(12) United States Patent
Wu et al.

(10) Patent No.: US 10,426,760 B2
(45) Date of Patent: *Oct. 1, 2019

(54) COMPOUNDS AND METHODS FOR KINASE MODULATION, AND INDICATIONS THEREFOR

(71) Applicant: Plexxikon Inc., Berkeley, CA (US)

(72) Inventors: Guoxian Wu, Foster City, CA (US); Jiazhong Zhang, Foster City, CA (US); Yong-Liang Zhu, Fremont, CA (US); Chao Zhang, Moraga, CA (US); Prabha N. Ibrahim, Mountain View, CA (US); Songyuan Shi, Fremont, CA (US); Wayne Spevak, Berkeley, CA (US); Dean R. Artis, Kensington, CA (US); James Tsai, Vallejo, CA (US)

(73) Assignee: Plexxikon Inc., Berkeley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/109,199

(22) Filed: Aug. 22, 2018

(65) Prior Publication Data

US 2019/0175567 A1  Jun. 13, 2019

Related U.S. Application Data

(63) Continuation of application No. 15/656,990, filed on Jul. 21, 2017, now abandoned, which is a (Continued)

(51) Int. Cl.
| | |
|---|---|
| A61K 31/44 | (2006.01) |
| A61K 31/41 | (2006.01) |
| A61K 31/42 | (2006.01) |
| A61K 31/415 | (2006.01) |
| C07D 213/75 | (2006.01) |
| C07D 213/82 | (2006.01) |
| C07D 215/12 | (2006.01) |
| C07D 215/20 | (2006.01) |
| C07D 215/38 | (2006.01) |
| C07D 239/48 | (2006.01) |
| C07D 263/48 | (2006.01) |
| C07D 417/12 | (2006.01) |
| C07D 471/04 | (2006.01) |
| A61K 31/437 | (2006.01) |
| A61K 31/444 | (2006.01) |
| A61K 31/47 | (2006.01) |
| A61K 31/5377 | (2006.01) |
| A61K 31/549 | (2006.01) |
| A61K 45/06 | (2006.01) |
| C07D 215/14 | (2006.01) |
| C07D 261/14 | (2006.01) |
| C07D 285/16 | (2006.01) |
| A61K 31/4439 | (2006.01) |
| A61K 31/505 | (2006.01) |
| C07D 213/76 | (2006.01) |
| C07D 239/49 | (2006.01) |
| A61K 31/506 | (2006.01) |

(Continued)

(52) U.S. Cl.
CPC ............ *A61K 31/44* (2013.01); *A61K 31/415* (2013.01); *A61K 31/42* (2013.01); *A61K 31/433* (2013.01); *A61K 31/437* (2013.01); *A61K 31/444* (2013.01); *A61K 31/4436* (2013.01); *A61K 31/4439* (2013.01); *A61K 31/4545* (2013.01); *A61K 31/47* (2013.01); *A61K 31/505* (2013.01); *A61K 31/506* (2013.01); *A61K 31/5377* (2013.01); *A61K 31/549* (2013.01); *A61K 45/06* (2013.01); *C07D 213/74* (2013.01); *C07D 213/75* (2013.01); *C07D 213/76* (2013.01); *C07D 213/82* (2013.01); *C07D 215/12* (2013.01); *C07D 215/14* (2013.01); *C07D 215/20* (2013.01); *C07D 215/38* (2013.01); *C07D 231/40* (2013.01); *C07D 239/48* (2013.01); *C07D 239/49* (2013.01); *C07D 261/14* (2013.01); *C07D 263/48* (2013.01); *C07D 285/135* (2013.01); *C07D 285/16* (2013.01); *C07D 401/12* (2013.01); *C07D 405/12* (2013.01); *C07D 409/12* (2013.01); *C07D 417/04* (2013.01); *C07D 417/12* (2013.01); *C07D 471/04* (2013.01)

(58) Field of Classification Search
CPC .............. A61K 31/4545; A61K 31/549; A61K 31/537; A61K 31/437
USPC .......................... 514/352, 349, 363, 378, 403
See application file for complete search history.

(56) References Cited

U.S. PATENT DOCUMENTS

| | | |
|---|---|---|
| 2,234,705 A | 3/1941 | Normington et al. |
| 2,413,258 A | 12/1946 | Soday et al. |

(Continued)

FOREIGN PATENT DOCUMENTS

| | | |
|---|---|---|
| CA | 2550361 | 7/2005 |
| DE | 24 13 258 | 10/1975 |

(Continued)

OTHER PUBLICATIONS

3OG7. "B-Raf Kinase V600E oncogenic mutant in complex with PLX4032," RCSB Protein Data Bank. Deposited: Aug. 16, 2010 Released: Sep. 22, 2010. https://www.rcsb.org/structure/3OG7.

(Continued)

*Primary Examiner* — Shengjun Wang
(74) *Attorney, Agent, or Firm* — Sheppard Mullin Richter & Hampton LLP

(57) ABSTRACT

Compounds active on protein kinases are described, as well as methods of using such compounds to treat diseases and conditions associated with aberrant activity of protein kinases.

52 Claims, No Drawings

Related U.S. Application Data continuation of application No. 15/260,042, filed on Sep. 8, 2016, now Pat. No. 9,844,539, which is a continuation of application No. 15/048,851, filed on Feb. 19, 2016, now Pat. No. 9,469,640, which is a continuation of application No. 13/926,959, filed on Jun. 25, 2013, now abandoned, which is a continuation of application No. 13/866,353, filed on Apr. 19, 2013, now abandoned, which is a continuation of application No. 12/669,450, filed as application No. PCT/US2008/070124 on Jul. 16, 2008, now abandoned.

(60) Provisional application No. 60/959,907, filed on Jul. 17, 2007.

(51) Int. Cl.

| | |
|---|---|
| *C07D 417/04* | (2006.01) |
| *C07D 213/74* | (2006.01) |
| *C07D 231/40* | (2006.01) |
| *C07D 285/135* | (2006.01) |
| *C07D 401/12* | (2006.01) |
| *C07D 405/12* | (2006.01) |
| *C07D 409/12* | (2006.01) |
| *A61K 31/433* | (2006.01) |
| *A61K 31/4436* | (2006.01) |
| *A61K 31/4545* | (2006.01) |

(56) References Cited

U.S. PATENT DOCUMENTS

| | | |
|---|---|---|
| 4,150,949 A | 4/1979 | Smith |
| 4,568,649 A | 2/1986 | Bertoglio-Matte |
| 4,595,780 A | 6/1986 | Ogata et al. |
| 4,626,513 A | 12/1986 | Burton et al. |
| 4,634,701 A | 1/1987 | De Vincentiis |
| 4,714,693 A | 12/1987 | Targos |
| 4,727,395 A | 2/1988 | Oda et al. |
| 4,863,945 A | 9/1989 | Friebe et al. |
| 5,120,782 A | 6/1992 | Hubsch et al. |
| 5,143,854 A | 9/1992 | Pirrung et al. |
| 5,338,849 A | 8/1994 | Festal et al. |
| 5,426,039 A | 6/1995 | Wallace et al. |
| 5,432,177 A | 7/1995 | Baker et al. |
| 5,434,049 A | 7/1995 | Okano et al. |
| 5,449,614 A | 9/1995 | Danos et al. |
| 5,474,935 A | 12/1995 | Chatterjee et al. |
| 5,486,525 A | 1/1996 | Summers et al. |
| 5,556,752 A | 9/1996 | Lockhart et al. |
| 5,576,319 A | 11/1996 | Baker et al. |
| 5,580,859 A | 12/1996 | Felgner et al. |
| 5,631,236 A | 5/1997 | Woo et al. |
| 5,632,957 A | 5/1997 | Heller et al. |
| 5,658,775 A | 8/1997 | Gilboa |
| 5,681,959 A | 10/1997 | Bishop et al. |
| 5,700,637 A | 12/1997 | Southern |
| 5,700,809 A | 12/1997 | Leeson et al. |
| 5,712,285 A | 1/1998 | Curtis et al. |
| 5,721,118 A | 2/1998 | Scheffler |
| 5,744,305 A | 4/1998 | Fodor et al. |
| 5,747,276 A | 5/1998 | Hoch et al. |
| 5,763,198 A | 6/1998 | Hirth et al. |
| 5,770,456 A | 6/1998 | Holmes |
| 5,800,992 A | 9/1998 | Fodor et al. |
| 5,807,522 A | 9/1998 | Brown et al. |
| 5,830,645 A | 11/1998 | Pinkel et al. |
| 5,840,485 A | 11/1998 | Lebl et al. |
| 5,856,174 A | 1/1999 | Lipshutz et al. |
| 5,858,995 A | 1/1999 | Kawai et al. |
| 5,877,007 A | 3/1999 | Housey |
| 5,952,362 A | 9/1999 | Cournoyer et al. |
| 5,959,098 A | 9/1999 | Goldberg et al. |
| 5,965,452 A | 10/1999 | Kovacs |
| 6,013,440 A | 1/2000 | Lipshutz et al. |
| 6,022,963 A | 2/2000 | McGall et al. |
| 6,025,155 A | 2/2000 | Hadlaczky et al. |
| 6,045,996 A | 4/2000 | Cronin et al. |
| 6,048,695 A | 4/2000 | Bradley et al. |
| 6,054,270 A | 4/2000 | Southern |
| 6,090,912 A | 7/2000 | Lebl et al. |
| 6,096,718 A | 8/2000 | Weitzman et al. |
| 6,107,478 A | 8/2000 | Pedersen et al. |
| 6,110,456 A | 8/2000 | During |
| 6,110,458 A | 8/2000 | Freeman et al. |
| 6,113,913 A | 9/2000 | Brough et al. |
| 6,117,681 A | 9/2000 | Salmons et al. |
| 6,161,776 A | 12/2000 | Byles |
| 6,178,384 B1 | 1/2001 | Kolossvary |
| 6,235,769 B1 | 5/2001 | Clary |
| 6,243,980 B1 | 6/2001 | Bronstein et al. |
| 6,258,606 B1 | 7/2001 | Kovacs |
| 6,261,776 B1 | 7/2001 | Pirrung et al. |
| 6,277,489 B1 | 8/2001 | Abbott et al. |
| 6,277,628 B1 | 8/2001 | Johann et al. |
| 6,288,234 B1 | 9/2001 | Griffin |
| 6,294,330 B1 | 9/2001 | Michnick et al. |
| 6,310,074 B1 | 10/2001 | Depreux et al. |
| 6,350,786 B1 | 2/2002 | Albano et al. |
| 6,545,014 B2 | 4/2003 | Verner |
| 6,653,309 B1 | 11/2003 | Saunders et al. |
| 6,858,860 B2 | 2/2005 | Hosono et al. |
| 6,897,207 B2 | 5/2005 | Cox et al. |
| 7,202,266 B2 | 4/2007 | Arnold et al. |
| 7,259,165 B2 | 8/2007 | Bernotas et al. |
| 7,348,338 B2 | 3/2008 | Arnold et al. |
| 7,361,763 B2 | 4/2008 | Arnold et al. |
| 7,361,764 B2 | 4/2008 | Arnold et al. |
| 7,452,993 B2 | 11/2008 | Arnold et al. |
| 7,476,746 B2 | 1/2009 | Artis et al. |
| 7,491,831 B2 | 2/2009 | Artis et al. |
| 7,498,342 B2 | 3/2009 | Ibrahim et al. |
| 7,504,509 B2 | 3/2009 | Ibrahim et al. |
| 7,517,970 B2 | 4/2009 | West et al. |
| 7,531,568 B2 | 5/2009 | Lin et al. |
| 7,572,806 B2 | 8/2009 | Arnold et al. |
| 7,582,637 B2 | 9/2009 | Arnold et al. |
| 7,585,859 B2 | 9/2009 | Ibrahim et al. |
| 7,601,839 B2 | 10/2009 | Arnold et al. |
| 7,605,168 B2 | 10/2009 | Ibrahim et al. |
| 7,626,021 B2 | 12/2009 | Arnold et al. |
| 7,723,374 B2 | 5/2010 | Artis et al. |
| 7,846,941 B2 | 12/2010 | Zhang et al. |
| 7,863,288 B2 | 1/2011 | Ibrahim et al. |
| 7,863,289 B2 | 1/2011 | Spevak et al. |
| 7,872,018 B2 | 1/2011 | Ibrahim et al. |
| 7,893,075 B2 | 2/2011 | Zhang et al. |
| 7,897,623 B2 | 3/2011 | Riedl |
| 7,947,708 B2 | 5/2011 | Ibrahim et al. |
| 7,994,185 B2 | 8/2011 | Rheault |
| 8,053,463 B2 | 11/2011 | Lin et al. |
| 8,067,434 B2 | 11/2011 | Ibrahim et al. |
| 8,067,638 B2 | 11/2011 | Kai et al. |
| 8,110,576 B2 | 2/2012 | Ibrahim et al. |
| 8,119,637 B2 | 2/2012 | Ibrahim et al. |
| 8,129,404 B2 | 3/2012 | Ibrahim et al. |
| 8,143,271 B2 | 3/2012 | Ibrahim et al. |
| 8,153,641 B2 | 4/2012 | Ibrahim et al. |
| 8,158,636 B2 | 4/2012 | Ibrahim et al. |
| 8,198,273 B2 | 6/2012 | Ibrahim et al. |
| 8,367,828 B2 | 2/2013 | Arnold et al. |
| 8,404,700 B2 | 3/2013 | Zhang et al. |
| 8,415,345 B2 | 4/2013 | Adjabeng et al. |
| 8,415,469 B2 | 4/2013 | Ibrahim et al. |
| 8,461,169 B2 | 6/2013 | Zhang et al. |
| 8,470,818 B2 | 6/2013 | Ibrahim et al. |
| 8,642,606 B2 | 2/2014 | Wu et al. |
| 8,673,928 B2 | 3/2014 | Ibrahim et al. |
| 8,722,702 B2 | 5/2014 | Zhang et al. |
| 8,865,735 B2 | 10/2014 | Ibrahim et al. |
| 8,901,118 B2 | 12/2014 | Zhang et al. |
| 8,901,301 B2 | 12/2014 | Ibrahim et al. |

(56) References Cited

U.S. PATENT DOCUMENTS

| | | | |
|---|---|---|---|
| 8,912,204 B2 | 12/2014 | Ibrahim et al. |
| 9,469,640 B2 | 10/2016 | Wu et al. |
| 9,730,918 B2 | 8/2017 | Bollag et al. |
| 9,745,298 B2 | 8/2017 | Ibrahim et al. |
| 9,776,998 B2 | 10/2017 | Ibrahim et al. |
| 9,802,932 B2 | 10/2017 | Ibrahim et al. |
| 9,814,714 B2 | 11/2017 | Ibrahim et al. |
| 9,822,109 B2 | 11/2017 | Zhang et al. |
| 9,844,539 B2 | 12/2017 | Wu et al. |
| 9,856,259 B2 | 1/2018 | Shi et al. |
| 2001/0001449 A1 | 5/2001 | Kiliany et al. |
| 2001/0008765 A1 | 7/2001 | Shinoki et al. |
| 2001/0012537 A1 | 8/2001 | Anderson et al. |
| 2001/0014448 A1 | 8/2001 | Chappa et al. |
| 2001/0014449 A1 | 8/2001 | Nerenberg et al. |
| 2001/0016322 A1 | 8/2001 | Caren et al. |
| 2001/0018642 A1 | 8/2001 | Balaban et al. |
| 2001/0019827 A1 | 9/2001 | Dawson et al. |
| 2003/0003004 A1 | 1/2003 | Stones et al. |
| 2003/0187001 A1 | 10/2003 | Calderwood et al. |
| 2003/0219489 A1 | 11/2003 | Curatolo et al. |
| 2003/0225106 A1 | 12/2003 | Askew et al. |
| 2004/0002534 A1 | 1/2004 | Lipson et al. |
| 2004/0022534 A1 | 2/2004 | Amano et al. |
| 2004/0077595 A1 | 4/2004 | Cheng et al. |
| 2004/0142864 A1 | 7/2004 | Bremer et al. |
| 2004/0167030 A1 | 8/2004 | Bernotas et al. |
| 2004/0171062 A1 | 9/2004 | Hirth et al. |
| 2005/0026792 A1 | 2/2005 | Cartwright |
| 2005/0031692 A1 | 2/2005 | Beyerinck et al. |
| 2005/0048573 A1 | 3/2005 | Artis et al. |
| 2005/0079548 A1 | 4/2005 | Artis et al. |
| 2005/0085463 A1 | 4/2005 | Weiner et al. |
| 2005/0154014 A1 | 7/2005 | Bloxham et al. |
| 2005/0164300 A1 | 7/2005 | Artis et al. |
| 2005/0170431 A1 | 8/2005 | Ibrahim et al. |
| 2005/0222171 A1 | 10/2005 | Bold et al. |
| 2005/0256151 A1 | 11/2005 | Salom et al. |
| 2006/0018726 A1 | 1/2006 | Hall |
| 2006/0024361 A1 | 2/2006 | Odidi et al. |
| 2006/0035898 A1 | 2/2006 | Arnold et al. |
| 2006/0058339 A1 | 3/2006 | Ibrahim et al. |
| 2006/0058340 A1 | 3/2006 | Ibrahim et al. |
| 2006/0135540 A1 | 6/2006 | Lin et al. |
| 2006/0160135 A1 | 7/2006 | Wang et al. |
| 2006/0270686 A1 | 11/2006 | Kelly et al. |
| 2007/0032519 A1 | 2/2007 | Zhang et al. |
| 2007/0049615 A1 | 3/2007 | Ibrahim et al. |
| 2007/0066641 A1 | 3/2007 | Ibrahim et al. |
| 2007/0072862 A1 | 3/2007 | Dimauro et al. |
| 2007/0072904 A1 | 3/2007 | Lin et al. |
| 2007/0218138 A1 | 9/2007 | Bittorf et al. |
| 2007/0287711 A1 | 12/2007 | Arnold et al. |
| 2008/0079906 A1 | 4/2008 | Finn |
| 2008/0167338 A1 | 7/2008 | Spevak et al. |
| 2008/0188514 A1 | 8/2008 | Wu et al. |
| 2008/0221127 A1 | 9/2008 | Lin et al. |
| 2008/0234349 A1 | 9/2008 | Lin et al. |
| 2008/0249137 A1 | 10/2008 | Lin et al. |
| 2009/0005356 A1 | 1/2009 | Blaney et al. |
| 2009/0076046 A1 | 3/2009 | Zhang et al. |
| 2009/0143352 A1 | 6/2009 | Arnold et al. |
| 2009/0306056 A1 | 12/2009 | Arnold et al. |
| 2010/0190777 A1 | 7/2010 | Wu et al. |
| 2010/0310659 A1 | 12/2010 | Desai et al. |
| 2011/0092538 A1 | 4/2011 | Spevak et al. |
| 2011/0112127 A1 | 5/2011 | Zhang et al. |
| 2011/0166174 A1 | 7/2011 | Ibrahim et al. |
| 2011/0183988 A1 | 7/2011 | Ibrahim et al. |
| 2012/0015966 A1 | 1/2012 | Lin et al. |
| 2012/0053177 A1 | 3/2012 | Ibrahim et al. |
| 2012/0122860 A1 | 5/2012 | Visor et al. |
| 2012/0165366 A1 | 6/2012 | Ibrahim et al. |
| 2012/0245174 A1 | 9/2012 | Ibrahim et al. |
| 2013/0237531 A1 | 9/2013 | Wu et al. |
| 2013/0261117 A1 | 10/2013 | Ibrahim et al. |
| 2013/0274259 A1 | 10/2013 | Zhang et al. |
| 2013/0303534 A1 | 11/2013 | Ibrahim et al. |
| 2014/0037617 A1 | 2/2014 | Bollag et al. |
| 2014/0038948 A1 | 2/2014 | Wu et al. |
| 2014/0045840 A1 | 2/2014 | Zhang et al. |
| 2014/0094611 A1 | 4/2014 | Ibrahim et al. |
| 2014/0128373 A1 | 5/2014 | Ibrahim et al. |
| 2014/0128390 A1 | 5/2014 | Lin et al. |
| 2014/0213554 A1 | 7/2014 | Wu et al. |
| 2014/0243365 A1 | 8/2014 | Zhang et al. |
| 2014/0288070 A1 | 9/2014 | Ibrahim et al. |
| 2014/0303121 A1 | 10/2014 | Zhang et al. |
| 2014/0303187 A1 | 10/2014 | Wu et al. |
| 2014/0357612 A1 | 12/2014 | Zhang et al. |
| 2015/0080372 A1 | 3/2015 | Ibrahim et al. |
| 2015/0284397 A1 | 3/2015 | Lin et al. |
| 2015/0133400 A1 | 5/2015 | Zhang et al. |
| 2015/0166547 A1 | 6/2015 | Ibrahim et al. |
| 2015/0265586 A1 | 6/2015 | Zhang et al. |
| 2015/0183793 A1 | 7/2015 | Zhang et al. |
| 2015/0368243 A1 | 8/2015 | Ibrahim |
| 2015/0290205 A1 | 10/2015 | Ibrahim et al. |
| 2016/0068528 A1 | 3/2016 | Zhang et al. |
| 2016/0075712 A1 | 3/2016 | Shi et al. |
| 2016/0176865 A1 | 6/2016 | Ibrahim et al. |
| 2016/0243092 A1 | 8/2016 | Bollag et al. |
| 2016/0326162 A1 | 11/2016 | Lin et al. |
| 2016/0326168 A1 | 11/2016 | Ibrahim et al. |
| 2016/0326169 A1 | 11/2016 | Ibrahim et al. |
| 2016/0339025 A1 | 11/2016 | Ibrahim et al. |
| 2016/0340357 A1 | 11/2016 | Ibrahim et al. |
| 2016/0340358 A1 | 11/2016 | Ibrahim et al. |
| 2016/0355513 A1 | 12/2016 | Desai et al. |
| 2017/0029413 A1 | 2/2017 | Holladay et al. |
| 2017/0081326 A1 | 3/2017 | Ibrahim et al. |
| 2017/0157120 A1 | 6/2017 | Ibrahim et al. |
| 2017/0158690 A1 | 6/2017 | Wu et al. |
| 2017/0247370 A1 | 8/2017 | Zhang et al. |
| 2017/0267660 A1 | 9/2017 | Lin et al. |
| 2017/0283423 A1 | 10/2017 | Zhang et al. |
| 2017/0319559 A1 | 11/2017 | Wu et al. |
| 2017/0320899 A1 | 11/2017 | Zhang et al. |
| 2017/0334909 A1 | 11/2017 | Ibrahim et al. |
| 2017/0349572 A1 | 12/2017 | Wu et al. |
| 2017/0362231 A1 | 12/2017 | Ibrahim et al. |
| 2018/0002332 A1 | 1/2018 | Ibrahim et al. |
| 2018/0030051 A1 | 2/2018 | Ibrahim et al. |
| 2018/0055828 A1 | 3/2018 | Bollag |
| 2018/0072722 A1 | 3/2018 | Zhang et al. |
| 2018/0099939 A1 | 4/2018 | Zhang et al. |
| 2018/0099975 A1 | 4/2018 | Zhang et al. |
| 2018/0111929 A1 | 4/2018 | Ibrahim |
| 2018/0111930 A1 | 4/2018 | Desai |
| 2018/0215763 A1 | 8/2018 | Wu et al. |
| 2018/0265508 A1 | 9/2018 | Lin |
| 2018/0305358 A1 | 10/2018 | Ibrahim et al. |
| 2018/0327403 A1 | 11/2018 | Ibrahim et al. |
| 2018/0354946 A1 | 12/2018 | Zhang et al. |
| 2019/0031654 A1 | 1/2019 | Ibrahim et al. |
| 2019/0119273 A1 | 4/2019 | Ibrahim et al. |
| 2019/0125747 A1 | 5/2019 | Rezaei et al. |
| 2019/0161484 A1 | 5/2019 | Ibrahim et al. |

FOREIGN PATENT DOCUMENTS

| | | |
|---|---|---|
| EP | 0 344 603 | 5/1989 |
| EP | 0 154 734 | 8/1990 |
| EP | 0 465 970 | 1/1992 |
| EP | 0 580 860 | 4/1992 |
| EP | 0 148 725 | 5/1994 |
| EP | 0 596 406 | 5/1994 |
| EP | 0 901 786 | 7/1998 |
| EP | 0 988 863 | 3/2000 |
| EP | 1 057 826 | 12/2000 |
| EP | 1 368 001 | 2/2002 |
| EP | 0 870 768 | 5/2002 |
| EP | 1 749 829 | 2/2007 |
| FR | 2264804 | 10/1975 |

(56) References Cited

FOREIGN PATENT DOCUMENTS

| | | |
|---|---|---|
| GB | 1 198 301 A | 5/1973 |
| GB | 2 292 143 | 2/1996 |
| GB | 2 292 145 | 2/1996 |
| GB | 2 298 198 | 8/1996 |
| GB | 2 299 581 | 10/1996 |
| JP | 06-135946 | 5/1994 |
| JP | 10-087629 | 4/1998 |
| JP | 10-130269 | 5/1998 |
| JP | 2001-278886 | 10/2001 |
| JP | 15-073357 | 3/2003 |
| WO | WO-93/13099 | 7/1993 |
| WO | WO-94/14808 | 7/1994 |
| WO | WO-94/20459 | 9/1994 |
| WO | WO-94/20497 | 9/1994 |
| WO | WO-95/04742 | 2/1995 |
| WO | WO-95/07910 | 3/1995 |
| WO | WO-95/28387 | 10/1995 |
| WO | WO-96/00226 | 1/1996 |
| WO | WO-96/11929 | 2/1996 |
| WO | WO-96/05200 | 4/1996 |
| WO | WO-96/17958 | 6/1996 |
| WO | WO-96/18738 | 6/1996 |
| WO | WO-96/30347 | 10/1996 |
| WO | WO-96/38131 | 12/1996 |
| WO | WO-97/03967 | 2/1997 |
| WO | WO-97/46313 | 12/1997 |
| WO | WO-97/46558 | 12/1997 |
| WO | WO-97/49703 | 12/1997 |
| WO | WO-98/06433 | 2/1998 |
| WO | WO-98/22457 | 5/1998 |
| WO | WO-98/47899 | 10/1998 |
| WO | WO-99/00386 | 1/1999 |
| WO | WO-99/09217 | 2/1999 |
| WO | WO-99/32433 | 7/1999 |
| WO | WO-99/51231 | 10/1999 |
| WO | WO-99/51232 | 10/1999 |
| WO | WO-99/51233 | 10/1999 |
| WO | WO-99/51234 | 10/1999 |
| WO | WO-99/51595 | 10/1999 |
| WO | WO-99/51596 | 10/1999 |
| WO | WO-99/51773 | 10/1999 |
| WO | WO-00/09162 | 2/2000 |
| WO | WO-00/12074 | 3/2000 |
| WO | WO-00/12514 | 3/2000 |
| WO | WO-00/17202 | 3/2000 |
| WO | WO-00/17203 | 3/2000 |
| WO | WO-00/29411 | 5/2000 |
| WO | WO-00/53582 | 9/2000 |
| WO | WO-00/55153 | 9/2000 |
| WO | WO-00/64898 | 11/2000 |
| WO | WO-00/71506 | 11/2000 |
| WO | WO-00/71537 | 11/2000 |
| WO | WO-00/75139 | 12/2000 |
| WO | WO-01/09121 | 2/2001 |
| WO | WO-01/19829 | 3/2001 |
| WO | WO-01/24236 | 4/2001 |
| WO | WO-01/29036 | 4/2001 |
| WO | WO-01/38324 | 5/2001 |
| WO | WO-01/46196 | 6/2001 |
| WO | WO-01/60822 | 8/2001 |
| WO | WO-01/62255 | 8/2001 |
| WO | WO-01/66539 | 9/2001 |
| WO | WO-01/66540 | 9/2001 |
| WO | WO-01/72778 | 10/2001 |
| WO | WO-01/74786 | 11/2001 |
| WO | WO-01/98299 | 12/2001 |
| WO | WO-02/00657 | 1/2002 |
| WO | WO-02/18346 | 3/2002 |
| WO | WO-02/24680 | 3/2002 |
| WO | WO-02/076396 | 10/2002 |
| WO | WO-02/083175 | 10/2002 |
| WO | WO-02/085896 | 10/2002 |
| WO | WO-02/094808 | 11/2002 |
| WO | WO-02/102783 | 12/2002 |
| WO | WO-03/000258 | 1/2003 |
| WO | WO-03/000267 | 1/2003 |
| WO | WO-03/003004 | 1/2003 |
| WO | WO-03/004472 | 1/2003 |
| WO | WO-03/006459 | 1/2003 |
| WO | WO-03/008422 | 1/2003 |
| WO | WO-03/011868 | 2/2003 |
| WO | WO-03/020698 | 3/2003 |
| WO | WO-03/022832 | 3/2003 |
| WO | WO-03/022833 | 3/2003 |
| WO | WO-03/022836 | 3/2003 |
| WO | WO-03/022837 | 3/2003 |
| WO | WO-03/022838 | 3/2003 |
| WO | WO-03/022840 | 3/2003 |
| WO | WO-03/028724 | 4/2003 |
| WO | WO-03/037862 | 5/2003 |
| WO | WO-03/051838 | 6/2003 |
| WO | WO-03/064413 | 8/2003 |
| WO | WO-03/068221 | 8/2003 |
| WO | WO-03/082289 | 10/2003 |
| WO | WO-03/082868 | 10/2003 |
| WO | WO-03/082869 | 10/2003 |
| WO | WO-03/087087 | 10/2003 |
| WO | WO-03/101990 | 12/2003 |
| WO | WO-2004/005283 | 1/2004 |
| WO | WO-2004/009600 | 1/2004 |
| WO | WO-2004/009601 | 1/2004 |
| WO | WO-2004/014369 | 2/2004 |
| WO | WO-2004/016609 | 2/2004 |
| WO | WO-2004/016610 | 2/2004 |
| WO | WO-2004/024895 | 3/2004 |
| WO | WO-2004/052880 | 6/2004 |
| WO | WO-2004/054581 | 7/2004 |
| WO | WO-2004/056830 A | 7/2004 |
| WO | WO-2004/065393 | 8/2004 |
| WO | WO-2004/065394 | 8/2004 |
| WO | WO-2004/069138 | 8/2004 |
| WO | WO-2004/072070 | 8/2004 |
| WO | WO-2004/074286 | 9/2004 |
| WO | WO 2004/076412 | 9/2004 |
| WO | WO-2004/078756 | 9/2004 |
| WO | WO-2004/078923 | 9/2004 |
| WO | WO-2004/101565 | 11/2004 |
| WO | WO-2005/002673 | 1/2005 |
| WO | WO-2005/026129 A1 | 3/2005 |
| WO | WO-2005/028475 | 3/2005 |
| WO | WO-2005/028624 | 3/2005 |
| WO | WO-2005/030128 | 4/2005 |
| WO | WO-2005/034869 | 4/2005 |
| WO | WO-2005/044181 | 5/2005 |
| WO | WO-2005/058891 | 6/2005 |
| WO | WO-2005/062795 | 7/2005 |
| WO | WO-2005/063746 | 7/2005 |
| WO | WO-2005/063747 | 7/2005 |
| WO | WO-2005/066347 | 7/2005 |
| WO | WO-2005/082367 | 9/2005 |
| WO | WO-2005/085244 | 9/2005 |
| WO | WO-2005/086904 | 9/2005 |
| WO | WO-2005/090328 | 9/2005 |
| WO | WO-2005/092896 | 10/2005 |
| WO | WO-2005/095400 | 10/2005 |
| WO | WO-2005/103050 | 11/2005 |
| WO | WO-2005/115363 | 12/2005 |
| WO | WO-2005/115374 | 12/2005 |
| WO | WO-2006/004984 | 1/2006 |
| WO | WO-2006/009755 | 1/2006 |
| WO | WO-2006/009797 | 1/2006 |
| WO | WO-2006/010637 | 2/2006 |
| WO | WO-2006/015123 | 2/2006 |
| WO | WO-2006/015124 | 2/2006 |
| WO | WO-2006/053121 | 5/2006 |
| WO | WO-2006/063167 | 6/2006 |
| WO | WO-2006/099075 | 9/2006 |
| WO | WO-2006/114180 | 11/2006 |
| WO | WO-2006/114520 | 11/2006 |
| WO | WO-2006/124874 | 11/2006 |
| WO | WO-2006/127587 | 11/2006 |
| WO | WO-2006/137376 | 12/2006 |
| WO | WO-2007/002325 | 1/2007 |
| WO | WO-2007/002433 | 1/2007 |

(56) References Cited

FOREIGN PATENT DOCUMENTS

| WO | WO-2007/013896 | 2/2007 |
| WO | WO-2007/021795 | 2/2007 |
| WO | WO-2007/022380 | 2/2007 |
| WO | WO-2007/106236 | 9/2007 |
| WO | WO-2008/058341 | 5/2008 |
| WO | WO-2008/079903 | 7/2008 |
| WO | WO-2008/079906 | 7/2008 |
| WO | WO-2008/079909 | 7/2008 |
| WO | WO-2008/138755 | 11/2008 |
| WO | WO-2009/012791 | 1/2009 |
| WO | WO-2009/111277 | 9/2009 |
| WO | WO-2009/111278 | 9/2009 |
| WO | WO-2009/111279 | 9/2009 |
| WO | WO-2009/111280 | 9/2009 |
| WO | WO-2009/137391 | 11/2009 |
| WO | WO-2010/104899 | 9/2010 |
| WO | WO-2010/111527 | 9/2010 |
| WO | WO-2010/114928 | 10/2010 |
| WO | WO-2010/129467 | 11/2010 |

OTHER PUBLICATIONS

4CQE. "B-Raf Kinase V600E mutant in complex with a diarylthiazole B-Raf Inhibitor," RCSB Protein Data Bank. Deposited: Feb. 14, 2014 Released: Dec. 10, 2014. https://www.rcsb.org/structure/4CQE.
4EX4. "Crystal Structure of B-Raf Kinase Domain in Complex with a Dihydropyrido[2,3-d]pyrimidinone-based Inhibitor," RCSB Protein Data Bank. Deposited: Mar. 13, 2012 Released: May 9, 2012. https://www.rcsb.org/structure/4e4x.
Aoki, et al. Hepatitis C virus core protein interacts with 14-3-3 protein and activates the kinase Raf-1. J Virol. Feb. 2000;74(4):1736-41.
Arnold, et al. Molecular Interactions in Crystal Structures of Potent Inhibitors Bound to the Kinase Domain of Tie-2. 93rd Annual American Association of Cancer Research Meeting, Apr. 2002, San Francisco, CA, Abs. # 4204.
Benn, et al. Hepatitis B virus HBx protein activates Ras-GTP complex formation and establishes a Ras, Raf, MAP kinase signaling cascade. PNAS Oct. 25, 1994 91 (22) 10350-10354.
Bollag, et al. Clinical efficacy of a RAF inhibitor needs broad target blockade in BRAF-mutant melanoma. Nature. Sep. 30, 2010;467(7315):596-9. doi: 10.1038/nature09454.
Cameron. A slow saga of success. Paradigm Magazine. (Spring 2007).
Cantwell-Dorris, et al. BRAFV600E: implications for carcinogenesis and molecular therapy. Mol Cancer Ther. Mar. 2011;10(3):385-94. doi: 10.1158/1535-7163.MCT-10-0799.
Cox, et al. Protodeboronation of Heteroaromatic, Vinyl, and Cyclopropyl Boronic Acids: pH-Rate Profiles, Autocatalysis, and Disproportionation. J Am Chem Soc. Jul. 27, 2016;138(29):9145-57. doi: 10.1021/jacs.6b03283. Epub Jul. 15, 2016.
Danson, et al. Improving Outcomes in Advanced Malignant Melanoma. Drugs. Apr. 2005, vol. 65, Issue 6, pp. 733-743.
Decision Denying Institution of Inter Partes Review—*Novartis Pharmaceuticals Corporation* v. *Plexxikon Inc.* Case IPR2018-01287. U.S. Pat. No. 9,469,640 B2. Dated Jan. 16, 2019. 16 pages.
Decision Denying Institution of Post-Grant Review—*Novartis Pharmaceuticals Corporation* v. *Plexxikon Inc.* Case PGR2018-00069. U.S. Pat. No. 9,844,539 B2. Dated Jan. 16, 2019. 22 pages.
Dufert, et al. Suzuki-Miyaura cross-coupling of unprotected, nitrogen-rich heterocycles: substrate scope and mechanistic investigation. J Am Chem Soc. Aug. 28, 2013;135(34):12877-85. doi: 10.1021/ja4064469. Epub Aug. 16, 2013.
Fabbro, et al. Ten things you should know about protein kinases: IUPHAR Review 14. Br J Pharmacol. Jun. 2015; 172(11): 2675-2700.
Fabbro. 25 years of small molecular weight kinase inhibitors: potentials and limitations. Mol Pharmacol. May 2015;87(5):766-75. doi: 10.1124/mol.114.095489. Epub Dec. 30, 2014.

Flaherty, et al. Inhibition of mutated, activated BRAF in metastatic melanoma. N Engl J Med. Aug. 26, 2010;363(9):809-19. doi: 10.1056/NEJMoa1002011.
Gandin, et al. Targeting kinases with anilinopyrimidines: discovery of N-phenyl-N'-[4-(pyrimidin-4-ylamino)phenyl]urea derivatives as selective inhibitors of class III receptor tyrosine kinase subfamily. Scientific Reports vol. 5, Article No. 16750 (2015).
Gao, et al. Using Machine Learning to Predict Suitable Conditions for Organic Reactions. 4 ACS Cent. Sci. 1465-76 (2018).
Garcia, et al. Impact of protein kinase PKR in cell biology: from antiviral to antiproliferative action. Microbiol Mol Biol Rev. Dec. 2006;70(4):1032-60.
Goodbourn, et al. Interferons: cell signalling, immune modulation, antiviral response and virus countermeasures. Oct. 1, 2000, Journal of General Virology 81: 2341-236.
Gross, et al. Targeting cancer with kinase inhibitors. J Clin Invest. May 2015;125(5):1780-9. doi: 10.1172/JCI76094. Epub May 1, 2015.
Hammerle, et al. A guideline for the arylation of positions 4 and 5 of thiazole via Pd-catalyzed cross-coupling reactions. Tetrahedron. vol. 66, Issue 40, Oct. 2, 2010, pp. 8051-8059.
Harmon. After Long Fight, Drug Gives Sudden Reprieve. New York Times (Feb. 23, 2010).
Harmon. Cycle of a Drug Trial: Recovery and Relapse, Then Reinvention. New York Times (Feb. 24, 2010).
Harmon. New Drugs Stir Debate on Rules of Clinical Trials. New York Times (Sep. 18, 2010).
Harmon. Urgent Chase for a Cure: Doggedly Testing a New Drug to Treat Melanoma. New York Times (Feb. 22, 2010).
Hubbard, et al. Protein tyrosine kinase structure and function. Annu. Rev. Biochem. 2000. 69:373-98.
Hubbard. Structural analysis of receptor tyrosine kinases. Prog Biophys Mol Biol. 1999;71(3-4):343-58.
Ibrahim et al., Discovery and Development of Vemurafenib: First-in-Class Inhibitor of Mutant BRAF for Treatment of Cancer, Medicinal Chemistry Approaches to Personalized Medicine (Karen Lackey & Bruce D. Roth, Eds., 1st ed. 2014) 91-100.
Jedinak, et al. The Suzuki-Miyaura Cross-Coupling Reaction of Halogenated Aminopyrazoles: Method Development, Scope, and Mechanism of Dehalogenation Side Reaction. J. Org. Chem., 2017, 82 (1), pp. 157-169.
Kannaiyan, et al. A comprehensive review of protein kinase inhibitors for cancer therapy. Expert Review of Anticancer Therapy. 2018; 18:1249-1270.
Keri, et al. Signal Transduction Therapy with Rationally Designed Kinase Inhibitors, 1 Curr. Signal Transduction Therapy 67-95 (2006).
King, et al. Demonstration of a genetic therapeutic index for tumors expressing oncogenic BRAF by the kinase inhibitor SB-590885. 66(23) Cancer Res. 11100-11105 (2006).
Kinzel, et al. A new palladium precatalyst allows for the fast Suzuki-Miyaura coupling reactions of unstable polyfluorophenyl and 2-heteroaryl boronic acids. J Am Chem Soc. Oct. 13, 2010;132(40):14073-5. doi: 10.1021/ja1073799.
Knockaert, et al. Pharmacological inhibitors of cyclin-dependent kinases. Trends in Pharmacological Sciences. vol. 23, Issue 9, Sep. 1, 2002, pp. 417-425.
Krosky, et al. The human cytomegalovirus UL97 protein kinase, an antiviral drug target, is required at the stage of nuclear egress. J Virol. Jan. 2003;77(2):905-14.
Kumar, et al. BRAF mutations are common somatic events in melanocytic nevi. J Invest Dermatol. Feb. 2004;122(2):342-8.
Levinson, et al. A conserved water-mediated hydrogen bond network defines bosutinib's kinase selectivity. Nat Chem Biol. Feb. 2014;10(2):127-32. doi: 10.1038/nchembio.1404. Epub Dec. 1, 2013.
Liu, et al. Rational design of inhibitors that bind to inactive kinase conformations. Nat Chem Biol. Jul. 2006;2(7):358-64.
Ludwig, et al. Influenza-virus-induced signaling cascades: targets for antiviral therapy? Trends Mol Med. Feb. 2003;9(2):46-52.
Marathon man: Genomics has not yet delivered the drugs, but it will. The Economist. Jun. 17, 2010. https://www.economist.com/node/16349422.

(56) References Cited

OTHER PUBLICATIONS

Martin, et al. Palladium-Catalyzed Suzuki-Miyaura Cross-Coupling Reactions Employing Dialkylbiaryl Phosphine Ligands. Acc. Chem. Res., 2008, 41 (11), pp. 1461-1473.
Mashhoon, et al. Crystal structure of a conformation-selective casein kinase-1 inhibitor. Jun. 30, 2000; The Journal of Biological Chemistry. 275, 20052-20060.
McInnes, et al. Strategies for the design of potent and selective kinase inhibitors. Curr Pharm Des. 2005;11(14):1845-63.
Merour, et al. The azaindole framework in the design of kinase inhibitors. Molecules. Nov. 28, 2014;19(12):19935-79. doi: 10.3390/molecules191219935.
Mijuk. Companies Aim to Personalize Therapy, Wall Street Journal (Oct. 26, 2010).
Noble, et al. Protein kinase inhibitors: insights into drug design from structure. Science. Mar. 19, 2004;303(5665):1800-5.
Pratilas, et al. Therapeutic Strategies for Targeting BRAF in Human Cancer. Reviews on Recent Clinical Trials, vol. 2, No. 2, May 2007, pp. 121-134(14).
Rheault, et al. Discovery of Dabrafenib: A Selective Inhibitor of Raf Kinases with Antitumor Activity against B-Raf-Driven Tumors. ACS Med Chem Lett. Feb. 7, 2013;4(3):358-62. doi: 10.1021/ml4000063. eCollection Mar. 14, 2013.
Roskoski, et al. Classification of small molecule protein kinase inhibitors based upon the structures of their drug-enzyme complexes. Pharmacological Research 103 (2016) 26-48.
Schang, et al. Pharmacological Cyclin-Dependent Kinase Inhibitors Inhibit Replication of Wild-Type and Drug-Resistant Strains of Herpes Simplex Virus and Human Immunodeficiency Virus Type 1 by Targeting Cellular, Not Viral, Proteins. Journal of Virology, Aug. 2002, vol. 76, No. 15, p. 7874-7882.
Shelledy, et al. Vemurafenib: First-in-Class BRAF-Mutated Inhibitor for the Treatment of Unresectable or Metastatic Melanoma. J Adv Pract Oncol. Jul.-Aug. 2015;6(4):361-5. Epub Jul. 1, 2015.
Singer, et al. Mutations in BRAF and KRAS characterize the development of low-grade ovarian serous carcinoma. J Natl Cancer Inst. Mar. 19, 2003;95(6):484-6.
Smalley, et al. Targeting Intracellular Signaling Pathways as a Novel Strategy in Melanoma Therapeutics. 1059 Ann. N.Y. Acad. Sci. 16-25 (2005).
Stellwagen, et al. Development of potent B-RafV600E inhibitors containing an arylsulfonamide headgroup. Bioorg Med Chem Lett. Aug. 1, 2011;21(15):4436-40. doi: 10.1016/j.bmcl.2011.06.021. Epub Jun. 16, 2011.
Suzuki. Cross-Coupling Reactions of Organoboranes: An Easy Way to Construct C☐C Bonds (Nobel Lecture). 50 Angew. Che. Int. Ed. 6723-6737 (2011).
Szabo. 'Breakthrough' melanoma drug shrinks tumors. USATODAY. Aug. 26, 2010. https://usatoday30.usatoday.com/news/health/2010-08-26-1Amelanoma26_ST_N.htm.
Taylor, et al. Roscovitine, a cyclin-dependent kinase inhibitor, prevents replication of varic ella-zoster virus. J Virol. Mar. 2004;78(6):2853-62.
Timmerman. Plexxikon Shows How New Drug Hits Molecular Target for Deadly Skin Cancer, XCONOMY (Sep. 7, 2010).
Vieth, et al. Kinomics-structural biology and chemogenomics of kinase inhibitors and targets. Biochim Biophys Acta. Mar. 11, 2004;1697(1-2):243-57.
Wan, et al. Mechanism of activation of the RAF-ERK signaling pathway by oncogenic mutations of B-RAF. Cell. Mar. 19, 2004;116(6):855-67.
Wu, et al. FDA-approved small-molecule kinase inhibitors. Trends in Pharmacological Sciences. vol. 36, Issue 7, Jul. 2015, pp. 422-439.
U.S. Appl. No. 14/798,167, filed Jul. 13, 2015, Ibrahim et al.
U.S. Appl. No. 14/846,545, filed Sep. 4, 2015, zhang et al.
U.S. Appl. No. 14/850,912, filed Sep. 10, 2015, Shi et al.
U.S. Appl. No. 15/093,660, filed Apr. 7, 2016, Lin et al.
U.S. Appl. No. 15/147,692, filed May 5, 2016, Ibrahim et al.
U.S. Appl. No. 15/147,709, filed May 5, 2016, Ibrahim et al.
U.S. Appl. No. 15/147,781, filed May 5, 2016, Bollag et al.
U.S. Appl. No. 15/160,551, filed May 20, 2016, Ibrahim et al.
U.S. Appl. No. 15/160,729, filed May 20, 2016, Ibrahim et al.
U.S. Appl. No. 15/161,103, filed May 20, 2016, Ibrahim.
Ahmad, K., "BRAF mutation common to 70% of thyroid carcinomas," The Lancet, Oncology, (2003), 4:330.
Alfthan, K., "Surface Plasmon Resonance Biosensors as a Tool in Antibody Engineering," Biosensors & Bioelectronics, (1998), 13:653-663.
Allegretti, et al., "Palladium-Catalysed Functionalisation at 4- and 6-Position of the 7-Azaindole System," Synlett, (2001), 5:609-612.
Al-Obeidi, et al., Peptide and Peptidomimetic Libraries, Mol Biotechnol., (1998), 9:205-223.
Alvarez, et al., "Synthesis of 3-Aryl- and 3-Heteroaryl-7-Azaindoles," Synthesis, (1999), 4:615-620.
Amersdorfer, et al., "Phage Libraries for Generation of Anti-Botulinum scFv Antibodies," Methods in Molecular Biology, (2000), 145:219-240.
Amiel, et al., "Hirschsprung disease, associated syndromes and genetics: a review," J Med Genet., (2008), 45:1-14.
Anderson, et al., "Cooperative Catalyst Effects in Palladium-Mediated Cyanation Reactions of Aryl Halides and Triflates," J. Org. Chem., (1998), 63:8224-8228.
Antonini, et al., "Synthesis of 4-Amino-1-β-D-Ribofuranosyl-1H-pyrrolo[2,3-b]pyridine (1-Deazatubercidin) as a Potential Antitumor Agent," J. Med. Chem., (1982), 25:1258-1261.
Arthan et al., "Leukemia inhibitory factor can mediate Ras/Raf/MEK/ERK-induced growth inhibitory signaling in medullary thyroid cancer cells," Cancer Letters (2010) 297:31-41.
Ashman, et al., "The biology of stem cell factor and its receptor C-kit," The International Journal of Biochemistry & Cell Biology, (1999), 31:1037-1051.
Baghestanian, et al., "A Case of Malignant Mastocytosis with Circulating Mast Cell Precursors: Biologic and Phenotypic Characterization of the Malignant Clone," Leuk., (1996), 10:159-166.
Bagshaw et al., "Measurement of Ligand Binding to Proteins," Spectrophotometry and Spectrofluorimetry: A Practical Approach, (1987), 4:91-113.
Bagshawe, K., "Antibody-Directed Enzyme Prodrug Therapy: A Review," Drug Dev. Res., (1995), 34:220-230.
Balak, et. al., "Novel D761Y and Common Secondary T790M Mutations in Epidermal Growth Factor Receptor 13 Mutant Lung Adenocarcinomas with Acquired Resistance to Kinase Inhibitors," Clin Cancer Res., (2006), 12:6494-501.
Bancalari, et al., "Blood Markers of Early and Late Airway Responses to Allergen in Asthmatic Subjects. Relationship with Functional Findings," Allergy, (1997), 52:32-40.
Bartlett, et al., "CAVEAT: A Program to Facilitate the Structure-Derived Design of Biologically Active Molecules," Royal Society of Chemistry, (1989), 78:I80-I96.
Barton, et al., "The chemistry of pentavalent organobismuth reagents. Part X. Studies on the phenylation and oxidation of phenols," Tetrahedron, (1987), 43(2):323-332.
Basta, et al., "High-dose Intravenous Immunoglobulin Exerts Its Beneficial Effect in Patients with Dermatomyositis by Blocking Endomysial Deposition of Activated Complement Fragments," J Clin Invest., (1994), 94:1729-1735.
Basto, et al., "Mutation analysis of B-RAF gene in human gliomas," Acta Neuropathol., (2005), 109:207-210.
Bedi, et al., "BCR-ABL-Mediated Inhibition of Apoptosis With Delay of G2/M Transition After DNA Damage: A Mechanism of Resistance to Multiple Anticancer Agents," Blood, (1995), 86:1148-1158.
Bell, J.E., "Fluorescence: Solution Studies" Spectroscopy in Biochemistry I, (1981),(4):155-194.
Bellone, et al., "Growth Stimulation of Colorectal Carcinoma Cells Via the c-Kit Receptor is Inhibited by TGF-β1," J. Cell Physiol., (1997), 172:1-11.
Berdel, et al., "Recombinant Human Stem Cell Factor Stimulates Growth of a Human Glioblastoma Cell Line Expressing c-kit Protooncogene," Canc. Res., (1992), 52:3498-3502.

(56) References Cited

OTHER PUBLICATIONS

Bertolini, et al., "A New Rational Hypothesis for the Pharmacophore of the Active Metabolite of Leflunomide, a Potent Immunosuppressive Drug," J. Med. Chem., (1997), 40:2011-2016.
Bjorntrop, "Neuroendocrine Pertuirbations as a Cause of Insulin Resistance," Diabetes Metab. Res. Rev., (1999), 15:427-441.
Bloom, et al., "The Preparation of 2-Alkylaminobenzimidazoles," J. Org. Chem., (1939), 14-19.
Blundell, et al., "Knowledge-Based Protein Modelling and Design," Eur. J. Biochem., (1988), 172:513-520.
Bode, et al., "Mutations in the tyrosine kinase domain of the EGFR gene are rare in synovial sarcoma," Modern Pathology, (2006), 19:541-547.
Bohm, H-J., "On the Use of LUDI to Search the Fine Chemicals Directory for Ligands of Proteins of Known Three-Dimensional Structure," J. Comp. Aided Molec. Design, (1994), 8:623-632.
Bokenmeyer, et al., "Expression of Stem-Cell Factor and Its Receptor c-kit Protein in Normal Testicular Tissue and Malignant Germ-Cell Tumours," J. Cancer Res. Clin. Oncol., (1996), 122:301-306.
Bolger, et al., "Computer Modeling of Combining Site Structure of Anti-Hapten Monoclonal Antibodies," Methods Enz., (1991), 203:21-45.
Bongarzone, et al., "High Frequency of Activation of Tyrosine Kinase Oncogenes in Human Papillary Thyroid Carcinoma," Oncogene, (1989), 4(12):1457-1462.
Bothwell, M., "Keeping Track of Neurotrophin Receptors," Cell, (1991), 65:915-918.
Bouzakri, et al., "MAP4K4 Gene silencing in Human Skeletal Muscle Prevents Tumor Necrosis Factor-a-induced Insulin Resistance," J. Biol. Chem., (2007), 282:7783-7789.
Bowtell, D., "Options Available From Start to Finish for Obtaining Expression Data by Microarray," Nature Genetics Supp., (1999), 21:25-32.
Brenner, et al., "Encoded Combinatorial Chemistry," Proc. Natl. Acad. Sci. USA, (1992), 89:5381-5383.
Broudy, V., "Stem Cell Factor and Hematopoiesis," Blood, (1997), 90:1345-1364.
Brunger, A. T., "Free R Value: a Novel Statistical Quantity for Assessing the Accuracy of Crystal Structures," Nature, (1992), 355:472-475.
Buchschacher, et al., "Human Immunodeficiency Virus Vectors for Inducible Expression of Foreign Genes," J. Virol., (1992), 66:2731-2739.
Calabresi, et al., "Section IX: Chemotherapy of neoplastic diseases," Goodman & Gilman's The Pharmacological Basis of Therapeutics, Tenth Edition, McGraw-Hill Medical Publishing Division (2001), pp. 1381, 1383-1385 and 1388.
Capon, et al., "Designing CD4 Immunoadhesins for AIDS Therapy," Nature, (1989), 337:525-531.
Carell, et al., "New Promise in Combinatorial Chemistry: Synthesis, Characterization, and Screening of Small-Molecule Libraries in Solution," Chem. Biol., (1995), 2:171-183.
Carpino, et al., "p62dok: A Constitutively Tyrosine-Phosphorylated, GAP-Associated Protein in Chronic Myelogenous Leukemia Progenitor Cells," Cell, (1997), 88:197-204.
Castelle, et al., "The Presence of Membrane-Bound Stem Cell Factor on Highly Immature Nonmetachromatic Mast Cells in the Peripheral Blood of a Patient with Aggressive Systemic Mastocytosis," J. Aller. Clin. Immunol., (1996), 98:831-840.
Castellone, et al., "A novel de novo germ-line V292M mutation in the extracellular region of RET in a patient with phaeochromocytoma and medullary thyroid carcinoma: functional characterization," Clinical Endocrinology, (2010), 73:529-534.
Castro, et al. "Utilizacion de dispersiones solidas como estrategia para aumentar la velocidad de disolucion de farmacos", Nuestra Farmcia, (2008), 25:24-29 (No English Translation Available).
Chabala, J., "Solid-Phase Combinatorial Chemistry and Novel Tagging Methods for Identifying Leads," Curr Opin Biotechnol., (1995), 6:632-639.

Chayer, et al., "Synthesis of Carboranylpyrroles," Tetrahedron Lett., (2001), 42(44):7759-7761.
Checovich, et al., "Fluorescence Polarization—a New Tool for Cell and Molecular Biology," Nature, (1995), 375:254-256.
Chou, et al., "Chemotherapeutic Synergism, Potentiation and Antagonism," Encyclopedia of Human Biology, Academic Press, (1991), 2:371-379.
Chou, et al., "Computerized Quantitation of Synergism and Antagonism of Taxol, Topotecan, and Cisplatin Against Human Teratocarcinoma Cell Growth: a Rational Approach to Clinical Protocol Design," J. Natl. Cancer Inst., (1994), 86:1517-1524.
Chou, et al., "Quantitative analysis of Dose-Effect Relationships: The Combined Effects of Multiple Drugs or Enzyme Inhibitors," Adv. Enzyme Regul., (1984), 22:27-55.
Chou, et al., "Synergism and Antagonism in Chemotherapy," Academic Press, (1991), Chapter 2, 61-102.
Clark, et al., "PRO_LIGAND: An Approach to De Novo Molecular Design. 1. Application to the Design of Organic Molecules," J. Comp. Aided Molec. Design, (1995), 9:13-32.
Clohisy, et al., "Review of Cellular Mechanisms of Tumor Osteolysis," Clin. Orthop., (2000), 373:104-114.
Coe, et al., "Solution-Phase Combinatorial Chemistry," Mol Divers., (1999), 4:31-38.
Coelho, et al., "Studies of RET gene expression and acetylcholinesterase activity in a series of sporadic Hirschsprung's disease," Pediatr Surg Int, (2008), 24:1017-1021.
Cohen, et al., "Expression of Stem Cell Factor and C-Kit in Human Neuroblastoma," Blood, (1994), 84:3465-3472.
Collins, et al., "A small interfereing RNA screen for modulators of tumor cell motility identifies MAP4K4 as a prommigratory kinase," Proc. Natl. Acad. Sci. USA, (2006), 103:3775-3780.
Collioud, et al., "Oriented and Covalent Immobilization of Target Molecules to Solid Supports: Synthesis and Application of a Light-Activatable and Thiol-Reactive Cross-Linking Reagent," Bioconjugate Chem., (1993), 4:528-536.
Colman, P.M., "Structure-Based Drug Design," Current Opinion in Struc. Biol., (1994), 4:868-874.
Columbo, et al., "The Human Recombinant c-kit Receptor Ligand, rhSCF, Induces Mediator Release From Human Cutaneous Mast Cells and Enhances IgE-Dependent Mediator Release From Both Skin Mast Cells and Peripheral Blood Basophils," J. Immunol., (1992), 149:599-608.
Communication Pursuant to Article 94(3) EPC for European Application No. 04814626.0 dated Jun. 6, 2011.
Communication Pursuant to Article 94(3) EPC for European Application No. 04814626.0 dated Dec. 15, 2009.
Communication Pursuant to Article 94(3) EPC for European Application No. 05789913.0 dated Feb. 15, 2010.
Communication Pursuant to Article 94(3) EPC for European Application No. 06773861.7 dated Apr. 22, 2010.
Communication Pursuant to Article 94(3) EPC for European Application No. 06773861.7 dated Jul. 9, 2009.
Communication Pursuant to Article 94(3) EPC for European Application No. 06773861.7 dated Dec. 21, 2009.
Communication Pursuant to Article 94(3) EPC for European Application No. 06813186.1 dated Sep. 15, 2009.
Communication Pursuant to Article 94(3) EPC for European Application No. 07864681.7 dated Dec. 2, 2009.
Communication Pursuant to Article 94(3) EPC for European Application No. 10722860.3 dated Mar. 27, 2013.
Costa, et al., "The Cells of the Allergic Response," JAMA, (1997), 278:1815-1822.
Coste, et al., "Coupling N-Methylated Amino Acids Using PyBroP1 and PyCloP Halogenophosphonium Salts: Mechanism and Fields of Application," Journal of Organic Chemistry, (1994), 59:2437-2446.
Coulie, et al., "Recombinant Human Neurotropic Factors Accelerate Colonic Transit and Relieve Constipation in Humans," Gastroenterology, (2000), 119:41-50.
Creighton, T., "An Empirical Approach to Protein Conformation Stability and Flexibility," Biopolymers, (1983), 22(1):49-58.
Crouch, et al., "The use of ATP bioluminescence as a measure of cell proliferation and cytotoxicity," Journal of Immunological Methods, (1993), 160:81-88.

(56) References Cited

OTHER PUBLICATIONS

Crump, M., "Inhibition of Raf Kinase in the Treatment of Acute Myeloid Leukemia," Curr. Pharm. Design, (2002), 8(25):2243-2248.
Cumming J.G. et al., "Novel, Potent and Selective Anilinoquinazoline and Anilinopyrimidine Inhibitors of p38 MAP Kinase," Bioorganic & Medicinal Chemistry Letters, (2004),14:5389-5394.
Curtin, et al., "Discovery and Evaluation of a Series of 3-Acylindole Imidazopyridine Platelet-Activating Factor Antagonists," J. Med. Chem., (1998), 41:74-95.
Cwirla, et al., "Peptides on Phage: A Vast Library of Peptides for Identifying Ligands," Biochemistry, (1990), 87:6378-6382.
Dai, et al., "Targeted disruption of the mouse colony-stimulating factor 1 receptor gene results in osteopetrosis, mononuclear phagocyte deficiency, increased primitive progenitor cell frequencies, and reproductive defects," Blood, (2002), 99: 111-120.
Dandliker, et al., "Equilibrium and Kinetic Inhibition Assays Based Upon Fluorescence Polarization," Methods in Enzymology, (1981), 74:3-28.
Das-Gupta et al., "Acridine Derivatives, Part VI," J. Indian Chem. Society, (1941), 18:25-28.
Dastych, et al., "Stem Cell Factor Induces Mast Cell Adhesion to Fibronectin," J. Immunol., (1994), 152:213-219.
Davies, et al., "Mutations of the BRAF gene in human cancer," Nature, (2002), 417:949-954.
Demetri, G.D., "Targeting c-kit mutations in solid tumors: Scientific rationale and novel therapeutic options," Seminars in Oncology, (2001), 28(5), Supp. 17, 19-26.
Dewar, et al., "Inhibition of c-fms by Imatinib Expanding the Spectrum of Treatment," Cell Cycle, (2005), 4(7):851-853.
Dobeli, et al., "Recombinant Fusion Proteins for the Industrial Production of Disulfide Bridge containing Peptides: Purification, Oxidation without Cancatamer Formation, and Selective Cleavage," Protein Expr. Purif., (1998), 12:404-414.
Dolle, et al., "Comprehensive Survey of Combinatorial Library Synthesis: 1998," J Comb Chem., (1999), 1:235-282.
Dong, et al., "BRAF Oncogenic Mutations Correlate with Progression rather than Initiation of Human Melanoma," Cancer Research, (2003), 63:3883-3885.
Donis-Keller, et al., "Mutations in the RET Proto-Oncogene are Associated with MEN 2A and FMTC," Hum Mol Genet., (1993), 2(7):851-856.
Douma, et al., "Suppression of anoikis and induction of metastasis by the neurotropic receptor TrkB," Nature, (2004), 430:1034-1039.
Doyle, eta al., "Alkyl Nitrite-metal halide Deamination Reactions. 6. Direct Synthesis of Arenediazonium Tetrafluoroborate Salts from Aromatic Amines, tert-Butyl Nitrite, and Boron Trifluoride Etherate in Anhydrous Media," J. Org. Chem., (1979), 44:1572.
Dube, et al., "Reductive N-Alkylation of Amides, Carbamates and Ureas," Tetrahedron Lett., (1999), 40:2295-2298.
Durbec, et al., "GDNF Signalling Through the Ret Receptor Tyrosine Kinase," Nature, (1996), 381:789-793.
Dutcher et al., "Studies of the C11H8N2OS Degradation Product of Gliotoxin," J. Am. Chem. Soc., (1951), 73:4139-4141.
Dyson, et al., "The Human Papilloma Virus 13 16 E7 Oncoprotein is Able to Bind to the Retinoblastoma Gene Product," Science, (1989), 243:934-937.
Eklund, et al., "Treatment of rheumatoid arthritis with imatinib mesylate: clinical improvements in three refractory cases," Annals of Medicine, (2003), 35:362-367.
Eliseev, et al., "Dynamic Combinatorial Chemistry: Evolutionary Formation and Screening of Molecular Libraries," Current Topics in Microbiology & Immunology, (1999), 243:159-172.
Enjalbal, et al., "Mass Spectrometry in Combinatorial Chemistry," Mass Spectrometry Reviews, (2000), 19:139-161.
Escribano, et al., "Expression of the c-kit (CD117) Molecule in Normal and Malignant Hematopoiesis," Leuk. Lymph., (1998), 30:459-466.

Felder, E.R., "The Challenge of Preparing and Testing Combinatorial Compound Libraries in the Fast Lane, at the Front End of Drug Development," Chimia., (1994), 48:531-541.
Feng, et al., "Stable in Vivo Gene Transduction Via a Novel Adenoviral/Retroviral Chimeric Vector," Nature Biotechnology, (1997), 15:866-870.
Feng, et al., "Tyrosines 559 and 807 in the Cytoplasmic Tail of the Macrophage colony-Stimulating Factor Receptor Play Distinct Roles in Osteoclast Differentiation and Function," Endocrinology, (2002), 143: 4868-4874.
Finotto, et al., "Glucocorticoids Disease Tissue Mast Cell Number by Reducing the Production of the c-kit Ligand, Stem Cell Factor, by Resident Cells," J. Clin. Invest., (1997), 99:1721-1728.
Fivash, et al., "BIAcore for macromolecular interaction," Current Opinion in Biotechnology, (1998), 9:97-101.
Flanagan, et al., "Update on the biologic effects of macrophage colony-stimulating factor," Curr Opin Hematol., (1998), 5:181-185.
Franz, et al., "Sulfuranes. X. A Reagent for the Facile Cleavage of Secondary Amides," JACS, (1973), 95(6):2017-2019.
Friesen et al., "Hydroxypropyl Methylcellulose Acetate Succinate-Based Spray-Dried Dispersions: An Overview," Molecular Pharmaceutics, 5(6):1003-1019 (2008).
Furitsu, et al., "Identification of Mutations in the Coding Sequence of the Proto-oncogene c-kit in a Human Mast Cell Leukemia Cell Line Causing Ligand-independent Activation of the c-kit Product," J. Clin. Invest., (1993), 92:1736-1744.
Furuta, et al., "Stem Cell Factor Influences Mast Cell Mediator Release in Response to Eosinophil-Derived Granule Major Basic Protein," Blood, (1998), 92:1055-1061.
Gallop, et al., "Applications of Combinatorial Technologies to Drug Discovery. 1. Background and Peptide Combinatorial Libraries," J. Med. Chem. (1994), 37:1233-1251.
Galofre, et al., "Evaluation and Treatment of Thyroid Nodules: A Clinical Guide," Mt Sinai J Med., (2008), 75:299-311.
Gassman, et al., "Specific Ortho Substitution of Aromatic Heterocyclic Amines," J Am Chem Society, (1973), 95(13):4453-4455.
Ghebre-Sellassie, Isaac; Martin, Charles., Pharmaceuticast Extrusion Technology. Marcer Dekker, Inc., New York. Basel. CRC Press, 2003 p. 238.
Gimbel, et al., "Braf mutations are associated with increased mortality in colorectal cancer," Journal of the American College of Surgeons, (2004), 199:S91-S92.
Girgis, et.al., "The Synthesis of 5-Azaindoles by Substitution-Rearrangement of 7-Azaindoles upon Treatment with Certain Primary Amines," J. Heterocyclic. Chem., (1989), 26:317-325.
Golkar, et al., "Mastocytosis," Lancet, (1997), 349:1379-1385.
Golub, et al., "Molecular Classifcation of Cancer: Class Discovery and Class Prediction by Gene Expression Monitoring," Science, (1999), 286:531-537.
Goodford, P.J., "A Computational Procedure for Determining Energetically Favorable Binding Sites on Biologically Important Macromolecules," J. Med. Chem., (1985), 28:849-857.
Goodsell, et al., "Automated Docking of Substrates to Proteins by Simulated Annealing," Proteins: Structure, Function, and Genetics, (1990), 8:195-202.
Gordon et al., "Detection of Peroxides and Their Removal," The Chemist's Companion: A Handbook of Practical Data, Techniques, and References, (1972), p. 437.
Gordon, et al., "Applications of Combinatorial Technologies to Drug Discovery. 2. Combinatorial Organic Synthesis, Library Screening Strategies, and Future Directions," J. Med. Chem., (1994), 37:1385-1401.
Gram, H., "Phage Display in Proteolysis and Signal Transduction," Combinatorial Chemistry & High Throughput Screening, (1999), 2:19-28.
Gravert, et al., "Synthesis on Soluble Polymers: New Reactions and the Construction of Small Molecules," Curr Opin Chem Biol., (1997), 1:107-113.
Greer, J., "Model Structure for the Inflammatory Protein C5a," Science, (1985), 228:1055-1060.
Grieco, et al., "PTC is a Novel Rearranged Form of the ret Proto-Oncogene and is Frequently Detected in Vivo in Human Thyroid Papillary Carcinomas," Cell, (1990), 60(4):557-563.

(56) References Cited

OTHER PUBLICATIONS

Guida, W., "Software for Structure-Based Drug Design," Current Opinion in Struc. Biol., (1994), 4:777-781.
Hafner, et al., "Isothermal Amplification and Multimerization of DNA by Bst DNA Polymerase," Biotechniques, (2001), 30(4):852-867.
Hallek, et al., "Interaction of the Receptor Tyrosine Kinase p145c-kit with the p210bcr/abl Kinase in Myeloid Cells," Brit. J Haem., (1996), 94:5-16.
Halvorson, et al., "A Blocking Antibody to Nerve Growth Factor Attenuates Skeletal Pain Induced by Prostate Tumor Cells Growing in Bone," Cancer Res., (2005), 65:9426-9435.
Hamel, et al., "The Road Less Traveled: c-kit and Stem Cell Factor," J. Neuro-Onc., (1997), 35:327-333.
Hancock et al., "Characteristics and Significance of the Amorphous State in Pharmaceutical Systems," Journal of Pharmaceutical Sciences 86(1):1-12 (1997).
Hands, et al., "A convenient Method for the Preparation of 5-, 6- and 7-Azaindoles and Their Derivatives," Synthesis, (1996), 877-882.
Hanselman, et al., "A cDNA-Dependant Scintillation Proximity Assay for Quantifying Apolipoprotein A1," J. Lipid Res., (1997), 38:2365-2373.
Hassan, et al., "Expression of Protooncogene c-kit and Its Ligand Stem Cell Factor (SCF) in Gastric Carcinoma Cell Lines," Digest. Dis. Science, (1998), 43:8-14.
Hassan, et al., "Stem Cell Factor as a Survival and Growth Factor in Human Normal and Malignant Hematopoiesis," Acta. Hem., (1996), 95:257-262.
Hayashi, et al., "Dichloro[1,1 19-bis(diphenylophosphino)ferrocene]palladium-(II), An Effective Catalyst for Cross-Coupling of Secondary and Primary Alkyl Grignard and Alkylzinc Reagents with Organic Halides," J. Am. Chem. Soc., (1984), 106:158-163.
Haydock et al., "Analogues of clofibrate and clobuzarit containing fluorine in the side chains," Eur. J. Med. Chem., (1984), 19(3):205-214.
He, et al., "Gamma-secretase activating protein, a therapeutic target for Alzheimer's disease," Nature (2010) 467(7311):95-98.
Heacock, et al., "Orientation and Relative Reaction rate Factors in aromatic Substitution by the Benzensulfonimido Radical," J. Am. Chem. Soc., (1960), 82:3460-3463.
Heim, et al., "Engineering Green Fluorescent Protein for Improved Brightness, Longer Wavelengths and Fluorescence Resonance Energy Transfer," Curr. Biol., (1996), 6:178-182.
Heinrich, et al., "PDGFRA Activating Mutations in Gastrointestinal Stromal Tumors," Science, (2003), 299:708-710.
Heinrich, M. C. et al., "Inhibition of KIT Tyrosine Kinase Activity: A Novel Molecular Approach to the Treatment of KIT-Positive Malignancies," J. Clin. Oncol., vol. 20, No. 6, pp. 1692-1703, Mar. 15, 2002.
Herbst, et al., "Differential Effects of W Mutations on p145c-kit Tyrosine Kinase Activity and Substrate Interaction," J. Biol. Chem., (1992), 267:13210-13216.
Hibi, et al., "Coexpression of the stem cell factor and the c-kit genes in small-cell lung cancer," Oncogene, (1991), 6:2291-2296.
Hirota, et al., "Gain-of-function Mutations of c-kit in Human Gastrointestinal Stromal Tumors," Science, (1998), 279:577-580.
Hoffmann, "m-Trifluoromethylbenzensulfonyl Chloride," Organic Syntheses, (1981), 60:121-126.
Hogaboam, et al., "Novel Role of Transmembrane SCF for Mast Cell Activation and Eotaxin Production in Mast Cell-Fibroblast Interactions," J. Immunol., (1998), 160:6166-6171.
Holmes, et al., "Long-term effects of Aβ42 immunisation in Alzheimer's disease: follow-up of a randomised, placebo-controlled phase I trail," Lancet (2008) 372:216-233.
Hood, et al., "Tumor Regression by Targeted Gene Delivery to the Neovasculature," Science, (2002), 296: 2404-2407.
Houghten, et al., "Generation and Use of Synthetic Peptide Combinatorial Libraries for Basic Research and Drug Discovery," Nature, (1991), 354:84-86.

Houghten, R., "Parallel Array and Mixture-Based Synthetic Combinatorial Chemistry: Tools for the Next Millennium," Annu Rev Pharmacol Toxicol., (2000), 40:273-282.
Houghten, R., "Peptide Libraries: Criteria and Trends," Trends Genet., (1993), 9:235-239.
Hudson, et al., "A Simple Method for the Determination of Serum Acid Phosphatase," J. Urology, (1947), 58:89-92.
Hughes-Jones, et al., "Synthesis of Rh Fv Phage-Antibodies Using VH and VL Germline Genes," British Journal of Haematology, (1999), 105:811-816.
Iemura, et al., "The c-kit Ligand, Stem Cell Factor, Promotes Mast Cell Survival by Suppressing Apoptosis," Amer. J. Pathol., (1994), 144:321-328.
Inoue, et al., "Coexpression of the c-kit Receptor and the Stem Cell Factor in Gynecological Tumors," Cancer Res., (1994), 54:3049-3053.
International Preliminary Report on Patentability and Written Opinion of the International Searching Authority, dated Jan. 19, 2010, in corresponding International Patent Application No. PCT/US2008/070124, 9 pages.
International Search Report and Written Opinion for PCT Application No. PCT/US2008/070124 dated Oct. 15, 2008 (12 pages).
International Search Report and Written Opinion of International Application No. PCT/US2004/042470 dated Nov. 25, 2005.
International Search Report and Written Opinion of International Application No. PCT/US2005/021231 dated Apr. 20, 2006.
International Search Report and Written Opinion of International Application No. PCT/US2006/018726 dated Apr. 4, 2007.
International Search Report and Written Opinion of International Application No. PCT/US2006/024361 dated Oct. 24, 2006.
International Search Report and Written Opinion of International Application No. PCT/US2006/024524 dated Oct. 24, 2006.
International Search Report and Written Opinion of International Application No. PCT/US2007/083910 dated Jun. 5, 2008.
International Search Report and Written Opinion of International Application No. PCT/US2007/085289 dated Jun. 5, 2008.
International Search Report and Written Opinion of International Application No. PCT/US2007/085299 dated Jul. 28, 2008.
International Search Report and Written Opinion of International Application No. PCT/US2007/088231 dated Jun. 4, 2008.
International Search Report and Written Opinion of International Application No. PCT/US2007/088237 dated Jun. 4, 2008.
International Search Report and Written Opinion of International Application No. PCT/US2007/088243 dated Jun. 5, 2008.
International Search Report and Written Opinion of International Application No. PCT/US2007/088412 dated Nov. 17, 2008.
International Search Report and Written Opinion of International Application No. PCT/US2007/088443 dated Jul. 25, 2008.
International Search Report and Written Opinion of International Application No. PCT/US2010/029489 dated Oct. 5, 2010.
International Search Report and Written Opinion of International Application No. PCT/US2012/025965 dated May 31, 2012.
Isbel, et al., "Local macrophage proliferation correlates with increased renal M-CSF expression in human glomerulonephritis," Nephrol Dial Transplant, (2001), 16:1638-1647.
Ishizaka, et al., "Human ret Proto-Oncogene Mapped to Chromsome 10q11.2," Oncogene, (1989), 4(12):1519-1521.
Isozaki, et al., "Deficiency of c-kit cells in patients with a myopathic form of chronic idiopathic intestinal pseudo-obstruction," Amer. J. of Gast., (1997), 9:332-334.
Ivanisevic et al., "Uses of X-Ray Powder Diffraction in the Pharmaceutical Industry," Pharm Sci Encyc:DDDM, (2010), 1-42.
Iwane, et al., "Myosin Subfragment-1 is Fully Equipped with Factors Essential for Motor Function," Biochem. and Biophys. Res. Comm., (1997), 230:76-80.
Izquierdo, et al., "Differential Expression of the c-kit Proto-Oncogene in Germ Cel Tumours," J. Pathol., (1995), 177:253-258.
Jarugula, et al., "Nonlinear Pharmacokinetics of 5-Fluorouracil in Rats," J Pharm Sci., (1997), 86(6):756-757.
Jensen, et al., "Pharmacological targeting of the KIT growth factor receptor: a therapeutic consideration for mast cell disorders," Brit J Pharmacology, (2008), 154:1572-1582.

(56) References Cited

OTHER PUBLICATIONS

Jing, et al., "GDNF-Induced Activation of the Ret Protein Tyrosine Kinase is Mediated by GDNFR-a, a Novel Receptor for GDNF," Cell, (1996), 85:1113-1124.

Johann, et al., "GLVR1, a Receptor for gibbon Ape Leukemia Virus, Is Homologous to a Phosphate Permease of Neurospora crassa and is Expressed at High Levels in the Brain and Thymus," J. Virol., (1992), 66:1635-1640.

Johnston, M., "Gene Chips: Array of hope for understanding gene regulation," Curr. Biol., (1998), 8:R171-R174.

Jones, et al., "Antiestrogens. 2. Structure-Activity Studies in a Series of 3-Aroyl-2-arylbenzo[b]thiophene Derivatives Leading to [6-Hydroxy-2-(4-hydroxyphenyl)benzo(b)thien-3-yl](4-[2-(1-piperidinyl)ethoxy]-phenyl]methanone Hydrochloride (LY156758), a Remarkably Effective Estrogen Antagonist with Only Minimal Intrinsic Estrogenicity," J. Med. Chem. (1984), 27(8):1057-1066.

Jones, R., "Biology and Treatment of Chronic Myeloid Leukemia," Curr. Opin. Onc., (1997), 9:3-7.

Jones, T., "Interactive Computer Graphics: FRODO," Methods in Enzymology, (1985), 115:157-171.

Jose, et al., "Blockade or Macrophage colony-Stimulating Factor Reduces Macrophage Proliferation and Accumulation in Renal Allograft Rejection," Am J Transplant, (2003), 3(3):294-300.

Joseph-McCarthy, D., "Computational Approaches to Structure-Based Ligand Design," Pharmacology & Therapeutics, (1999), 84:179-191.

Kahl, et al., "A Multiple-Approach Scintillation Proximity Assay to Measure the Association Between Ras and Raf," Anal. Biochem., (1996), 243:282-283.

Kassel, et al., "Local increase in the number of mast cells and expression of nerve growth factor in the bronchus of asthmatic patients after repeated inhalation of allergen at low-dose," Clin. Exp. Allergy, (2001), 31:1432-1440.

Katritzky, et al., "Regiospecific C-Acylation of Pyrroles and Indoles Using N-Acylbenzotriazoles," J. Org. Chem., (2003), 68:5720-5723.

Kay, et al., "Eosinophils and Eosinophil-Associated Cytokines in Allergic Inflammation," Int. Arch. Aller. Immunol., (1997), 113:196-199.

Kern, et al., "Direct Hybridization of Large-Insert Genomic Clones on High-Density Gridded cDNA Filter Arrays," Biotechniques, (1997), 23:120-124.

Kim, et al., "A Merger of Rational Drug Design and Combinatorial Chemistry: Development and Application of Peptide Secondary Structure Mimetics," Combinatorial Chemistry & High Throughput Screening, (2000), 3:167-183.

Kim, et al., Database CAS on STN (Columbus, OH, USA) No. 138:55974, Preparation of 2-anilino-4-indolyl pyrimidines as tyrosine kinase inhibitors, abstract, 2002) see whole article.

Kinashi, et al., "Steel Factor and c-kit Cell-Matrix Adhesion," Blood, (1994), 83:1033-1038.

Kirkpatrick, et al., "Structure-Based Drug Design: Combinatorial Chemistry and Molecular Modeling," Combinatorial Chemistry & High Throughput Screening, (1999), 2:211-221.

Kitamura, et al., "Synthesis of Quinolines and 2H-Dihydropyrroles by Nucleophilic Substitution at the Nitrogen Atom of Oxime Derivatives," Synthesis, (2003), 15:2415-2426.

Kline, et al., "Studies by 1H Nuclear Magnetic Resonance and Distance Geometry of the Solution Conformation of the x-Amylase Inhibitor Tendamistat," J. Mol. Biol., (1986), 189:377-382.

Knighton, et al., "Structural Basis of the Intrasteric Regulation of Myosin Light Chain Kinases," Science, (1992), 258:130-135.

Kodama, et al., "Congenital Osteoclast Deficiency in Osteopetrotic (op/op) Mice Is Cured by Injections of Macrophage colony-stimulating Factor," J. Exp,. Med.,(1991), 173:269-272.

Kolaskar, et al., "A Semi-Empirical Method for Prediction of Antigenic Determinants on Protein Antigens," FEBS Lett., (1990), 276:172-174.

Komoyira, et al., "Design, synthesis and biological activity of amidinobicyclic compounds (derivatives of DX-9065a) as a factor Xa inhibitors: SAR study of S1 and aryl binding sites," Bioorg. Med. Chem., (2004), 12: 2099-2114.

Kondoh, et al., "An in vivo model for receptor tyrosine kinase autocrine/paracrine activation: auto-stimulated Kit receptor acts as a tumor promoting factor in papillomavirinduced tumorigenesis," Oncogene, (1995), 10:341-347.

Kondoh, et al., "Establishment and Further Characterization of a Line of Transgenic Mice Showing Testicular Tumorigenesis at 100% Incidence," J. Urol., (1994), 152:2151-2154.

Kondoh, et al., "Very High Incidence of Germ Cell tumorigenesis (Seminomagenesis) in Human Papillomavirus Type 16 Transgenic Mice," J. Virol., (1991), 65:3335-3339.

Konishi, et al., "Overexpression of leucocyte common antigen (LAR) P-subunit in thyroid carcinomas," Brit J Cancer, (2003), 88:1223-1228.

Konno et al., "Influence of Different Polymers on the Crystallization Tendency of Molecularly Dispersed Amorphous Felodipine," Journal of Pharmaceutical Sciences 95(12):2692-2705 (2006).

Kroll, et al., "A Malfunctional Prokaryotic Protein Expression System: Overproduction, Affinity Purification, and Selective Detection," DNA Cell. Biol., (1993), 12:441-453.

Kundu, et al., "Combinatorial Chemistry: Polymer Supported Synthesis of Peptide and Non-Peptide Libraries," Progress in Drug Research, (1999), 53:89-156.

Kunisada, et al., "Murine Cutaneous Mastocytosis and Epidermal Melanocytosis Induced by Keratinocyte Expression of Transgenic Stem Cell Factor," J. Exp. Med., (1998), 187:1565-1573.

Kunkel, T., "Rapid and Efficient Site-Specific Mutagenesis Without Phenotypic Selection," Methods in Enzymology, (1987), 154:367-382.

Kunnimalaiyaan, et al., "The Raf-1 pathway: a molecular target for treatment of select neuroendocrine tumors?" Anticancer Drugs, (2006), 17(2):139-42.

Kuntz, et al., "A Geometric Approach to Macromolecule-Ligand Interactions," J. Mol. Biol., (1982), 161:269-288.

Kuntz, et al., "Structure-Based Molecular Design," Acc. Chem. Res., (1994), 27:117-123.

Lahm, et al., "Interleukin 4 Down-Regulates Expression of c-kit and Autocrine Stem Cell Factor in Human Colorectal Carcinoma Cells," Cell Growth & Differ., (1995), 6:1111-1118.

Lala, et al., "Role of nitric oxide in tumor progression: Lessons from experimental tumors," Cancer and Metastasis Reviews, (1998), 17:91-106.

Lam, et al., "A new type of synthetic peptide library for identifying ligand-binding activity," Nature, (1991), 354: 82-84.

Langham et al., "Metalation and Halogen-Metal Interconversion Reactions of Some Halogenated Phenyl Ethers," J. of the Am. Chem. Society, (1941), 63:545-549.

Lawicki, et al., "The pretreratment plasma level and disgnostic utility of M-CSF in benign breast tumor and breast cancer patients," Clinica Chimica Acta., (2006), 371:112-116.

Le Meur, et al., "Macrophage accumulation at a site of renal inflammation is dependent on the M-CSF/c-fms pathway," J Leukocyte Biology, (2002), 72:530-537.

Lebl, et al., "One-Bead-One-Structure Combinatorial Libraries," Biopolymers, (1995), 37:177-198.

Lee, et al., "HLA-DR-Triggered Inhibition of Hemopoiesis Involves Fas/Fas Ligand Interactions and is Prevented by c-kit Ligand," J. Immunol., (1997), 159:3211-3219.

Lee, et al., "Mast Cells: A Cellular Link Between Autoantibodies and Inflammatory Arthritis," Science, (2002), 297:1689-1692.

Leuner, et al., "Improving drug solubility for oral delivery using solid dispersions," European Journal of Pharma. and Biopharma., (2000), 50(1):47-60.

Levin, et al., "Neoplasms of the Central Nervous System," Cancer Principles & Practice of Oncology, (1997), 2:2022-2082.

Li, et al., "Abrogation of c-kit/Steel Factor-Dependent Tumorigenesis by Kinase Defective Mutants of the c-kit Receptor: c-kit Kinase Defective Mutants as Candidate Tools for Cancer Gene Therapy," Canc. Res., (1996), 56:4343-4346.

Libby, P., "Inflammation in atherosclerosis," Nature, (2002), 420:868-874.

(56) References Cited

OTHER PUBLICATIONS

Liparoto, et al., "Biosensor Analysis of the Interleukin-2 Receptor Complex," Journal of Molecular Recognition, (1999), 12:316-321.
Lipinski, et al., "Experimental and Computational Approaches to Estimate Solubility and Permeability in Drug Discovery and Development Settings," Advanced Drug Delivery Reviews, (1997), 23:3-25.
Lipschultz, et al., "Experimental design for analysis of complex kinetics using surface plasmon resonance," Methods, (2000), 20(3):310-318.
Liu, et al., "Sorafenib Blocks the RAF/MEK/ERK Pathway, Inhibits Tumor Angiogenesis, and Induces Tumor Cell Apoptosis in Hepatocellular Carcinoma Model PLC/PRF/5," Cancer Res., (2006), 66:11852-11858.
Liu, et al., "Rational Design of Inhibitors that Bind to Inactive Conformations," Nature Chemical Biology, (2006), 2(7):358-364.
London, et al., "Expression of Stem Cell Factor Receptor (c-kit) by the Malignant Mast Cells from Spontaneous Canine Mast Cell Tumors," J. Compar. Pathol., (1996), 115:399-414.
Longley, et al., "Altered Metabolism of Mast-cell Growth Factor (c-kit Ligand) in Cutaneous Mastocytosis," New Engl. J. Med., (1993), 328:1302-1307.
Longley, et al., "Chymase Cleavage of Stem Cell Factor Yields a Bioactive Soluble Product," Proc. Natl. Acad. Sci., (1997), 94:9017-9021.
Longley, et al., "Somatic c-KIT Activating Mutation in Urticaria Pigmentosa and Aggressive Mastocytosis: Establishment of Clonality in a Human Mast Cell Neoplasm," Nat. Gen., (1996), 12:312-314.
Loveland, et al., "Stem Cell Factor and c-kit in the Mammalian Testis: Lessons Originating from Mother Nature 19s Gene Knockouts," J. Endocrinol., (1997), 153:337-344.
Lu, et al., "Oriented Immobilization of Fab 19 Fragments on Silica Surfaces," Anal. Chem., (1995), 67:83-87.
Lukacs, et al., "Stem Cell Factor (c-kit Ligand) Influences Eosinophil Recruitment and Histamine Levels in Allergic Airway Inflammation," J. Immunol., (1996), 156:3945-3951.
Luo, et al., "Close Linkage with the RET Proto-Oncogene and Boundaries of Deletion Mutations in Autosomal Dominant Hirschsprung Disease," Hum Mol Genet., (1993), 2(11):1803-1808.
Lyman, et al., "c-kit Ligand and Flt3 Ligand: Stem/Progenitor Cell Factors With Overlapping Yet Distinct Activities," Blood, (1998), 91:1101-1134.
Ma, et al., "Indolinone Derivatives Inhibit Constitutively Activated KIT Mutants and Kill Neoplastic Mast Cells," J Invest Dermatol., (2000), 114:392-394.
Ma, et al., "The c-KIT Mutation Causing Human Mastocytosis is Resistant to ST1571 and Other KIT Kinase Inhibitors; Kinases with Enzymatic Site Mutations Show Different Inhibitor Sensitivity Profiles Than Wild-type Kinases and Those With Regulatory-Type Mutations," Blood, (2002), 99:1741-1744.
Machens, et al., "Modification of multiple endocrine neoplasia 2A phenotype by cell membrane proximity of RET mutations in exon 10," Endocrine-Related Cancer, (2009), 16:171-177.
Machida, et al., "Mitogen-activated Protein Kinase Kinase Kinase Kinase 4 as a Putative Effector of Rap2 to Activate the c-Jun N-terminal Kinase," J. Biol. Chem., (2004), 279:15711-15714.
Mack, et al., "Functional identification of kinases essential for T-cell activation through a genetic suppression screen," Immunol. Lett., (2005), 96:129-145.
Madden, et al., "Synthetic Combinatorial Libraries: Views on Techniques and Their Application," Perspectives in Drug Discovery and Design, (1994), 2:269-285.
Malmborg, et al., "BIAcore as a Tool in Antibody Engineering," Journal of Immunological Methods, (1995), 183:7-13.
Malmqvist, et al., "Biomolecular Interaction Analysis: Affinity Biosensor Technologies for Functional Analysis of Proteins," Current Opinion in Chemical Biology, (1997), 1:378-383.
Malmqvist, M., "BIACORE: An Affinity Biosensor System for Characterization of Biomolecular Interactions," Biochemical Society Transactions, (1999), 27:335-340.
Markiewicz, et al., "Synthetic Oligonucleotide Combinatorial Libraries and Their Applications," Il Farmaco, (2000), 55:174-177.
Martin, Y., "Computer-Assisted Rational Drug Design," Methods Enz., (1991), 203:587-613.
Matayoshi, et al., "Actions of brain-derived neurotrophic factor on spinal nociceptive transmission during inflammation in the rat," J Physiol., (2005), 569:685-95.
Matsumoto, et al., "Physical properties of solid molecular dispersions of indomethacin with poly(vinylpyrrolindone) and poly(vinylpyrrolidone-co-vinyl-acetate) in relation to indomethacin crystallization," Pharmaceutical Research, (1999), 16(11):1722-1728.
Mazeas, et. al., "Synthesis of new melatoninergic ligands including azaindole moiety," Heterocycles, (1999), 50:1065-1080.
McCall, et al., "Characterization of Anti-Mouse FcγRII Single-Chain Fv Fragments Derived from Human Phage Display Libraries," Immunotechnology, (1998), 4:71-87.
McPherson, A., "Current Approaches to Macromolecule Crystallization," Eur. J. Biochem., (1990), 189:1-23.
Mekori, et al., "The Role of c-Kit and Its Ligand, Stem Cell Factor, in Mast Cell Apoptosis," Int. Arch. Allergy Immunol., (1995), 107:136-138.
Mekori, et al., "Transforming Growth Factor-β Prevents Stem Cell Factor-Mediated Rescue of Mast Cells from Apoptosis After IL-3 Deprivation," J. Immunol., (1994), 153:2194-2203.
Meltzer, E. O., "The pharmacological basis for the treatment of perennial allergic rhinitis and non-allergic rhinitis with topical corticosteroids," Aller., (1997), 52:33-40.
Meng, et al., "Automated Docking with Grid-Based Energy Evaluation," J. Compt. Chem., (1992), 13:505-524.
Merour, et al., "Synthesis and Reactivity of 7-Azaindoles (1H-Pyrrolo[2,3-b]pyridine)," Curr. Org. Chem., (2001), 5:471-506.
Merritt, A., "Solution Phase Combinatorial Chemistry," Comb Chem High Throughput Screen, (1998), 1:57-72.
Metcalf, D., "Lineage Commitment in the Progeny of Murine Hematopoietic Preprogenitor Cells: Influence of Thrombopoietin and Interleukin 5," Proc. Natl. Acad. Sci., (1998), 95:6408-6412.
Metcalfe, D. "Classification and Diagnosis of Mastocytosis: Current Status," J. Invest. Derm., (1991), 93:2S-4S.
Metcalfe, et al., "Mast Cells," Physiol. Rev., (1997), 77:1033-1079.
Meula Pomeda, et al., "Efecto De Codisolventes Y Dispersiones Solida De Polivinilpirrolidona K-30 En La Solubilidad Tel Tiabendazol," Departamento de Farmacia y Tecnologia Farmaceutica. Facultad de Farmacia. Universidad de Alcala, pp. 85-87 (2002) (No English Translation Available).
Miller et al., "FLOG: A System to Select Quasi-Flexible Ligands Complementary to a Receptor of Known Three-Dimensional Structure," J. Comp. Aided Molec. Design, (1994), 8:153-174.
Minakata, et al., "Functionalization of 1H-Pyrrolo[2,3-b]pyridine," Bulletin of the Chemical Society of Japan, (1992), 65(11):2992-2997.
Minakata, et al., "Regioselective Funtionalization of 1H-Pyrrolo[2,3-b]pyridine Via its N-Oxide," Synthesis, (1992), 661-663.
Miranker, at al., "Functionality Maps of Binding Sites: A Multiple Copy Simultaneous Search Method," Proteins: Structure, Function, and Genetics, (1991), 11:29-34.
Mitra, et al., "Fluorescence Resonance Energy Transfer Between Blue-Emitting and Red-Shifted Excitation Derivatives of the Green Fluorescent Protein," Gene, (1996), 173:13-17.
Miyaura, et al., "Palladium-Catalyzed Cross-Coupling Reactions of Organoboron Compounds," Chem. Rev., (1995), 95:2457-2483.
Mokhtari, et al., "Potential utility of small tyrosine kinase inhibitors in the treatment of diabetes," Clinical Science, (2010), 118(4):241-247.
Mol, et al., "Structural Basis for the Autoinhibition and STI-571 Inhibition of c-Kit Tyrosine Kinase," J. Biol. Chem., (2004), 279:31655-31663.
Mol, et al., "Structure of a c-Kit Product Complex Reveals the Basis for Kinase Transactivation," J. Biol. Chem., (2003), 278:31461-31464.

(56) References Cited

OTHER PUBLICATIONS

Morgan, et al., "Isolation and Characterization of a Cloned Growth Factor Dependent Macrophage Cell Line, BAC1.2F5," J. of Cell. Physiology, (1987), 130:420-427.
Motoyoshi, K., "Biological activities and clinical application of M-CSF," Int J Hematol. (1998), 67:109-122.
Murty, et al., "A Genetic Perspective of Male Germ Cell Tumors," Sem. Oncol., (1998), 25:133-144.
Naclerio, et al., "Rhinitis and Inhalant Allergens," JAMA, (1997), 278:1842-1848.
Nagafuji, et al., "A General Synthesis of Pyrroles and Fused Pyrrole Systems from Ketones and Amino Acids," J. Org. Chem., (1996), 61:4999-5003.
Nagata, et al., "Elevated Expression of the Proto-Oncogene c-kit in Patients with Mastocytosis," Leukemia, (1998), 12:175-181.
Nahm et al., "N-Methoxy-N-Methylamides as Effective Acylating Agents," Tetrahedron Lett., (1981), 22(39):3815-3818.
Nakagawara, et al., "Expression and Function of TRK-B an BDNF in Human Neuroblastomas," Mol. Cell Biol., (1994), 14:759-767.
Nakai et al., "New Potent Antagonists of Leukotrienes C4 and D4. 01. Synthesis and Structure-Activity Relationships," J. Med. Chem., (1988), 31:(1):84-91.
Nassentein, et al., "The Neurotrophins Nerve Growth Factor, Brain-derived Neurotrophic Factor, Neurotrophin-3, and Neurotrophin-4 Are Survival and Activation Factors for Eosinophils in Patients with Allergic Bronchial Asthma," J. Exp. Med., (2003), 198:455-467.
Natali, et al., "Breast cancer is associated with loss of the c-kit oncogene product," Int. J. Cancer (1992) 52:713-717.
Navaza, J., "AMoRe: an Automated Package for Molecular Replacement," Acta Cryst., (1994), A50:157-163.
Neidle, et al., "Molecular Modeling to Study DNA Intercalation by Anti-Tumor Drugs," Methods Enz., (1991), 203:433-458.
Newbatt Y. et al., Identification of Inhibitors of the Kinase Activity of Oncogenic V600EBRAF in an Enzyme Cascade High-Throughput Screen. Journal of Biomolecular Screening, 2006, vol. 11, No. 2, p. 145-154.
Ng, et al., "Engineering Protein-Lipid Interactions: Targeting of Histidine-Tagged Proteins to Metal-Chelating Lipid Monolayers," Langmuir, (1995), 11:4048-4055.
Nicholls, et al., "Protein Folding and Association: Insights From the Interfacial and Thermodynamic Properties of Hydrocarbons," Proteins, (1991), 11:281-296.
Nichols, et al., "Development of a Scintillation Proximity Assay for Peroxisome Proliferator-Activated Receptor γ Ligand Binding Domain," Anal. Biochem., (1998), 257:112-119.
Niihori, et al., "Germline KRAS and BRAF mutations in cardio-facio-cutaneous syndrome," Nature Genet., (2006), 38(3):294-296.
Ochs, et al., "A phase I/II trial of recombinant methionyl human brain derived neurotrophic factor administered by intrathecal infusion to patients with amyotrophic lateral sclerosis," Amyotroph Lateral Scler Other Motor Neuron Disord., (2000), 1:201-206.
Okada, et al., "Gene Therapy Against an Experimental Glioma Using Adeno-Associated Virus Vectors," Gene Ther., (1996), 3:957-964.
Okayama, et al., "Activation of Eosinophils with Cytokines Produced by Lung Mast Cells," Int. Arch. Aller. Immunol., (1997), 114(suppl. 1):75-77.
Okayama, et al., "Human Lung Mast Cells are Enriched in the Capacity to Produce Granulocyte-Macrophage Colony-Stimulating Factor in Response to IgE-Dependent Stimulation," Eur. J. Immunol., (1998), 28:708-715.
Olah, et al., "Synthetic Methods and Reactions: Part 209. Improved Preparation of Aldehydes and Ketones from N,N-Dimethylamides and Grignard Reagents," Synthesis, (1984), 228-230.
O'Shannessy, D., "Determination of Kinetic Rate and Equilibrium Binding Constants for Macromolecular Interactions: a Critique of the Surface Plasmon Resonance Literature," Current Opinions in Biotechnology, (1994), 5:65-71.

O'Shannessy, et al., "Interpretation of Deviations From Pseudo-First-Order Kinetic Behavior in the Characterization of Ligand Binding by Biosensor Technology," Analytical Biochemistry, (1996), 236:275-283.
Ottoni, et al., "Efficient and Simple Methods for the Introduction of the Sulfonyl, Acyl and Alkyl Protecting Groups on the Nitrogen of Indole and its Derivatives," Tetrahedron, (1998), 54:13915-13928.
Otwinowski, Z., "Maximum Likelihood Refinement of Heavy Atom Parameters," Dept. of Molecular Biophysics and Biochemistry, (1991), 80-86.
Owicki, et al., Application of Fluorescence Polarization Assays in High-Throughput Screening, Genetic Engineering News, (1997), 17:27.
Parker, et al., "Development of High Throughput Screening Assays Using Fluorescence Polarization: Nuclear Receptor-Ligand-Binding and Kinase/Phosphatase Assays," J Biomol Screen, (2000), 5:77-88.
Patani et al, "Bioisosterism: a rational approach in drug design," Chem Rev, (1996), 96:3147-3176.
Perrin, D., "Nucleic Acids for Recognition and Catalysis: Landmarks, Limitations, and Looking to the Future," Combinatorial Chemistry & High Throughput Screening, (2000), 3:243-269.
Petty, et al., "The effect of systemically administered recombinant human nerve growth factor in healthy human subjects," Ann Neurol., (1994), 36:244-246.
Pflugrath, et al., "Crystal Structure Determination, Refinement and the Molecular Model of the x-Amylase Inhibitor Hoe-467A," J. Mol. Biol., (1986), 189:383-386.
Pierce, et al., "Local anesthetics. I. beta-Monoaklylaminoethyl Esters of Alkoxybenzoic Acids," J. Am. Chem. Soc., (1942), 64:1691-1694.
Pignon, J.M., "C-kit mutations and mast cell disorders A model of activating mutations of growth factor receptors," Hermatol Cell Ther., (1997), 39:114-116.
Plunkett, et al., "A Silicon-Based Linker for Traceless Solid-Phase Synthesis," J. Org. Chem., (1995), 60:6006-6007.
Poul, et al., "Selection of Tumor-Specific Internalizing Human Antibodies from Phage Libraries," J. Mol. Biol., (2000), 301:1149-1161.
Price, et al., "Summary report on the ISOBM TD-4 Workshop: analysis of 56 monoclonal antibodies against the MUC1 mucin," Tumour Biology, (1998), 19:1-20.
Qiao, et. al., "Role of Macrophage Colony-Stimulating Factor in Atherosclerosis," Am. J. Path., (1997), 150:1687-1699.
Rajavashisth, et. al., "Heterozygous Osteopetrotic (op) Mutation Reduces Atherosclerosis in LDL Receptor-deficient Mice," J. Clin. Invest., (1998), 101:2702-2710.
Rajpert-De Meyts, et al., "Expression of the c-kit Protein Product in Carcinoma-in-situ and Invasive Testicular Germ Cell Tumours," Int. J. Androl., (1994), 17:85-92.
Rapp, et al., "Raf kinases in lung tumor development," Advan. Enzyme Regul. (2003) 43:183-195.
Remington: The Science and Practice of Pharmacy, vol. II, pp. 1454-1460 (1995).
Ricotti, et al., "c-kit Is Expressed in Soft Tissue Sarcoma of Neuroectodermic Origin and Its Ligand Prevents Apoptosis of Neoplastic Cells," Blood, (1998), 91:2397-2405.
Ridge, et al., "FMS mutations in myelodysplastic, leukemic, and normal subjects," Proc. Nat. Acad. Sci., (1990), 87:1377-1380.
Roberts et al., "Targeting the Raf-MEK-ERK mitogen-activated protein kinase cascade for the treatment of cancer," Oncogene (2007) 26:3291-3310.
Roberts, et al., "Generation of an antibody with enhanced affinity and specificity for its antigen by protein engineering," Nature, (1987), 328:731-734.
Robinson, et al., "Stimulation of Bone Marrow Colony Growth In Vitro by Human Urine," Blood, (1969), 33:396-399.
Robison, et al., "7-Azaindole. I. Synthesis and Conversion to 7-Azatryptophan and Other Derivatives," J. Am. Chem. Soc., (1955), 77:457-460.
Rodan, et al., "Therapeutic Approaches to Bone Diseases," Science, (2000), 289:1508-1514.

(56) References Cited

OTHER PUBLICATIONS

Rodriguez-Viciana, et al., "Germline Mutations in Genes Within the MAPK Pathway Cause Cardio-facio-cutaneous Syndrome," Science, (2006), 311:1287-1290.
Rosenfeld, M.A., "Human artificial chromosomes get real," Nat. Genet., (1997), 15:333-335.
Ryan, et al., "Role for the Stem Cell Factor/KIT Complex in Schwann Cell Neoplasia and Mast Cell Proliferation Associated with Neurofibromatosis," J. Neuro. Res. (1994), 37:415-432.
Saify, et al., "Database CAS on STN (Columbus, OH, USA) No. 124:170379, Synthesis of some 2-azaindole derivatives: their cyctotoxicity and antibacterial activity," abstract, (1996), See RN 271-63-6.
Saify, et al., "Synthesis of some 7-azaindole derivatives: Their cytotoxicity and antibacterial activity," Pakistan Journal of Scientific and Industrial Research, (1994), 37(10):439-441.
Saiki, R.K., "Amplification of Genomic DNA," PCR Protocols, A Guide to Methods and Applications, (1990), 13-20.
Sambrook, et al., "Introduction of Recombinant Vectors into Mammalian Cells," Molecular Cloning: A Laboratory Manual, (1989), 2:16.30-16.37.
Samowitz et al., "Poor Survival Associated with the BRAF V600E Mutation in Microsatellite-Stable Colon Cancer," Cancer Research, (2005), 65(14): 6063-6070.
Sandlow, et al., "Expression of c-KIT and its Ligand, Stem Cell Factor, in Normal and Subfertile Human Testicular Tissue," J. Androl., (1996), 17:403-408.
Santoro, et al., "The ret Proto-Oncogene is Consistently Expressed in Human Pheochromocytomas and Thyroid Medullary Carcinomas," Oncogene, (1990), 5(10):1595-1598.
Sathornsumetee, et al., "AAL881, a Novel Small Molecule Inhibitor of RAF and Vascular Endothelial Growth Factor Receptor Activities, Blocks the Growth of Malignant Glioma," Cancer Res., (2006), 66:8722-8730.
Sawada, et al., "4-(Benzoylindolizinyl)butyric acids; Novel nonsteroidal inhibitors of steroid 5;1-reductase. III," Chemical and Pharmaceutical Bulletin, (2001), 49(7):799-813.
Sawada, et al., "Role of Cytokines in Leukemic type Growth of Myelodysplastic CD34+ Cells," Blood, (1996), 88:319-327.
Sawai, et al., "Aberrant growth of granulocyte-macrophage progenitors in juvenile chronic myelogenous leukemia in serum-free culture," Exp. Hem., (1996), 2:116-122.
Scheffner, et al., "The E6 Oncoprotein Encoded by Human Papillomavirus Types 16 and 18 Promotes the Degradation of p53," Cell, (1990), 63:1129-1136.
Schiemann, et al., "p-Fluorobenzoic Acid," Org. Syn. Coll., (1943), 2:299-301.
Schneider, et al., "Functional Purification of a Bacterial ATP-Binding Cassette Transporter Protein (MalK) from the Cytoplasmic Fraction of an Overproducing Strain," Protein Expr. Purif., (1995), 6:10-14.
Schneller, et. al., "Synthesis of 4-Amino-1 H-pyrrolo[2,3-b]pyridine {1,7-Dideazaadenine) and 1H-Pyrrolo[2,3-b]pyridine-4-ol (1,7-Dideazahypoxanthine)," J. Org. Chem., (1980), 45:4045-4048.
Schuhmann, et al., "Immobilization of Enzymes on Langmuir-Blodgett Films via a Membrane-Bound Receptor. Possible Applications for Amperometric Biosensors," Adv. Mater., (1991), 3:388-391.
Schummer, et al., "Inexpensive Handheld Device for the Construction of High-Density Nucleic Acid Arrays," Biotechniques, (1997), 23:1087-1092.
Schweizer, et al., "Combinatorial Synthesis of Carbohydrates," Curr Opin Chem Biol, (1999), 3(3):291-298.
Sclabas, et al., "Overexpression of Tropomyosin-Related Kinase B in Metastatic Human Pancreatic Cancer Cells," Clin. Cancer. Res., (2005), 11:440-449.
Search Report for European Application No. 04814626.0 dated Aug. 4, 2009.
Search Report for European Application No. 11173701.1 dated Mar. 6, 2012.
Search Report for European Application No. 11173701.1 dated Oct. 26, 2011.
Secor, et al., "Mast cells are essential for early onset and severe disease in a murine model of multiple sclerosis," J. Exp. Med., (2000), 5:813-821.
Selvin, P., "Fluorescence Resonance Energy Transfer," Meth. Enzymol., (1995), 246:300-345.
Shan, et al., "Prodrug strategies based on intramolecular cyclization reactions," Journal of Pharmaceutical Sciences, (1997), 86(7):765-767.
Sheets, et al., "Efficient Construction of a Large Nonimmune Phage Antibody Library: The Production of High-Affinity Human Single-Chain Antibodies to Protein Antigens," Proc Natl Acad Sci USA., (1998), 95:6157-6162.
Shibata, et al., "Alveolar macrophage deficiency in osteopetrotic mice deficient in macrophage colony-stimulating factor is spontaneously corrected with age and associated with matrix metalloproteinase expression and emphysema," Blood, (2001), 98:2845-2852.
Siegel, et al., "Mass Spectral Analysis of a Protein Complex Using Single-Chain Antibodies Selected on a Peptide Target: Applications to Functional Genomics," Journal of Molecular Biology, (2000), 302:285-293.
Sigal, et al., "A Self-Assembled Monolayer for the Binding and Study of histidine-Tagged Proteins by Surface Plasmon Resonance," Anal. Chem., (1996), 68:490-497.
Smalley, et al., "c-KIT signaling as the driving oncogenic event in sub-groups of melanomas," Histol Histopathol, (2009), 24:643-650.
Solinas-Toldo, et al., "Matrix-Based Comparative Genomic Hybridization Biochips to Screen for Genomic Imbalances," Genes, Chromosomes & Cancer, (1997), 20:399-407.
Song, et al., "Isomerism of Bis(7-azaindolyl)methane," Organic Letters (2002), 4(23):4049-4052, Table of content p. 1-16 and Supporting information p. 1-15.
Sperling, et al., "Expression of the Stem Cell Factor Receptor C-Kit (CD117) in Acute Leukemias," Haemat., (1997), 82:617-621.
Stanulla, et al., "Coexpression of Stem Cell Factor and Its Receptor c-Kit in Human Malignant Glioma Cell Lines," Act Neuropath., (1995), 89:158-165.
Steinman, L., "Multiple sclerosis: A coordinated immunological attack against myelin in the central nervous system," Cell, (1996), 85:299-302.
Strohmeyer, et al., "Expression of the C-kit Proto-Oncogene and its Ligand Stem Cell Factor (SCF) in Normal and Malignant Human Testicular Tissue," J. Urol., (2005), 153:511-515.
Strohmeyer, et al., "Expression of the hst-1 and c-kit Protooncogenes in Human Testicular Germ Cell Tumors," Canc. Res., (1991), 51:1811-1816.
Su, et al., "Synthesis of bromo-substituted Idoxyl Esters for Cytochemical Demonstration of Enzyme Activity," J. Am. Chem. Soc., (1960), 82:1187-1189.
Sun, C., "Recent Advances in Liquid-Phase Combinatorial Chemistry," Comb. Chem. & High Throughput Screening, (1999), 2:299-318.
Sun, et al., "Design, Synthesis, and Evaluations of Substituted 3-[(3- or 4-Carboxyethylpyrrol-2-yl) Methylidenyl]indolin-2-Ones as Inhibitors of VEGF, PGF, and PDGF Receptor Tyrosine Kinases," J. Med. Chem., (1999), 42:5120-5130.
Tada, et al., "Analysis of Cytokine Receptor Messenger RNA Expression in Human Glioblastoma Cells and Normal Astrocytes by Reverse-Transcription Polymerase Chain Reaction," J. Neuro., (1994), 80:1063-1073.
Takahashi, et al., "Activation of a Novel Human Transforming Gene, ret, by DNA Rearrangement," Cell, (1985), 42(2):581-588.
Takahashi, et al., "Cloning and Expression of the ret Proto-Oncogene Encoding a Tyrosine Kinase with Two Potential Transmembrane Domains," Oncogene, (1988), 3(5):571-578.
Takahashi, et al., "ret Transforming Gene Encodes a Fusion Protein Homologous to Tyrosine Kinases," Mol Cell Biol., (1987), 7:1378-1385.

(56) References Cited

OTHER PUBLICATIONS

Tang, et al., "An RNA interference-based screen identifies MAP4K4/NIK as a negative regulator of PPARγ, adipogenesis, and insulin-responsive hexose transport," Proc. Natl. Acad. Sci., (2006), 103:2087-2092.
Tanno et al., "Evaluation of Hypromellose Acetate Succinate (HPMCAS) as a Carrier in Solid Dispersions," Drug Development and Industrial Pharmacy 30(1):9-17 (2004).
Taylor, et al., "The Rapid Generation of Oligonucleotide-directed Mutations at High Frequency Using Phosphorothloate-Modified DNA," Nucl. Acids Res., (1985), 13:8764-8785.
Teitelbaum, S.L., "Bone Resorption by Osteoclasts," Science, (2000), 289:1504-1508.
Thibault, et. al., "Concise and Efficient Synthesis of 4-fluoro-1H-pyrrolo[2,3-b] pyridine," Org. Lett., (2003), 5:5023-5025.
Thomas, et al., "The Eosinophil and its Role in Asthma," Gen. Pharmac., (1996), 27:593-597.
Thomas, et. al., "Light-Emitting Carbazole Derivatives: Potential Electroluminescent Materials," J. Am. Chem. Soc., (2001), 123:9404-9411.
Toste, et al., "A Versatile Procedure for the Preparation of Aryl Thiocyanates Using N-Thiocyanatosuccinimide (NTS)," Synth. Comm., (1995), 25(8):1277-1286.
Toyota, et al., "Expression of c-kit and kit Ligand in Human Colon Carcinoma Cells," Turn Biol., (1993), 14:295-302.
Trupp, et al., "Functional Receptor for GDNF Encoded by the c-ret Proto-Oncogene," Nature., (1996), 381:785-789.
Tsai, et al., "Discovery of a Selective Inhibitor of Oncogenic B-Raf Kinase with Potent Antimelanoma Activity," PNAS, (2008), 105(8):3041-3046.
Tsujimura, et al., "Ligand-Independent Activation of c-kit Receptor Tyrosine Kinase in a Murine Mastocytoma Cell Line P-815 Generated by a Point Mutation," Blood, (1994), 9:2619-2626.
Tsujimura, et al., "Substitution of an Aspartic Acid Results in Constitutive Activation of c-kit Receptor Tyrosine Kinase in a Rat Tumor Mast Cell Line RBL-2H3," Int. Arch. Aller. Immunol., (1995), 106:377-385.
Tsujimura, T., "Role of c-kit Receptor Tyrosine Kinase in the Development, Survival and Neoplastic Transformation of Mast Cells," Pathol Int., (1996), 46:933-938.
Turner, et al., "Nonhematopoeietic Tumor Cell Lines Express Stem Cell Factor and Display c-kit Receptors," Blood, (1992), 80:374-381.
Udenfriend, et al., "Scintillation Proximity Assay: A Sensitive and Continuous Isotopic Method for Monitoring Ligand/Receptor and Antigen/Antibody Interactions," Anal. Biochem, (1987), 161:494-500.
Uritskaya, et al., STN Accession No. 1974-27133; Document No. 08:27133; Abstract of Khimiya Geterotsiklicheskikh Soedinenii (1973), 10:1370-1373.
U.S. Notice of Allowance of U.S. Appl. No. 11/016,350 dated Dec. 26, 2007.
U.S. Notice of Allowance of U.S. Appl. No. 11/154,988 dated Jun. 6, 2008.
U.S. Notice of Allowance of U.S. Appl. No. 11/154,988 dated Jul. 23, 2008.
U.S. Notice of Allowance of U.S. Appl. No. 11/154,988 dated Sep. 8, 2008.
U.S. Notice of Allowance of U.S. Appl. No. 11/435,381 dated May 27, 2010.
U.S. Notice of Allowance of U.S. Appl. No. 11/435,381 dated Jul. 27, 2010.
U.S. Notice of Allowance of U.S. Appl. No. 11/473,347 dated Jun. 18, 2010.
U.S. Notice of Allowance of U.S. Appl. No. 11/473,347 dated Sep. 8, 2010.
U.S. Notice of Allowance of U.S. Appl. No. 11/960,590 dated Aug. 11, 2010.
U.S. Notice of Allowance of U.S. Appl. No. 11/961,901 dated May 17, 2012.
U.S. Notice of Allowance of U.S. Appl. No. 11/962,044 dated Aug. 13, 2010.
U.S. Notice of Allowance of U.S. Appl. No. 11/986,667 dated Aug. 6, 2010.
U.S. Notice of Allowance of U.S. Appl. No. 12/244,730 dated Jan. 6, 2011.
U.S. Notice of Allowance of U.S. Appl. No. 12/616,079 dated Oct. 25, 2012.
U.S. Notice of Allowance of U.S. Appl. No. 13/216,200 dated Dec. 8, 2011.
U.S. Office Action in U.S. Appl. No. 11/016,350 dated Jun. 6, 2007.
U.S. Office Action in U.S. Appl. No. 11/016,350 dated Aug. 2, 2007.
U.S. Office Action in U.S. Appl. No. 11/016,350 dated Oct. 26, 2007.
U.S. Office Action in U.S. Appl. No. 11/154,988 dated Jan. 4, 2008.
U.S. Office Action in U.S. Appl. No. 11/154,988 dated Oct. 19, 2007.
U.S. Office Action in U.S. Appl. No. 11/435,381 dated Feb. 19, 2010.
U.S. Office Action in U.S. Appl. No. 11/435,381 dated Mar. 4, 2009.
U.S. Office Action in U.S. Appl. No. 11/435,381 dated Jun. 1, 2009.
U.S. Office Action in U.S. Appl. No. 11/473,347 dated Dec. 18, 2009.
U.S. Office Action in U.S. Appl. No. 11/487,134 dated May 15, 2008.
U.S. Office Action in U.S. Appl. No. 11/487,134 dated Aug. 22, 2007.
U.S. Office Action in U.S. Appl. No. 11/962,044 dated Feb. 17, 2010.
U.S. Office Action in U.S. Appl. No. 11/962,044 dated Sep. 23, 2009.
U.S. Office Action in U.S. Appl. No. 11/986,667 dated Feb. 26, 2010.
U.S. Office Action in U.S. Appl. No. 11/986,667 dated Sep. 22, 2009.
U.S. Office Action in U.S. Appl. No. 12/082,665 dated Nov. 8, 2010.
U.S. Office Action in U.S. Appl. No. 12/244,730 dated Jul. 22, 2010.
U.S. Office Action in U.S. Appl. No. 12/616,079 dated Feb. 9, 2012.
U.S. Office Action in U.S. Appl. No. 12/616,079 dated Jun. 29, 2012.
U.S. Office Action in U.S. Appl. No. 12/669,450 dated Dec. 27, 2012.
U.S. Office Action in U.S. Appl. No. 12/752,035 dated Jun. 18, 2013.
U.S. Office Action in U.S. Appl. No. 12/752,035 dated Oct. 3, 2012.
U.S. Office Action in U.S. Appl. No. 12/906,980 dated Feb. 29, 2012.
U.S. Office Action in U.S. Appl. No. 12/906,980 dated Oct. 17, 2012.
U.S. Office Action in U.S. Appl. No. 12/958,376 dated Apr. 18, 2012.
U.S. Office Action in U.S. Appl. No. 12/958,379 dated Jul. 17, 2012.
U.S. Office Action in U.S. Appl. No. 12/958,379 dated Nov. 14, 2012.
U.S. Office Action in U.S. Appl. No. 12/981,427 dated Mar. 5, 2013.
U.S. Office Action in U.S. Appl. No. 13/243,748 dated Jun. 27, 2013.
U.S. Office Action in U.S. Appl. No. 13/546,923 dated Sep. 18, 2012.
Vachon, et al., "The influence of microencapsulation using Eudragit RS100 on the hydrolysis kinetics of acetylsalicylic acid," J. Microencapsulation, (1997), 14(3):281-301.
Valent, P., "Biology, Classification and Treatment of Human Mastocytosis," Wein/Klin Wochenschr., (1996), 108:385-397.
Van Heyningen, V., "One Gene—Four Syndromes," Nature, (1994), 367:319-320.
Van Regenmortel, M.H.V., "Use of biosensors to characterize recombinant proteins," Developments in Biological Standardization, (1994), 83:143-151.
Vandelli, et al., "Analysis of release data in the evaluation of the physical state of progesterone in matrix systems," J. Microencapsulation, (1993), 10(1):55-65.

(56) References Cited

OTHER PUBLICATIONS

Vely, et al., "BIAcore Analysis to Test Phosphopeptide-SH2 Domain Interactions," Methods in Molecular Biology, (2000), 121:313-321.
Verfaillie, C.M., "Chronic myelogenous leukemia: too much or too little growth, or both?" Leukemia, (1998), 12:136-138.
Viskochil, D., "It Takes Two to Tango: Mast Cell and Schwann Cell Interactions in Neurofibromas," J Clin Invest., (2003), 112:1791-1793.
Vliagoftis, et al., "The protooncogene c-kit and c-kit ligand in human disease," Journ. Clin. Immunol, (1997), 100:435-440.
Weber, P., "Physical Principles of Protein Crystallization," Adv. Protein Chem., (1991), 41:1-36.
Wells, et al., "Targeting the RET Pathway in Thyroid Cancer," Clin Cancer Res., (2009), 15(23):7119-7123.
Wendt, et al., "Identification of novel binding interactions in the development of potent, selective 2-naphthamidine inhibitors of urokinase, synthesis, structural analysis, and SAR of y-Phenyl amide 6-substitution," J. Med. Chem., (2004), 47(2):303-324.
Wermuth. Saishin Souyaku Kagaku (The Practice of Medicinal Chemistry), 1998, first volume, p. 375-80. (in Japanese with English Translation).
Wermuth. Saishin Souyaku Kagaku (The Practice of Medicinal Chemistry), 1998, first volume, p. 235-271. (in Japanese with English Translation).
Werness, et al., "Association of Human Papillomavirus Types 16 and 18 E6 Proteins with p53," Science, (1990), 248:76-79.
Wessjohann, L., "Synthesis of Natural-Product-Based Compound Libraries," Curr Opin Chem Biol., (2000), 4:303-309.
Wharam, et al., "Specific Detection of DNA and RNA Targets Using a Novel Isothermal Nucleic Acid Amplification Assay Based on the Formation of a Three-Way Junction Structure," Nucleic Acids Res., (2001), 29:1-8.
Wild, et al., "Antibodies to Nerve Growth Factor Reverse Established Tactile Allodynia in Rodent Models of Neuropathic Pain without Tolerance," J. Pharmacol. Exp. Ther., (2007), 322:282-287.
Williams, et al., "Dissection of the Extracellular Human Interferon y Receptor a-Chain into two Immunoglobulin-like domains. Production in an *Escherichia coli* Thioredoxin Gene Fusion Expression system and Recognition by Neutralizing Antibodies," Biochemistry, (1995), 34:1787-1797.
Woon, et al., "Construction and Characterization of a 10-Fold Genome Equivalent Rat P1-Derived Artificial Chromosome Library," Genomics, (1998), 50:306-316.
Wright, et al., "The STE20 Kinase KGK Is Broadly Expressed in Human tumor Cells and Can Modulate Cellular Transformation, Invasion, and Adhesion," Mol. Cell. Biol., (2003), 23:2068-2082.
Wuthrich, K., "Chapter 10: Three-Dimensional Protein Structures by NMR," NMR of Proteins and Nucleic Acids, (1986), 10:176-199.
Wyckoff, et al., "Direct visualization of macrophage-assisted tumor cell intravasation in mammary tumors," Cancer Research, (2007), 67(6):2649-2656.
Xing, et al., "BRAF Mutation Predicts a Poorer Clinical Prognosis for Papillary Thyroid Cancer," J. Clin. Endocrinol. Metab., (2005), 90(12):6373-6379.
Xing, M., "BRAF mutation in thyroid cancer," Endocrine-Related Cancer, (2005), 12:245-262.
Xu, et al., "Modulation of Endothelial Cell function by Normal Polyspecific Human Intraveneous immunoglobulins," Am. J. Path., (1998), 153:1257-1266.
Yakhontov, et al., "Derivatives of 7-azaindole. XV. Electrophilic substitution of 4-methyl-7-azaindole and its derivatives," Zhurnal Obshchei Khimii, (1965), 1(11):2032-2040 (English abstract only).
Yamaguchi, et al., "Calcium Restriction Allows cAMP Activation of the B-Raf/ERK Pathway, Switching Cells to a cAMP-dependent Growth-stimulated Phenotype," The Journal of Biological Chemistry, (2004), 279:40419-40430.
Yamaguchi, et al., "Cyclic AMP activates B-Raf and ERK in cyst epithelial cells from autosomal-dominant polycystic kidneys," Kidney International, (2003), 63:1983-1994.
Yang, et al., "Identification of Brain-Derived Neurotrophic Factor as a Novel Functional Protein in Hepatocellular Carcinoma," Cancer Res., (2005), 65:219-225.
Yang, et al., "Neurofibromin-Deficient Schwann Cells Secrete a Potent Migratory Stimulus for NF1+/− Mast Cells," J Clin Invest., (2003), 112:1851-1861.
Yang, et al., "Nf1-Dependent tumors require a microenvironment containing Nf1+/−-and c-kit-Dependent bone marrow," Cell, (2008), 135:437-448.
Yang, et al., "Synthesis of some 5-substituted indoles," Heterocycles, (1992), 34:1169-1175.
Yao, et al., "A Novel Human STE20-related Protein Kinase, HGK, That Specifically Activates the c-Jun N-terminal Kinase Signaling Pathway," J. Biol. Chem., (1999), 274:2118-2125.
Yee, et al., "Role of kit-Ligand in Proliferation and Suppression of Apoptosis in Mast Cells: Basis for Radiosensitivity of White Spotting and Steel Mutant Mice," J. Exp. Med., (1994), 179:1777-1787.
Yeung, et al., "Friedel-Crafts acylation of indoles in acidic imidazolium chloroaluminate ionic liquid at room temperature," Tetrahedron Letters, (2002), 43(33), 5793-5795.
Yoshida et al., "Studies on anti-helicobacter pylori agents, Part 1: Benzyloxyisoquinoline derivatives," Bioorganic & Medicinal Chemistry, Elsevier Science Ltd, 7(11):2647-2666 (1999).
Yuan, et al., Human Peripheral Blood Eosinophils Express a Functional c-kit Receptor for Stem Cell Factor that Stimulates Very Late Antigen 4 (VLA-4)-Mediated Cell Adhesion to Fibronectin and Vascular Cell Adhesion Molecule 1 (VCAM-1), J. Exp. Med., (1997), 186:313-323.
Zanon, et. al., "Copper-Catalyzed Domino Halide Exchange-Cyanation of Aryl Bromides," J. Am. Chem. Soc., (2003), 125:2890-2891.
Zhang, et al., "An effective procedure for the acylation of azaindoles at C-3," Journal of Organic Chemistry, (2002), 67(17):6226-6227.
U.S. Appl. No. 16/058,945, filed Aug. 8, 2018, Wu.
U.S. Appl. No. 16/123,612, filed Sep. 6, 2018, Desai et al.
U.S. Appl. No. 16/148,244, filed Oct. 1, 2018, Zhang et al.
U.S. Appl. No. 16/358,608, filed Mar. 19, 2019, Zhang et al.
U.S. Appl. No. 16/400,801, filed May 1, 2019, Ibrahim et al.
U.S. Appl. No. 16/441,610, filed Jun. 14, 2019, Ibrahim et al.
Robubi, et al. RAF Kinase inhibitors in cancer treatment: like a Bull in a China shop?, Chem BioChem, 2010; 11:1645-1648.

COMPOUNDS AND METHODS FOR KINASE MODULATION, AND INDICATIONS THEREFOR

This application is a continuation application of U.S. application Ser. No. 15/656,990, filed Jul. 21, 2017, which is a continuation of U.S. application Ser. No. 15/260,042, filed Sep. 8, 2016, now U.S. Pat. No. 9,884,539, which is a continuation application of U.S. application Ser. No. 15/048,851, filed Feb. 19, 2016, now U.S. Pat. No. 9,469,640, which is a continuation of U.S. application Ser. No. 13/926,959, filed Jun. 25, 2013, which is a continuation of U.S. application Ser. No. 13/866,353, filed Apr. 19, 2013, which is a continuation application of Ser. No. 12/669,450, filed Jan. 15, 2010, which application is a National Phase application under 35 U.S.C. § 371 of PCT/US2008/070124, filed Jul. 16, 2008, which claims the benefit under 35 U.S.C. § 119(e) from U.S. Application No. 60/959,907, filed Jul. 17, 2007, which applications are hereby incorporated by reference in their entirety.

FIELD OF THE INVENTION

Background of the Invention

The present invention relates to kinases and compounds which modulate kinases, and uses therefor. Particular embodiments contemplate disease indications which are amenable to treatment by modulation of kinase activity by the compounds of the present invention.

SUMMARY OF THE INVENTION

Compounds are contemplated that are active on protein kinases in general, including, but not limited to, Abl, Akt1, Akt2, Akt3, ALK, Alk5, A-Raf, B-Raf, Brk, Btk, Cdk2, CDK4, CDK5, CDK6, CHK1, c-Raf-1, Csk, EGFR, EphA1, EphA2, EphB2, EphB4, Erk2, Fak, FGFR1, FGFR2, FGFR3, FGFR4, Flt1, Flt3, Flt4, Fms, Frk, Fyn, Gsk3α, Gsk3β, HCK, Her2/Erbb2, Her4/Erbb4, IGF1R, IKK beta, Irak4, Itk, Jak1, Jak2, Jak3, Jnk1, Jnk2, Jnk3, Kdr, Kit, Lck, Lyn, MAP2K1, MAP2K2, MAP4K4, MAPKAPK2, Met, Mnk1, MLK1, p38, PDGFRA, PDGFRB, PDPK1, Pim1, Pim2, Pim3, PKC alpha, PKC beta, PKC theta, Plk1, Pyk2, Ret, ROCK1, ROCK2, Ron, Src, Stk6, Syk, TEC, Tie2, TrkA, TrkB, Yes, and/or Zap70, including any mutations of these kinases. In some aspects, the compounds are active on Raf protein kinases including A-Raf, B-Raf and/or c-Raf-1, including any mutations thereof. In some aspects, compounds are of Formula I as described below.

Also contemplated in accordance with the present invention are methods for the use of the above-described compounds in treating diseases and conditions associated with regulation of the activity of the above-described kinases. Thus, the use of compounds for therapeutic methods involving modulation of protein kinases are provided, as well as compounds that can be used for therapeutic methods involving modulation of protein kinases.

In some embodiments, compounds have the structure according to the following Formula I:

Formula I

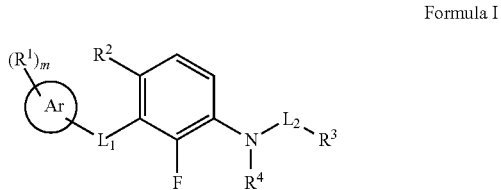

or a salt, a prodrug, a tautomer or an isomer thereof, wherein:
Ar is optionally substituted heteroaryl;
$R^1$ at each occurrence is independently selected from the group consisting of halogen, optionally substituted lower alkyl, optionally substituted lower alkenyl, optionally substituted lower alkynyl, optionally substituted cycloalkyl, optionally substituted heterocycloalkyl, optionally substituted aryl, optionally substituted heteroaryl, $-NR_2$, $-CN$, $-O-R^5$, $-N(R^5)-R^6$, $-C(X)-N(R^5)-R^6$, $-C(X)-R^7$, $-S(O)_2-N(R^5)-R^6$, $-S(O)_n-R^7$, $-O-C(X)-R^7$, $-C(X)-O-R^5$, $-C(NH)-N(R^8)-R^9$, $-N(R^5)-C(X)-R^7$, $-N(R^5)-S(O)_2-R^7$, $-N(R^5)-C(X)-N(R^5)-R^6$, and $-N(R^5)-S(O)_2-N(R^5)-R^6$;
m is 0, 1, 2, 3, 4 or 5;
n is 0, 1 or 2;
$R^2$ is hydrogen, lower alkyl or halogen;
$L_2$ is selected from the group consisting of $-S(O)_2-$, $-C(X)-$, $-C(X)-N(R^{10})-$, and $-S(O)_2-N(R^{10})-$;
$R^3$ is optionally substituted lower alkyl, optionally substituted $C_{3-6}$ cycloalkyl, optionally substituted heterocycloalkyl, optionally substituted aryl or optionally substituted heteroaryl;
$L_1$ is selected from the group consisting of a bond, $-N(R^{11})-$, $-O-$, $-S-$, $-C(X)-$, $-C(R^{12}R^{13})-X-$, $-X-C(R^{12}R^{13})-$, $-C(R^{12}R^{13})-N(R^{11})-$, $-N(R^{11})-C(R^{12}R^{13})-$, $-O-C(X)-$, $-C(X)-O-$, $-C(X)-N(R^{11})-$, $-N(R^{11})-C(X)-$, $-S(O)-$, $-S(O)_2-$, $-S(O)_2-N(R^{11})-$, $-N(R^{11})-S(O)_2-$, $-C(NH)-N(R^{11})-$, $-N(R^{11})-C(NH)-$, $-N(R^{11})-C(X)-N(R^{11})-$, and $-N(R^{11})-S(O)_2-N(R^{11})-$;
X is O or S;
$R^4$, $R^{10}$ and each $R^{11}$ are independently hydrogen or lower alkyl, wherein lower alkyl is optionally substituted with one or more substituents selected from the group consisting of fluoro, $-OH$, $-NH_2$, lower alkoxy, fluoro substituted lower alkoxy, lower alkylthio, fluoro substituted lower alkylthio, mono-alkylamino, fluoro substituted mono-alkylamino, di-alkylamino, fluoro substituted di-alkylamino, and $-NR^{14}R^{15}$;
$R^5$, $R^6$, $R^8$, and $R^9$ at each occurrence are independently selected from the group consisting of hydrogen, optionally substituted lower alkyl, optionally substituted $C_{3-6}$ alkenyl, optionally substituted $C_{3-6}$ alkynyl, optionally substituted cycloalkyl, optionally substituted heterocycloalkyl, optionally substituted aryl, and optionally substituted heteroaryl, or
$R^8$ and $R^9$ combine with the nitrogen to which they are attached to form a 5-7 membered optionally substituted nitrogen containing heterocycloalkyl or a 5 or 7 membered optionally substituted nitrogen containing heteroaryl;
$R^7$ at each occurrence is independently selected from the group consisting of optionally substituted lower alkyl, optionally substituted $C_{3-6}$ alkenyl, optionally substituted $C_{3-6}$ alkynyl, optionally substituted cycloalkyl, optionally substituted heterocycloalkyl, optionally substituted aryl, and optionally substituted heteroaryl;

$R^{12}$ and $R^{13}$ are independently selected from the group consisting of hydrogen, fluoro, —OH, —NH$_2$, lower alkyl, lower alkoxy, lower alklylthio, mono-alkylamino, di-alkylamino, and —NR$^{14}$R$^{15}$, wherein the alkyl chain(s) of lower alkyl, lower alkoxy, lower alkylthio, mono-alkylamino, or di-alkylamino are optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and cycloalkylamino; or $R^{12}$ and $R^{13}$ combine with the carbon to which they are attached to form a 3-7 membered monocyclic cycloalkyl or 5-7 membered monocyclic heterocycloalkyl, wherein the monocyclic cycloalkyl or monocyclic heterocycloalkyl are optionally substituted with one or more substituents selected from the group consisting of halogen, —OH, —NH$_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino; and $R^{14}$ and $R^{15}$ at each occurrence independently combine with the nitrogen to which they are attached to form a 5-7 membered heterocycloalkyl or 5-7 membered heterocycloalkyl substituted with one or more substituents selected from the group consisting of fluoro, —OH, —NH$_2$, lower alkyl, fluoro substituted lower alkyl, lower alkoxy, fluoro substituted lower alkoxy, lower alkylthio, and fluoro substituted lower alkylthio, provided, however, that when $L_1$ is a bond, —NR$^{11}$—, —O—, —S—, —C(X)—, —S(O)—, or —S(O)$_2$—, Ar is not 1H-pyrrolo[2,3-b]pyridine-3-yl, 1H-pyrazolo[3,4-b]pyridine-3-yl, 5H-pyrrolo[2,3-b]pyrazine-7-yl, 7H-pyrrolo[2,3-d]pyrimidine-5-yl, or 7H-pyrrolo[2,3-c]pyridazine-5-yl, i.e. is not

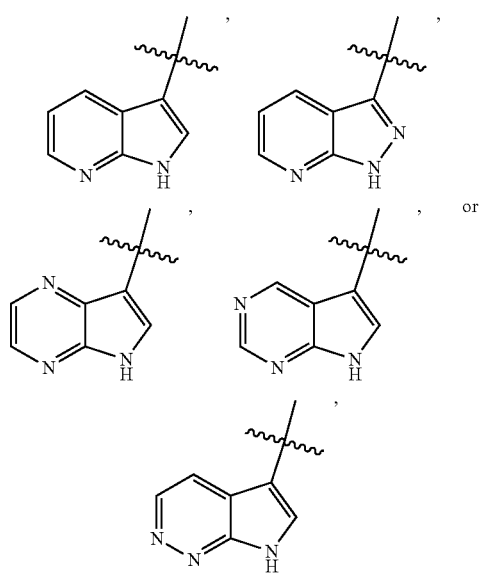

wherein

indicates the attachment point to $L_1$.

In some embodiments, the compound of Formula I has a structure according to the following sub-generic structure Formula Ia:

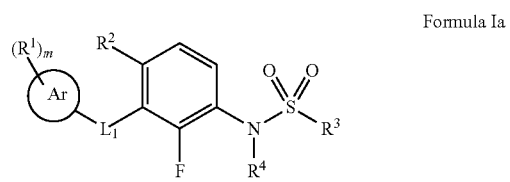

Formula Ia or a salt, a prodrug, a tautomer or an isomer thereof, wherein m, Ar, $R^1$, $R^2$, $R^3$, $R^4$, and $L_1$ are as defined for Formula I.

In some embodiments of compounds of Formula I or Ia, $L_1$ is a bond, —N(R$^{11}$)—, —N(R$^{11}$)—C(X)—, —N(R$^{11}$)—S(O)$_2$—, —N(R$^{11}$)—C(NH)—, —N(R$^{11}$)—C(X)—N(R$^{11}$)—, or —N(R$^{11}$)—S(O)$_2$—N(R$^{11}$)—, also —N(R$^{11}$)—, —N(R$^{11}$)—C(X)—, or —N(R$^{11}$)—S(O)$_2$—, also —N(R$^{11}$)—C(O)—, wherein the left side (i.e. —N(R$^{11}$)—) of $L_1$ is attached to Ar and the right side of $L_1$ is attached to the phenyl ring of Formula I or Ia. In some embodiments, $L_1$ is a bond, —N(R$^{11}$)—, —N(R$^{11}$)—C(X)—, —N(R$^{11}$)—S(O)$_2$—, —N(R$^{11}$)—C(NH)—, —N(R$^{11}$)—C(X)—N(R$^{11}$)—, or —N(R$^{11}$)—S(O)$_2$—N(R$^{11}$)—, also —N(R$^{11}$)—, —N(R$^{11}$)—C(X)—, or —N(R$^{11}$)—S(O)$_2$—, also —N(R$^{11}$)—C(O)—, and each R$^{11}$ and R$^4$ are independently hydrogen or lower alkyl, wherein lower alkyl is optionally substituted with one or more substituents selected from the group consisting of fluoro, lower alkoxy, fluoro substituted lower alkoxy, lower alkylthio, and fluoro substituted lower alkylthio, preferably each R$^{11}$ and R$^4$ are H.

In some embodiments of compounds of Formula I or Ia, $L_1$ is —C(X)—N(R$^{11}$)—, —C(R$^{12}$R$^{13}$)—X—, —X—C(R$^{12}$R$^{13}$)—, —C(R$^{12}$R$^{13}$)—N(R$^{11}$)—, or —N(R$^{11}$)—C(R$^{12}$R$^{13}$)—, wherein the left side of $L_1$ is attached to Ar and the right side of $L_1$ is attached to the phenyl ring of Formula I or Ia. In some embodiments, $L_1$ is —C(X)—N(R$^{11}$)—, —C(R$^{12}$R$^{13}$)—X—, —X—C(R$^{12}$R$^{13}$)—, —C(R$^{12}$R$^{13}$)—N(R$^{11}$)—, or —N(R$^{11}$)—C(R$^{12}$R$^{13}$)—, and each R$^{11}$ and R$^4$ are independently hydrogen or lower alkyl, wherein lower alkyl is optionally substituted with one or more substituents selected from the group consisting of fluoro, lower alkoxy, fluoro substituted lower alkoxy, lower alkylthio, and fluoro substituted lower alkylthio, preferably each R$^{11}$ and R$^4$ are H.

In some embodiments of compounds of Formula I or Ia, $R^2$ is hydrogen, fluoro or chloro, preferably fluoro or chloro. In some embodiments, R$^2$ is hydrogen, fluoro or chloro, each R$^{11}$ and R$^4$ are independently hydrogen or lower alkyl, wherein lower alkyl is optionally substituted with one or more substituents selected from the group consisting of fluoro, lower alkoxy, fluoro substituted lower alkoxy, lower alkylthio, and fluoro substituted lower alkylthio, preferably R$^2$ is fluoro or chloro and each R$^{11}$ and R$^4$ are H. In some embodiments, R$^2$ is hydrogen, fluoro or chloro, preferably fluoro or chloro, and $L_1$ is a bond, $-N(R^{11})-$, $-N(R^{11})-C(X)-$, $-N(R^{11})-S(O)_2-$, $-N(R^{11})-C(NH)-$, $-N(R^{11})-C(X)-N(R^{11})-$, or $-N(R^{11})-S(O)_2-N(R^{11})-$, also $-N(R^{11})-$, $-N(R^{11})-C(X)-$, or $-N(R^{11})-S(O)_2-$, also $-N(R^{11})-C(O)-$, wherein the left side (i.e. $-N(R^{11})-$) of $L_1$ is attached to Ar and the right side of $L_1$ is attached to the phenyl ring of Formula I or Ia. In some embodiments, $R^2$ is hydrogen, fluoro or chloro, preferably fluoro or chloro; $L_1$ is a bond, $-N(R^{11})-$, $-N(R^{11})-C(X)-$, $-N(R^{11})-S(O)_2-$, $-N(R^{11})-C(NH)-$, $-N(R^{11})-C(X)-N(R^{11})-$, or $-N(R^{11})-S(O)_2-N(R^{11})-$, also $-N(R^{11})-$, $-N(R^1)-C(X)-$, or $-N(R^{11})-S(O)_2-$, also $-N(R^{11})-C(O)-$; and each $R^{11}$ and $R^4$ are independently hydrogen or lower alkyl, wherein lower alkyl is optionally substituted with one or more substituents selected from the group consisting of fluoro, lower alkoxy, fluoro substituted lower alkoxy, lower alkylthio, and fluoro substituted lower alkylthio, preferably each $R^{11}$ and $R^4$ are H.

In some embodiments of compounds of Formula I or Ia, $R^2$ is hydrogen, fluoro or chloro, preferably fluoro or chloro. In some embodiments, $R^2$ is hydrogen, fluoro or chloro, each $R^{11}$ and $R^4$ are independently hydrogen or lower alkyl, wherein lower alkyl is optionally substituted with one or more substituents selected from the group consisting of fluoro, lower alkoxy, fluoro substituted lower alkoxy, lower alkylthio, and fluoro substituted lower alkylthio, preferably $R^2$ is fluoro or chloro and each $R^{11}$ and $R^4$ are H. In some embodiments, $R^2$ is hydrogen, fluoro or chloro, preferably fluoro or chloro, and $L_1$ is $-C(X)-N(R^{11})-$, $-C(R^{12}R^{13})-X-$, $-X-C(R^{12}R^{13})-$, $-C(R^{12}R^{13})-N(R^{11})-$, or $-N(R^{11})-C(R^{12}R^{13})-$, wherein the left side of $L_1$ is attached to Ar and the right side of $L_1$ is attached to the phenyl ring of Formula I or Ia. In some embodiments, $R^2$ is hydrogen, fluoro or chloro, preferably fluoro or chloro; $L_1$ is $-C(X)-N(R^{11})-$, $-C(R^{12}R^{13})-X-$, $-X-C(R^{12}R^{13})-$, $-C(R^{12}R^{13})-N(R^{11})-$, or $-N(R^{11})-C(R^{12}R^{13})-$; and each $R^{11}$ and $R^4$ are independently hydrogen or lower alkyl, wherein lower alkyl is optionally substituted with one or more substituents selected from the group consisting of fluoro, lower alkoxy, fluoro substituted lower alkoxy, lower alkylthio, and fluoro substituted lower alkylthio, preferably each $R^{11}$ and $R^4$ are H.

In some embodiments, the compound of Formula I has a structure according to the following sub-generic structure Formula Ib:

Formula Ib

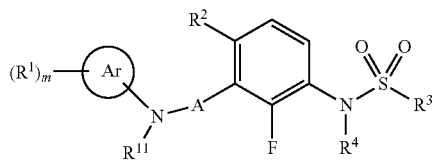

or a salt, a prodrug, a tautomer or an isomer thereof,
wherein A is $-C(O)-$ or $-C(R^{12}R^{13})-$; and
m, Ar, $R^1$, $R^2$, $R^3$, $R^4$, $R^{11}$, $R^{12}$ and $R^{13}$ are as defined for Formula I.

In some embodiments of compounds of Formula Ib, $R^4$, $R^{11}$, $R^{12}$ and $R^{13}$ are independently hydrogen or lower alkyl, wherein lower alkyl is optionally substituted with one or more substituents selected from the group consisting of fluoro, lower alkoxy, fluoro substituted lower alkoxy, lower alkylthio, and fluoro substituted lower alkylthio, preferably $R^4$, $R^{11}$, $R^{12}$ and $R^{13}$ are H. In some embodiments, $R^2$ is hydrogen, fluoro or chloro, preferably fluoro or chloro. In some embodiments, $R^2$ is hydrogen, fluoro or chloro, and $R^4$, $R^{11}$, $R^{12}$ and $R^{13}$ are independently hydrogen or lower alkyl, wherein lower alkyl is optionally substituted with one or more substituents selected from the group consisting of fluoro, lower alkoxy, fluoro substituted lower alkoxy, lower alkylthio, and fluoro substituted lower alkylthio, preferably $R^2$ is fluoro or chloro and $R^4$, $R^{11}$, $R^{12}$ and $R^{13}$ are H.

In some embodiments of compounds of Formula Ib, A is $-C(O)-$, and $R^4$ and $R^{11}$ are independently hydrogen or lower alkyl, wherein lower alkyl is optionally substituted with one or more substituents selected from the group consisting of fluoro, lower alkoxy, fluoro substituted lower alkoxy, lower alkylthio, and fluoro substituted lower alkylthio, preferably $R^4$ and $R^{11}$ are H. In some embodiments, A is $-C(O)-$, and $R^2$ is hydrogen, fluoro or chloro, preferably fluoro or chloro. In some embodiments, A is $-C(O)-$, $R^2$ is hydrogen, fluoro or chloro, preferably fluoro or chloro; and $R^4$ and $R^{11}$ are independently hydrogen or lower alkyl, wherein lower alkyl is optionally substituted with one or more substituents selected from the group consisting of fluoro, lower alkoxy, fluoro substituted lower alkoxy, lower alkylthio, and fluoro substituted lower alkylthio, preferably $R^4$ and $R^{11}$ are H.

In some embodiments of compounds of Formula Ib, A is $-C(R^{12}R^{13})-$, and $R^4$, $R^{11}$, $R^{12}$ and $R^{13}$ are independently hydrogen or lower alkyl, wherein lower alkyl is optionally substituted with one or more substituents selected from the group consisting of fluoro, lower alkoxy, fluoro substituted lower alkoxy, lower alkylthio, and fluoro substituted lower alkylthio, preferably $R^4$, $R^{11}$, $R^{12}$ and $R^{13}$ are H. In some embodiments, A is $-C(R^{12}R^{13})-$, $R^{12}$ and $R^{13}$ are independently hydrogen or lower alkyl, wherein lower alkyl is optionally substituted with one or more substituents selected from the group consisting of fluoro, lower alkoxy, fluoro substituted lower alkoxy, lower alkylthio, and fluoro substituted lower alkylthio, preferably $R^{12}$ and $R^{13}$ are H, and $R^2$ is hydrogen, fluoro or chloro, preferably fluoro or chloro. In some embodiments, A is $-C(R^{12}R^{13})-$; $R^2$ is hydrogen, fluoro or chloro, preferably fluoro or chloro; and $R^4$, $R^{11}$, $R^{12}$ and $R^{13}$ are independently hydrogen or lower alkyl, wherein lower alkyl is optionally substituted with one or more substituents selected from the group consisting of fluoro, lower alkoxy, fluoro substituted lower alkoxy, lower alkylthio, and fluoro substituted lower alkylthio, preferably $R^4$, $R^{11}$, $R^{12}$ and $R^{13}$ are H.

In some embodiments, the compound of Formula I has a structure according to the following sub-generic structure Formula Ic:

Formula Ic

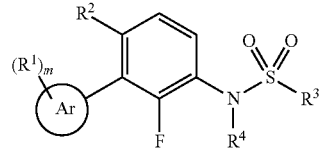

or a salt, a prodrug, a tautomer or an isomer thereof,
wherein m, Ar, $R^1$, $R^2$, $R^3$, and $R^4$, are as defined for Formula I.

In some embodiments of compounds of Formula Ic, $R^4$ is hydrogen or lower alkyl, wherein lower alkyl is optionally substituted with one or more substituents selected from the group consisting of fluoro, lower alkoxy, fluoro substituted lower alkoxy, lower alkylthio, and fluoro substituted lower alkylthio, preferably $R^4$ is H. In some embodiments, $R^2$ is hydrogen, fluoro or chloro, preferably fluoro or chloro. In some embodiments, $R^2$ is hydrogen, fluoro or chloro and $R^4$ is hydrogen or lower alkyl, wherein lower alkyl is optionally substituted with one or more substituents selected from the group consisting of fluoro, lower alkoxy, fluoro substituted lower alkoxy, lower alkylthio, and fluoro substituted lower alkylthio, preferably $R^2$ is fluoro or chloro and $R^4$ is H.

In some embodiments, the compound of Formula I has a structure according to the following sub-generic structure Formula Id:

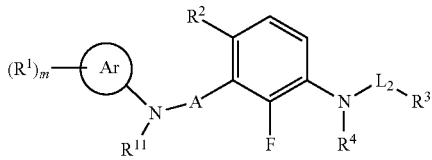

Formula Id or a salt, a prodrug, a tautomer or an isomer thereof, wherein A is —C(O)— or —C($R^{12}R^{13}$)—; and
m, Ar, $R^1$, $R^2$, $R^3$, $R^4$, $R^{11}$, $R^{12}$, $R^{13}$ and $L_2$ are as defined for Formula I.

In some embodiments of compounds of Formula Id, $R^4$, $R^{11}$, $R^{12}$ and $R^{13}$ are independently hydrogen or lower alkyl, wherein lower alkyl is optionally substituted with one or more substituents selected from the group consisting of fluoro, lower alkoxy, fluoro substituted lower alkoxy, lower alkylthio, and fluoro substituted lower alkylthio, preferably $R^4$, $R^{11}$, $R^{12}$ and $R^{13}$ are H. In some embodiments, $R^2$ is hydrogen, fluoro or chloro, preferably fluoro or chloro. In some embodiments, $R^2$ is hydrogen, fluoro or chloro, and $R^4$, $R^{11}$, $R^{12}$ and $R^{13}$ are independently hydrogen or lower alkyl, wherein lower alkyl is optionally substituted with one or more substituents selected from the group consisting of fluoro, lower alkoxy, fluoro substituted lower alkoxy, lower alkylthio, and fluoro substituted lower alkylthio, preferably $R^2$ is fluoro or chloro and $R^4$, $R^{11}$, $R^{12}$ and $R^{13}$ are H.

In some embodiments of compounds of Formula Id, A is —C(O)—, and $R^4$ and $R^{11}$ are independently hydrogen or lower alkyl, wherein lower alkyl is optionally substituted with one or more substituents selected from the group consisting of fluoro, lower alkoxy, fluoro substituted lower alkoxy, lower alkylthio, and fluoro substituted lower alkylthio, preferably $R^4$ and $R^{11}$ are H. In some embodiments, A is —C(O)—, and $R^2$ is hydrogen, fluoro or chloro, preferably fluoro or chloro. In some embodiments, A is —C(O)—, $R^2$ is hydrogen, fluoro or chloro, preferably fluoro or chloro; and $R^4$ and $R^{11}$ are hydrogen or lower alkyl, wherein lower alkyl is optionally substituted with one or more substituents selected from the group consisting of fluoro, lower alkoxy, fluoro substituted lower alkoxy, lower alkylthio, and fluoro substituted lower alkylthio, preferably $R^4$ and $R^{11}$ are H.

In some embodiments of compounds of Formula Id, A is —C($R^{12}R^{13}$)—, and $R^4$, $R^{11}$, $R^{12}$ and $R^{13}$ are independently hydrogen or lower alkyl, wherein lower alkyl is optionally substituted with one or more substituents selected from the group consisting of fluoro, lower alkoxy, fluoro substituted lower alkoxy, lower alkylthio, and fluoro substituted lower alkylthio, preferably $R^4$, $R^{11}$, $R^{12}$ and $R^{13}$ are H. In some embodiments, A is —C($R^{12}R^{13}$)—, $R^{12}$ and $R^{13}$ are independently hydrogen or lower alkyl, wherein lower alkyl is optionally substituted with one or more substituents selected from the group consisting of fluoro, lower alkoxy, fluoro substituted lower alkoxy, lower alkylthio, and fluoro substituted lower alkylthio, preferably $R^{12}$ and $R^{13}$ are H, and $R^2$ is hydrogen, fluoro or chloro, preferably fluoro or chloro. In some embodiments, A is —C($R^{12}R^{13}$)—; $R^2$ is hydrogen, fluoro or chloro, preferably fluoro or chloro; and $R^4$, $R^{11}$, $R^{12}$ and $R^{13}$ are independently hydrogen or lower alkyl, wherein lower alkyl is optionally substituted with one or more substituents selected from the group consisting of fluoro, lower alkoxy, fluoro substituted lower alkoxy, lower alkylthio, and fluoro substituted lower alkylthio, preferably $R^4$, $R^{11}$, $R^{12}$ and $R^{13}$ are H.

In some embodiments, the compound of Formula I has a structure according to the following sub-generic structure Formula Ie:

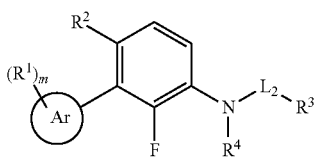

Formula Ie or a salt, a prodrug, a tautomer or an isomer thereof,
wherein m, Ar, $R^1$, $R^2$, $R^3$, $R^4$, and $L_2$ are as defined for Formula I.

In some embodiments of compounds of Formula Ie, $R^4$ is hydrogen or lower alkyl, wherein lower alkyl is optionally substituted with one or more substituents selected from the group consisting of fluoro, lower alkoxy, fluoro substituted lower alkoxy, lower alkylthio, and fluoro substituted lower alkylthio, preferably $R^4$ is H. In some embodiments, $R^2$ is hydrogen, fluoro or chloro, preferably fluoro or chloro. In some embodiments, $R^2$ is hydrogen, fluoro or chloro and $R^4$ is hydrogen or lower alkyl, wherein lower alkyl is optionally substituted with one or more substituents selected from the group consisting of fluoro, lower alkoxy, fluoro substituted lower alkoxy, lower alkylthio, and fluoro substituted lower alkylthio, preferably $R^2$ is fluoro or chloro and $R^4$ is H.

In some embodiments, the compound of Formula I has a structure according to the following sub-generic structure Formula If:

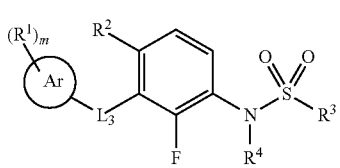

Formula If or a salt, a prodrug, a tautomer or an isomer thereof,
wherein:
$L_3$ is —C(X)—N($R^{11}$)—, —C($R^{12}R^{13}$)—X—, —X—C($R^{12}R^{13}$)—, —C($R^{12}R^{13}$)—N($R^{11}$)—, or —N($R^{11}$)—C($R^{12}R^{13}$)—; and
m, Ar, $R^1$, $R^2$, $R^3$, $R^4$, $R^{11}$, $R^{12}$, $R^{13}$, and X are as defined for Formula I.

In some embodiments of compounds of Formula If, $L_3$ is —C(O)—N($R^{11}$)—, —C($R^{12}R^{13}$)—O—, —O—C($R^{12}R^{13}$)—, —C($R^{12}R^{13}$)—N($R^{11}$)—, or —N($R^{11}$)—C($R^{12}R^{13}$)—, wherein the left side of $L_3$ is attached to Ar and the right side of $L_3$ is attached to the phenyl ring of Formula If. In some embodiments, $L_3$ is —C(O)—N($R^{11}$)—, —C($R^{12}R^{13}$)—O—, —O—C($R^{12}R^{13}$)—, —C($R^{12}R^{13}$)—N($R^{11}$)—, or —N($R^{11}$)—C($R^{12}R^{13}$)—, and $R^4$, $R^{11}$, $R^{12}$ and $R^{13}$ are independently hydrogen or lower alkyl, wherein lower alkyl is optionally substituted with one or more substituents selected from the group consisting of fluoro, lower alkoxy, fluoro substituted lower alkoxy, lower alkylthio, and fluoro substituted lower alkylthio, preferably $R^4$, $R^{11}$, $R^{12}$ and $R^{13}$ are H.

In some embodiments, the compound of Formula I has a structure according to the following sub-generic structure Formula Ig:

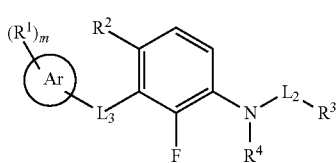

Formula Ig or a salt, a prodrug, a tautomer or an isomer thereof, wherein:
$L_3$ is —C(X)—N($R^{11}$)—, —C($R^{12}R^{13}$)—X—, —X—C($R^{12}R^{13}$)—, —C($R^{12}R^{13}$)—N($R^{11}$)—, or —N($R^{11}$)—C($R^{12}R^{13}$)—; and
m, Ar, $R^1$, $R^2$, $R^3$, $R^4$, $R^{11}$, $R^{12}$, $R^{13}$, X and $L_2$ are as defined for Formula I.

In some embodiments of compounds of Formula Ig, $L_3$ is —C(O)—N($R^{11}$)—, —C($R^{12}R^{13}$)—O—, —O—C($R^{12}R^{13}$)—, —C($R^{12}R^{13}$)—N($R^{11}$)—, or —N($R^{11}$)—C($R^{12}R^{13}$)—, wherein the left side of $L_3$ is attached to Ar and the right side of $L_3$ is attached to the phenyl ring of Formula Ig. In some embodiments, $L_3$ is —C(O)—N($R^{11}$)—, —C($R^{12}R^{13}$)—O—, —O—C($R^{12}R^{13}$)—, —C($R^{12}R^{13}$)—N($R^{11}$)—, or —N($R^{11}$)—C($R^{12}R^{13}$)—, and $R^4$, $R^{11}$, $R^{12}$ and $R^{13}$ are independently hydrogen or lower alkyl, wherein lower alkyl is optionally substituted with one or more substituents selected from the group consisting of fluoro, lower alkoxy, fluoro substituted lower alkoxy, lower alkylthio, and fluoro substituted lower alkylthio, preferably $R^4$, $R^{11}$, $R^{12}$ and $R^{13}$ are H.

In some embodiments, the compound of Formula I has a structure according to the following sub-generic structure Formula Ih:

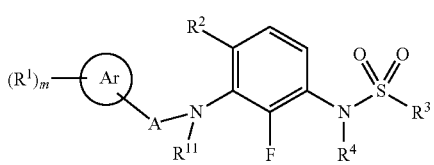

Formula Ih or a salt, a prodrug, a tautomer or an isomer thereof,
wherein A is —C(O)— or —C($R^{12}R^{13}$)—; and
m, Ar, $R^1$, $R^2$, $R^3$, $R^4$, $R^{11}$, $R^{12}$ and $R^{13}$ are as defined for Formula I.

In some embodiments of compounds of Formula Ih, $R^4$, $R^{11}$, $R^{12}$ and $R^{13}$ are independently hydrogen or lower alkyl, wherein lower alkyl is optionally substituted with one or more substituents selected from the group consisting of fluoro, lower alkoxy, fluoro substituted lower alkoxy, lower alkylthio, and fluoro substituted lower alkylthio, preferably $R^4$, $R^{11}$, $R^{12}$ and $R^{13}$ are H. In some embodiments, $R^2$ is hydrogen, fluoro or chloro, preferably fluoro or chloro. In some embodiments, $R^2$ is hydrogen, fluoro or chloro, and $R^4$, $R^{11}$, $R^{12}$ and $R^{13}$ are independently hydrogen or lower alkyl, wherein lower alkyl is optionally substituted with one or more substituents selected from the group consisting of fluoro, lower alkoxy, fluoro substituted lower alkoxy, lower alkylthio, and fluoro substituted lower alkylthio, preferably $R^2$ is fluoro or chloro and $R^4$, $R^{11}$, $R^{12}$ and $R^{13}$ are H.

In some embodiments of compounds of Formula Ih, A is —C(O)—, and $R^4$ and $R^{11}$ are independently hydrogen or lower alkyl, wherein lower alkyl is optionally substituted with one or more substituents selected from the group consisting of fluoro, lower alkoxy, fluoro substituted lower alkoxy, lower alkylthio, and fluoro substituted lower alkylthio, preferably $R^4$ and $R^{11}$ are H. In some embodiments, A is —C(O)—, and $R^2$ is hydrogen, fluoro or chloro, preferably fluoro or chloro. In some embodiments, A is —C(O)—, $R^2$ is hydrogen, fluoro or chloro, preferably fluoro or chloro; and $R^4$ and $R^{11}$ are independently hydrogen or lower alkyl, wherein lower alkyl is optionally substituted with one or more substituents selected from the group consisting of fluoro, lower alkoxy, fluoro substituted lower alkoxy, lower alkylthio, and fluoro substituted lower alkylthio, preferably $R^4$ and $R^{11}$ are H.

In some embodiments of compounds of Formula Ih, A is —C($R^{12}R^{13}$)—, and $R^4$, $R^{11}$, $R^{12}$ and $R^{13}$ are independently hydrogen or lower alkyl, wherein lower alkyl is optionally substituted with one or more substituents selected from the group consisting of fluoro, lower alkoxy, fluoro substituted lower alkoxy, lower alkylthio, and fluoro substituted lower alkylthio, preferably $R^4$, $R^{11}$, $R^{12}$ and $R^{13}$ are H. In some embodiments, A is —C($R^{12}R^{13}$)—, $R^{12}$ and $R^{13}$ are independently hydrogen or lower alkyl, wherein lower alkyl is optionally substituted with one or more substituents selected from the group consisting of fluoro, lower alkoxy, fluoro substituted lower alkoxy, lower alkylthio, and fluoro substituted lower alkylthio, preferably $R^{12}$ and $R^{13}$ are H, and $R^2$ is hydrogen, fluoro or chloro, preferably fluoro or chloro. In some embodiments, A is —C($R^{12}R^{13}$)—; $R^2$ is hydrogen, fluoro or chloro, preferably fluoro or chloro; and $R^4$, $R^{11}$, $R^{12}$ and $R^{13}$ are independently hydrogen or lower alkyl, wherein lower alkyl is optionally substituted with one or more substituents selected from the group consisting of fluoro, lower alkoxy, fluoro substituted lower alkoxy, lower alkylthio, and fluoro substituted lower alkylthio, preferably $R^4$, $R^{11}$, $R^{12}$ and $R^{13}$ are H.

In some embodiments, the compound of Formula I has a structure according to the following sub-generic structure Formula Ii:

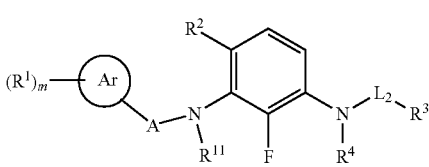

Formula Ii or a salt, a prodrug, a tautomer or an isomer thereof,
wherein A is —C(O)— or —C($R^{12}R^{13}$)—; and
m, Ar, $R^1$, $R^2$, $R^3$, $R^4$, $R^{11}$, $R^{12}$, $R^{13}$ and $L_2$ are as defined for Formula I.

In some embodiments of compounds of Formula Ii, $R^4$, $R^{11}$, $R^{12}$ and $R^{13}$ are independently hydrogen or lower alkyl, wherein lower alkyl is optionally substituted with one or more substituents selected from the group consisting of fluoro, lower alkoxy, fluoro substituted lower alkoxy, lower alkylthio, and fluoro substituted lower alkylthio, preferably $R^4$, $R^{11}$, $R^{12}$ and $R^{13}$ are H. In some embodiments, $R^2$ is hydrogen, fluoro or chloro, preferably fluoro or chloro. In some embodiments, $R^2$ is hydrogen, fluoro or chloro, and $R^4$, $R^{11}$, $R^{12}$ and $R^{13}$ are independently hydrogen or lower alkyl, wherein lower alkyl is optionally substituted with one or more substituents selected from the group consisting of fluoro, lower alkoxy, fluoro substituted lower alkoxy, lower alkylthio, and fluoro substituted lower alkylthio, preferably $R^2$ is fluoro or chloro and $R^4$, $R^{11}$, $R^{12}$ and $R^{13}$ are H.

In some embodiments of compounds of Formula Ii, A is —C(O)—, and $R^4$ and $R^{11}$ are independently hydrogen or lower alkyl, wherein lower alkyl is optionally substituted with one or more substituents selected from the group consisting of fluoro, lower alkoxy, fluoro substituted lower alkoxy, lower alkylthio, and fluoro substituted lower alkylthio, preferably $R^4$ and $R^{11}$ are H. In some embodiments, A is —C(O)—, and $R^2$ is hydrogen, fluoro or chloro, preferably fluoro or chloro. In some embodiments, A is —C(O)—, $R^2$ is hydrogen, fluoro or chloro, preferably fluoro or chloro; and $R^4$ and $R^{11}$ are hydrogen or lower alkyl, wherein lower alkyl is optionally substituted with one or more substituents selected from the group consisting of fluoro, lower alkoxy, fluoro substituted lower alkoxy, lower alkylthio, and fluoro substituted lower alkylthio, preferably $R^4$ and $R^{11}$ are H.

In some embodiments of compounds of Formula Ii, A is —C($R^{12}R^{13}$)—, and $R^4$, $R^{11}$, $R^{12}$ and $R^{13}$ are independently hydrogen or lower alkyl, wherein lower alkyl is optionally substituted with one or more substituents selected from the group consisting of fluoro, lower alkoxy, fluoro substituted lower alkoxy, lower alkylthio, and fluoro substituted lower alkylthio, preferably $R^4$, $R^{11}$, $R^{12}$ and $R^{13}$ are H. In some embodiments, A is —C($R^{12}R^{13}$)—, $R^{12}$ and $R^{13}$ are independently hydrogen or lower alkyl, wherein lower alkyl is optionally substituted with one or more substituents selected from the group consisting of fluoro, lower alkoxy, fluoro substituted lower alkoxy, lower alkylthio, and fluoro substituted lower alkylthio, preferably $R^{12}$ and $R^{13}$ are H, and $R^2$ is hydrogen, fluoro or chloro, preferably fluoro or chloro. In some embodiments, A is —C($R^{12}R^{13}$)—; $R^2$ is hydrogen, fluoro or chloro, preferably fluoro or chloro; and $R^4$, $R^{11}$, $R^{12}$ and $R^{13}$ are independently hydrogen or lower alkyl, wherein lower alkyl is optionally substituted with one or more substituents selected from the group consisting of fluoro, lower alkoxy, fluoro substituted lower alkoxy, lower alkylthio, and fluoro substituted lower alkylthio, preferably $R^4$, $R^{11}$, $R^{12}$ and $R^{13}$ are H.

In some embodiments, the compound of Formula I has a structure according to the following sub-generic structure Formula Ij:

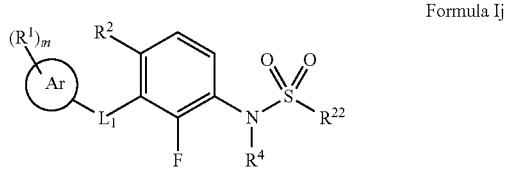

Formula Ij or a salt, a prodrug, a tautomer or an isomer thereof, wherein:

m, Ar, $R^1$, $R^2$, $R^4$, and $L_1$ are as defined for Formula I; and $R^{22}$ is selected from the group consisting of mono-alkylamino, di-alkylamino, optionally substituted lower alkyl, optionally substituted cycloalkyl, optionally substituted heterocycloalkyl, optionally substituted aryl and optionally substituted heteroaryl, wherein the alkyl chain(s) of mono-alkylamino or di-alkylamino are independently optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino and cycloalkylamino.

In some embodiments of compounds of Formula Ij, $L_1$ is a bond, —N($R^{11}$)—, —N($R^{11}$)—C(X)—, —N($R^{11}$)—S(O)$_2$—, —N($R^{11}$)—C(NH)—, —N($R^{11}$)—C(X)—N($R^{11}$)—, or —N($R^{11}$)—S(O)$_2$—N($R^{11}$)—, also —N($R^{11}$)—, —N($R^{11}$)—C(X)—, or —N($R^{11}$)—S(O)$_2$—, also —N($R^{11}$)—C(O)—, wherein the left side (i.e. —N($R^{11}$)—) of $L_1$ is attached to Ar and the right side of $L_1$ is attached to the phenyl ring of Formula Ij. In some embodiments, $L_1$ is a bond, —N($R^1$)—, —N($R^1$)—C(X)—, —N($R^{11}$)—S(O)$_2$—, —N($R^{11}$)—C(NH)—, —N($R^{11}$)—C(X)—N($R^{11}$)—, or —N($R^{11}$)—S(O)$_2$—N($R^{11}$)—, also —N($R^{11}$)—, —N($R^{11}$)—C(X)—, or —N($R^{11}$)—S(O)$_2$—, also —N($R^{11}$)—C(O)—, and each $R^{11}$ and $R^4$ are independently hydrogen or lower alkyl, wherein lower alkyl is optionally substituted with one or more substituents selected from the group consisting of fluoro, lower alkoxy, fluoro substituted lower alkoxy, lower alkylthio, and fluoro substituted lower alkylthio, preferably each $R^{11}$ and $R^4$ are H.

In some embodiments of compounds of Formula Ij, $L_1$ is —C(X)—N($R^{11}$)—, —C($R^{12}R^{13}$)—X—, —X—C($R^{12}R^{13}$)—, —C($R^{12}R^{13}$)—N($R^{11}$)—, or —N($R^{11}$)—C($R^{12}R^{13}$)—, wherein the left side of $L_1$ is attached to Ar and the right side of $L_1$ is attached to the phenyl ring of Formula Ij. In some embodiments, $L_1$ is —C(X)—N($R^{11}$)—, —C($R^{12}R^{13}$)—X—, —X—C($R^{12}R^{13}$)—, —C($R^{12}R^{13}$)—N($R^{11}$)—, or —N($R^{11}$)—C($R^{12}R^{13}$)—, and each $R^{11}$ and $R^4$ are independently hydrogen or lower alkyl, wherein lower alkyl is optionally substituted with one or more substituents selected from the group consisting of fluoro, lower alkoxy, fluoro substituted lower alkoxy, lower alkylthio, and fluoro substituted lower alkylthio, preferably each $R^{11}$ and $R^4$ are H.

In some embodiments of compounds of Formula Ij, $R^2$ is hydrogen, fluoro or chloro, preferably fluoro or chloro. In some embodiments, $R^2$ is hydrogen, fluoro or chloro, each $R^1$ and $R^4$ are independently hydrogen or lower alkyl, wherein lower alkyl is optionally substituted with one or more substituents selected from the group consisting of fluoro, lower alkoxy, fluoro substituted lower alkoxy, lower alkylthio, and fluoro substituted lower alkylthio, preferably $R^2$ is fluoro or chloro and each $R^{11}$ and $R^4$ are H. In some embodiments, $R^2$ is hydrogen, fluoro or chloro, preferably fluoro or chloro, and $L_1$ is a bond, —N($R^{11}$)—, —N($R^{11}$)—C(X)—, —N($R^{11}$)—S(O)$_2$—, —N($R^{11}$)—C(NH)—, —N($R^{11}$)—C(X)—N($R^{11}$)—, or —N($R^{11}$)—S(O)$_2$—N($R^{11}$)—, also —N($R^{11}$)—, —N($R^{11}$)—C(X)—, or —N($R^{11}$)—S(O)$_2$—, also —N($R^{11}$)—C(O)—, wherein the left side (i.e. —N($R^{11}$)—) of $L_1$ is attached to Ar and the right side of $L_1$ is attached to the phenyl ring of Formula Ij. In some embodiments, $R^2$ is hydrogen, fluoro or chloro, preferably fluoro or chloro; $L_1$ is a bond, —N($R^{11}$)—, —N($R^{11}$)—C(X)—, —N($R^{11}$)—S(O)$_2$—, —N($R^{11}$)—C(NH)—, —N($R^{11}$)—C(X)—N($R^{11}$)—, or —N($R^{11}$)—S(O)$_2$—N($R^{11}$)—, also —N($R^{11}$)—, —N($R^{11}$)—C(X)—, or —N($R^{11}$)—S(O)$_2$—, also —N($R^{11}$)—C(O)—; and each $R^{11}$ and $R^4$ are independently hydrogen or lower alkyl, wherein lower alkyl is optionally substituted with one or fluoro, lower alkoxy, fluoro substituted lower alkoxy, lower alkylthio, and fluoro substituted lower alkylthio, preferably each $R^{11}$ and $R^4$ are H.

In some embodiments of compounds of Formula Ij, $R^2$ is hydrogen, fluoro or chloro, preferably fluoro or chloro. In some embodiments, $R^2$ is hydrogen, fluoro or chloro, each $R^{11}$ and $R^4$ are independently hydrogen or lower alkyl, wherein lower alkyl is optionally substituted with one or more substituents selected from the group consisting of fluoro, lower alkoxy, fluoro substituted lower alkoxy, lower alkylthio, and fluoro substituted lower alkylthio, preferably $R^2$ is fluoro or chloro and each $R^{11}$ and $R^4$ are H. In some embodiments, $R^2$ is hydrogen, fluoro or chloro, preferably fluoro or chloro, and $L_1$ is —C(X)—N($R^1$)—, —C($R^{12}R^{13}$)—X—, —X—C($R^{12}R^{13}$)—, —C($R^{12}R^{13}$)—N($R^{11}$)—, or —N($R^{11}$)—C($R^{12}R^{13}$)—, wherein the left side of $L_1$ is attached to Ar and the right side of $L_1$ is attached to the phenyl ring of Formula Ij. In some embodiments, $R^2$ is hydrogen, fluoro or chloro, preferably fluoro or chloro; $L_1$ is —C(X)—N($R^1$)—, —C($R^{12}R^{13}$)—X—, —X—C($R^{12}R^{13}$)—, —C($R^{12}R^{13}$)—N($R^{11}$)—, or —N($R^{11}$)—C($R^{12}R^{13}$)—; and each $R^{11}$ and $R^4$ are independently hydrogen or lower alkyl, wherein lower alkyl is optionally substituted with one or more substituents selected from the group consisting of fluoro, lower alkoxy, fluoro substituted lower alkoxy, lower alkylthio, and fluoro substituted lower alkylthio, preferably each $R^{11}$ and $R^4$ are H.

In some embodiments of compounds of Formula Ij, further to any of the above embodiments of Formula Ij, $R^{22}$ is mono-alkylamino, di-alkylamino, or optionally substituted heterocycloalkyl, preferably wherein heterocycloalkyl is a 5 or 6 membered nitrogen containing heterocycloalkyl, wherein a nitrogen of the heterocycloalkyl is bound to the $S(O)_2$ of Formula Ij. In some embodiments, $R^{22}$ is mono-alkylamino, di-alkylamino or 5 or 6 membered nitrogen containing heterocycloalkyl, wherein the heterocycloalkyl is substituted with one or more substituents selected from the group consisting of fluoro, —OH, —$NH_2$, lower alkyl, lower alkoxy, lower alkylthio, mono-alkylamino, di-alkylamino, and cycloalkylamino, wherein lower alkyl or the alkyl chain(s) of lower alkoxy, lower alkylthio, mono-alkylamino, or di-alkylamino are optionally substituted with one or more substituents selected from the group consisting of fluoro, —OH, —$NH_2$, lower alkoxy, fluoro substituted lower alkoxy, lower alkylthio, fluoro substituted lower alkylthio, mono-alkylamino, di-alkylamino and cycloalkylamino, preferably wherein the 5 or 6 membered nitrogen containing heterocycloalkyl is optionally substituted with one or more substituents selected from the group consisting of fluoro, lower alkyl, fluoro substituted lower alkyl, lower alkoxy, fluoro substituted lower alkoxy, lower alkylthio, and fluoro substituted lower alkylthio.

In some embodiments of compounds of Formula I, Ia, Ib, Ic, Id, Ie, If, Ig, Ih, Ii, or Ij, further to any of the above embodiments of Formula I, Ia, Ib, Ic, Id, Ie, If, Ig, Ih, Ii or Ij, Ar is monocyclic or bicyclic nitrogen containing heteroaryl. In some embodiments, Ar is selected from the group consisting of

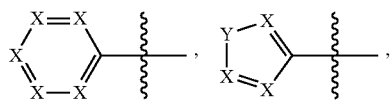

-continued

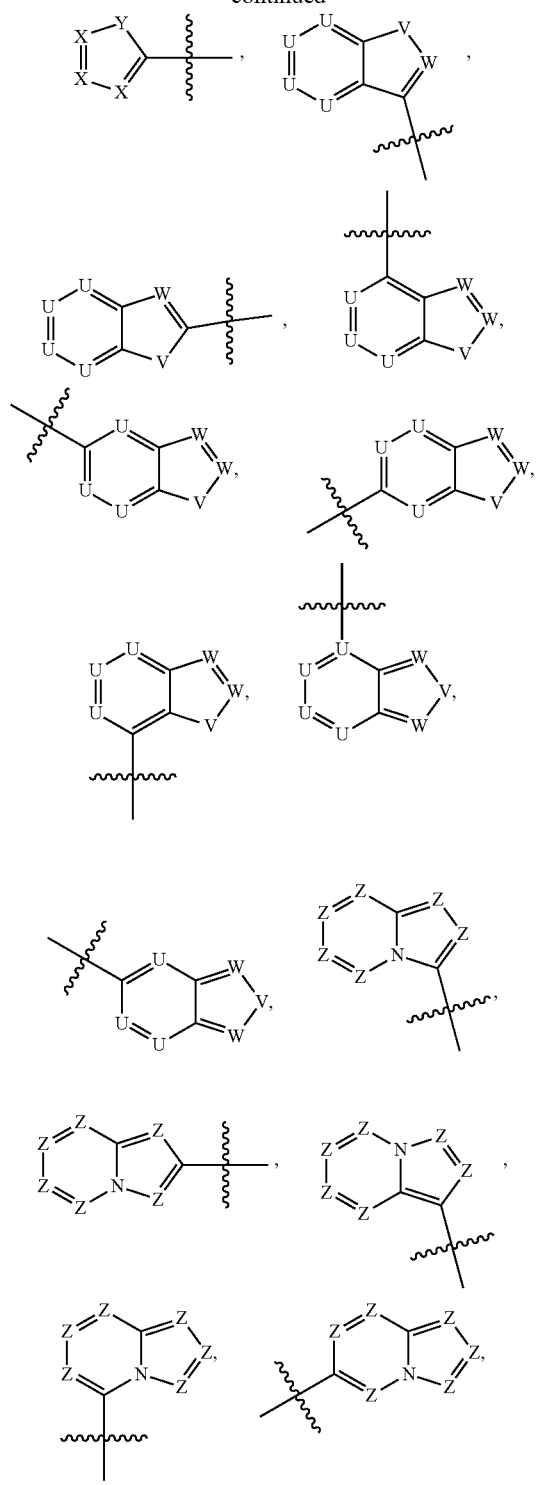

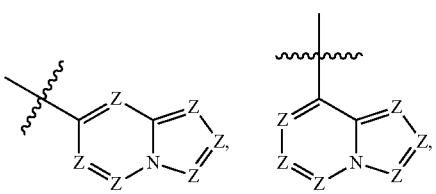

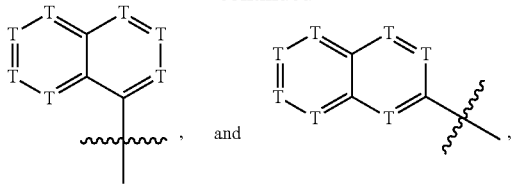

wherein

indicates the attachment point of the Ar ring to $L_1$ in Formula I, Ia or Ij, to $L_3$ in Formula If or Ig, to the nitrogen of Ar—N— in Formula Ib or Id, to A of Formula Ih or Ii, or to the phenyl ring of Formula Ic or Ie, and wherein:

T, U, X, and Z at each occurrence are independently N or CH, provided, however, that at least one, and no more than 2 of X in any ring is N, no more than 2 of U in any ring is N, at least one T is N and no more than two of T within any six-membered ring is N, and at least one Z is N and no more than 2 of Z within any bicyclic ring is N;

Y is NH, O, or S;

W at each occurrence is independently N or CH;

V is O, S, or NH, provided, however, that when V is O or S, at least one of U in any ring or W in any ring is N; and any $R^1$ is bound to Ar at any available NH or CH, preferably any $R^1$ is independently $R^{16}$, wherein $R^{16}$ at each occurrence is independently selected from the group consisting of —OH, —NH$_2$, —CN, —NO$_2$, —C(O)—OH, —S(O)$_2$—NH$_2$, —C(O)—NH$_2$, —O—$R^{17}$, —S—$R^{17}$, —N($R^{19}$)—$R^{17}$, —N($R^{19}$)—C(O)—$R^{17}$, —N($R^{19}$)—S(O)$_2$—$R^{17}$, —S(O)$_2$—$R^{17}$, —C(O)—$R^{17}$, —C(O)—O—$R^{17}$, —C(O)—N($R^{19}$)—$R^{17}$, —S(O)$_2$—N($R^{19}$)—$R^{17}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as $R^{16}$, or as substituents of lower alkyl, are optionally substituted with one or more substituents selected from the group consisting of —OH, —NH$_2$, —CN, —NO$_2$, —C(O)—OH, —S(O)$_2$—NH$_2$, —C(O)—NH$_2$, —O—$R^{18}$, —S—$R^{18}$, —N($R^{19}$)—$R^{18}$, —N($R^{19}$)—C(O)—$R^{18}$, —N($R^{19}$)—S(O)$_2$—$R^{18}$, —S(O)$_2$—$R^{18}$, —C(O)—$R^{18}$, —C(O)—O—$R^{18}$, —C(O)—N($R^{19}$)—$R^{18}$, —S(O)$_2$—N($R^{19}$)—$R^{18}$, halogen, lower alkyl, fluoro substituted lower alkyl, and cycloalkylamino;

$R^{17}$ at each occurrence is independently selected from the group consisting of lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as $R^{17}$ or as substituents of lower alkyl are optionally substituted with one or more substituents selected from the group consisting of —OH, —NH$_2$, —CN, —NO$_2$, —C(O)—OH, —S(O)$_2$—NH$_2$, —C(O)—NH$_2$, —O—$R^{18}$, —S—$R^{18}$, —N($R^{19}$)—$R^{18}$, —N($R^{19}$)—C(O)—$R^{18}$, —N($R^{19}$)—S(O)$_2$—$R^{18}$, —S(O)$_2$—$R^{18}$, —C(O)—$R^{18}$, —C(O)—O—$R^{18}$, —C(O)—N($R^{19}$)—$R^{18}$, —S(O)$_2$—N($R^{19}$)—$R^{18}$, halogen, lower alkyl, fluoro substituted lower alkyl, and cycloalkylamino;

$R^{18}$ at each occurrence is independently selected from the group consisting of lower alkyl, heterocycloalkyl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino; and $R^{19}$ at each occurrence is independently hydrogen or lower alkyl, wherein lower alkyl is optionally substituted with one or more substituents selected from the group consisting of fluoro, lower alkoxy, fluoro substituted lower alkoxy, lower alkylthio, and fluoro substituted lower alkylthio.

In some embodiments of compounds of Formula I, Ia, Ib, Id, If, Ig, Ih, Ii, or Ij, further to any of the above embodiments of Formula I, Ia, Ib, Id, If, Ig, Ih, Ii, or Ij, when $L_1$ is other than a bond, Ar is selected from the group consisting of

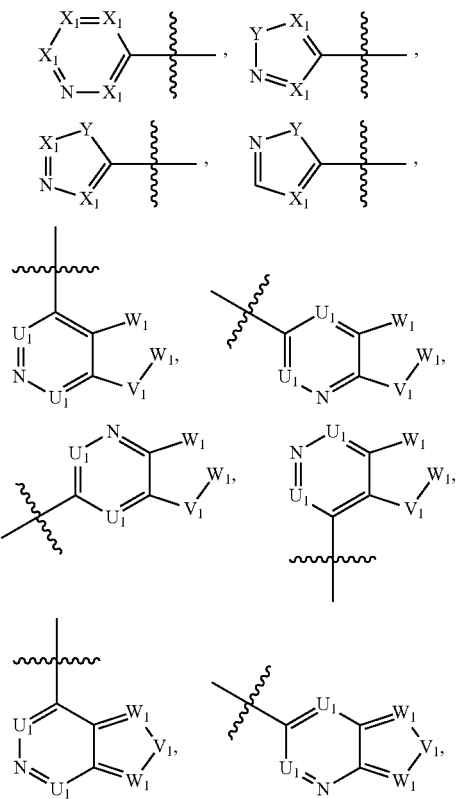

-continued

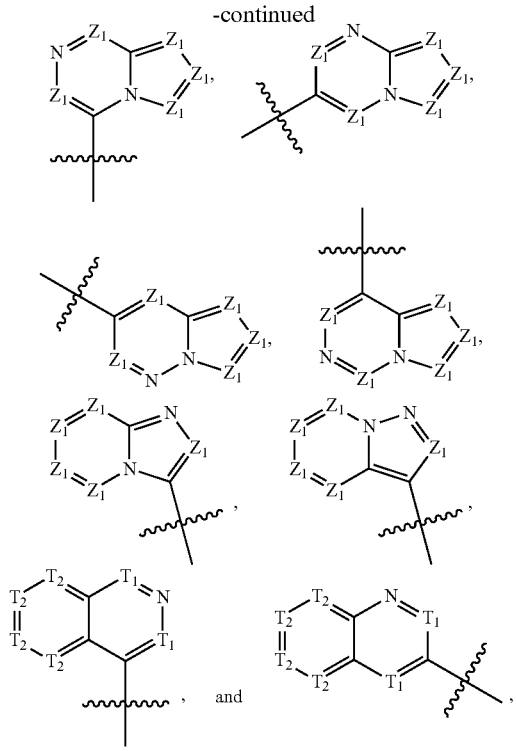

wherein

indicates the attachment point of the Ar ring to $L_1$ in Formula I, Ia or Ij, to $L_3$ in Formula If or Ig, to the nitrogen of Ar—N— in Formula Ib or Id, or to A of Formula Ih or Ii, and wherein:

$T_1$, $U_1$, $W_1$, $X_1$, and $Z_1$ at each occurrence are independently N or CH, provided, however, that at most 1 of $T_1$, $U_1$, $X_1$, and $Z_1$ is N;

$T_2$ at each occurrence is independently N or CH, provided, however, that at most 2 of $T_2$ are N;

Y and $V_1$ are O, S, or NH;

any $R_1$ is bound to Ar at any available NH or CH, preferably any $R_1$ is independently $R^{16}$, as defined in paragraph [0041], preferably wherein $R^{16}$ at each occurrence is independently selected from the group consisting of halogen, —OH, —NH$_2$, —CN, lower alkyl, lower alkoxy, lower alkylthio, mono-alkylamino, di-alkylamino, and —NR$^{20}$R$^{21}$, wherein lower alkyl and the alkyl chain(s) of lower alkoxy, lower alkylthio, mono-alkylamino or di-alkylamino are optionally substituted with one or more, preferably 1, 2, or 3 substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, or cycloalkylamino; and $R^{20}$ and $R^{21}$ at each occurrence independently combine with the nitrogen to which they are attached to form a 5-7 membered heterocycloalkyl or 5-7 membered heterocycloalkyl substituted with one or more substituents selected from the group consisting of fluoro, —OH, —NH$_2$, lower alkyl, fluoro substituted lower alkyl, lower alkoxy, fluoro substituted lower alkoxy, lower alkylthio, and fluoro substituted lower alkylthio.

In some embodiments of compounds of Formula I, Ia, Ib, Id, If, Ig, Ih, Ii, or Ij, further to any of the above embodiments of Formula I, Ia, Ib, Id, If, Ig, Ih, Ii, or Ij, when $L_1$ is other than a bond, Ar is selected from the group consisting of

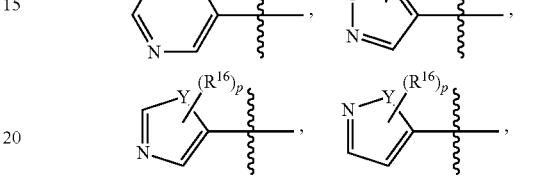

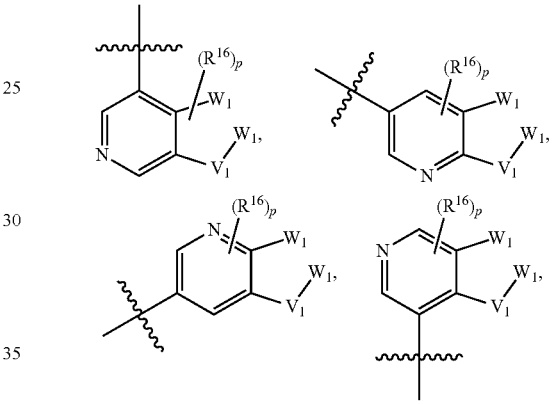

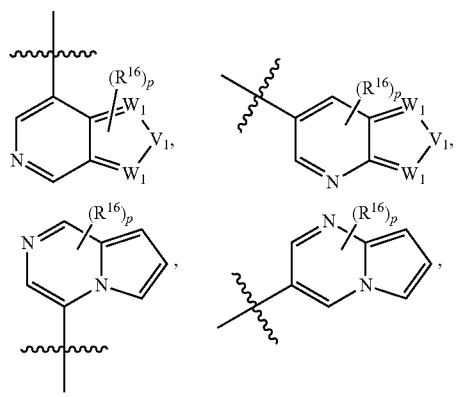

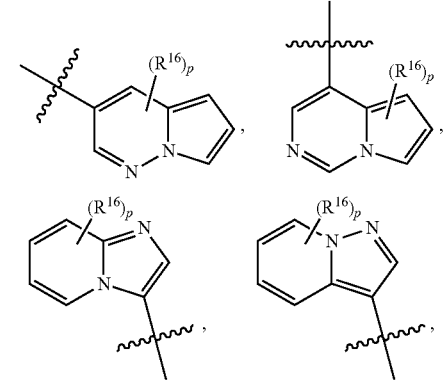

-continued

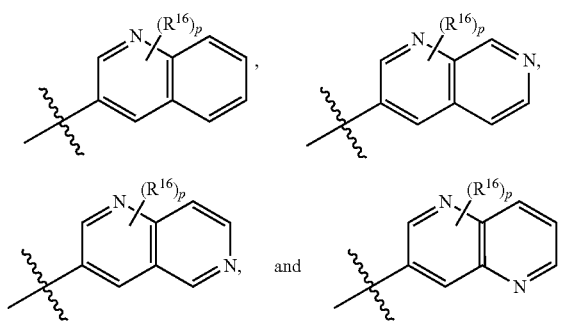

wherein

indicates the attachment point of the Ar ring to L₁ in Formula I, Ia or Ij, to L₃ in Formula If or Ig, to the nitrogen of Ar—N— in Formula Ib or Id, or to A of Formula Ih or Ii, and wherein:

W₁ at each occurrence is independently N or CH;

Y and V₁ are O, S, or NH;

p is 0, 1, 2 or 3; and

R¹⁶, substituting at any available CH or NH, is as defined in paragraph [0041], preferably wherein R¹⁶ at each occurrence is independently selected from the group consisting of halogen, —OH, —NH₂, —CN, lower alkyl, lower alkoxy, lower alkylthio, mono-alkylamino, di-alkylamino, and —NR²⁰R²¹, wherein lower alkyl and the alkyl chain(s) of lower alkoxy, lower alkylthio, mono-alkylamino or di-alkylamino are optionally substituted with one or more, preferably 1, 2, or 3 substituents selected from the group consisting of fluoro, —OH, —NH₂, lower alkoxy, fluoro substituted lower alkoxy, lower alkylthio, fluoro substituted lower alkylthio, mono-alkylamino, di-alkylamino, or cycloalkylamino, wherein R²⁰ and R²¹ are as defined in paragraph [0042].

In some embodiments of compounds of Formula I, Ia, Ib, Id, If, Ig, Ih, Ii, or Ij, further to any of the above embodiments of Formula I, Ia, Ib, Id, If, Ig, Ih, Ii, or Ij, when L₁ is other than a bond, Ar is selected from the group consisting of

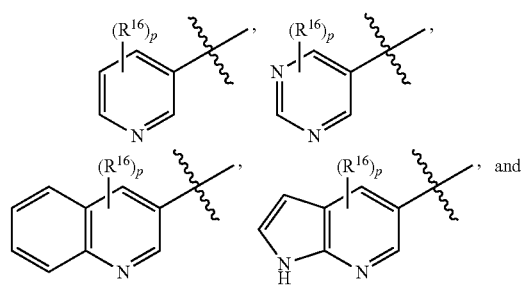

-continued

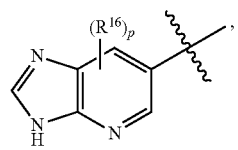

wherein

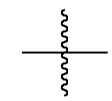

indicates the attachment point of the Ar ring to L₁ in Formula I, Ia or Ij, to L₃ in Formula If or Ig, to the nitrogen of Ar—N— in Formula Ib or Id, or to A of Formula Ih or Ii, and wherein:

p is 0, 1, 2 or 3; and

R¹⁶, substituting at any available CH or NH, is as defined in paragraph [0041].

In some embodiments of compounds of Formula Ic or Ie, further to any of the above embodiments of Formula Ic or Ie, Ar is selected from the group consisting of

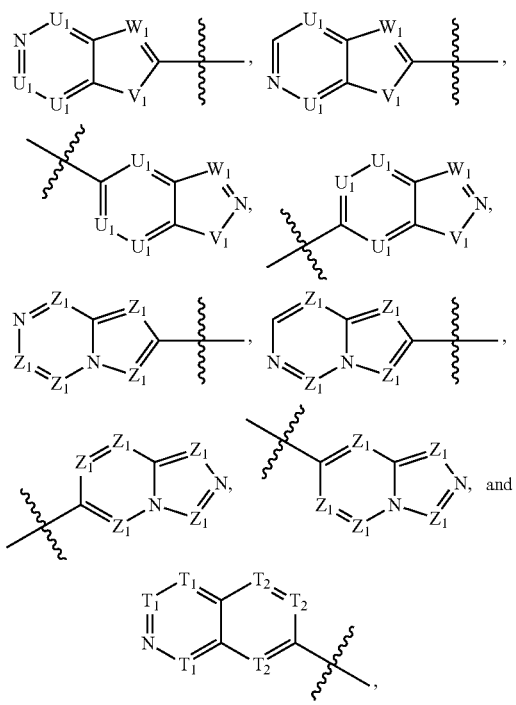

wherein

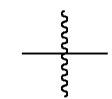

indicates the attachment point of the Ar ring to the phenyl ring of Formula Ic or Ie, and wherein:

$T_1$, $U_1$, $W_1$ and $Z_1$ at each occurrence is independently N or CH, provided, however, that at most 1 of $T_1$, $U_1$, and $Z_1$ is N;

$T_2$ is N or CH, provided, however, that no more than 2 of $T_2$ are N;

$V_1$ is O, S, or NH; and any $R^1$ is bound to Ar at any available NH or CH, preferably any $R^1$ is independently $R^{16}$, as defined in paragraph [0041], preferably wherein $R^{16}$ at each occurrence is independently selected from the group consisting of halogen, —OH, —NH$_2$, —CN, lower alkyl, lower alkoxy, lower alkylthio, mono-alkylamino, di-alkylamino, and —NR$^{20}$R$^{21}$, wherein lower alkyl and the alkyl chain(s) of lower alkoxy, lower alkylthio, mono-alkylamino or di-alkylamino are optionally substituted with one or more, preferably 1, 2, or 3 substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, or cycloalkylamino, wherein $R^{20}$ and $R^{21}$ are as defined in paragraph [0042].

In some embodiments of compounds of Formula Ic or Ie, further to any of the above embodiments of Formula Ic or Ie, $R^1$ is selected from the group consisting of

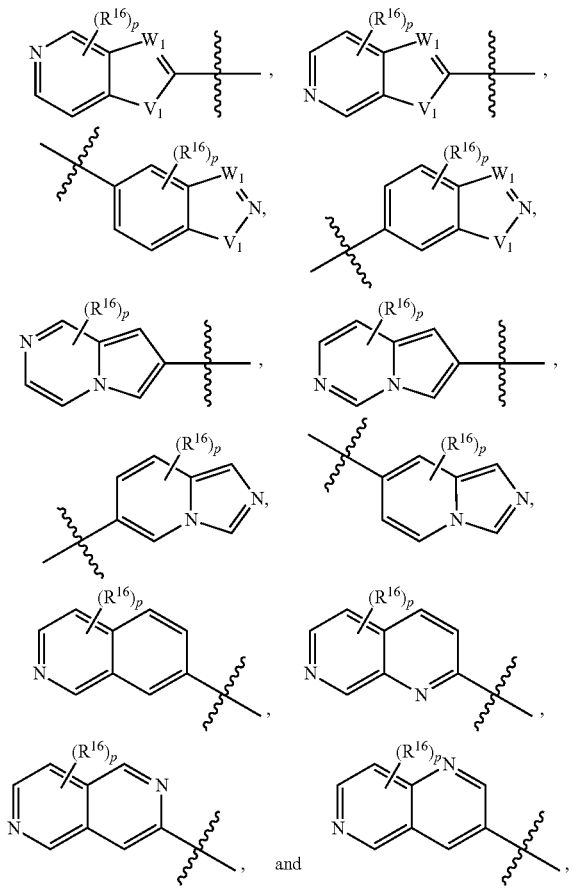

wherein

indicates the attachment point of the Ar ring to the phenyl ring of Formula Ic or Ie, and wherein:

$W_1$ is N or CH;

$V_1$ is O, S, or NH;

p is 0, 1, 2 or 3; and $R^{16}$, substituting at any available CH or NH, is as defined in paragraph [0041], preferably wherein $R^{16}$ at each occurrence is independently selected from the group consisting of halogen, —OH, —NH$_2$, —CN, lower alkyl, lower alkoxy, lower alkylthio, mono-alkylamino, di-alkylamino, and —NR$^{20}$R$^{21}$, wherein lower alkyl and the alkyl chain(s) of lower alkoxy, lower alkylthio, mono-alkylamino or di-alkylamino are optionally substituted with one or more, preferably 1, 2, or 3 substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, or cycloalkylamino, wherein $R^{20}$ and $R^{21}$ are as defined in paragraph [0042].

In some embodiments of compounds of Formula I, Ia, Ib, Ic, Id, Ie, If, Ig, Ih, or Ii, further to any of the above embodiments of Formula I, Ia, Ib, Ic, Id, Ie, If, Ig, Ih, or Ii, $R^3$ is optionally substituted lower alkyl or optionally substituted $C_{3-6}$ cycloalkyl. In some embodiments, $R^3$ is lower alkyl or $C_{3-6}$ cycloalkyl, wherein lower alkyl is optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, fluoro substituted mono-alkylamino, di-alkylamino, fluoro substituted di-alkylamino, cycloalkylamino, and $C_{3-5}$ cycloalkyl, and wherein $C_{3-6}$ cycloalkyl is optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, fluoro substituted mono-alkylamino, di-alkylamino, and fluoro substituted di-alkylamino. In some embodiments, $R^3$ is lower alkyl or $C_{3-6}$ cycloalkyl, wherein lower alkyl or $C_{3-6}$ cycloalkyl are optionally substituted with one or more substituents selected from the group consisting of fluoro, lower alkoxy, fluoro substituted lower alkoxy, lower alkylthio, and fluoro substituted lower alkylthio. In some embodiments, $R^3$ is optionally fluoro substituted lower alkyl or optionally fluoro substituted $C_{3-6}$ cycloalkyl. In some embodiments, $R^3$ is lower alkyl, wherein lower alkyl is optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, fluoro substituted mono-alkylamino, di-alkylamino, fluoro substituted di-alkylamino, cycloalkylamino, also one or more substituents selected from the group consisting of fluoro, —OH, —NH$_2$, lower alkoxy, fluoro substituted lower alkoxy, lower alkylthio, fluoro substituted lower alkylthio, mono-alkylamino, fluoro substituted mono-alkylamino, di-alkylamino, and fluoro substituted di-alkylamino, also one or more substituents selected from the group consisting of fluoro, lower alkoxy, fluoro substituted lower alkoxy, lower alkylthio, and fluoro substituted lower alkylthio. In some embodiments, $R^3$ is optionally fluoro substituted lower alkyl.

In some embodiments of compounds of Formula I, Ia, Ib, Ic, Id, Ie, If, Ig, Ih, or Ii, further to any of the above embodiments of Formula I, Ia, Ib, Ic, Id, Ie, If, Ig, Ih, or Ii, $R^3$ is optionally substituted phenyl, also phenyl mono-substituted at the para position, also phenyl mono-substituted at the meta position. In some embodiments, $R^3$ is phenyl optionally substituted with one or more substituents selected from the group consisting of halogen, —CN, —NO$_2$, —OH, —NH$_2$, lower alkyl, lower alkoxy, lower alkylthio, mono-alkylamino, di-alkylamino, and cycloalkylamino, wherein lower alkyl or the alkyl chain(s) of lower alkoxy, lower alkylthio, mono-alkylamino, or di-alkylamino are optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino and cycloalkylamino, preferably wherein the phenyl is mono-substituted at either the para or meta position. In some embodiments, $R^3$ is phenyl optionally substituted with one or more substituents selected from the group consisting of fluoro, lower alkyl, fluoro substituted lower alkyl, lower alkoxy, fluoro substituted lower alkoxy, lower alkylthio, and fluoro substituted lower alkylthio, preferably wherein the phenyl is mono-substituted at either the para or meta position.

In one embodiment of compounds of Formula I, the compound is selected from the group consisting of:

6-Chloro-2-fluoro-3-(propane-1-sulfonylamino)-N-pyridin-3-yl-benzamide (P-0001),
N-(6-Acetylamino-pyridin-3-yl)-6-chloro-2-fluoro-3-(propane-1-sulfonylamino)-benzamide (P-0002),
6-Chloro-2-fluoro-N-(6-methoxy-pyridin-3-yl)-3-(propane-1-sulfonylamino)-benzamide (P-0003),
N-(2-Acetylamino-pyrimidin-5-yl)-6-chloro-2-fluoro-3-(propane-1-sulfonylamino)-benzamide (P-0004),
6-Chloro-2-fluoro-N-(6-isopropylamino-pyridin-3-yl)-3-(propane-1-sulfonylamino)-benzamide (P-0005),
Pyrrolidine-1-carboxylic acid {5-[6-chloro-2-fluoro-3-(propane-1-sulfonylamino)-benzoylamino]-pyridin-2-yl}-amide (P-0006),
6-Chloro-N-(3,5-dimethyl-isoxazol-4-yl)-2-fluoro-3-(propane-1-sulfonylamino)-benzamide (P-0007),
N-(6-Acetylamino-pyridin-3-yl)-2,6-difluoro-3-(propane-1-sulfonylamino)-benzamide (P-0008),
6-Chloro-N-(6-cyclopentylamino-pyridin-3-yl)-2-fluoro-3-(propane-1-sulfonylamino)-benzamide (P-0009),
6-Chloro-N-[5-(4-chloro-phenyl)-2H-pyrazol-3-yl]-2-fluoro-3-(propane-1-sulfonylamino)-benzamide (P-0010),
6-Chloro-2-fluoro-N-[6-(5-methyl-thiazol-2-ylamino)-pyridin-3-yl]-3-(propane-1-sulfonylamino)-benzamide (P-0011),
6-Chloro-N-[5-(4-chloro-benzyl)-[1,3,4]thiadiazol-2-yl]-2-fluoro-3-(propane-1-sulfonylamino)-benzamide (P-0012),
6-Chloro-2-fluoro-3-(propane-1-sulfonylamino)-N-quinolin-3-yl-benzamide (P-0013),
[2-[6-Chloro-2-fluoro-3-(propane-1-sulfonylamino)-benzoylamino]-4H-[1,3,4]thiadiazin-(5E)-ylidene]-acetic acid ethyl ester (P-0014),
6-Chloro-N-(6-cyclopropylamino-pyridin-3-yl)-2-fluoro-3-(propane-1-sulfonylamino)-benzamide (P-0015),
6-Chloro-2-fluoro-3-(propane-1-sulfonylamino)-N-{6-[(thiophen-2-ylmethyl)-amino]-pyridin-3-yl}-benzamide (P-0016),
N-(6-Benzylamino-pyridin-3-yl)-6-chloro-2-fluoro-3-(propane-1-sulfonylamino)-benzamide (P-0017),
6-Chloro-2-fluoro-N-imidazo[1,2-a]pyridin-3-yl-3-(propane-1-sulfonylamino)-benzamide (P-0018),
Propane-1-sulfonic acid {2,4-difluoro-3-[(5-methyl-isoxazol-3-ylamino)-methyl]-phenyl}-amide (P-0019),
N-{5-[2,6-Difluoro-3-(propane-1-sulfonylamino)-benzylamino]-pyridin-2-yl}-acetamide (P-0020),
Propane-1-sulfonic acid [2,4-difluoro-3-(quinolin-3-ylaminomethyl)-phenyl]-amide (P-0021),
Propane-1-sulfonic acid {3-[(6-chloro-pyridin-3-ylamino)-methyl]-2,4-difluoro-phenyl}-amide (P-0022),
Propane-1-sulfonic acid {2,4-difluoro-3-[(6-methoxy-pyridin-3-ylamino)-methyl]-phenyl}-amide (P-0023),
Quinoline-3-carboxylic acid [2,6-difluoro-3-(propane-1-sulfonylamino)-phenyl]-amide (P-0024),
Propane-1-sulfonic acid {2,4-difluoro-3-[(quinolin-3-ylmethyl)-amino]-phenyl}-amide (P-0025),
Propane-1-sulfonic acid [2,4-difluoro-3-(quinolin-3-yloxymethyl)-phenyl]-amide (P-0026),
2,6-Difluoro-3-(propane-1-sulfonylamino)-N-quinolin-3-yl-benzamide (P-0027),
6-Acetylamino-N-[2,6-difluoro-3-(2-fluoro-benzenesulfonylamino)-phenyl]-nicotinamide (P-0028),
6-Acetylamino-N-[2,6-difluoro-3-(3-fluoro-benzenesulfonylamino)-phenyl]-nicotinamide (P-0029),
6-Acetylamino-N-[3-(2,6-difluoro-benzenesulfonylamino)-2,6-difluoro-phenyl]-nicotinamide (P-0030),
6-Acetylamino-N-[3-(2,4-difluoro-benzenesulfonylamino)-2,6-difluoro-phenyl]-nicotinamide (P-0031),
6-Acetylamino-N-[3-(2,5-difluoro-benzenesulfonylamino)-2,6-difluoro-phenyl]-nicotinamide (P-0032),
6-Acetylamino-N-[2,6-difluoro-3-(3-fluoro-4-methoxy-benzenesulfonylamino)-phenyl]-nicotinamide (P-0033),
6-Acetylamino-N-[2,6-difluoro-3-(4-trifluoromethyl-benzenesulfonylamino)-phenyl]-nicotinamide (P-0034),
6-Acetylamino-N-[3-(4-difluoromethoxy-benzenesulfonylamino)-2,6-difluoro-phenyl]-nicotinamide (P-0035),
6-Acetylamino-N-[3-(3-difluoromethoxy-benzenesulfonylamino)-2,6-difluoro-phenyl]-nicotinamide (P-0036),
6-Acetylamino-N-[2,6-difluoro-3-(4-isopropyl-benzenesulfonylamino)-phenyl]-nicotinamide (P-0037),
6-Acetylamino-N-[3-(4-tert-butyl-benzenesulfonylamino)-2,6-difluoro-phenyl]-nicotinamide (P-0038),
6-Acetylamino-N-[2,6-difluoro-3-(4-propyl-benzenesulfonylamino)-phenyl]-nicotinamide (P-0039),
6-Acetylamino-N-[2,6-difluoro-3-(pyridine-2-sulfonylamino)-phenyl]-nicotinamide (P-0040),
6-Acetylamino-N-[2,6-difluoro-3-(pyridine-3-sulfonylamino)-phenyl]-nicotinamide (P-0041),
6-Acetylamino-N-[2,6-difluoro-3-(dimethylaminosulfonylamino)-phenyl]-nicotinamide (P-0042),
6-Acetylamino-N-[2,6-difluoro-3-(piperidine-1-sulfonylamino)-phenyl]-nicotinamide (P-0043),
6-Acetylamino-N-[2,6-difluoro-3-(morpholine-4-sulfonylamino)-phenyl]-nicotinamide (P-0044),
6-Acetylamino-N-[2,6-difluoro-3-(tetrahydro-pyran-4-sulfonylamino)-phenyl]-nicotinamide (P-0045),
6-Acetylamino-N-(3-cyclopentanesulfonylamino-2,6-difluoro-phenyl)-nicotinamide (P-0046),
6-Acetylamino-N-[2,6-difluoro-3-(pyrrolidine-1-sulfonylamino)-phenyl]-nicotinamide (P-0047),
6-Acetylamino-N-[2,6-difluoro-3-(3,3,3-trifluoro-propane-1-sulfonylamino)-phenyl]-nicotinamide (P-0048), 1H-Pyrrolo[2,3-b]pyridine-5-carboxylic acid [2,6-difluoro-3-(2-fluoro-benzenesulfonylamino)-phenyl]-amide (P-0049),
1H-Pyrrolo[2,3-b]pyridine-5-carboxylic acid [2,6-difluoro-3-(3-fluoro-benzenesulfonylamino)-phenyl]-amide (P-0050),
1H-Pyrrolo[2,3-b]pyridine-5-carboxylic acid [3-(2,6-difluoro-benzenesulfonylamino)-2,6-difluoro-phenyl]-amide (P-0051),
1H-Pyrrolo[2,3-b]pyridine-5-carboxylic acid [3-(2,4-difluoro-benzenesulfonylamino)-2,6-difluoro-phenyl]-amide (P-0052),
1H-Pyrrolo[2,3-b]pyridine-5-carboxylic acid [3-(2,5-difluoro-benzenesulfonylamino)-2,6-difluoro-phenyl]-amide (P-0053),
1H-Pyrrolo[2,3-b]pyridine-5-carboxylic acid [2,6-difluoro-3-(3-fluoro-4-methoxy-benzenesulfonylamino)-phenyl]-amide (P-0054),
1H-Pyrrolo[2,3-b]pyridine-5-carboxylic acid [2,6-difluoro-3-(4-trifluoromethyl-benzenesulfonylamino)-phenyl]-amide (P-0055),
1H-Pyrrolo[2,3-b]pyridine-5-carboxylic acid [3-(4-difluoromethoxy-benzenesulfonylamino)-2,6-difluoro-phenyl]-amide (P-0056),
1H-Pyrrolo[2,3-b]pyridine-5-carboxylic acid [3-(3-difluoromethoxy-benzenesulfonylamino)-2,6-difluoro-phenyl]-amide (P-0057),
1H-Pyrrolo[2,3-b]pyridine-5-carboxylic acid [2,6-difluoro-3-(4-isopropyl-benzenesulfonylamino)-phenyl]-amide (P-0058),
1H-Pyrrolo[2,3-b]pyridine-5-carboxylic acid [3-(4-tert-butyl-benzenesulfonylamino)-2,6-difluoro-phenyl]-amide (P-0059),
1H-Pyrrolo[2,3-b]pyridine-5-carboxylic acid [2,6-difluoro-3-(4-propyl-benzenesulfonylamino)-phenyl]-amide (P-0060),
1H-Pyrrolo[2,3-b]pyridine-5-carboxylic acid [2,6-difluoro-3-(pyridine-2-sulfonylamino)-phenyl]-amide (P-0061),
1H-Pyrrolo[2,3-b]pyridine-5-carboxylic acid [2,6-difluoro-3-(pyridine-3-sulfonylamino)-phenyl]-amide (P-0062),
1H-Pyrrolo[2,3-b]pyridine-5-carboxylic acid [2,6-difluoro-3-(dimethylaminosulfonylamino)-phenyl]-amide (P-0063),
1H-Pyrrolo[2,3-b]pyridine-5-carboxylic acid [2,6-difluoro-3-(piperidine-1-sulfonylamino)-phenyl]-amide (P-0064),
1H-Pyrrolo[2,3-b]pyridine-5-carboxylic acid [2,6-difluoro-3-(morpholine-4-sulfonylamino)-phenyl]-amide (P-0065),
1H-Pyrrolo[2,3-b]pyridine-5-carboxylic acid [2,6-difluoro-3-(tetrahydro-pyran-4-sulfonylamino)-phenyl]-amide (P-0066),
1H-Pyrrolo[2,3-b]pyridine-5-carboxylic acid (3-cyclopentanesulfonylamino-2,6-difluoro-phenyl)-amide (P-0067),
1H-Pyrrolo[2,3-b]pyridine-5-carboxylic acid [2,6-difluoro-3-(pyrrolidine-1-sulfonylamino)-phenyl]-amide (P-0068),
1H-Pyrrolo[2,3-b]pyridine-5-carboxylic acid [2,6-difluoro-3-(3,3,3-trifluoro-propane-1-sulfonylamino)-phenyl]-amide (P-0069),
3H-Imidazo[4,5-b]pyridine-6-carboxylic acid [2,6-difluoro-3-(2-fluoro-benzenesulfonylamino)-phenyl]-amide (P-0070),
3H-Imidazo[4,5-b]pyridine-6-carboxylic acid [2,6-difluoro-3-(3-fluoro-benzenesulfonylamino)-phenyl]-amide (P-0071),
3H-Imidazo[4,5-b]pyridine-6-carboxylic acid [3-(2,6-difluoro-benzenesulfonylamino)-2,6-difluoro-phenyl]-amide (P-0072),
3H-Imidazo[4,5-b]pyridine-6-carboxylic acid [3-(2,4-difluoro-benzenesulfonylamino)-2,6-difluoro-phenyl]-amide (P-0073),
3H-Imidazo[4,5-b]pyridine-6-carboxylic acid [3-(2,5-difluoro-benzenesulfonylamino)-2,6-difluoro-phenyl]-amide (P-0074),
3H-Imidazo[4,5-b]pyridine-6-carboxylic acid [2,6-difluoro-3-(3-fluoro-4-methoxy-benzenesulfonylamino)-phenyl]-amide (P-0075),
3H-Imidazo[4,5-b]pyridine-6-carboxylic acid [2,6-difluoro-3-(4-trifluoromethyl-benzenesulfonylamino)-phenyl]-amide (P-0076),
3H-Imidazo[4,5-b]pyridine-6-carboxylic acid [3-(4-difluoromethoxy-benzenesulfonylamino)-2,6-difluoro-phenyl]-amide (P-0077),
3H-Imidazo[4,5-b]pyridine-6-carboxylic acid [3-(3-difluoromethoxy-benzenesulfonylamino)-2,6-difluoro-phenyl]-amide (P-0078),
3H-Imidazo[4,5-b]pyridine-6-carboxylic acid [2,6-difluoro-3-(4-isopropyl-benzenesulfonylamino)-phenyl]-amide (P-0079),
3H-Imidazo[4,5-b]pyridine-6-carboxylic acid [3-(4-tert-butyl-benzenesulfonylamino)-2,6-difluoro-phenyl]-amide (P-0080),
3H-Imidazo[4,5-b]pyridine-6-carboxylic acid [2,6-difluoro-3-(4-propyl-benzenesulfonylamino)-phenyl]-amide (P-0081),
3H-Imidazo[4,5-b]pyridine-6-carboxylic acid [2,6-difluoro-3-(pyridine-2-sulfonylamino)-phenyl]-amide (P-0082),
3H-Imidazo[4,5-b]pyridine-6-carboxylic acid [2,6-difluoro-3-(pyridine-3-sulfonylamino)-phenyl]-amide (P-0083),
3H-Imidazo[4,5-b]pyridine-6-carboxylic acid [2,6-difluoro-3-(dimethylaminosulfonylamino)-phenyl]-amide (P-0084),
3H-Imidazo[4,5-b]pyridine-6-carboxylic acid [2,6-difluoro-3-(piperidine-1-sulfonylamino)-phenyl]-amide (P-0085),
3H-Imidazo[4,5-b]pyridine-6-carboxylic acid [2,6-difluoro-3-(morpholine-4-sulfonylamino)-phenyl]-amide (P-0086),
3H-Imidazo[4,5-b]pyridine-6-carboxylic acid [2,6-difluoro-3-(tetrahydro-pyran-4-sulfonylamino)-phenyl]-amide (P-0087),
3H-Imidazo[4,5-b]pyridine-6-carboxylic acid (3-cyclopentanesulfonylamino-2,6-difluoro-phenyl)-amide (P-0088),
3H-Imidazo[4,5-b]pyridine-6-carboxylic acid [2,6-difluoro-3-(pyrrolidine-1-sulfonylamino)-phenyl]-amide (P-0089),
3H-Imidazo[4,5-b]pyridine-6-carboxylic acid [2,6-difluoro-3-(3,3,3-trifluoro-propane-1-sulfonylamino)-phenyl]-amide (P-0090),
N-{5-[2,6-Difluoro-3-(propane-1-sulfonylamino)-benzyloxy]-pyridin-2-yl}-acetamide (P-0091),
Propane-1-sulfonic acid [3-(2-amino-pyridin-3-yloxymethyl)-2,4-difluoro-phenyl]-amide (P-0092),
Propane-1-sulfonic acid [2,4-difluoro-3-(1H-pyrrolo[2,3-b]pyridin-5-yloxymethyl)-phenyl]-amide (P-0093),
N-{5-[2,6-Difluoro-3-(4-trifluoromethyl-benzenesulfonylamino)-benzyloxy]-pyridin-2-yl}-acetamide (P-0094),
N-[3-(2-Amino-pyridin-3-yloxymethyl)-2,4-difluoro-phenyl]-4-trifluoromethyl-benzenesulfonamide (P-0095),
N-[2,4-Difluoro-3-(1H-pyrrolo[2,3-b]pyridin-5-yloxymethyl)-phenyl]-4-trifluoromethyl-benzenesulfonamide (P-0096), N-(6-Acetylamino-pyridin-3-yl)-2,6-difluoro-3-(2-fluoro-benzenesulfonylamino)-benzamide (P-0097),
N-(6-Acetylamino-pyridin-3-yl)-2,6-difluoro-3-(3-fluoro-benzenesulfonylamino)-benzamide (P-0098),
N-(6-Acetylamino-pyridin-3-yl)-3-(2,6-difluoro-benzenesulfonylamino)-2,6-difluoro-benzamide (P-0099),
N-(6-Acetylamino-pyridin-3-yl)-3-(2,4-difluoro-benzenesulfonylamino)-2,6-difluoro-benzamide (P-0100),
N-(6-Acetylamino-pyridin-3-yl)-3-(2,5-difluoro-benzenesulfonylamino)-2,6-difluoro-benzamide (P-0101),
6-Acetylamino-N-[2,6-difluoro-3-(3-fluoro-4-methoxy-benzenesulfonylamino)-phenyl]-nicotinamide (P-0102),
N-(6-Acetylamino-pyridin-3-yl)-2,6-difluoro-3-(4-trifluoromethyl-benzenesulfonylamino)-benzamide (P-0103),
N-(6-Acetylamino-pyridin-3-yl)-3-(4-difluoromethoxy-benzenesulfonylamino)-2,6-difluoro-benzamide (P-0104),
N-(6-Acetylamino-pyridin-3-yl)-3-(3-difluoromethoxy-benzenesulfonylamino)-2,6-difluoro-benzamide (P-0105),
N-(6-Acetylamino-pyridin-3-yl)-2,6-difluoro-3-(4-isopropyl-benzenesulfonylamino)-benzamide (P-0106),
N-(6-Acetylamino-pyridin-3-yl)-3-(4-tert-butyl-benzenesulfonylamino)-2,6-difluoro-benzamide (P-0107),
N-(6-Acetylamino-pyridin-3-yl)-2,6-difluoro-3-(4-propyl-benzenesulfonylamino)-benzamide (P-0108),
N-(6-Acetylamino-pyridin-3-yl)-2,6-difluoro-3-(pyridine-2-sulfonylamino)-benzamide (P-0109),
N-(6-Acetylamino-pyridin-3-yl)-2,6-difluoro-3-(pyridine-3-sulfonylamino)-benzamide (P-0110),
N-(6-Acetylamino-pyridin-3-yl)-2,6-difluoro-3-(dimethylaminosulfonylamino)-benzamide (P-0111),
N-(6-Acetylamino-pyridin-3-yl)-2,6-difluoro-3-(piperidine-1-sulfonylamino)-benzamide (P-0112),
N-(6-Acetylamino-pyridin-3-yl)-2,6-difluoro-3-(morpholine-4-sulfonylamino)-benzamide (P-0113),
N-(6-Acetylamino-pyridin-3-yl)-2,6-difluoro-3-(tetrahydropyran-4-sulfonylamino)-benzamide (P-0114),
N-(6-Acetylamino-pyridin-3-yl)-3-cyclopentanesulfonylamino-2,6-difluoro-benzamide (P-0115),
N-(6-Acetylamino-pyridin-3-yl)-2,6-difluoro-3-(pyrrolidine-1-sulfonylamino)-benzamide (P-0116),
N-(6-Acetylamino-pyridin-3-yl)-2,6-difluoro-3-(3,3,3-trifluoro-propane-1-sulfonylamino)-benzamide (P-0117),
6-Acetylamino-N-[2,6-difluoro-3-(propane-1-sulfonylamino)-phenyl]-nicotinamide (P-0118),
1H-Pyrrolo[2,3-b]pyridine-5-carboxylic acid [2,6-difluoro-3-(propane-1-sulfonylamino)-phenyl]-amide (P-0119),
3H-Imidazo[4,5-b]pyridine-6-carboxylic acid [2,6-difluoro-3-(propane-1-sulfonylamino)-phenyl]-amide (P-0120), and
any salt, prodrug, tautomer, or isomer thereof.

In reference to compounds herein, unless clearly indicated to the contrary, specification of a compound or group of compounds includes pharmaceutically acceptable salts of such compound(s), pharmaceutically acceptable formulations of such compound(s), prodrug(s), and all stereoisomers thereof. In reference to compositions, kits, methods of use, etc. of compounds of Formula I described herein, it is understood (unless indicated otherwise) that a compound of Formula I includes all sub-embodiments thereof (e.g. including Formula Ia, Ib, Ic, Id, Ie, If, Ig, Ih, Ii, and Ij and all embodiments as described above).

In one aspect, methods are provided for treating a protein kinase mediated disease or condition in an animal subject, wherein the method involves administering to the subject an effective amount of one or more compound(s) of Formula I.

The terms "treat," "therapy," and like terms refer to the administration of material, e.g., one or more compound(s) of Formula I, in an amount effective to prevent, alleviate, or ameliorate one or more symptoms of a disease or condition, i.e., indication, and/or to prolong the survival of the subject being treated. The term "protein kinase mediated disease or condition" refers to a disease or condition in which the biological function of a protein kinase affects the development, and/or course, and/or symptoms of the disease or condition, and/or in which modulation of the protein kinase alters the development, course, and/or symptoms of the disease or condition. A protein kinase mediated disease or condition includes a disease or condition for which modulation provides a therapeutic benefit, e.g. wherein treatment with protein kinase modulators, including compounds described herein, provides a therapeutic benefit to the subject suffering from or at risk of the disease or condition. In one aspect, the protein kinase modulator is an inhibitor of the protein kinase. In one aspect, the method involves administering to the subject an effective amount of one or more compound(s) of Formula I in combination with one or more other therapies for the disease or condition.

In one aspect, methods are provided for treating a protein kinase mediated disease or condition in an animal subject, wherein the method involves administering to the subject an effective amount of any one or more compound(s) of Formula I.

In one aspect, the invention provides methods for treating a Raf protein kinase mediated disease or condition in an animal subject, wherein the method involves administering to the subject an effective amount of one or more compound(s) of Formula I. The terms "Raf protein kinase mediated disease or condition," "Raf mediated disease or condition," and the like refer to a disease or condition in which the biological function of a Raf kinase, including any mutations thereof, affects the development, course, and/or symptoms of the disease or condition, and/or in which modulation of the Raf protein kinase alters the development, course, and/or symptoms of the disease or condition. The Raf protein kinase includes, but is not limited to, A-Raf, mutations of A-Raf, B-Raf, mutations of B-Raf, c-Raf-1 and mutations of c-Raf-1. In some embodiments, the Raf protein kinase is B-Raf mutation V600E. In some embodiments, the Raf protein kinase is B-Raf mutation V600E/T529I. In some embodiments, the disease or condition is a cancer that is amenable to treatment by an inhibitor of the V600E mutant B-Raf. In some embodiments, the disease or condition is a cancer that is amenable to treatment by an inhibitor of the V600E/T529I mutant B-Raf. The Raf protein kinase mediated disease or condition includes a disease or condition for which Raf modulation provides a therapeutic benefit, e.g. wherein treatment with Raf modulators, including compounds described herein, provides a therapeutic benefit to the subject suffering from or at risk of the disease or condition. In one aspect, the Raf modulator is a Raf inhibitor. In one aspect, the method involves administering to the subject an effective amount of a compound of Formula I in combination with one or more other therapies for the disease or condition. Similarly, the terms "A-Raf, B-Raf or c-Raf-1 protein kinase mediated disease or condition," "A-Raf, B-Raf or c-Raf-1 mediated disease or condition," and the like refer to a disease or condition in which the biological function of an A-Raf, B-Raf or c-Raf-1 kinase, respectively, including any mutations thereof, affects the development, course, and/or symptoms of the disease or condition, and/or in which modulation of the A-Raf, B-Raf or c-Raf-1 protein kinase, respectively, alters the development, course, and/or symptoms of the disease or condition.

In some embodiments, a compound of Formula I will have an $IC_{50}$ of less than 500 nm, less than 100 nM, less than 50 nM, less than 20 nM, less than 10 nM, less than 5 nM, or less than 1 nM as determined in a generally accepted kinase activity assay. In some embodiments, a compound of Formula I will have an $IC_{50}$ of less than 500 nm, less than 100 nM, less than 50 nM, less than 20 nM, less than 10 nM, less than 5 nM, or less than 1 nM with respect to at least one kinase selected from the group consisting of Abl, Akt1, Akt2, Akt3, ALK, Alk5, A-Raf, B-Raf, Brk, Btk, Cdk2, CDK4, CDK5, CDK6, CHK1, c-Raf-1, Csk, EGFR, EphA1, EphA2, EphB2, EphB4, Erk2, Fak, FGFR1, FGFR2, FGFR3, FGFR4, Flt1, Flt3, Flt4, Fms, Frk, Fyn, Gsk3a, Gsk33, HCK, Her2/Erbb2, Her4/Erbb4, IGF1R, IKK beta, Irak4, Itk, Jak1, Jak2, Jak3, Jnk1, Jnk2, Jnk3, Kdr, Kit, Lck, Lyn, MAP2K1, MAP2K2, MAP4K4, MAPKAPK2, Met, Mnk1, MLK1, p38, PDGFRA, PDGFRB, PDPK1, Pim1, Pim2, Pim3, PKC alpha, PKC beta, PKC theta, Plk1, Pyk2, Ret, ROCK1, ROCK2, Ron, Src, Stk6, Syk, TEC, Tie2, TrkA, TrkB, Yes, and Zap70, including any mutations thereof.

In some embodiments, a compound of Formula I will have an $IC_{50}$ of less than 500 nm, less than 100 nM, less than 50 nM, less than 20 nM, less than 10 nM, less than 5 nM, or less than 1 nM with respect to at least one kinase selected from the group consisting of Abl, Akt1, Akt2, Akt3, ALK, Alk5, A-Raf, B-Raf, Btk, Cdk2, CDK4, CDK5, CDK6, CHK1, c-Raf-1, Csk, EGFR, EphA1, EphA2, EphB2, EphB4, Erk2, Fak, Fms, Fyn, Gsk3a, Gsk33, HCK, Her2/Erbb2, Her4/Erbb4, IGF1R, IKK beta, Irak4, Itk, Jak1, Jak2, Jak3, Jnk1, Jnk2, Jnk3, Kit, Lck, Lyn, MAP2K1, MAP2K2, MAP4K4, MAPKAPK2, Met, Mnk1, MLK1, p38, PDPK1, Pim1, Pim2, Pim3, PKC alpha, PKC beta, PKC theta, Plk1, Pyk2, Ron, Src, Stk6, Syk, TEC, Tie2, TrkA, TrkB, Yes, and Zap70, including any mutations thereof.

In some embodiments, a compound of Formula I will have an $IC_{50}$ of less than 500 nm, less than 100 nM, less than 50 nM, less than 20 nM, less than 10 nM, less than 5 nM, or less than 1 nM with respect to at least one kinase selected from the group consisting of Abl, A-Raf, B-Raf, Btk, c-Raf-1, EGFR, EphB2, Erk2, Fak, FGFR1, Flt1, Flt3, Flt4, Fms, Irak4, Jnk1, Jnk2, Jnk3, Kdr, Kit, Lck, Lyn, MAP2K1, MAP4K4, MAPKAPK2, Met, p38, PDGFRB, Pim1, PKC theta, Pyk2, Ret, Src, Stk6, TrkA, TrkB, Yes, and Zap70, including any mutations thereof.

In some embodiments, a compound of Formula I will have an $IC_{50}$ of less than 500 nm, less than 100 nM, less than 50 nM, less than 20 nM, less than 10 nM, less than 5 nM, or less than 1 nM with respect to at least one kinase selected from the group consisting of Abl, A-Raf, B-Raf, Btk, c-Raf-1, EGFR, EphB2, Erk2, Fak, Fms, Irak4, Jnk1, Jnk2, Jnk3, Kit, Lck, Lyn, MAP2K1, MAP4K4, MAPKAPK2, Met, p38, Pim1, PKC theta, Pyk2, Src, Stk6, TrkA, TrkB, Yes, and Zap70, including any mutations thereof.

In some embodiments, a compound of Formula I will have an $IC_{50}$ of less than 500 nm, less than 100 nM, less than 50 nM, less than 20 nM, less than 10 nM, less than 5 nM, or less than 1 nM with respect to at least one kinase selected from the group consisting of A-Raf, B-Raf, B-Raf V600E mutant, B-Raf V600E/T529I mutant, c-Raf-1, Fak, FGFR1, FGFR2, FGFR3, FGFR4, Jnk1, Jnk2, Jnk3, Lck, Lyn, Met, Pim1, Pim2, Pim3, Pyk2, Kdr, Src and Ret, including any mutations thereof.

In some embodiments, a compound of Formula I is an inhibitor of a Raf kinase and has an $IC_{50}$ of less than 500 nm, less than 100 nM, less than 50 nM, less than 20 nM, less than 10 nM, less than 5 nM, or less than 1 nM as determined in a generally accepted Raf kinase activity assay. In some embodiments, a compound of Formula I will have an $IC_{50}$ of less than 500 nm, less than 100 nM, less than 50 nM, less than 20 nM, less than 10 nM, less than 5 nM, or less than 1 nM with respect to A-Raf, B-Raf, c-Raf-1, B-Raf V600E mutant, or B-Raf V600E/T529I mutant. In some embodiments, a compound of Formula I will selectively inhibit one Raf kinase relative to one or more other Raf kinases. In some embodiments, the compound of Formula I will selectively inhibit a mutation of the Raf kinase relative to the wild type kinase, for example B-Raf V600E mutant relative to wild type B-Raf.

Further to any of the above mentioned embodiments, a compound of Formula I will also inhibit the effects of a mutation of the kinase, including, but not limited to, a mutation that is related to a disease state, such as a cancer. For example, B-Raf V600E mutant is present in a high percentage of some cancers, such as melanoma, and compounds will inhibit the kinase activity of this mutant.

Further to any of the above embodiments, a compound of Formula I may selectively inhibit one kinase relative to one or more other kinases, where preferably inhibition is selective with respect to any of the other kinases, whether a kinase discussed herein, or other kinases. In some embodiments, the compound may selectively inhibit the effects of a mutation of the kinase relative to the wild type kinase, for example B-Raf V600E mutant relative to wild type B-Raf. Selective inhibition of one kinase relative to another is such that the $IC_{50}$ for the one kinase may be at least about 2-fold, also 5-fold, also 10-fold, also 20-fold, also 50-fold, or at least about 100-fold less than the $IC_{50}$ for any of the other kinases as determined in a generally accepted kinase activity assay.

In another aspect, compositions are provided that include a therapeutically effective amount of one or more compound(s) of Formula I and at least one pharmaceutically acceptable carrier, excipient, and/or diluent, including combinations of any two or more compounds of Formula I. The composition can further include a plurality of different pharmacologically active compounds, which can include a plurality of compounds of Formula I. In another aspect, the composition can include one or more compounds of Formula I along with one or more compounds that are therapeutically effective for the same disease indication. In one aspect, the composition includes one or more compounds of Formula I along with one or more compounds that are therapeutically effective for the same disease indication, wherein the compounds have a synergistic effect on the disease indication. In one aspect, the composition includes one or more compounds of Formula I effective in treating a cancer and one or more other compounds that are effective in treating the cancer, further wherein the compounds are synergistically effective in treating the cancer.

In another aspect, methods are provided for modulating the activity of a protein kinase selected from the group consisting of Abl, Akt1, Akt2, Akt3, ALK, Alk5, A-Raf, B-Raf, Brk, Btk, Cdk2, CDK4, CDK5, CDK6, CHK1, c-Raf-1, Csk, EGFR, EphA1, EphA2, EphB2, EphB4, Erk2, Fak, FGFR1, FGFR2, FGFR3, FGFR4, Flt1, Flt3, Flt4, Fms, Frk, Fyn, Gsk3a, Gsk33, HCK, Her2/Erbb2, Her4/Erbb4, IGF1R, IKK beta, Irak4, Itk, Jak1, Jak2, Jak3, Jnk1, Jnk2, Jnk3, Kdr, Kit, Lck, Lyn, MAP2K1, MAP2K2, MAP4K4, MAPKAPK2, Met, Mnk1, MLK1, p38, PDGFRA, PDGFRB, PDPK1, Pim1, Pim2, Pim3, PKC alpha, PKC beta, PKC theta, Plk1, Pyk2, Ret, ROCK1, ROCK2, Ron, Src, Stk6, Syk, TEC, Tie2, TrkA, TrkB, Yes, and Zap70, including any mutations thereof, by contacting the protein kinase with an effective amount of one or more compound(s) of Formula I.

In another aspect, methods are provided for treating a protein kinase mediated disease or condition in an animal subject, wherein the method involves administering to the subject an effective amount of a composition including one or more compound(s) of Formula I.

In one aspect, methods are provided for treating a disease or condition mediated by a protein kinase selected from the group consisting of Abl, Akt1, Akt2, Akt3, ALK, Alk5, A-Raf, B-Raf, Brk, Btk, Cdk2, CDK4, CDK5, CDK6, CHK1, c-Raf-1, Csk, EGFR, EphA1, EphA2, EphB2, EphB4, Erk2, Fak, FGFR1, FGFR2, FGFR3, FGFR4, Flt1, Flt3, Flt4, Fms, Frk, Fyn, Gsk3a, Gsk33, HCK, Her2/Erbb2, Her4/Erbb4, IGF1R, IKK beta, Irak4, Itk, Jak1, Jak2, Jak3, Jnk1, Jnk2, Jnk3, Kdr, Kit, Lck, Lyn, MAP2K1, MAP2K2, MAP4K4, MAPKAPK2, Met, Mnk1, MLK1, p38, PDGFRA, PDGFRB, PDPK1, Pim1, Pim2, Pim3, PKC alpha, PKC beta, PKC theta, Plk1, Pyk2, ROCK1, ROCK2, Ron, Src, Stk6, Syk, TEC, Tie2, TrkA, TrkB, Yes, and Zap70, including any mutations thereof, by administering to the subject an effective amount of a composition including one or more compound(s) of Formula I.

In one aspect, the invention provides methods for treating a disease or condition mediated by a protein kinase selected from the group consisting of Abl, Akt1, Akt2, Akt3, ALK, Alk5, A-Raf, B-Raf, Btk, Cdk2, CDK4, CDK5, CDK6, CHK1, c-Raf-1, Csk, EGFR, EphA1, EphA2, EphB2, EphB4, Erk2, Fak, Fms, Fyn, Gsk3α, Gsk3β, HCK, Her2/Erbb2, Her4/Erbb4, IGF1R, IKK beta, Irak4, Itk, Jak1, Jak2, Jak3, Jnk1, Jnk2, Jnk3, Kit, Lck, Lyn, MAP2K1, MAP2K2, MAP4K4, MAPKAPK2, Met, Mnk1, MLK1, p38, PDPK1, Pim1, Pim2, Pim3, PKC alpha, PKC beta, PKC theta, Plk1, Pyk2, Ron, Src, Stk6, Syk, TEC, Tie2, TrkA, TrkB, Yes, and Zap70, including any mutations thereof, by administering to the subject an effective amount of a composition including one or more compound(s) of Formula I.

In one aspect, the invention provides methods for treating a disease or condition mediated by a protein kinase selected from the group consisting of Abl, A-Raf, B-Raf, Btk, c-Raf-1, EGFR, EphB2, Erk2, Fak, FGFR1, Flt1, Flt3, Flt4, Fms, Irak4, Jnk1, Jnk2, Jnk3, Kdr, Kit, Lck, Lyn, MAP2K1, MAP4K4, MAPKAPK2, Met, p38, PDGFRB, Pim1, PKC theta, Pyk2, Ret, Src, Stk6, TrkA, TrkB, Yes, and Zap70, including any mutations thereof, by administering to the subject an effective amount of a composition including one or more compound(s) of Formula I.

In one aspect, the invention provides methods for treating a disease or condition mediated by a protein kinase selected from the group consisting of Abl, A-Raf, B-Raf, Btk, c-Raf-1, EGFR, EphB2, Erk2, Fak, Fms, Irak4, Jnk1, Jnk2, Jnk3, Kit, Lck, Lyn, MAP2K1, MAP4K4, MAPKAPK2, Met, p38, Pim1, PKC theta, Pyk2, Src, Stk6, TrkA, TrkB, Yes, and Zap70, including any mutations thereof, by administering to the subject an effective amount of a composition including one or more compound(s) of Formula I.

In one aspect, the invention provides methods for treating a disease or condition mediated by a protein kinase selected from the group consisting of A-Raf, B-Raf, B-Raf V600E mutant, B-Raf V600E/T529I mutant, c-Raf-1, Fak, FGFR1, FGFR2, FGFR3, FGFR4, Jnk1, Jnk2, Jnk3, Lck, Lyn, Met, Pim1, Pim2, Pim3, Pyk2, Kdr, Src and Ret, including any mutations thereof, by administering to the subject an effective amount of a composition including one or more compound(s) of Formula I.

In one aspect, the invention provides methods for treating a disease or condition mediated by A-Raf, B-Raf, c-Raf-1, B-Raf V600E mutant, or B-Raf V600E/T529I mutant by administering to the subject an effective amount of a composition including one or more compound(s) of Formula I. In one aspect, the invention provides methods for treating a disease or condition mediated by A-Raf, B-Raf, c-Raf-1, B-Raf V600E mutant, or B-Raf V600E/T529I mutant by administering to the subject an effective amount of a composition including one or more compound(s) of Formula I in combination with one or more other suitable therapies for treating the disease. In one aspect, the invention provides methods for treating a cancer mediated by B-Raf V600E mutant or B-Raf V600E/T529I mutant by administering to the subject an effective amount of a composition including one or more compound(s) of Formula I in combination with one or more suitable anticancer therapies, such as one or more chemotherapeutic drugs.

In one aspect, the invention provides a method of treating a cancer by administering to the subject an effective amount of a composition including one or more compound(s) of Formula I, in combination with one or more other therapies or medical procedures effective in treating the cancer. Other therapies or medical procedures include suitable anticancer therapy (e.g. drug therapy, vaccine therapy, gene therapy, photodynamic therapy) or medical procedure (e.g. surgery, radiation treatment, hyperthermia heating, bone marrow or stem cell transplant). In one aspect, the one or more suitable anticancer therapies or medical procedures is selected from treatment with a chemotherapeutic agent (e.g. chemotherapeutic drug), radiation treatment (e.g. x-ray, □-ray, or electron, proton, neutron, or □ particle beam), hyperthermia heating (e.g. microwave, ultrasound, radiofrequency ablation), Vaccine therapy (e.g. AFP gene hepatocellular carcinoma vaccine, AFP adenoviral vector vaccine, AG-858, allogeneic GM-CSF-secretion breast cancer vaccine, dendritic cell peptide vaccines), gene therapy (e.g. Ad5CMV-p53 vector, adenovector encoding MDA7, adenovirus 5-tumor necrosis factor alpha), photodynamic therapy (e.g. aminolevulinic acid, motexafin lutetium), surgery, and bone marrow and stem cell transplantation.

In a preferred embodiment, the invention provides a method of treating a cancer by administering to the subject an effective amount of a composition including one or more compound(s) of Formula I in combination with one or more suitable chemotherapeutic agents. In one aspect, the one or more suitable chemotherapeutic agents is selected from an alkylating agent, including, but not limited to, adozelesin, altretamine, bizelesin, busulfan, carboplatin, carboquone, carmustine, chlorambucil, cisplatin, cyclophosphamide, dacarbazine, estramustine, fotemustine, hepsulfam, ifosfamide, improsulfan, irofulven, lomustine, mechlorethamine, melphalan, oxaliplatin, piposulfan, semustine, streptozocin, temozolomide, thiotepa, and treosulfan; an antibiotic, including, but not limited to, bleomycin, dactinomycin, daunorubicin, doxorubicin, epirubicin, idarubicin, menogaril, mitomycin, mitoxantrone, neocarzinostatin, pentostatin, and plicamycin; an antimetabolite, including, but not limited to, azacitidine, capecitabine, cladribine, clofarabine, cytarabine, decitabine, floxuridine, fludarabine, 5-fluorouracil, ftorafur, gemcitabine, hydroxyurea, mercaptopurine, methotrexate, nelarabine, pemetrexed, raltitrexed, thioguanine, and trimetrexate; an immunotherapy, including, but not limited to, alemtuzumab, bevacizumab, cetuximab, galiximab, gemtuzumab, panitumumab, pertuzumab, rituximab, tositumomab, trastuzumab, and 90 Y ibritumomab tiuxetan; a hormone or hormone antagonist, including, but not limited to, anastrozole, androgens, buserelin, diethylstilbestrol, exemestane, flutamide, fulvestrant, goserelin, idoxifene, letrozole, leuprolide, magestrol, raloxifene, tamoxifen, and toremifene; a taxane, including, but not limited to, DJ-927, docetaxel, TPI 287, paclitaxel and DHA-paclitaxel; a retinoid, including, but not limited to, alitretinoin, bexarotene, fenretinide, isotretinoin, and tretinoin; an alkaloid, including, but not limited to, etoposide, homoharringtonine, teniposide, vinblastine, vincristine, vindesine, and vinorelbine; an antiangiogenic agent, including, but not limited to, AE-941 (GW786034, Neovastat), ABT-510, 2-methoxyestradiol, lenalidomide, and thalidomide; a topoisomerase inhibitor, including, but not limited to, amsacrine, edotecarin, exatecan, irinotecan (also active metabolite SN-38 (7-ethyl-10-hydroxy-camptothecin)), rubitecan, topotecan, and 9-aminocamptothecin; a kinase inhibitor, including, but not limited to, erlotinib, gefitinib, flavopiridol, imatinib mesylate, lapatinib, sorafenib, sunitinib malate, AEE-788, AG-013736, AMG 706, AMN107, BMS-354825, BMS-599626, UCN-01 (7-hydroxy-staurosporine), and vatalanib; a targeted signal transduction inhibitor including, but not limited to bortezomib, geldanamycin, and rapamycin; a biological response modifier, including, but not limited to, imiquimod, interferon-0, and interleukin-2; and other chemotherapeutics, including, but not limited to 3-AP (3-amino-2-carboxyaldehyde thiosemicarbazone), aminoglutethimide, asparaginase, bryostatin-1, cilengitide, E7389, ixabepilone, procarbazine, sulindac, temsirolimus, tipifarnib. Preferably, the method of treating a cancer involves administering to the subject an effective amount of a composition including one or more compound(s) of Formula I in combination with a chemotherapeutic agent selected from 5-fluorouracil, carboplatin, dacarbazine, gefitinib, oxaliplatin, paclitaxel, SN-38, temozolomide, vinblastine, bevacizumab, cetuximab, or erlotinib.

In another aspect, the invention provides a method of treating or prophylaxis of a disease or condition in a mammal, by administering to the mammal a therapeutically effective amount of one or more compound(s) of Formula I, a prodrug of such compound, a pharmaceutically acceptable salt of such compound or prodrug, or a pharmaceutically acceptable formulation of such compound or prodrug. The compound can be alone or can be part of a composition. In another aspect, the invention provides a method of treating or prophylaxis of a disease or condition in a mammal, by administering to the mammal a therapeutically effective amount of one or more compound(s) of Formula I, a prodrug of such compound, a pharmaceutically acceptable salt of such compound or prodrug, or a pharmaceutically acceptable formulation of such compound or prodrug in combination with one or more other suitable therapies for the disease or condition.

In a related aspect, the invention provides kits that include a composition as described herein. In some embodiments, the composition is packaged, e.g., in a vial, bottle, flask, which may be further packaged, e.g., within a box, envelope, or bag; the composition is approved by the U.S. Food and Drug Administration or similar regulatory agency for administration to a mammal, e.g., a human; the composition is approved for administration to a mammal, e.g., a human, for a protein kinase mediated disease or condition; the invention kit includes written instructions for use and/or other indication that the composition is suitable or approved for administration to a mammal, e.g., a human, for a protein kinase-mediated disease or condition; and the composition is packaged in unit dose or single dose form, e.g., single dose pills, capsules, or the like.

In aspects involving treatment or prophylaxis of a disease or condition with the compounds of Formula I, the disease or condition is, for example without limitation, neurologic diseases, including, but not limited to, cerebrovascular ischemia, multi-infarct dementia, head injury, spinal cord injury, Alzheimer's disease (AD), Parkinson's disease, amyotrophic lateral sclerosis, dementia, senile chorea, and Huntington's disease; neoplastic diseases and associated complications, including, but not limited to, chemotherapy-induced hypoxia, gastrointestinal stromal tumors (GISTs), prostate tumors, mast cell tumors (including canine mast cell tumors), acute myeloid leukemia, acute lymphocytic leukemia, chronic myeloid leukemia, chronic lymphocytic leukemia, multiple myeloma, melanoma, mastocytosis, gliomas, glioblastoma, astrocytoma, neuroblastoma, sarcomas (e.g. sarcomas of neuroectodermal origin, leiomyosarcoma), carcinomas (e.g. lung, breast, pancreatic, colon, hepatocellular, renal, female genital tract, squamous cell, carcinoma in situ), lymphoma (e.g. histiocytic lymphoma, non-Hodgkin's lymphoma), MEN2 syndromes, neurofibromatosis (including Schwann cell neoplasia), myelodysplastic syndrome, leukemia, tumor angiogenesis, cancers of the thyroid, liver, bone, skin, brain, central nervous system, pancreas, lung (e.g. small cell lung cancer, non small cell lung cancer), breast, colon, bladder, prostate, gastrointestinal tract, endometrium, fallopian tube, testes and ovary, and metastasis of tumors to other tissues; pain of neuropathic or inflammatory origin, including, but not limited to, acute pain, chronic pain, bone pain, cancer-related pain and migraine; cardiovascular diseases, including, but not limited to, heart failure, ischemic stroke, cardiac hypertrophy, thrombosis (e.g. thrombotic microangiopathy syndromes), atherosclerosis, reperfusion injury and ischemia (e.g. cerebrovascular ischemia, liver ischemia); inflammation including, but not limited to, age-related macular degeneration, rheumatoid arthritis, allergic rhinitis, inflammatory bowel disease (e.g. ulcerative colitis, Crohn's disease), systemic lupus erythematosis, Sjogren's Syndrome, Wegener's granulomatosis, psoriasis, scleroderma, chronic thyroiditis, Grave's disease, myasthenia gravis, multiple sclerosis, osteoarthritis, endometriosis, scarring (e.g. dermal, tissue), vascular restenosis, fibrotic disorders, hypereosinophilia, CNS inflammation, pancreatitis, nephritis, atopic dermatitis, and hepatitis; immunodeficiency diseases, including, but not limited to, severe combined immunodeficiency (SCID), organ transplant rejection, and graft versus host disease; renal or prostatic diseases, including, but not limited to, diabetic nephropathy, polycystic kidney disease, nephrosclerosis, glomerulonephritis, interstitial nephritis, Lupus nephritis, prostate hyperplasia, chronic renal failure, tubular necrosis, diabetes-associated renal complications, and hypertrophy; metabolic diseases, including, but not limited to, type 1 diabetes, type 2 diabetes, metabolic syndrome, obesity, hepatic steatosis, insulin resistance, hyperglycemia, lipolysis and obesity; infection, including, but not limited to, *Helicobacter pylori*, Hepatitis and Influenza viruses, fever, and sepsis; pulmonary diseases, including, but not limited to, chronic obstructive pulmonary disease (COPD), acute respiratory distress syndrome (ARDS), asthma, allergy, bronchitis, emphysema, and pulmonary fibrosis; genetic developmental diseases, including, but not limited to, Noonan's syndrome, Crouzon syndrome, acrocephalo-syndactyly type I, Pfeiffer's syndrome, Jackson-Weiss syndrome, Costello syndrome, (faciocutaneoskeletal syndrome), LEOPARD syndrome, cardio-faciocutaneous syndrome (CFC) and neural crest syndrome abnormalities causing cardiovascular, skeletal, intestinal, skin, hair and endocrine diseases; disorders of bone structure, mineralization and bone reformation and resorption, including, but not limited to, osteoporosis, increased risk of fracture, Paget's disease, hypercalcemia, and metastatis of cancer to bone; Grave's disease; Hirschsprung's disease; lymphoedema; selective T-cell defect (STD); X-linked agammaglobulinemia; diabetic retinopathy; alopecia; erectile dysfunction; tuberous sclerosis, and diseases associated with muscle regeneration or degeneration, including, but not limited to, sarcopenia, muscular dystrophies (including, but not limited to, Duchenne, Becker, Emery-Dreifuss, Limb-Girdle, Facioscapulohumeral, Myotonic, Oculopharyngeal, Distal and Congenital Muscular Dystrophies), motor neuron diseases (including, but not limited to, amyotrophic lateral sclerosis, infantile progressive spinal muscular atrophy, intermediate spinal muscular atrophy, juvenile spinal muscular atrophy, spinal bulbar muscular atrophy, and adult spinal muscular atrophy), inflammatory myopathies (including, but not limited to, dermatomyositis, polymyositis, and inclusion body myositis), diseases of the neuromuscular junction (including, but not limited to, myasthenia gravis, Lambert-Eaton syndrome, and congenital myasthenic syndrome), myopathies due to endocrine abnormalities (including, but not limited to, hyperthyroid myopathy and hypothyroid myopathy) diseases of peripheral nerve (including, but not limited to, Charcot-Marie-Tooth disease, Dejerine-Sottas disease, and Friedreich's ataxia), other myopathies (including, but not limited to, myotonia congenita, paramyotonia congenita, central core disease, nemaline myopathy, myotubular myopathy, and periodic paralysis), and metabolic diseases of muscle (including, but not limited to, phosphorylase deficiency, acid maltase deficiency, phosphofructokinase deficiency, debrancher enzyme deficiency, mitochondrial myopathy, carnitine deficiency, carnitine palmatyl transferase deficiency, phosphoglycerate kinase deficiency, phosphoglycerate mutase deficiency, lactate dehydrogenase deficiency, and myoadenylate deaminase deficiency).

In some aspects, compounds of Formula I can be used in the preparation of a medicament for the treatment of a disease or condition is, for example without limitation, neurologic diseases, including, but not limited to, cerebrovascular ischemia, multi-infarct dementia, head injury, spinal cord injury, Alzheimer's disease (AD), Parkinson's disease, amyotrophic lateral sclerosis, dementia, senile chorea, and Huntington's disease; neoplastic diseases and associated complications, including, but not limited to, chemotherapy-induced hypoxia, gastrointestinal stromal tumors (GISTs), prostate tumors, mast cell tumors (including canine mast cell tumors), acute myeloid leukemia, acute lymphocytic leukemia, chronic myeloid leukemia, chronic lymphocytic leukemia, multiple myeloma, melanoma, mastocytosis, gliomas, glioblastoma, astrocytoma, neuroblastoma, sarcomas (e.g. sarcomas of neuroectodermal origin, leiomyosarcoma), carcinomas (e.g. lung, breast, pancreatic, colon, hepatocellular, renal, female genital tract, squamous cell, carcinoma in situ), lymphoma (e.g. histiocytic lymphoma, non-Hodgkin's lymphoma), MEN2 syndromes, neurofibromatosis (including Schwann cell neoplasia), myelodysplastic syndrome, leukemia, tumor angiogenesis, cancers of the thyroid, liver, bone, skin, brain, central nervous system, pancreas, lung (e.g. small cell lung cancer, non small cell lung cancer), breast, colon, bladder, prostate, gastrointestinal tract, endometrium, fallopian tube, testes and ovary, and metastasis of tumors to other tissues; pain of neuropathic or inflammatory origin, including, but not limited to, acute pain, chronic pain, bone pain, cancer-related pain and migraine; cardiovascular diseases, including, but not limited to, heart failure, ischemic stroke, cardiac hypertrophy, thrombosis (e.g. thrombotic microangiopathy syndromes), atherosclerosis, reperfusion injury and ischemia (e.g. cerebrovascular ischemia, liver ischemia); inflammation including, but not limited to, age-related macular degeneration, rheumatoid arthritis, allergic rhinitis, inflammatory bowel disease (e.g. ulcerative colitis, Crohn's disease), systemic lupus erythematosis, Sjogren's Syndrome, Wegener's granulomatosis, psoriasis, scleroderma, chronic thyroiditis, Grave's disease, myasthenia gravis, multiple sclerosis, osteoarthritis, endometriosis, scarring (e.g. dermal, tissue), vascular restenosis, fibrotic disorders, hypereosinophilia, CNS inflammation, pancreatitis, nephritis, atopic dermatitis, and hepatitis; immunodeficiency diseases, including, but not limited to, severe combined immunodeficiency (SCID), organ transplant rejection, and graft versus host disease; renal or prostatic diseases, including, but not limited to, diabetic nephropathy, polycystic kidney disease, nephrosclerosis, glomerulonephritis, interstitial nephritis, Lupus nephritis, prostate hyperplasia, chronic renal failure, tubular necrosis, diabetes-associated renal complications, and hypertrophy; metabolic diseases, including, but not limited to, type 1 diabetes, type 2 diabetes, metabolic syndrome, obesity, hepatic steatosis, insulin resistance, hyperglycemia, lipolysis and obesity; infection, including, but not limited to, *Helicobacter pylori*, Hepatitis and Influenza viruses, fever, and sepsis; pulmonary diseases, including, but not limited to, chronic obstructive pulmonary disease (COPD), acute respiratory distress syndrome (ARDS), asthma, allergy, bronchitis, emphysema, and pulmonary fibrosis; genetic developmental diseases, including, but not limited to, Noonan's syndrome, Crouzon syndrome, acrocephalo-syndactyly type I, Pfeiffer's syndrome, Jackson-Weiss syndrome, Costello syndrome, (faciocutaneoskeletal syndrome), LEOPARD syndrome, cardio-faciocutaneous syndrome (CFC) and neural crest syndrome abnormalities causing cardiovascular, skeletal, intestinal, skin, hair and endocrine diseases; disorders of bone structure, mineralization and bone reformation and resorption, including, but not limited to, osteoporosis, increased risk of fracture, Paget's disease, hypercalcemia, and metastatis of cancer to bone; Grave's disease; Hirschsprung's disease; lymphoedema; selective T-cell defect (STD); X-linked agammaglobulinemia; diabetic retinopathy; alopecia; erectile dysfunction; tuberous sclerosis, and diseases associated with muscle regeneration or degeneration, including, but not limited to, sarcopenia, muscular dystrophies (including, but not limited to, Duchenne, Becker, Emery-Dreifuss, Limb-Girdle, Facioscapulohumeral, Myotonic, Oculopharyngeal, Distal and Congenital Muscular Dystrophies), motor neuron diseases (including, but not limited to, amyotrophic lateral sclerosis, infantile progressive spinal muscular atrophy, intermediate spinal muscular atrophy, juvenile spinal muscular atrophy, spinal bulbar muscular atrophy, and adult spinal muscular atrophy), inflammatory myopathies (including, but not limited to, dermatomyositis, polymyositis, and inclusion body myositis), diseases of the neuromuscular junction (including, but not limited to, myasthenia gravis, Lambert-Eaton syndrome, and congenital myasthenic syndrome), myopathies due to endocrine abnormalities (including, but not limited to, hyperthyroid myopathy and hypothyroid myopathy) diseases of peripheral nerve (including, but not limited to, Charcot-Marie-Tooth disease, Dejerine-Sottas disease, and Friedreich's ataxia), other myopathies (including, but not limited to, myotonia congenita, paramyotonia congenita, central core disease, nemaline myopathy, myotubular myopathy, and periodic paralysis), and metabolic diseases of muscle (including, but not limited to, phosphorylase deficiency, acid maltase deficiency, phosphofructokinase deficiency, debrancher enzyme deficiency, mitochondrial myopathy, carnitine deficiency, carnitine palmatyl transferase deficiency, phosphoglycerate kinase deficiency, phosphoglycerate mutase deficiency, lactate dehydrogenase deficiency, and myoadenylate deaminase deficiency).

In aspects involving treatment or prophylaxis of a disease or condition with the compounds of Formula I, the invention provides methods for treating an A-Raf-mediated, B-Raf-mediated and/or c-Raf-1-mediated disease or condition in an animal subject (e.g. a mammal such as a human, other primates, sports animals, animals of commercial interest such as cattle, farm animals such as horses, or pets such as dogs and cats), e.g., a disease or condition characterized by abnormal A-Raf, B-Raf, and/or c-Raf-1 activity (e.g. kinase activity). Invention methods involve administering to the subject suffering from or at risk of an A-Raf-mediated, B-Raf-mediated and/or c-Raf-1-mediated disease or condition an effective amount of compound of Formula I. In one embodiment, the A-Raf-mediated, B-Raf-mediated, and/or c-Raf-1-mediated disease is selected from the group consisting of neurologic diseases, including, but not limited to, multi-infarct dementia, head injury, spinal cord injury, Alzheimer's disease (AD), Parkinson's disease; neoplastic diseases including, but not limited to, melanoma, glioma, sarcoma, carcinoma (e.g. colorectal, lung, breast, pancreatic, thyroid, renal, ovarian), lymphoma (e.g. histiocytic lymphoma) neurofibromatosis, acute myeloid leukemia, myelodysplastic syndrome, leukemia, tumor angiogenesis, neuroendocrine tumors such as medullary thyroid cancer, carcinoid, small cell lung cancer and pheochromocytoma; pain of neuropathic or inflammatory origin, including, but not limited to, acute pain, chronic pain, cancer-related pain, and migraine; cardiovascular diseases including, but not limited to, heart failure, ischemic stroke, cardiac hypertrophy, thrombosis (e.g. thrombotic microangiopathy syndromes), atherosclerosis, and reperfusion injury; inflammation including, but not limited to, psoriasis, arthritis and autoimmune diseases and conditions, osteoarthritis, endometriosis, scarring, vascular restenosis, fibrotic disorders, rheumatoid arthritis, inflammatory bowel disease; immunodeficiency diseases, including, but not limited to, organ transplant rejection, graft versus host disease; renal or prostatic diseases, including, but not limited to, diabetic nephropathy, polycystic kidney disease, nephrosclerosis, glomerulonephritis, prostate hyperplasia; metabolic disorders, including, but not limited to, obesity; infection, including, but not limited to *Helicobacter pylori*, Hepatitis and Influenza viruses, fever, and sepsis; pulmonary diseases including, but not limited to, chronic obstructive pulmonary disease (COPD) and acute respiratory distress syndrome (ARDS); genetic developmental diseases, including, but not limited to, Noonan's syndrome, Costello syndrome, (faciocutaneoskeletal syndrome), LEOPARD syndrome, cardio-faciocutaneous syndrome (CFC), and neural crest syndrome abnormalities causing cardiovascular, skeletal, intestinal, skin, hair and endocrine diseases; and diseases associated with muscle regeneration or degeneration, including, but not limited to, sarcopenia, muscular dystrophies (including, but not limited to, Duchenne, Becker, Emery-Dreifuss, Limb-Girdle, Facioscapulohumeral, Myotonic, Oculopharyngeal, Distal and Congenital Muscular Dystrophies), motor neuron diseases (including, but not limited to, amyotrophic lateral sclerosis, infantile progressive spinal muscular atrophy, intermediate spinal muscular atrophy, juvenile spinal muscular atrophy, spinal bulbar muscular atrophy, and adult spinal muscular atrophy), inflammatory myopathies (including, but not limited to, dermatomyositis, polymyositis, and inclusion body myositis), diseases of the neuromuscular junction (including, but not limited to, myasthenia gravis, Lambert-Eaton syndrome, and congenital myasthenic syndrome), myopathies due to endocrine abnormalities (including, but not limited to, hyperthyroid myopathy and hypothyroid myopathy) diseases of peripheral nerve (including, but not limited to, Charcot-Marie-Tooth disease, Dejerine-Sottas disease, and Friedreich's ataxia), other myopathies (including, but not limited to, myotonia congenita, paramyotonia congenita, central core disease, nemaline myopathy, myotubular myopathy, and periodic paralysis), and metabolic diseases of muscle (including, but not limited to, phosphorylase deficiency, acid maltase deficiency, phosphofructokinase deficiency, debrancher enzyme deficiency, mitochondrial myopathy, carnitine deficiency, carnitine palmatyl transferase deficiency, phosphoglycerate kinase deficiency, phosphoglycerate mutase deficiency, lactate dehydrogenase deficiency, and myoadenylate deaminase deficiency).

In some aspects, compounds of Formula I can be used in the preparation of a medicament for the treatment of an A-Raf-mediated, B-Raf-mediated or c-Raf-1-mediated disease or condition selected from the group consisting of neurologic diseases, including, but not limited to, multi-infarct dementia, head injury, spinal cord injury, Alzheimer's disease (AD), Parkinson's disease; neoplastic diseases including, but not limited to, melanoma, glioma, sarcoma, carcinoma (e.g. colorectal, lung, breast, pancreatic, thyroid, renal, ovarian), lymphoma (e.g. histiocytic lymphoma) neurofibromatosis, acute myeloid leukemia, myelodysplastic syndrome, leukemia, tumor angiogenesis, neuroendocrine tumors such as medullary thyroid cancer, carcinoid, small cell lung cancer and pheochromocytoma; pain of neuropathic or inflammatory origin, including, but not limited to, acute pain, chronic pain, cancer-related pain, and migraine; cardiovascular diseases, including, but not limited to, heart failure, ischemic stroke, cardiac hypertrophy, thrombosis (e.g. thrombotic microangiopathy syndromes), atherosclerosis, and reperfusion injury; inflammation including, but not limited to, psoriasis, arthritis and autoimmune diseases and conditions, osteoarthritis, endometriosis, scarring, vascular restenosis, fibrotic disorders, rheumatoid arthritis, inflammatory bowel disease; immunodeficiency diseases, including, but not limited to, organ transplant rejection, graft versus host disease; renal or prostatic diseases, including, but not limited to, diabetic nephropathy, polycystic kidney disease, nephrosclerosis, glomerulonephritis, prostate hyperplasia; metabolic disorders, including, but not limited to, obesity; infection, including, but not limited to, *Helicobacter pylori*, Hepatitis and Influenza viruses, fever, and sepsis; pulmonary diseases, including, but not limited to, chronic obstructive pulmonary disease (COPD) and acute respiratory distress syndrome (ARDS); genetic developmental diseases, including, but not limited to, Noonan's syndrome, Costello syndrome, (faciocutaneoskeletal syndrome), LEOPARD syndrome, cardio-faciocutaneous syndrome (CFC), and neural crest syndrome abnormalities causing cardiovascular, skeletal, intestinal, skin, hair and endocrine diseases; and diseases associated with muscle regeneration or degeneration, including, but not limited to, sarcopenia, muscular dystrophies (including, but not limited to, Duchenne, Becker, Emery-Dreifuss, Limb-Girdle, Facioscapulohumeral, Myotonic, Oculopharyngeal, Distal and Congenital Muscular Dystrophies), motor neuron diseases (including, but not limited to, amyotrophic lateral sclerosis, infantile progressive spinal muscular atrophy, intermediate spinal muscular atrophy, juvenile spinal muscular atrophy, spinal bulbar muscular atrophy, and adult spinal muscular atrophy), inflammatory myopathies (including, but not limited to, dermatomyositis, polymyositis, and inclusion body myositis), diseases of the neuromuscular junction (including, but not limited to, myasthenia gravis, Lambert-Eaton syndrome, and congenital myasthenic syndrome), myopathies due to endocrine abnormalities (including, but not limited to, hyperthyroid myopathy and hypothyroid myopathy) diseases of peripheral nerve (including, but not limited to, Charcot-Marie-Tooth disease, Dejerine-Sottas disease, and Friedreich's ataxia), other myopathies (including, but not limited to, myotonia congenita, paramyotonia congenita, central core disease, nemaline myopathy, myotubular myopathy, and periodic paralysis), and metabolic diseases of muscle (including, but not limited to, phosphorylase deficiency, acid maltase deficiency, phosphofructokinase deficiency, debrancher enzyme deficiency, mitochondrial myopathy, carnitine deficiency, carnitine palmatyl transferase deficiency, phosphoglycerate kinase deficiency, phosphoglycerate mutase deficiency, lactate dehydrogenase deficiency, and myoadenylate deaminase deficiency).

The compounds of Formula I with kinase activity $IC_{50}$ less than 10 □M as determined in a standard assay described herein can be used to treat protein kinase mediated diseases and conditions related to the following protein kinases, including any mutations thereof, for example without limitation:

Abl, related to chronic myeloid leukemia (CML), acute lymphoblastic leukemia (ALL) and acute myelogenous leukemia (AML);

Akt1, related to gastric, prostate, colorectal, ovarian, pancreatic and breast cancer, glioblastoma and leukemia, as well as schizophrenia and bipolar disorders, and also use in combination with other chemotherapeutic drugs;

Akt2, related to hyperglycemia due to peripheral insulin resistance and nonsuppressible hepatic glucose production accompanied by inadequate compensatory hyperinsulinemia, also related to pancreatic, ovarian and breast cancer;

Akt3, related to melanoma, prostate and breast cancer;

ALK, related to non-Hodgkin lymphomas such as diffuse large B-cell lymphoma and anaplastic large cell lymphoma;

Alk5, related to pancreatic and biliary cancers, and cutaneous T-cell lymphoma;

A-Raf, related to neurologic diseases such as multi-infarct dementia, head injury, spinal cord injury, Alzheimer's disease (AD), Parkinson's disease; neoplastic diseases including, but not limited to, melanoma, glioma, sarcoma, carcinoma (e.g. colorectal, lung, breast, pancreatic, thyroid, renal, ovarian), lymphoma (e.g. histiocytic lymphoma), neurofibromatosis, myelodysplastic syndrome, leukemia, tumor angiogenesis; pain of neuropathic or inflammatory origin, including acute pain, chronic pain, cancer-related pain and migraine; and diseases associated with muscle regeneration or degeneration, including, but not limited to, vascular restenosis, sarcopenia, muscular dystrophies (including, but not limited to, Duchenne, Becker, Emery-Dreifuss, Limb-Girdle, Facioscapulohumeral, Myotonic, Oculopharyngeal, Distal and Congenital Muscular Dystrophies), motor neuron diseases (including, but not limited to, amyotrophic lateral sclerosis, infantile progressive spinal muscular atrophy, intermediate spinal muscular atrophy, juvenile spinal muscular atrophy, spinal bulbar muscular atrophy, and adult spinal muscular atrophy), inflammatory myopathies (including, but not limited to, dermatomyositis, polymyositis, and inclusion body myositis), diseases of the neuromuscular junction (including, but not limited to, myasthenia gravis, Lambert-Eaton syndrome, and congenital myasthenic syndrome), myopathies due to endocrine abnormalities (including, but not limited to, hyperthyroid myopathy and hypothyroid myopathy) diseases of peripheral nerve (including, but not limited to, Charcot-Marie-Tooth disease, Dejerine-Sottas disease, and Friedreich's ataxia), other myopathies (including, but not limited to, myotonia congenita, paramyotonia congenita, central core disease, nemaline myopathy, myotubular myopathy, and periodic paralysis), and metabolic diseases of muscle (including, but not limited to, phosphorylase deficiency, acid maltase deficiency, phosphofructokinase deficiency, debrancher enzyme deficiency, mitochondrial myopathy, carnitine deficiency, carnitine palmatyl transferase deficiency, phosphoglycerate kinase deficiency, phosphoglycerate mutase deficiency, lactate dehydrogenase deficiency, and myoadenylate deaminase deficiency);

B-Raf or c-Raf-1, related to neurologic diseases, including, but not limited to, as multi-infarct dementia, head injury, spinal cord injury, Alzheimer's disease (AD), Parkinson's disease; neoplastic diseases including, but not limited to, melanoma, glioma, sarcoma, carcinoma (e.g. colorectal, lung, breast, pancreatic, thyroid, renal, ovarian), lymphoma (e.g. histiocytic lymphoma) neurofibromatosis, acute myeloid leukemia, myelodysplastic syndrome, leukemia, tumor angiogenesis, neuroendocrine tumors such as medullary thyroid cancer, carcinoid, small cell lung cancer and pheochromocytoma; pain of neuropathic or inflammatory origin, including, but not limited to, acute pain, chronic pain, cancer-related pain, and migraine; cardiovascular diseases including, but not limited to, heart failure, ischemic stroke, cardiac hypertrophy, thrombosis (e.g. thrombotic microangiopathy syndromes), atherosclerosis, reperfusion injury; inflammation including, but not limited to, psoriasis, arthritis and autoimmune diseases and conditions, osteoarthritis, endometriosis, scarring, vascular restenosis, fibrotic disorders, rheumatoid arthritis, inflammatory bowel disease; immunodeficiency diseases, including, but not limited to, organ transplant rejection, graft versus host disease; renal or prostatic diseases, including, but not limited to, diabetic nephropathy, polycystic kidney disease, nephrosclerosis, glomerulonephritis, prostate hyperplasia; metabolic disorders, including, but not limited to, obesity; infection, including, but not limited to, *Helicobacter pylori*, Hepatitis and Influenza viruses, fever, and sepsis; pulmonary diseases including, but not limited to, chronic obstructive pulmonary disease (COPD) and acute respiratory distress syndrome (ARDS); genetic developmental diseases, including, but not limited to, Noonan's syndrome, Costello syndrome, (faciocutaneoskeletal syndrome), LEOPARD syndrome, cardiofaciocutaneous syndrome (CFC), and neural crest syndrome abnormalities causing cardiovascular, skeletal, intestinal, skin, hair and endocrine diseases;

Brk, related to breast and colon cancer, and head and neck squamous cell carcinoma;

Btk, related to X-linked agammaglobulinemia, acute lymphocytic leukemia, autoimmune diseases such as multiple sclerosis, systemic lupus erythematosis, rheumatoid arthritis, and Graves' disease, immune suppression in organ transplant, and drug sensitivity of B-lineage cells;

Cdk2, related to prostate, breast, colorectal and ovarian cancer;

Cdk4, related to glioblastoma (e.g. glioblastoma multiforme), anaplastic astrocytoma, and breast cancer;

Cdk5, related to Alzheimer's disease, amyotrophic lateral sclerosis and Lewy body disease;

Cdk6, related to glioblastoma multiforme, non-Hodgkin's lymphoma, splenic marginal zone lymphoma, T-cell lymphoblastic lymphoma (T-LBL) and T-cell acute lymphoblastic leukemia (T-ALL);

CHK1, related to DNA damage repair, sensitizes cells to chemotherapeutic agents;

Csk, related to colon and pancreatic carcinomas and autoimmune pathology such as type 1 diabetes, rheumatoid arthritis and systemic lupus erythematosus;

EGFR, related to breast, colorectal, bladder, prostate and non small cell lung cancer, squamous cell carcinomas of the head and neck cancer, oral cavity, and esophagus, and glioblastoma multiforme;

EphA1, related to head and neck squamous cell carcinoma, hepatoma and lung cancer;

EphA2, related to aberrant short-range contact-mediated axonal guidance, bladder, breast, prostate, colon, skin, cervical, ovarian, pancreatic and lung cancers, and metastatic melanoma;

EphB2, related to angiogenesis disorder (e.g. ocular angiogenesis disease such as retinopathy), and cancer (e.g. glioblastoma, breast and liver cancer);

EphB4, related to colorectal cancer (CRC), head and neck squamous cell carcinoma, and tumours of the prostate, breast, endometrium, and bladder;

Erk2, related to aberrant proliferation, differentiation, transcription regulation and development, and may be useful in treating inflammation, for example inflammation associated with Lyme neuroborreliosis, and in treating cancers, such as gastric cancer;

Fak, related to colon and breast tumors, and is also related to esophageal squamous cell carcinoma, melanoma, anaplastic astrocytoma, glioblastoma, ductal carcinoma in situ, prostate and hepatocellular carcinoma, and tumor metastases, and may also provide synergistic effects when used with other chemotherapeutic drugs;

FGFR1, related to 8p11 myeloproliferative syndrome;

FGFR2, related to Crouzon Syndrome, Jackson-Weiss Syndrome, Apert Syndrome, craniosynostosis, Pfeiffer Syndrome, acrocephalo syndactyly type V, and Beare-Stevenson Cutis Gyrata Syndrome;

FGFR3, related to angiogenesis, wound healing, achondroplasia, Muenke craniosynostosis, Crouzon syndrome, acanthosis *nigricans*, thanatophoric dysplasia, bladder carcinomas, and multiple myeloma;

FGFR4, related to cancer of the breast, lung, colon, medullary thyroid, pancreas, ovary, prostate, endometrium, and fallopian tube, head and neck squamous cell carcinomas and leiomyosarcoma;

Flt1, related to non-small cell lung carcinoma, prostate carcinoma and colorectal cancer;

Flt3, related to acute myeloid leukemia, myelodysplastic syndrome, acute lymphoblastic leukemia;

Flt4, related to primary lymphoedema;

Fms, related to immune disorders, including rheumatoid arthritis, systemic lupus erythematosis (SLE), and transplant rejection, inflammatory diseases including inflammatory bowel disease (e.g. ulcerative colitis, Crohn's disease), chronic obstructive pulmonary disease (COPD), emphysema, and atherosclerosis, metabolic disorders, including Type I diabetes, Type II diabetes, insulin resistance, hyperglycemia, and lipolysis, disorders of bone structure, mineralization and bone formation and resorption, including osteoporosis, increased risk of fracture, Paget's disease, hypercalcemia, and metastasis of cancer to bone, kidney diseases, including nephritis (e.g. glomerulonephritis, interstitial nephritis, Lupus nephritis), tubular necrosis, diabetes-associated renal complications (e.g. diabetic nephropathy), and hypertrophy, disorders of the central nervous system, including multiple sclerosis, stroke, Alzheimer's disease and Parkinson's disease; inflammatory and chronic pain, including bone pain; and cancers, including multiple myeloma, acute myeloid leukemia, chronic myeloid leukemia (CML), prostate cancer, breast cancer, ovarian cancer, and metastasis of tumors to other tissues;

Frk, related to acute myeloid leukemia and type 1 diabetes;

Fyn, related to Alzheimer's disease, schizophrenia and prevention of metastases, e.g. in melanoma and squamous cell carcinoma;

GSK3 (Gsk3α and/or Gsk3β), related to CNS disorders such as Alzheimer's disease, Parkinson's disease, amyotrophic lateral sclerosis, diabetes type II, bipolar disorders, stroke, cancer, chronic inflammatory disease, leucopenia, schizophrenia, chronic pain, neuropathic pain, and traumatic head injury;

HCK, related to chronic myelogenous leukemia and acute lymphocytic leukemia;

Her2/Erbb2, related to prostate and breast cancer;

Her4/Erbb4, related to childhood medulloblastoma;

IGF1R, related to prostate cancer, hepatocellular carcinoma;

IKK beta, related to leukemia of T-cells, necrosis, insulin resistance, and malignant neoplasms;

Irak4, related to bacterial infections, immunodeficiency syndrome, inflammatory bowel disease (e.g. ulcerative colitis, Crohn's disease), asthma, chronic bronchitis, cardio hypertrophy, and kidney hypertension;

Itk, related to allergic asthma;

Jak1, related to Hepatitis C virus infection;

Jak2, related to myeloproliferative disorders such as polycythaemia vera, myelofibrosis, essential thrombocythemia, myeloid metaplasia and leukemias, including acute lymphoblastic leukemia, chronic neutrophilic leukemia, juvenile myelomonocytic leukemia, CMML, Philadelphia chromosome-negative CML, megakaryocytic leukemia, and acute erythroid leukemia;

Jak3, related to X-linked severe combined immunodeficiency, myeloproliferative disorders, transplant rejection and autoimmune diseases such as rheumatoid arthritis, inflammatory bowel disease (e.g. ulcerative colitis, Crohn's disease), systemic lupus erythematosis, psoriasis and multiple sclerosis;

Jnk (Jnk1, Jnk2, Jnk3), related to metabolic diseases including type 1 diabetes, type 2 diabetes, metabolic syndrome, obesity, and hepatic steatosis; cardiovascular diseases such as atherosclerosis, ischemia (e.g. cerebrovascular ischemia, liver ischemia), reperfusion injury, cardiac hypertrophy; renal diseases such as chronic renal failure; neoplastic diseases and associated complications, including chemotherapy-induced hypoxia, prostate tumors, myeloid leukemia and cancers of the liver, bone, skin, brain, pancreas, lung breast, colon, prostate and ovary; transplant rejection; pain of neuropathic or inflammatory origin including acute and chronic pain; inflammatory and autoimmune diseases including age-related macular degeneration, rheumatoid arthritis, inflammatory bowel disease (e.g. ulcerative colitis, Crohn's disease), systemic lupus erythematosis, Sjogren's Syndrome, psoriasis, scleroderma, chronic thyroiditis, Grave's disease, myasthenia gravis, and multiple sclerosis, and inflammation in other organs including CNS inflammation, pancreatitis, nephritis, atopic dermatitis, and hepatitis; airway inflammatory diseases such as asthma, allergy, bronchitis, pulmonary fibrosis, chronic obstructive pulmonary disease; neurologic diseases such as stroke, cerebrovascular ischemia, neurodegenerative diseases such as Parkinson's disease, Alzheimer's disease, amyotrophic lateral sclerosis, dementia, senile chorea, head and spinal cord trauma, and Huntington's disease. More particularly, Jnk1 is related to type 1 diabetes, type 2 diabetes, metabolic syndrome, obesity and hepatic steatosis, Jnk2 is related to atherosclerosis, and Jnk3 is related to inflammatory diseases including autoimmune diseases such as rheumatoid arthritis, inflammatory bowel disease (e.g. ulcerative colitis, Crohn's disease), systemic lupus erythematosis, Sjogren's Syndrome, psoriasis and multiple sclerosis, airway inflammatory diseases such as asthma, allergy, pulmonary fibrosis, and chronic obstructive pulmonary disease, and inflammation in other organs, such as CNS inflammation, pancreatitis, nephritis, and hepatitis; neurologic diseases such as stroke, cerebrovascular ischemia, and neurodegenerative diseases such as Parkinson's disease, Alzheimer's disease, and Huntington's disease; and neoplastic diseases such as prostate tumors and myeloid leukemia;

Kdr, related to anti-angiogenesis for treating solid tumor growth (e.g. ovarian, lung, breast, pancreatic, prostate, colon, gastrointestinal stromal tumor, non small cell lung cancer, and epidermoid cancer), metastasis, psoriasis, rheumatoid arthritis, diabetic retinopathy and age related macular degeneration;

Kit, related to malignancies, including mast cell tumors, small cell lung cancer, testicular cancer, gastrointestinal stromal tumors (GISTs), glioblastoma, astrocytoma, neuroblastoma, carcinomas of the female genital tract, sarcomas of neuroectodermal origin, colorectal carcinoma, carcinoma in situ, Schwann cell neoplasia associated with neurofibromatosis, acute myelocytic leukemia, acute lymphocytic leukemia, chronic myelogenous leukemia, mastocytosis, melanoma, and canine mast cell tumors, and inflammatory diseases, including asthma, rheumatoid arthritis, allergic rhinitis, multiple sclerosis, inflammatory bowel disease (e.g. ulcerative colitis, Crohn's disease), transplant rejection, and hypereosinophilia;

Lck, related to acute lymphoblastic leukemia, T-cell lymphoma, lymphopenia, renal carcinoma, colon carcinoma, severe combined immunodeficiency, multiple sclerosis, inflammatory bowel disease (e.g. ulcerative colitis, Crohn's disease) and type I diabetes;

Lyn, related to cancers such as glioblastoma.

MAP2K1, related to acute myeloid leukemia, breast, ovarian and liver cancer;

MAP2K2, related to cancer and inflammation;

MAP4K4, related to metabolic indications, including re-sensitizing fat and muscle cells to insulin, ameliorating the pathology in adipocytes, ameliorating the pathology in muscle cells, metabolic syndrome, and type II diabetes; a broad range of oncology indications, including blocking the migration, invasion and metastasis in many different tumor types; and T-cell mediated autoimmune diseases;

MAPKAPK2, cancer (e.g. prostate, breast), stroke, menengitis, and inflammatory disorders;

Met, related to kidney, breast, bladder, non-small-cell lung, colorectal, and bladder cancers, and hepatocellular carcinoma;

Mnk1, related to conditions associated with heat shock, nutrient deprivation, oxidative or osmotic stress, and infection of mammalian cells (e.g. with viruses such as adenovirus (Ad) or influenza virus), and autoimmune diseases;

MLK1, related to neurodegenerative diseases such as Alzheimer's disease and Parkinson's disease, and inflammatory disorders;

p38, related to acute coronary syndrome, stroke, atherosclerosis, and inflammatory autoimmune diseases such as rheumatoid arthritis, and inflammatory bowel disease (e.g. ulcerative colitis, Crohn's disease); PDGFR (PDGFRA, PDGFRB), related to idiopathic hypereosinophilic syndrome, chronic eosinophilic leukemia, glioma, gastrointestinal stromal tumors (GISTs), juvenile myelomonocytic leukemia, metastatic medulloblastoma, atherogenesis, and restenosis. More particularly, PDGFRA related to idiopathic hypereosinophilic syndrome, chronic eosinophilic leukemia, glioma, gastrointestinal stromal tumors (GISTs), juvenile myelomonocytic leukemia, metastatic medulloblastoma, atherogenesis, and restenosis, and PDGFRB related to idiopathic hypereosinophilic syndrome, chronic eosinophilic leukemia, juvenile myelomonocytic leukemia, and metastatic medulloblastoma;

PDPK1, related to cancer and diabetes;

Pim1, related to cancers such as hematopoietic (e.g. acute myeloid and acute lymphoid leukemias) and prostate cancers, and non-Hodgkin's lymphomas;

Pim2, related to lymphomas;

Pim3, related to hepatocellular carcinoma;

PKC alpha, related to pituitary tumors and prefrontal cortical dysfunction such as distractibility, impaired judgment, impulsivity, and thought disorder, also may be used to sensitize chemotherapy in breast, colon, and non small cell lung cancers;

PKC beta, related to diabetic retinopathy;

PKC-theta, related to insulin resistance, T-cell lymphoma;

Plk1, related to cancers (e.g. lymphoma of the thyroid, non-Hodgkin's lymphomas, colorectal cancers, leukemias and melanoma), also useful as sensitizer in chemotherapy;

Pyk2, related to inflammation (e.g. osteoporosis, polycystic kidney disease, rheumatoid arthritis and inflammatory bowel disease), CNS disease (e.g. Parkinson's disease and Alzheimer's disease), stroke and cancers (e.g. gliomas, breast cancer, and pancreatic cancer);

Ret, related to cancer of the thyroid, neuroblastoma, familial medullary thyroid carcinoma (FMTC), multiple endocrine neoplasia type IIA and IIB (MEN2A, MEN2B), and neurodegenerative disorders (e.g. Hirschsprung's disease, Parkinson's disease, Alzheimer's disease, and amyotrophic lateral sclerosis);

ROCK (ROCK-1, ROCK-2), related to cancers (e.g. ovarian cancer, hepatocellular carcinoma, pancreatic cancer), ocular disease (e.g. glaucoma), cardiac hypertrophy, improved renal perfusion, transplant rejection, and acute respiratory distress syndrome;

Ron, related to cancer and inflammation;

Src, related to cancer and osteoporosis;

Stk6, related to gastric, bladder, breast, lung, CNS, ovarian, kidney, colon, prostate, pancreas, and cervical cancers, melanoma, leukemia, and neuroblastoma;

Syk, related to lymphomas (e.g. mantle cell lymphoma);

TEC, related to sepsis, septic shock, inflammation, rheumatoid arthritis, Crohn's disease, irritable bowel disease (IBD) and ulcerative colitis;

Tie2 (TEK), related to cancer, arthritis (e.g. rheumatoid arthritis), and atherosclerosis;

TrkA, related to pain (e.g. chronic pain, neuropathic pain), cancer (e.g. prostate cancer, lung cancer, pancreatic cancer), allergic disorders (e.g. asthma), arthritis, diabetic retinopathy, macular degeneration and psoriasis;

TrkB, related to obesity, hyperphagia, developmental delays, cancer (e.g. prostate cancer, lung cancer, Wilms tumors, neuroblastoma, pancreatic cancer), various neuropathies (e.g. stroke, multiple sclerosis, transverse myelitis, and encephalitis), and diabetes.

Yes, related to various cancers including esophageal squamous cell carcinoma; and Zap70, related to AIDS, systemic lupus erythematosus, myasthenia gravis, atherosclerosis, rejection of transplanted organs or tissues, allograft rejection including acute and chronic allograft rejection, graft versus host disease, rheumatoid arthritis, psoriasis, systemic sclerosis, atopic dermatitis, eczematous dermatitis, alopecia, and inflammation of the nasal mucus membrane, including all forms of rhinitis.

Additional aspects and embodiments will be apparent from the following Detailed Description of the Invention and from the claims.

DETAILED DESCRIPTION OF THE PREFERRED EMBODIMENTS

As used herein the following definitions apply unless clearly indicated otherwise:

"Halogen" refer to all halogens, that is, chloro (Cl), fluoro (F), bromo (Br), or iodo (I).

"Hydroxyl" or "hydroxy" refer to the group —OH.

"Thiol" refers to the group —SH.

"Lower alkyl" alone or in combination means an alkane-derived radical containing from 1 to 6 carbon atoms (unless specifically defined) that includes a straight chain alkyl or branched alkyl. The straight chain or branched alkyl group is chemically feasible and attached at any available point to produce a stable compound. In many embodiments, a lower alkyl is a straight or branched alkyl group containing from 1-6, 1-4, or 1-2, carbon atoms, such as methyl, ethyl, propyl, isopropyl, butyl, t-butyl, and the like. An "optionally substituted lower alkyl" denotes lower alkyl that is optionally independently substituted, unless indicated otherwise, with one or more, preferably 1, 2, 3, 4 or 5, also 1, 2, or 3 substituents, attached at any available atom to produce a stable compound, wherein the substituents are selected from the group consisting of —F, —OH, —NH$_2$, —NO$_2$, —CN, —C(O)—OH, —C(S)—OH, —C(O)—NH$_2$, —C(S)—NH$_2$, —S(O)$_2$—NH$_2$, —N(H)—C(O)—NH$_2$, —N(H)—C(S)—NH$_2$, —N(H)—S(O)$_2$—NH$_2$, —C(NH)—NH$_2$, —O—R$^o$, —S—R$^o$, —O—C(O)—R$^o$, —O—C(S)—R$^o$, —C(O)—R$^o$, —C(S)—R$^o$, —C(O)—O—R$^o$, —C(S)—O—R$^o$, —S(O)—R$^o$, —S(O)$_2$—R$^o$, —C(O)—N(H)—R$^o$, —C(S)—N(H)—R$^o$, —C(O)—N(R$^o$)—R$^o$, —C(S)—N(R$^o$)—R$^o$, —S(O)$_2$—N(H)—R$^o$, —S(O)$_2$—N(R$^o$)—R$^o$, —C(NH)—N(H)—R$^o$, —C(NH)—N(R$^P$)—R$^o$, —N(H)—C(O)—R$^o$, —N(H)—C(S)—R$^o$, —N(R$^o$)—C(O)—R$^o$, —N(R$^o$)—C(S)—R$^o$, —N(H)—S(O)$_2$—R$^o$, —N(R$^o$)—S(O)$_2$—R$^o$, —N(H)—C(O)—N(H)—R$^o$, —N(H)—C(S)—N(H)—R$^o$, —N(R$^o$)—C(O)—NH$_2$, —N(R$^o$)—C(S)—NH$_2$, —N(R$^o$)—C(O)—N(H)—R$^o$, —N(R$^o$)—C(S)—N(H)—R$^o$, —N(H)—C(O)—N(R$^o$)—R$^o$, —N(H)—C(S)—N(R$^o$)—R$^o$, —N(R$^o$)—C(O)—N(R$^o$)—R$^o$, —N(R$^o$)—C(S)—N(R$^o$)—R$^o$, —N(H)—S(O)$_2$—N(H)—R$^o$, —N(R$^o$)—S(O)$_2$—NH$_2$, —N(R$^o$)—S(O)$_2$—N(H)—R$^o$, —N(H)—S(O)$_2$—N(R$^o$)—R$^o$, —N(R$^o$)—S(O)$_2$—N(R$^o$)—R$^o$, —N(H)—R$^o$, —N(R$^o$)—R$^o$, —R$^e$, —R$^f$, and —R$^g$. Furthermore, possible substitutions include subsets of these substitutions, such as are indicated herein, for example, in the description of compounds of Formula I, attached at any available atom to produce a stable compound. For example "fluoro substituted lower alkyl" denotes a lower alkyl group substituted with one or more fluoro atoms, such as perfluoroalkyl, where preferably the lower alkyl is substituted with 1, 2, 3, 4 or 5 fluoro atoms, also 1, 2, or 3 fluoro atoms. It is understood that substitutions are chemically feasible and attached at any available atom to provide a stable compound.

"Lower alkenyl" alone or in combination means a straight or branched hydrocarbon containing 2-6 carbon atoms (unless specifically defined) and at least one, preferably 1-3, more preferably 1-2, most preferably one, carbon to carbon double bond. Carbon to carbon double bonds may be either contained within a straight chain or branched portion. The straight chain or branched lower alkenyl group is chemically feasible and attached at any available point to provide a stable compound. Examples of lower alkenyl groups include ethenyl, propenyl, isopropenyl, butenyl, and the like. An "optionally substituted lower alkenyl" denotes lower alkenyl that is optionally independently substituted, unless indicated otherwise, with one or more, preferably 1, 2, 3, 4 or 5, also 1, 2, or 3 substituents, attached at any available atom to produce a stable compound, wherein the substituents are selected from the group consisting of —F, —OH, —NH$_2$, —NO$_2$, —CN, —C(O)—OH, —C(S)—OH, —C(O)—NH$_2$, —C(S)—NH$_2$, —S(O)$_2$—NH$_2$, —N(H)—C(O)—NH$_2$, —N(H)—C(S)—NH$_2$, —N(H)—S(O)$_2$—NH$_2$, —C(NH)—NH$_2$, —O—R$^o$, —S—R$^o$, —O—C(O)—R$^o$, —O—C(S)—R$^o$, —C(O)—R$^o$, —C(S)—R$^o$, —C(O)—O—R$^o$, —C(S)—O—R$^o$, —S(O)—R$^o$, —S(O)$_2$—R$^o$, —C(O)—N(H)—R$^o$, —C(S)—N(H)—R$^o$, —C(O)—N(R$^o$)—R$^o$, —C(S)—N(R$^o$)—R$^o$, —S(O)$_2$—N(H)—R$^o$, —S(O)$_2$—N(R$^o$)—R$^o$, —C(NH)—N(H)—R$^o$, —C(NH)—N(R$^P$)—R$^o$, —N(H)—C(O)—R$^o$, —N(H)—C(S)—R$^o$, —N(R$^o$)—C(O)—R$^o$, —N(R$^o$)—C(S)—R$^o$, —N(H)—S(O)$_2$—R$^o$, —N(R$^o$)—S(O)$_2$—R$^o$, —N(H)—C(O)—N(H)—R$^o$, —N(H)—C(S)—N(H)—R$^o$, —N(R$^o$)—C(O)—NH$_2$, —N(R$^o$)—C(S)—NH$_2$, —N(R$^o$)—C(O)—N(H)—R$^o$, —N(R$^o$)—C(S)—N(H)—R$^o$, —N(H)—C(O)—N(R$^o$)—R$^o$, —N(H)—C(S)—N(R$^o$)—R$^o$, —N(R$^o$)—C(O)—N(R$^o$)—R$^o$, —N(R$^o$)—C(S)—N(R$^o$)—R$^o$, —N(H)—S(O)$_2$—N(H)—R$^o$, —N(R$^o$)—S(O)$_2$—NH$_2$, —N(R$^o$)—S(O)$_2$—N(H)—R$^o$, —N(H)—S(O)$_2$—N(R$^o$)—R$^o$, —N(R$^o$)—S(O)$_2$—N(R$^o$)—R$^o$, —N(H)—R$^o$, —N(R$^o$)—R$^o$, —R$^d$, —R$^f$, and —R$^g$. Further, possible substitutions include subsets of these substitutions, such as are indicated herein, for example, in the description of compounds of Formula I, attached at any available atom to produce a stable compound. For example "fluoro substituted lower alkenyl" denotes a lower alkenyl group substituted with one or more fluoro atoms, where preferably the lower alkenyl is substituted with 1, 2, 3, 4 or 5 fluoro atoms, also 1, 2, or 3 fluoro atoms. "$C_{3-6}$ alkenyl" denotes lower alkenyl containing 3-6 carbon atoms. An "optionally substituted $C_{3-6}$ alkenyl" denotes optionally substituted lower alkenyl containing 3-6 carbon atoms. It is understood that substitutions are chemically feasible and attached at any available atom to provide a stable compound.

"Lower alkynyl" alone or in combination means a straight or branched hydrocarbon containing 2-6 carbon atoms (unless specifically defined) containing at least one, preferably one, carbon to carbon triple bond. The straight chain or branched lower alkynyl group is chemically feasible and attached at any available point to provide a stable compound. Examples of alkynyl groups include ethynyl, propynyl, butynyl, and the like. An "optionally substituted lower alkynyl" denotes lower alkynyl that is optionally independently substituted, unless indicated otherwise, with one or more, preferably 1, 2, 3, 4 or 5, also 1, 2, or 3 substituents, attached at any available atom to produce a stable compound, wherein the substituents are selected from the group consisting of —F, —OH, —$NH_2$, —$NO_2$, —CN, —C(O)—OH, —C(S)—OH, —C(O)—$NH_2$, —C(S)—$NH_2$, —S(O)$_2$—$NH_2$, —N(H)—C(O)—$NH_2$, —N(H)—C(S)—$NH_2$, —N(H)—S(O)$_2$—$NH_2$, —C(NH)—$NH_2$, —O—$R^o$, —S—$R^o$, —O—C(O)—$R^o$, —O—C(S)—$R^o$, —C(O)—$R^o$, —C(S)—$R^o$, —C(O)—O—$R^o$, —C(S)—O—$R^o$, —S(O)—$R^o$, —S(O)$_2$—$R^o$, —C(O)—N(H)—$R^o$, —C(S)—N(H)—$R^o$, —C(O)—N($R^o$)—$R^o$, —C(S)—N($R^o$)—$R^o$, —S(O)$_2$—N(H)—$R^o$, —S(O)$_2$—N($R^o$)—$R^o$, —C(NH)—N(H)—$R^o$, —C(NH)—N($R^P$)—$R^o$, —N(H)—C(O)—$R^o$, —N(H)—C(S)—$R^o$, —N($R^o$)—C(O)—$R^o$, —N($R^o$)—C(S)—$R^o$, —N(H)—S(O)$_2$—$R^o$, —N($R^o$)—S(O)$_2$—$R^o$, —N(H)—C(O)—N(H)—$R^o$, —N(H)—C(S)—N(H)—$R^o$, —N($R^o$)—C(O)—$NH_2$, —N($R^o$)—C(S)—$NH_2$, —N($R^o$)—C(O)—N(H)—$R^o$, —N($R^o$)—C(S)—N(H)—$R^o$, —N(H)—C(O)—N($R^o$)—$R^o$, —N(H)—C(S)—N($R^o$)—$R^o$, —N($R^o$)—C(O)—N($R^o$)—$R^o$, —N($R^o$)—C(S)—N($R^o$)—$R^o$, —N(H)—S(O)$_2$—N(H)—$R^o$, —N($R^o$)—S(O)$_2$—$NH_2$, —N($R^o$)—S(O)$_2$—N(H)—$R^o$, —N(H)—S(O)$_2$—N($R^o$)—$R^o$, —N($R^o$)—S(O)$_2$—N($R^o$)—$R^o$, —N(H)—$R^o$, —N($R^o$)—$R^o$, —$R^d$, —$R^e$, and —$R^g$. Further, possible substitutions include subsets of these substitutions, such as are indicated herein, for example, in the description of compounds of Formula I, attached at any available atom to produce a stable compound. For example "fluoro substituted lower alkynyl" denotes a lower alkynyl group substituted with one or more fluoro atoms, where preferably the lower alkynyl is substituted with 1, 2, 3, 4 or 5 fluoro atoms, also 1, 2, or 3 fluoro atoms. "$C_{3-6}$ alkynyl" denotes lower alkynyl containing 3-6 carbon atoms. An "optionally substituted $C_{3-6}$ alkynyl" denotes optionally substituted lower alkynyl containing 3-6 carbon atoms. It is understood that substitutions are chemically feasible and attached at any available atom to provide a stable compound.

"Cycloalkyl" refers to saturated or unsaturated, non-aromatic monocyclic, bicyclic or tricyclic carbon ring systems of 3-10, also 3-8, more preferably 3-6, ring members per ring, such as cyclopropyl, cyclopentyl, cyclohexyl, adamantyl, and the like. An "optionally substituted cycloalkyl" is a cycloalkyl that is optionally independently substituted, unless indicated otherwise, with one or more, preferably 1, 2, 3, 4 or 5, also 1, 2, or 3 substituents, attached at any available atom to produce a stable compound, wherein the substituents are selected from the group consisting of halogen, —OH, —$NH_2$, —$NO_2$, —CN, —C(O)—OH, —C(S)—OH, —C(O)—$NH_2$, —C(S)—$NH_2$, —S(O)$_2$—$NH_2$, —N(H)—C(O)—$NH_2$, —N(H)—C(S)—$NH_2$, —N(H)—S(O)$_2$—$NH_2$, —C(NH)—$NH_2$, —O—$R^o$, —S—$R^o$, —O—C(O)—$R^o$, —O—C(S)—$R^o$, —C(O)—$R^o$, —C(S)—$R^o$, —C(O)—O—$R^o$, —C(S)—O—$R^o$, —S(O)—$R^o$, —S(O)$_2$—$R^o$, —C(O)—N(H)—$R^o$, —C(S)—N(H)—$R^o$, —C(O)—N($R^o$)—$R^o$, —C(S)—N($R^o$)—$R^o$, —S(O)$_2$—N(H)—$R^o$, —S(O)$_2$—N($R^o$)—$R^o$, —C(NH)—N(H)—$R^o$, —C(NH)—N($R^P$)—$R^o$, —N(H)—C(O)—$R^o$, —N(H)—C(S)—$R^o$, —N($R^o$)—C(O)—$R^o$, —N($R^o$)—C(S)—$R^o$, —N(H)—S(O)$_2$—$R^o$, —N($R^o$)—S(O)$_2$—$R^o$, —N(H)—C(O)—N(H)—$R^o$, —N(H)—C(S)—N(H)—$R^o$, —N($R^o$)—C(O)—$NH_2$, —N($R^o$)—C(S)—$NH_2$, —N($R^o$)—C(O)—N(H)—$R^o$, —N($R^o$)—C(S)—N(H)—$R^o$, —N(H)—C(O)—N($R^o$)—$R^o$, —N(H)—C(S)—N($R^o$)—$R^o$, —N($R^o$)—C(O)—N($R^o$)—$R^o$, —N($R^o$)—C(S)—N($R^o$)—$R^o$, —N(H)—S(O)$_2$—N(H)—$R^o$, —N($R^o$)—S(O)$_2$—$NH_2$, —N($R^o$)—S(O)$_2$—N(H)—$R^o$, —N(H)—S(O)$_2$—N($R^o$)—$R^o$, —N($R^o$)—S(O)$_2$—N($R^o$)—$R^o$, —N(H)—$R^o$, —N($R^o$)—$R^o$, —$R^d$, —$R^e$, —$R^f$, and —$R^g$. "$C_{3-6}$ cycloalkyl" denotes cycloalkyl containing 3-6 carbon atoms. "$C_{3-5}$ cycloalkyl" denotes cycloalkyl containing 3-5 carbon atoms. It is understood that substitutions are chemically feasible and attached at any available atom to provide a stable compound.

"Heterocycloalkyl" refers to a saturated or unsaturated non-aromatic cycloalkyl group having from 5 to 10 atoms in which from 1 to 3 carbon atoms in the ring are replaced by heteroatoms of O, S or N, and are optionally fused with benzo or heteroaryl of 5-6 ring members. Heterocycloalkyl is also intended to include oxidized S or N, such as sulfinyl, sulfonyl and N-oxide of a tertiary ring nitrogen. Heterocycloalkyl is also intended to include compounds in which a ring carbon may be oxo substituted, i.e. the ring carbon is a carbonyl group, such as lactones and lactams. The point of attachment of the heterocycloalkyl ring is at a carbon or nitrogen atom such that a stable ring is retained. Examples of heterocycloalkyl groups include, but are not limited to, morpholino, tetrahydrofuranyl, dihydropyridinyl, piperidinyl, pyrrolidinyl, pyrrolidonyl, piperazinyl, dihydrobenzofuryl, and dihydroindolyl. "Nitrogen containing heterocycloalkyl" refers to heterocycloalkyl wherein at least one heteroatom is N. An "optionally substituted heterocycloalkyl" is a heterocycloalkyl that is optionally independently substituted, unless indicated otherwise, with one or more, preferably 1, 2, 3, 4 or 5, also 1, 2, or 3 substituents, attached at any available atom to produce a stable compound, wherein the substituents are selected from the group consisting of halogen, —OH, —$NH_2$, —$NO_2$, —CN, —C(O)—OH, —C(S)—OH, —C(O)—$NH_2$, —C(S)—$NH_2$, —S(O)$_2$—$NH_2$, —N(H)—C(O)—$NH_2$, —N(H)—C(S)—$NH_2$, —N(H)—S(O)$_2$—$NH_2$, —C(NH)—$NH_2$, —O—$R^o$, —S—$R^o$, —O—C(O)—$R^o$, —O—C(S)—$R^o$, —C(O)—$R^o$, —C(S)—$R^o$, —C(O)—O—$R^o$, —C(S)—O—$R^o$, —S(O)—$R^o$, —S(O)$_2$—$R^o$, —C(O)—N(H)—$R^o$, —C(S)—N(H)—$R^o$, —C(O)—N($R^o$)—$R^o$, —C(S)—N($R^o$)—$R^o$, —S(O)$_2$—N(H)—$R^o$, —S(O)$_2$—N($R^o$)—$R^o$, —C(NH)—N(H)—$R^o$, —C(NH)—N($R^P$)—$R^o$, —N(H)—C(O)—$R^o$, —N(H)—C(S)—$R^o$, —N($R^o$)—C(O)—$R^o$, —N($R^o$)—C(S)—$R^o$, —N(H)—S(O)$_2$—$R^o$, —N($R^o$)—S(O)$_2$—$R^o$, —N(H)—C(O)—N(H)—$R^o$, —N(H)—C(S)—N(H)—$R^o$, —N($R^o$)—C(O)—$NH_2$, —N($R^o$)—C(S)—$NH_2$, —N($R^o$)—C(O)—N(H)—$R^o$, —N($R^o$)—C(S)—N(H)—$R^o$, —N(H)—C(O)—N($R^o$)—$R^o$, —N(H)—C(S)—N($R^o$)—$R^o$, —N($R^o$)—C(O)—N($R^o$)—$R^o$, —N($R^o$)—C(S)—N($R^o$)—$R^o$, —N(H)—S(O)$_2$—N(H)—$R^o$, —N($R^o$)—S(O)$_2$—$NH_2$, —N($R^o$)—S(O)$_2$—N(H)—$R^o$, —N(H)—S(O)$_2$—N($R^o$)—$R^o$, —N($R^o$)—S(O)$_2$—N($R^o$)—$R^o$, —N(H)—$R^o$, —N($R^o$)—$R^o$, —$R^d$, —$R^e$, —$R^f$, and —$R^g$. It is understood that substitutions are chemically feasible and attached at any available atom to provide a stable compound.

"Aryl" alone or in combination refers to a monocyclic or bicyclic ring system containing aromatic hydrocarbons such as phenyl or naphthyl, which may be optionally fused with a cycloalkyl of preferably 5-7, more preferably 5-6, ring members. An "optionally substituted aryl" is an aryl that is optionally independently substituted, unless indicated otherwise, with one or more, preferably 1, 2, 3, 4 or 5, also 1, 2, or 3 substituents, attached at any available atom to produce a stable compound, wherein the substituents are selected from the group consisting of halogen, —OH, —NH$_2$, —NO$_2$, —CN, —C(O)—OH, —C(S)—OH, —C(O)—NH$_2$, —C(S)—NH$_2$, —S(O)$_2$—NH$_2$, —N(H)—C(O)—NH$_2$, —N(H)—C(S)—NH$_2$, —N(H)—S(O)$_2$—NH$_2$, —C(NH)—NH$_2$, —O—R$^o$, —S—R$^o$, —O—C(O)—R$^o$, —O—C(S)—R$^o$, —C(O)—R$^o$, —C(S)—R$^o$, —C(O)—O—R$^o$, —C(S)—O—R$^o$, —S(O)—R$^o$, —S(O)$_2$—R$^o$, —C(O)—N(H)—R$^o$, —C(S)—N(H)—R$^o$, —C(O)—N(R$^o$)—R$^o$, —C(S)—N(R$^o$)—R$^o$, —S(O)$_2$—N(H)—R$^o$, —S(O)$_2$—N(R$^o$)—R$^o$, —C(NH)—N(H)—R$^o$, —C(NH)—N(R$^P$)—R$^o$, —N(H)—C(O)—R$^o$, —N(H)—C(S)—R$^o$, —N(R$^o$)—C(O)—R$^o$, —N(R$^o$)—C(S)—R$^o$, —N(H)—S(O)$_2$—R$^o$, —N(R$^o$)—S(O)$_2$—R$^o$, —N(H)—C(O)—N(H)—R$^o$, —N(H)—C(S)—N(H)—R$^o$, —N(R$^o$)—C(O)—NH$_2$, —N(R$^o$)—C(S)—NH$_2$, —N(R$^o$)—C(O)—N(H)—R$^o$, —N(R$^o$)—C(S)—N(H)—R$^o$, —N(H)—C(O)—N(R$^o$)—R$^o$, —N(H)—C(S)—N(R$^o$)—R$^o$, —N(R$^o$)—C(O)—N(R$^o$)—R$^o$, —N(R$^o$)—C(S)—N(R$^o$)—R$^o$, —N(H)—S(O)$_2$—N(H)—R$^o$, —N(R$^o$)—S(O)$_2$—NH$_2$, —N(R$^o$)—S(O)$_2$—N(H)—R$^o$, —N(H)—S(O)$_2$—N(R$^o$)—R$^o$, —N(R$^o$)—S(O)$_2$—N(R$^o$)—R$^o$, —N(H)—R$^o$, —N(R$^o$)—R$^o$, —R$^d$, —R$^e$, —R$^f$, and —R$^g$. It is understood that substitutions are chemically feasible and attached at any available atom to provide a stable compound.

"Heteroaryl" alone or in combination refers to a monocyclic aromatic ring structure containing 5 or 6 ring atoms, or a bicyclic aromatic group having 8 to 10 atoms, containing one or more, preferably 1-4, more preferably 1-3, even more preferably 1-2, heteroatoms independently selected from the group consisting of O, S, and N. Heteroaryl is also intended to include oxidized S or N, such as sulfinyl, sulfonyl and N-oxide of a tertiary ring nitrogen. A carbon or nitrogen atom is the point of attachment of the heteroaryl ring structure such that a stable compound is produced. Examples of heteroaryl groups include, but are not limited to, pyridinyl, pyridazinyl, pyrazinyl, quinoaxalyl, indolizinyl, benzo[b]thienyl, quinazolinyl, purinyl, indolyl, quinolinyl, pyrimidinyl, pyrrolyl, pyrazolyl, oxazolyl, thiazolyl, thienyl, isoxazolyl, oxathiadiazolyl, isothiazolyl, tetrazolyl, imidazolyl, triazolyl, furanyl, benzofuryl, and indolyl. "Nitrogen containing heteroaryl" refers to heteroaryl wherein at least one heteroatom is N. In some instances, for example when R groups of a nitrogen combine with the nitrogen to form a 5 or 7 membered nitrogen containing heteroaryl, any heteroatoms in such 5 or 7 membered heteroaryl are N. An "optionally substituted heteroaryl" is a heteroaryl that is optionally independently substituted, unless indicated otherwise, with one or more, preferably 1, 2, 3, 4 or 5, also 1, 2, or 3 substituents, attached at any available atom to produce a stable compound, wherein the substituents are selected from the group consisting of halogen, —OH, —NH$_2$, —NO$_2$, —CN, —C(O)—OH, —C(S)—OH, —C(O)—NH$_2$, —C(S)—NH$_2$, —S(O)$_2$—NH$_2$, —N(H)—C(O)—NH$_2$, —N(H)—C(S)—NH$_2$, —N(H)—S(O)$_2$—NH$_2$, —C(NH)—NH$_2$, —O—R$^o$, —S—R$^o$, —O—C(O)—R$^o$, —O—C(S)—R$^o$, —C(O)—R$^o$, —C(S)—R$^o$, —C(O)—O—R$^o$, —C(S)—O—R$^o$, —S(O)—R$^o$, —S(O)$_2$—R$^o$, —C(O)—N(H)—R$^o$, —C(S)—N(H)—R$^o$, —C(O)—N(R$^o$)—R$^o$, —C(S)—N(R$^o$)—R$^o$, —S(O)$_2$—N(H)—R$^o$, —S(O)$_2$—N(R$^o$)—R$^o$, —C(NH)—N(H)—R$^o$, —C(NH)—N(R$^P$)—R$^o$, —N(H)—C(O)—R$^o$, —N(H)—C(S)—R$^o$, —N(H)—C(S)—R$^o$, —N(R$^o$)—C(O)—R$^o$, —N(R$^o$)—C(S)—R$^o$, —N(H)—S(O)$_2$—R$^o$, —N(R$^o$)—S(O)$_2$—R$^o$, —N(H)—C(O)—N(H)—R$^o$, —N(H)—C(S)—N(H)—R$^o$, —N(R$^o$)—C(O)—NH$_2$, —N(R$^o$)—C(S)—NH$_2$, —N(R$^o$)—C(O)—N(H)—R$^o$, —N(R$^o$)—C(S)—N(H)—R$^o$, —N(H)—C(O)—N(R$^o$)—R$^o$, —N(H)—C(S)—N(R$^o$)—R$^o$, —N(R$^o$)—C(O)—N(R$^o$)—R$^o$, —N(R$^o$)—C(S)—N(R$^o$)—R$^o$, —N(H)—S(O)$_2$—N(H)—R$^o$, —N(R$^o$)—S(O)$_2$—NH$_2$, —N(R$^o$)—S(O)$_2$—N(H)—R$^o$, —N(H)—S(O)$_2$—N(R$^o$)—R$^o$, —N(R$^o$)—S(O)$_2$—N(R$^o$)—R$^o$, —N(H)—R$^o$, —N(R$^o$)—R$^o$, —R$^d$, —R$^e$, —R$^f$, and —R$^g$. It is understood that substitutions are chemically feasible and attached at any available atom to provide a stable compound.

The variables R$^o$, R$^P$, R, R$^d$, R$^e$, R$^f$ and R$^g$ as used in the description of optional substituents for alkyl, alkenyl, alkynyl, cycloalkyl, heterocycloalkyl, aryl and heteroaryl are defined as follows:

each R$^o$, R$^P$, and R$^c$ are independently selected from the group consisting of R$^d$, R$^e$, R$^f$, and R$^g$, or R$^P$ and R$^c$ combine with the nitrogen to which they are attached to form a 5-7 membered heterocycloalkyl or a 5 or 7 membered nitrogen containing heteroaryl, wherein the 5-7 membered heterocycloalkyl or 5 or 7 membered nitrogen containing heteroaryl are optionally substituted with one or more, preferably 1, 2, 3, 4 or 5, also 1, 2, or 3 substituents selected from the group consisting of halogen, —NO$_2$, —CN, —OH, —NH$_2$, —O—R$^u$, —S—R$^u$, —N(H)—R$^u$, —N(R$^u$)—R$^u$, —R$^x$, and —R$^y$;

each R$^d$ is independently lower alkyl, wherein lower alkyl is optionally substituted with one or more, preferably 1, 2, 3, 4 or 5, also 1, 2 or 3 substituents selected from the group consisting of fluoro, —OH, —NH$_2$, —NO$_2$, —CN, —C(O)—OH, —C(S)—OH, —C(O)—NH$_2$, —C(S)—NH$_2$, —S(O)$_2$—NH$_2$, —N(H)—C(O)—NH$_2$, —N(H)—C(S)—NH$_2$, —N(H)—S(O)$_2$—NH$_2$, —C(NH)—NH$_2$, —O—R$^k$, —S—R$^k$, —O—C(O)—R$^k$, —O—C(S)—R$^k$, —C(O)—R$^k$, —C(S)—R$^k$, —C(O)—O—R$^k$, —C(S)—O—R$^k$, —S(O)—R$^k$, —S(O)$_2$—R$^k$, —C(O)—N(H)—R$^k$, —C(S)—N(H)—R$^k$, —C(O)—N(R$^k$)—R$^k$, —C(S)—N(R$^k$)—R$^k$, —S(O)$_2$—N(H)—R$^k$, —S(O)$_2$—N(R$^k$)—R$^k$, —C(NH)—N(H)—R$^k$, —C(NH)—N(R$^m$)—R$^n$, —N(H)—C(O)—R$^k$, —N(H)—C(S)—R$^k$, —N(R$^k$)—C(O)—R$^k$, —N(R$^k$)—C(S)—R$^k$, —N(H)—S(O)$_2$—R$^k$, —N(R$^k$)—S(O)$_2$—R$^k$, —N(H)—C(O)—N(H)—R$^k$, —N(H)—C(S)—N(H)—R$^k$, —N(R$^k$)—C(O)—NH$_2$, —N(R$^k$)—C(S)—NH$_2$, —N(R$^k$)—C(O)—N(H)—R$^k$, —N(R$^k$)—C(S)—N(H)—R$^k$, —N(H)—C(O)—N(R$^k$)—R$^k$, —N(H)—C(S)—N(R$^o$)—R$^k$, —N(R$^k$)—C(O)—N(R$^k$)—R$^k$, —N(R$^k$)—C(S)—N(R$^k$)—R$^k$, —N(H)—S(O)$_2$—N(H)—R$^k$, —N(R$^k$)—S(O)$_2$—NH$_2$, —N(R$^k$)—S(O)$_2$—N(H)—R$^k$, —N(H)—S(O)$_2$—N(R$^k$)—R$^k$, —N(R$^k$)—S(O)$_2$—N(R$^k$)—R$^k$, —N(H)—R$^k$, —N(R$^k$)—R$^k$, —R$^i$, and —R$^i$;

each R$^e$ is independently lower alkenyl, wherein lower alkenyl is optionally substituted with one or more, preferably 1, 2, 3, 4 or 5, also 1, 2 or 3 substituents selected from the group consisting of fluoro, —OH, —NH$_2$, —NO$_2$, —CN, —C(O)—OH, —C(S)—OH, —C(O)—NH$_2$, —C(S)—NH$_2$, —S(O)$_2$—NH$_2$, —N(H)—C(O)—NH$_2$, —N(H)—C(S)—NH$_2$, —N(H)—S(O)$_2$—NH$_2$, —C(NH)—NH$_2$, —O—R$^k$, —S—R$^k$, —O—C(O)—R$^k$, —O—C(S)—R$^k$, —C(O)—R$^k$, —C(S)—R$^k$, —C(O)—

O—R$^k$, —C(S)—O—R$^k$, —S(O)—R$^k$, —S(O)$_2$—R$^k$, —C(O)—N(H)—R$^k$, —C(S)—N(H)—R$^k$, —C(O)—N(R$^k$)—R$^k$, —C(S)—N(R$^k$)—R$^k$, —S(O)$_2$—N(H)—R$^k$, —S(O)$_2$—N(R$^k$)—R$^k$, —C(NH)—N(H)—R$^k$, —C(NH)—N(R$^m$)—R$^n$, —N(H)—C(O)—R$^k$, —N(H)—C(S)—R$^k$, —N(R$^k$)—C(O)—R$^k$, —N(R$^k$)—C(S)—R$^k$, —N(H)—S(O)$_2$—R$^k$, —N(R$^k$)—S(O)$_2$—R$^k$, —N(H)—C(O)—N(H)—R$^k$, —N(H)—C(S)—N(H)—R$^k$, —N(R$^k$)—C(O)—NH$_2$, —N(R$^k$)—C(S)—NH$_2$, —N(R$^k$)—C(O)—N(H)—R$^k$, —N(R$^k$)—C(S)—N(H)—R$^k$, —N(H)—C(O)—N(R$^k$)—R$^k$, —N(H)—C(S)—N(R$^k$)—R$^k$, —N(R$^k$)—C(O)—N(R$^k$)—R$^k$, —N(R$^k$)—C(S)—N(R$^k$)—R$^k$, —N(H)—S(O)$_2$—N(H)—R$^k$, —N(R$^k$)—S(O)$_2$—NH$_2$, —N(R$^k$)—S(O)$_2$—N(H)—R$^k$, —N(H)—S(O)$_2$—N(R$^k$)—R$^k$, —N(R$^k$)—S(O)$_2$—N(R$^k$)—R$^k$, —N(H)—R$^k$, —N(R$^k$)—R$^k$, —R$^h$, and —R;

each R$^f$ is independently lower alkynyl, wherein lower alkynyl is optionally substituted with one or more, preferably 1, 2, 3, 4 or 5, also 1, 2 or 3 substituents selected from the group consisting of fluoro, —OH, —NH$_2$, —NO$_2$, —CN, —C(O)—OH, —C(S)—OH, —C(O)—NH$_2$, —C(S)—NH$_2$, —S(O)$_2$—NH$_2$, —N(H)—C(O)—NH$_2$, —N(H)—C(S)—NH$_2$, —N(H)—S(O)$_2$—NH$_2$, —C(NH)—NH$_2$, —O—R$^k$, —S—R$^k$, —O—C(O)—R$^k$, —O—C(S)—R$^k$, —C(O)—R$^k$, —C(S)—R$^k$, —C(O)—O—R$^k$, —C(S)—O—R$^k$, —S(O)—R$^k$, —S(O)$_2$—R$^k$, —C(O)—N(H)—R$^k$, —C(S)—N(H)—R$^k$, —C(O)—N(R$^k$)—R$^k$, —C(S)—N(R$^k$)—R$^k$, —S(O)$_2$—N(H)—R$^k$, —S(O)$_2$—N(R$^k$)—R$^k$, —C(NH)—N(H)—R$^k$, —C(NH)—N(R$^m$)—R$^n$, —N(H)—C(O)—R$^k$, —N(H)—C(S)—R$^k$, —N(R$^k$)—C(O)—R$^k$, —N(R$^k$)—C(S)—R$^k$, —N(H)—S(O)$_2$—R$^k$, —N(R$^k$)—S(O)$_2$—R$^k$, —N(H)—C(O)—N(H)—R$^k$, —N(H)—C(S)—N(H)—R$^k$, —N(R$^k$)—C(O)—NH$_2$, —N(R$^k$)—C(S)—NH$_2$, —N(R$^k$)—C(O)—N(H)—R$^k$, —N(R$^k$)—C(S)—N(H)—R$^k$, —N(H)—C(O)—N(R$^k$)—R$^k$, —N(H)—C(S)—N(R$^k$)—R$^k$, —N(R$^k$)—C(O)—N(R$^k$)—R$^k$, —N(R$^k$)—C(S)—N(R$^k$)—R$^k$, —N(H)—S(O)$_2$—N(H)—R$^k$, —N(R$^k$)—S(O)$_2$—NH$_2$, —N(R$^k$)—S(O)$_2$—N(H)—R$^k$, —N(H)—S(O)$_2$—N(R$^k$)—R$^k$, —N(R$^k$)—S(O)$_2$—N(R$^k$)—R$^k$, —N(H)—R$^k$, —N(R$^k$)—R$^k$, —R$^h$, and —R$^i$;

each R$^g$ is independently selected from the group consisting of cycloalkyl, heterocycloalkyl, aryl, and heteroaryl, wherein cycloalkyl, heterocycloalkyl, aryl, and heteroaryl are optionally substituted with one or more, preferably 1, 2, 3, 4 or 5, also 1, 2 or 3 substituents selected from the group consisting of halogen, —OH, —NH$_2$, —NO$_2$, —CN, —C(O)—OH, —C(S)—OH, —C(O)—NH$_2$, —C(S)—NH$_2$, —S(O)$_2$—NH$_2$, —N(H)—C(O)—NH$_2$, —N(H)—C(S)—NH$_2$, —N(H)—S(O)$_2$—NH$_2$, —C(NH)—NH$_2$, —O—R$^k$, —S—R$^k$, —O—C(O)—R$^k$, —O—C(S)—R$^k$, —C(O)—R$^k$, —C(S)—R$^k$, —C(O)—O—R$^k$, —C(S)—O—R$^k$, —S(O)—R$^k$, —S(O)$_2$—R$^k$, —C(O)—N(H)—R$^k$, —C(S)—N(H)—R$^k$, —C(O)—N(R$^k$)—R$^k$, —C(S)—N(R$^k$)—R$^k$, —S(O)$_2$—N(H)—R$^k$, —S(O)$_2$—N(R$^k$)—R$^k$, —C(NH)—N(H)—R$^k$, —C(NH)—N(R$^m$)—R$^n$, —N(H)—C(O)—R$^k$, —N(H)—C(S)—R$^k$, —N(R$^k$)—C(O)—R$^k$, —N(R$^k$)—C(S)—R$^k$, —N(H)—S(O)$_2$—R$^k$, —N(R$^k$)—S(O)$_2$—R$^k$, —N(H)—C(O)—N(H)—R$^k$, —N(H)—C(S)—N(H)—R$^k$, —N(R$^k$)—C(O)—NH$_2$, —N(R$^k$)—C(S)—NH$_2$, —N(R$^k$)—C(O)—N(H)—R$^k$, —N(R$^k$)—C(S)—N(H)—R$^k$, —N(H)—C(O)—N(R$^k$)—R$^k$, —N(H)—C(S)—N(R$^k$)—R$^k$, —N(R$^k$)—C(O)—N(R$^k$)—R$^k$, —N(R$^k$)—C(S)—N(R$^k$)—R$^k$, —N(H)—S(O)$_2$—N(H)—R$^k$, —N(R$^k$)—S(O)$_2$—NH$_2$, —N(R$^k$)—S(O)$_2$—N(H)—R$^k$, —N(H)—S(O)$_2$—N(R$^k$)—R$^k$, —N(R$^k$)—S(O)$_2$—N(R$^k$)—R$^k$, —N(H)—R$^k$, —N(R$^k$)—R$^k$, —R$^h$, —R$^i$, and —R$^j$;

wherein R$^k$, R$^m$, and R$^n$ at each occurrence are independently selected from the group consisting of R$^h$, R$^i$, and R$^j$, or R$^m$ and R$^n$ combine with the nitrogen to which they are attached to form a 5-7 membered heterocycloalkyl or a 5 or 7 membered nitrogen containing heteroaryl, wherein the 5-7 membered heterocycloalkyl or 5 or 7 membered nitrogen containing heteroaryl are optionally substituted with one or more, preferably 1, 2, 3, 4 or 5, also 1, 2, or 3 substituents selected from the group consisting of halogen, —NO$_2$, —CN, —OH, —NH$_2$, O—R$^u$, —S—R$^u$, —N(H)—R$^u$, —NR$^u$R$^u$, —R$^x$, and —R$^y$;

wherein each R$^h$ is independently lower alkyl optionally substituted with one or more, preferably 1, 2, 3, 4 or 5, also 1, 2, or 3 substituents selected from the group consisting of fluoro, —OH, —NH$_2$, —NO$_2$, —CN, —C(O)—OH, —C(S)—OH, —C(O)—NH$_2$, —C(S)—NH$_2$, —S(O)$_2$—NH$_2$, —N(H)—C(O)—NH$_2$, —N(H)—C(S)—NH$_2$, —N(H)—S(O)$_2$—NH$_2$, —C(NH)—NH$_2$, —O—R$^r$, —S—R$^r$, —O—C(O)—R$^r$, —O—C(S)—R$^r$, —C(O)—R$^r$, —C(S)—R$^r$, —C(O)—O—R$^r$, —C(S)—O—R$^r$, —S(O)—R$^r$, —S(O)$_2$—R$^r$, —C(O)—N(H)—R$^r$, —C(S)—N(H)—R$^r$, —C(O)—N(R$^r$)—R$^r$, —C(S)—N(R$^r$)—R$^r$, —S(O)$_2$—N(H)—R$^r$, —S(O)$_2$—N(R$^r$)—R$^r$, —C(NH)—N(H)—R$^r$, —C(NH)—N(R$^s$)—R$^t$, —N(H)—C(O)—R$^r$, —N(H)—C(S)—R$^r$, —N(R$^r$)—C(O)—R$^r$, —N(R$^r$)—C(S)—R$^r$, —N(H)—S(O)$_2$—R$^r$, —N(R$^r$)—S(O)$_2$—R$^r$, —N(H)—C(O)—N(H)—R$^r$, —N(H)—C(S)—N(H)—R$^r$, —N(R$^r$)—C(O)—NH$_2$, —N(R$^r$)—C(S)—NH$_2$, —N(R$^r$)—C(O)—N(H)—R$^o$, —N(R$^r$)—C(S)—N(H)—R$^o$, —N(H)—C(O)—N(R$^r$)—R$^r$, —N(H)—C(S)—N(O)R$^r$, —N(R$^r$)—C(O)—N(R$^r$)—R$^r$, —N(R$^r$)—C(S)—N(R$^r$)—R$^r$, —N(H)—S(O)$_2$—N(H)—R$^r$, —N(R$^r$)—S(O)$_2$—NH$_2$, —N(R$^r$)—S(O)$_2$—N(H)—R$^r$, —N(H)—S(O)$_2$—N(R$^r$)—R$^r$, —N(R$^r$)—S(O)$_2$—N(R$^r$)—R$^r$, —N(H)—R$^r$, —N(R$^r$)—, —R$^i$, and —R$^j$;

wherein each R is independently selected from the group consisting of lower alkenyl and lower alkynyl, wherein lower alkenyl or lower alkynyl are optionally substituted with one or more, preferably 1, 2, 3, 4 or 5, also 1, 2 or 3 substituents selected from the group consisting of fluoro, —OH, —NH$_2$, —NO$_2$, —CN, —C(O)—OH, —C(S)—OH, —C(O)—NH$_2$, —C(S)—NH$_2$, —S(O)$_2$—NH$_2$, —N(H)—C(O)—NH$_2$, —N(H)—C(S)—NH$_2$, —N(H)—S(O)$_2$—NH$_2$, —C(NH)—NH$_2$, —O—R$^r$, —S—R$^r$, —O—C(O)—R$^r$, —O—C(S)—R$^r$, —C(O)—R$^r$, —C(S)—R$^r$, —C(O)—O—R$^r$, —C(S)—O—R$^r$, —S(O)—R$^r$, —S(O)$_2$—R$^r$, —C(O)—N(H)—R$^r$, —C(S)—N(H)—R$^r$, —C(O)—N(R$^r$)—R$^r$, —C(S)—N(R$^r$)—R$^r$, —S(O)$_2$—N(H)—R$^r$, —S(O)$_2$—N(R$^r$)—R$^r$, —C(NH)—N(H)—R$^r$, —C(NH)—N(R$^r$)—R$^r$, —N(H)—C(O)—R$^r$, —N(H)—C(S)—R$^r$, —N(R$^r$)—C(O)—R$^r$, —N(R$^r$)—C(S)—R$^r$, —N(H)—S(O)$_2$—R$^r$, —N(R$^r$)—S(O)$_2$—R$^r$, —N(H)—C(O)—N(H)—R$^r$, —N(H)—C(S)—N(H)—R$^r$, —N(R$^r$)—C(O)—NH$_2$, —N(R$^r$)—C(S)—NH$_2$, —N(R$^r$)—C(O)—N(H)—R$^r$, —N(R$^r$)—C(S)—N(H)—R$^r$, —N(H)—C(O)—N(R$^r$)—R$^r$, —N(H)—C(S)—N(R$^r$)—R$^r$, —N(R$^r$)—C(O)—N(R$^r$)—R$^r$, —N(R$^r$)—C(S)—N(R$^r$)—R$^r$, —N(H)—S(O)$_2$—N(H)—, —N(R$^r$)—S(O)$_2$—NH$_2$, —N(R$^r$)—S(O)$_2$—N (H)—, —N(H)—S(O)₂—N(Rʳ)—Rʳ, —N(Rʳ)—S(O)₂—N(Rʳ)—Rʳ, —N(H)—Rʳ, —N(Rʳ)—Rʳ, and —Rʲ;

wherein each Rʲ is independently selected from the group consisting of cycloalkyl, heterocycloalkyl, aryl, and heteroaryl, wherein cycloalkyl, heterocycloalkyl, aryl, and heteroaryl are optionally substituted with one or more, preferably 1, 2, 3, 4 or 5, also 1, 2 or 3 substituents selected from the group consisting of halogen, —OH, —NH₂, —NO₂, —CN, —C(O)—OH, —C(S)—OH, —C(O)—NH₂, —C(S)—NH₂, —S(O)₂—NH₂, —N(H)—C(O)—NH₂, —N(H)—C(S)—NH₂, —N(H)—S(O)₂—NH₂, —C(NH)—NH₂, —O—Rʳ, —S—Rʳ, —O—C(O)—Rʳ, —O—C(S)—Rʳ, —C(O)—Rʳ, —C(S)—Rʳ, —C(O)—O—Rʳ, —C(S)—O—Rʳ, —S(O)—Rʳ, —S(O)₂—Rʳ, —C(O)—N(H)—Rʳ, —C(S)—N(H)—Rʳ, —C(O)—N(Rʳ)—Rʳ, —C(S)—N(Rʳ)—Rʳ, —S(O)₂—N(H)—Rʳ, —S(O)₂—N(Rʳ)—Rʳ, —C(NH)—N(H)—Rʳ, —C(NH)—N(Rˢ)—Rᵗ, —N(H)—C(O)—Rʳ, —N(H)—C(S)—Rʳ, —N(Rʳ)—C(O)—Rᵒ, —N(Rʳ)—C(S)—Rʳ, —N(H)—S(O)₂—Rʳ, —N(Rʳ)—S(O)₂—Rʳ, —N(H)—C(O)—N(H)—Rʳ, —N(H)—C(S)—N(H)—Rʳ, —N(Rʳ)—C(O)—NH₂, —N(Rʳ)—C(S)—NH₂, —N(Rʳ)—C(O)—N(H)—Rʳ, —N(Rʳ)—C(S)—N(H)—Rʳ, —N(H)—C(O)—N(Rʳ)—Rʳ, —N(H)—C(S)—N(Rʳ)—Rʳ, —N(Rʳ)—C(O)—N(Rʳ)—Rʳ, —N(Rʳ)—C(S)—N(Rʳ)—Rʳ, —N(H)—S(O)₂—N(H)—Rʳ, —N(Rʳ)—S(O)₂—NH₂, —N(Rʳ)—S(O)₂—N(H)—Rʳ, —N(H)—S(O)₂—N(Rʳ)—Rʳ, —N(Rʳ)—S(O)₂—N(Rʳ)—Rʳ, —N(H)—Rʳ, —N(Rʳ)—Rʳ, cycloalkylamino, and —Rˣ;

wherein each Rʳ, Rˢ, and Rᵗ at each occurrence are independently selected from the group consisting of lower alkyl, C₃₋₆ alkenyl, C₃₋₆ alkynyl, cycloalkyl, heterocycloalkyl, aryl and heteroaryl, wherein lower alkyl is optionally substituted with one or more, preferably 1, 2, 3, 4 or 5, also 1, 2, or 3 substituents selected from the group consisting of —Rʸ, fluoro, —OH, —NH₂, lower alkoxy, fluoro substituted lower alkoxy, lower alkylthio, fluoro substituted lower alkylthio, mono-alkylamino, di-alkylamino, and cycloalkylamino, and wherein C₃₋₆ alkenyl or C₃₋₆ alkynyl are optionally substituted with one or more, preferably 1, 2, 3, 4 or 5, also 1, 2, or 3 substituents selected from the group consisting of —Rʸ, fluoro, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino, and wherein cycloalkyl, heterocycloalkyl, aryl, and heteroaryl are optionally substituted with one or more, preferably 1, 2, 3, 4 or 5, also 1, 2, or 3 substituents selected from the group consisting of halogen, —OH, —NH₂, —NO₂, —CN, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino, or Rˢ and Rᵗ combine with the nitrogen to which they are attached to form a 5-7 membered heterocycloalkyl or a 5 or 7 membered nitrogen containing heteroaryl, wherein the 5-7 membered heterocycloalkyl or 5 or 7 membered nitrogen containing heteroaryl are optionally substituted with one or more, preferably 1, 2, 3, 4 or 5, also 1, 2, or 3 substituents selected from the group consisting of halogen, —NO₂, —CN, —OH, —NH₂, O—Rᵘ, —S—Rᵘ, —N(H)—Rᵘ, —N(Rᵘ)—Rᵘ, —Rˣ, and —Rʸ;

wherein each Rᵘ is independently selected from the group consisting of lower alkyl, C₃₋₆ alkenyl, C₃₋₆ alkynyl, cycloalkyl, heterocycloalkyl, aryl, and heteroaryl, wherein lower alkyl is optionally substituted with one or more, preferably 1, 2, 3, 4 or 5, also 1, 2, or 3 substituents selected from the group consisting of —Rʸ, fluoro, —OH, —NH₂, lower alkoxy, fluoro substituted lower alkoxy, lower alkylthio, fluoro substituted lower alkylthio, mono-alkylamino, di-alkylamino, and cycloalkylamino, and wherein C₃₋₆ alkenyl or C₃₋₆ alkynyl are optionally substituted with one or more, preferably 1, 2, 3, 4 or 5, also 1, 2, or 3 substituents selected from the group consisting of —Rʸ, fluoro, —OH, —NH₂, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino, and wherein cycloalkyl, heterocycloalkyl, aryl, and heteroaryl are optionally substituted with one or more, preferably 1, 2, 3, 4 or 5, also 1, 2, or 3 substituents selected from the group consisting of halogen, —OH, —NH₂, —NO₂, —CN, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;

wherein each Rˣ is selected from the group consisting of lower alkyl, lower alkenyl and lower alkynyl, wherein lower alkyl is optionally substituted with one or more, preferably 1, 2, 3, 4 or 5, also 1, 2, or 3 substituents selected from the group consisting of —Rʸ, fluoro, —OH, —NH₂, lower alkoxy, fluoro substituted lower alkoxy, lower alkylthio, fluoro substituted lower alkylthio, mono-alkylamino, di-alkylamino, and cycloalkylamino, and wherein lower alkenyl or lower alkynyl are optionally substituted with one or more, preferably 1, 2, 3, 4 or 5, also 1, 2, or 3 substituents selected from the group consisting of —Rʸ, fluoro, —OH, —NH₂, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;

wherein each Rʸ is selected from the group consisting of cycloalkyl, heterocycloalkyl, aryl, and heteroaryl, wherein cycloalkyl, heterocycloalkyl, aryl, and heteroaryl are optionally substituted with one or more, preferably 1, 2, 3, 4 or 5, also 1, 2, or 3 substituents selected from the group consisting of halogen, —OH, —NH₂, —NO₂, —CN, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino.

In some embodiments, all occurrences of optionally substituted lower alkyl, optionally substituted lower alkenyl, optionally substituted C₃₋₆ alkenyl, optionally substituted lower alkynyl, or optionally substituted C₃₋₆ alkynyl are optionally substituted with one or more, also 1, 2 or 3 groups or substituents selected from the group consisting of fluoro, —NO₂, —CN, —O—R¹ᵃ, —S—R¹ᵃ, —N(R¹ᵃ)—R¹ᵃ, —O—C(O)—R¹ᵃ, —O—C(S)—R¹ᵃ, —C(O)—R¹ᵃ, —C(S)—R¹ᵃ, —C(O)—O—R¹ᵃ, —C(S)—O—R¹ᵃ, —C(O)—N(R¹ᵃ)—R¹ᵃ, —C(S)—N(R¹ᵃ)—R¹ᵃ, —S(O)₂—N(R¹ᵃ)—R¹ᵃ, —C(NH)—N(R¹ᵃ)—R¹ᵃ, —N(R¹ᵃ)—C(O)—R¹ᵃ, —N(R¹ᵃ)—C(S)—R¹ᵃ, —N(R¹ᵃ)—S(O)₂—Rᵃ, —N(R¹ᵃ)—C(O)—N(R¹ᵃ)—R¹ᵃ, —N(R¹ᵃ)—C(S)—N(R¹ᵃ)—R¹ᵃ, —N(R¹ᵃ)—S(O)₂—N(R¹ᵃ)—R¹ᵃ, —S(O)—

$R^{1a}$, —S(O)$_2$—$R^{1a}$, cycloalkyl, heterocycloalkyl, aryl and heteroaryl; wherein cycloalkyl, heterocycloalkyl, aryl and heteroaryl are optionally substituted with one or more, also 1, 2 or 3 groups or substituents selected from the group consisting of halogen, —NO$_2$, —CN, —O—$R^{1a}$, —S—$R^{1a}$, —N($R^{1a}$)—$R^{1a}$, —O—C(O)—$R^{1a}$, —O—C(S)—$R^{1a}$, —C(O)—$R^{1a}$, —C(S)—$R^{1a}$, —C(O)—O—$R^{1a}$, —C(S)—O—$R^{1a}$, —C(O)—N($R^{1a}$)—$R^{1a}$, —C(S)—N($R^{1a}$)—$R^{1a}$, —S(O)$_2$—N($R^{1a}$)—$R^{1a}$, —C(NH)—N($R^{1a}$)—$R^{1a}$, —N($R^{1a}$)—C(O)—$R^{1a}$, —N($R^{1a}$)—C(S)—$R^{1a}$, —N($R^{1a}$)—S(O)$_2$—$R^{1a}$, —N($R^{1a}$)—C(O)—N($R^{1a}$)—$R^{1a}$, —N($R^{1a}$)—C(S)—N($R^{1a}$)—$R^{1a}$, —N($R^{1a}$)—S(O)$_2$—N($R^{1a}$)—$R^{1a}$, —S(O)—$R^{1a}$, —S(O)$_2$—$R^{1a}$, —$R^{1b}$, and lower alkyl optionally substituted with one or more, also 1, 2 or 3 groups or substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and —$R^{1b}$; and all occurrences of optionally substituted cycloalkyl, optionally substituted heterocycloalkyl, optionally substituted 5-7 membered heterocycloalkyl, optionally substituted aryl, optionally substituted heteroaryl, or optionally substituted 5 or 7 membered nitrogen containing heteroaryl are optionally substituted with one or more, also 1, 2, or 3 groups or substituents selected from the group consisting of halogen, —NO$_2$, —CN, —O—$R^{1a}$, —S—$R^{1a}$, —N($R^{1a}$)—$R^{1a}$, —O—C(O)—$R^{1a}$, —O—C(S)—$R^{1a}$, —C(O)—$R^{1a}$, —C(S)—$R^{1a}$, —C(O)—O—$R^{1a}$, —C(S)—O—$R^{1a}$, —C(O)—N($R^{1a}$)—$R^{1a}$, —C(S)—N($R^{1a}$)—$R^{1a}$, —S(O)$_2$—N($R^{1a}$)—$R^{1a}$, —C(NH)—N($R^{1a}$)—$R^{1a}$, —N($R^{1a}$)—C(O)—$R^{1a}$, —N($R^{1a}$)—C(S)—$R^{1a}$, —N($R^{1a}$)—S(O)$_2$—$R^{1a}$, —N($R^{1a}$)—C(O)—N($R^{1a}$)—$R^{1a}$, —N($R^{1a}$)—C(S)—N($R^{1a}$)—$R^{1a}$, —N($R^{1a}$)—S(O)$_2$—N($R^{1a}$)—$R^{1a}$, —S(O)—$R^{1a}$, —S(O)$_2$—$R^{1a}$, —$R^{1b}$, and lower alkyl optionally substituted with one or more, also 1, 2 or 3 groups or substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and —$R^{1b}$; wherein $R^{1a}$ is selected from the group consisting of hydrogen, —$R^{1b}$, and lower alkyl optionally substituted with one or more, also 1, 2 or 3 groups or substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and —$R^{1b}$, and wherein —$R^{1b}$ is selected from the group consisting of cycloalkyl, heterocycloalkyl, aryl and heteroaryl, wherein cycloalkyl, heterocycloalkyl, aryl and heteroaryl are optionally substituted with one or more, also 1, 2 or 3 groups or substituents selected from the group consisting of halogen, —CN, —OH, —NH$_2$, lower alkoxy, fluoro substituted lower alkoxy, lower alkylthio, fluoro substituted lower alkylthio, mono-alkylamino, di-alkylamino, and cycloalkylamino.

In some embodiments, all occurrences of optionally substituted lower alkyl, optionally substituted lower alkenyl, optionally substituted C$_{3-6}$ alkenyl, optionally substituted lower alkynyl, or optionally substituted C$_{3-6}$ alkynyl are optionally substituted with one or more, also 1, 2 or 3 groups or substituents selected from the group consisting of fluoro, —CN, —O—$R^{1a}$, —S—$R^{1a}$, —N($R^{1a}$)—$R^{1a}$, —C(O)—$R^{1a}$, —C(S)—$R^{1a}$, —C(O)—O—$R^{1a}$, —C(O)—N($R^{1a}$)—$R^{1a}$, —C(S)—N($R^{1a}$)—$R^{1a}$, —S(O)$_2$—N($R^{1a}$)—$R^{1a}$, —N($R^{1a}$)—C(O)—$R^{1a}$, —N($R^{1a}$)—C(S)—$R^{1a}$, —N($R^{1a}$)—S(O)$_2$—$R^{1a}$, —S(O)—$R^{1a}$, —S(O)$_2$—$R^{1a}$, cycloalkyl, heterocycloalkyl, aryl and heteroaryl, wherein cycloalkyl, heterocycloalkyl, aryl and heteroaryl are optionally substituted with one or more, also 1, 2 or 3 groups or substituents selected from the group consisting of halogen, —CN, —O—$R^{1a}$, —S—$R^{1a}$, —N($R^{1a}$)—$R^{1a}$, —C(O)—$R^{1a}$, —C(S)—$R^{1a}$, —C(O)—O—$R^{1a}$, —C(O)—N($R^{1a}$)—$R^{1a}$, —C(S)—N($R^{1a}$)—$R^{1a}$, —S(O)$_2$—N($R^{1a}$)—$R^{1a}$, —N($R^{1a}$)—C(O)—$R^{1a}$, —N($R^{1a}$)—C(S)—$R^{1a}$, —N($R^{1a}$)—S(O)$_2$—$R^{1a}$, —S(O)—$R^{1a}$, —S(O)$_2$—$R^{1a}$, —$R^{1b}$, and lower alkyl optionally substituted with one or more, also 1, 2 or 3 groups or substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and —$R^{1b}$; and all occurrences of optionally substituted cycloalkyl, optionally substituted heterocycloalkyl, optionally substituted 5-7 membered heterocycloalkyl, optionally substituted aryl, optionally substituted heteroaryl, or optionally substituted 5 or 7 membered nitrogen containing heteroaryl are optionally substituted with one or more, also 1, 2, or 3 groups or substituents selected from the group consisting of halogen, —CN, —O—$R^{1a}$, —S—$R^{1a}$, —N($R^{1a}$)—$R^{1a}$, —C(O)—$R^{1a}$, —C(S)—$R^{1a}$, —C(O)—O—$R^{1a}$, —C(O)—N($R^{1a}$)—$R^{1a}$, —C(S)—N($R^{1a}$)—$R^{1a}$, —S(O)$_2$—N($R^{1a}$)—$R^{1a}$, —N($R^{1a}$)—C(O)—$R^{1a}$, —N($R^{1a}$)—C(S)—$R^{1a}$, —N($R^{1a}$)—S(O)$_2$—$R^{1a}$, —S(O)—$R^{1a}$, —S(O)$_2$—$R^{1a}$, —$R^{1b}$, and lower alkyl optionally substituted with one or more, also 1, 2 or 3 groups or substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and —$R^{1b}$; wherein $R^{1a}$ is selected from the group consisting of hydrogen, —$R^{1b}$, and lower alkyl optionally substituted with one or more, also 1, 2 or 3 groups or substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and —$R^{1b}$, and wherein —$R^{1b}$ is selected from the group consisting of cycloalkyl, heterocycloalkyl, aryl and heteroaryl, wherein cycloalkyl, heterocycloalkyl, aryl and heteroaryl are optionally substituted with one or more, also 1, 2 or 3 groups or substituents selected from the group consisting of halogen, —CN, —OH, —NH$_2$, lower alkoxy, fluoro substituted lower alkoxy, lower alkylthio, fluoro substituted lower alkylthio, mono-alkylamino, di-alkylamino, and cycloalkylamino.

"Lower alkoxy" denotes the group —OR$^z$, where R$^z$ is lower alkyl. "Substituted lower alkoxy" denotes lower alkoxy in which R$^z$ is lower alkyl substituted with one or more substituents as indicated herein, for example, in the description of compounds of Formula I, including descriptions of substituted cycloalkyl, heterocycloalkyl, aryl and heteroaryl, attached at any available atom to provide a stable compound. Preferably, substitution of lower alkoxy is with 1, 2, 3, 4, or 5 substituents, also 1, 2, or 3 substituents. For example "fluoro substituted lower alkoxy" denotes lower alkoxy in which the lower alkyl is substituted with one or more fluoro atoms, where preferably the lower alkoxy is substituted with 1, 2, 3, 4 or 5 fluoro atoms, also 1, 2, or 3 fluoro atoms. It is understood that substitutions on alkoxy are chemically feasible and attached at any available atom to provide a stable compound.

"Lower alkylthio" denotes the group —SR$^{aa}$, where R$^{aa}$ is lower alkyl. "Substituted lower alkylthio" denotes lower alkylthio in which R$^{aa}$ is lower alkyl substituted with one or more substituents as indicated herein, for example, in the description of compounds of Formula I, including descriptions of substituted cycloalkyl, heterocycloalkyl, aryl and heteroaryl, attached at any available atom to provide a stable compound. Preferably, substitution of lower alkylthio is with 1, 2, 3, 4, or 5 substituents, also 1, 2, or 3 substituents. For example "fluoro substituted lower alkylthio" denotes lower alkylthio in which the lower alkyl is substituted with one or more fluoro atoms, where preferably the lower alkylthio is substituted with 1, 2, 3, 4 or 5 fluoro atoms, also 1, 2, or 3 fluoro atoms. It is understood that substitutions on alkylthio are chemically feasible and attached at any available atom to provide a stable compound.

"Amino" or "amine" denotes the group —$NH_2$. "Mono-alkylamino" denotes the group —$NHR^{bb}$ where $R^{bb}$ is lower alkyl. "Di-alkylamino" denotes the group —$NR^{bb}R^{cc}$, where $R^{bb}$ and $R^{cc}$ are independently lower alkyl. "Cycloalkylamino" denotes the group —$NR^{dd}R^{ee}$, where $R^{dd}$ and $R^{ee}$ combine with the nitrogen to form a 5-7 membered heterocycloalkyl, where the heterocycloalkyl may contain an additional heteroatom within the ring, such as O, N, or S, and may also be further substituted with lower alkyl. Examples of 5-7 membered heterocycloalkyl include, but are not limited to, piperidine, piperazine, 4-methylpiperazine, morpholine, and thiomorpholine. It is understood that when mono-alkylamino, di-alkylamino, or cycloalkylamino are substituents on other moieties, these are chemically feasible and attached at any available atom to provide a stable compound.

As used herein, the term "composition" refers to a formulation suitable for administration to an intended animal subject for therapeutic purposes that contains at least one pharmaceutically active compound and at least one pharmaceutically acceptable carrier or excipient.

The term "pharmaceutically acceptable" indicates that the indicated material does not have properties that would cause a reasonably prudent medical practitioner to avoid administration of the material to a patient, taking into consideration the disease or conditions to be treated and the respective route of administration. For example, it is commonly required that such a material be essentially sterile, e.g., for injectables.

In the present context, the term "therapeutically effective" or "effective amount" indicates that the materials or amount of material is effective to prevent, alleviate, or ameliorate one or more symptoms of a disease or medical condition, and/or to prolong the survival of the subject being treated.

In the present context, the terms "synergistically effective" or "synergistic effect" indicate that two or more compounds that are therapeutically effective, when used in combination, provide improved therapeutic effects greater than the additive effect that would be expected based on the effect of each compound used by itself.

As used herein, the terms "ligand" and "modulator" are used equivalently to refer to a compound that changes (i.e., increases or decreases) the activity of a target biomolecule, e.g., an enzyme such as a kinase. The term "inhibitor" refers to a modulator that decreases the activity of the target biomolecule. Generally a ligand or modulator will be a small molecule, where "small molecule refers to a compound with a molecular weight of 1500 daltons or less, or preferably 1000 daltons or less, 800 daltons or less, or 600 daltons or less.

In the context of compounds binding to a target, the terms "greater affinity" and "selective" indicates that the compound binds more tightly than a reference compound, or than the same compound in a reference condition, i.e., with a lower dissociation constant. In some embodiments, the greater affinity (i.e. selectivity) is at least 2, 3, 4, 5, 8, 10, 50, 100, 200, 400, 500, 1000, or 10,000-fold greater affinity.

As used herein in connection with compounds of the invention, the term "synthesizing" and like terms means chemical synthesis from one or more precursor materials.

By "assaying" is meant the creation of experimental conditions and the gathering of data regarding a particular result of the experimental conditions. For example, enzymes can be assayed based on their ability to act upon a detectable substrate. A compound or ligand can be assayed based on its ability to bind to a particular target molecule or molecules.

As used herein, the term "modulating" or "modulate" refers to an effect of altering a biological activity, especially a biological activity associated with a particular biomolecule such as a protein kinase. For example, an agonist or antagonist of a particular biomolecule modulates the activity of that biomolecule, e.g., an enzyme, by either increasing (e.g. agonist, activator), or decreasing (e.g. antagonist, inhibitor) the activity of the biomolecule, such as an enzyme. Such activity is typically indicated in terms of an inhibitory concentration ($IC_{50}$) or excitation concentration ($EC_{50}$) of the compound for an inhibitor or activator, respectively, with respect to, for example, an enzyme.

In the context of the use, testing, or screening of compounds that are or may be modulators, the term "contacting" means that the compound(s) are caused to be in sufficient proximity to a particular molecule, complex, cell, tissue, organism, or other specified material that potential binding interactions and/or chemical reaction between the compound and other specified material can occur.

As used herein in connection with amino acid or nucleic acid sequence, the term "isolate" indicates that the sequence is separated from at least a portion of the amino acid and/or nucleic acid sequences with which it would normally be associated.

In connection with amino acid or nucleic sequences, the term "purified" indicates that the subject molecule constitutes a significantly greater proportion of the biomolecules in a composition than the proportion observed in a prior composition, e.g., in a cell culture. The greater proportion can be 2-fold, 5-fold, 10-fold, or more than 10-fold, with respect to the proportion found in the prior composition.

The present invention concerns compounds of Formula I, and all sub-generic formulae, that are modulators of protein kinases, for example without limitation, the compounds are modulators of at least one of the kinases selected from the group consisting of Abl, Akt1, Akt2, Akt3, ALK, Alk5, A-Raf, B-Raf, Brk, Btk, Cdk2, CDK4, CDK5, CDK6, CHK1, c-Raf-1, Csk, EGFR, EphA1, EphA2, EphB2, EphB4, Erk2, Fak, FGFR1, FGFR2, FGFR3, FGFR4, Flt1, Flt3, Flt4, Fms, Frk, Fyn, Gsk3α, Gsk3β, HCK, Her2/Erbb2, Her4/Erbb4, IGF1R, IKK beta, Irak4, Itk, Jak1, Jak2, Jak3, Jnk1, Jnk2, Jnk3, Kdr, Kit, Lck, Lyn, MAP2K1, MAP2K2, MAP4K4, MAPKAPK2, Met, Mnk1, MLK1, p38, PDGFRA, PDGFRB, PDPK1, Pim1, Pim2, Pim3, PKC alpha, PKC beta, PKC theta, Plk1, Pyk2, Ret, ROCK1, ROCK2, Ron, Src, Stk6, Syk, TEC, Tie2, TrkA, TrkB, Yes, and Zap70, and any mutations thereof, and the use of such compounds in the treatment of diseases or conditions.

Kinase Targets and Indications of the Invention

Protein kinases play key roles in propagating biochemical signals in diverse biological pathways. More than 500 kinases have been described, and specific kinases have been implicated in a wide range of diseases or conditions (i.e., indications), including for example without limitation, cancer, cardiovascular disease, inflammatory disease, neurological disease, and other diseases. As such, kinases represent important control points for small molecule therapeutic intervention. Specific target protein kinases contemplated by the present invention are described in the art, including, without limitation, protein kinases as described in U.S. patent application Ser. No. 11/473,347 (see also, PCT publication WO2007002433), the disclosure of which is hereby incorporated by reference in its entirety, including all specifications, figures, and tables, and for all purposes, as well as the following:

A-Raf:

Target kinase A-Raf (i.e., v-raf murine sarcoma 3611 viral oncogene homolog 1) is a 67.6 kDa serine/threonine kinase encoded by chromosome Xp11.4-p11.2 (symbol: ARAF). The mature protein comprises RBD (i.e., Ras binding domain) and phorbol-ester/DAG-type zinc finger domain and is involved in the transduction of mitogenic signals from the cell membrane to the nucleus. A-Raf inhibitors may be useful in treating neurologic diseases such as multi-infarct dementia, head injury, spinal cord injury, Alzheimer's disease (AD), Parkinson's disease; neoplastic diseases including, but not limited to, melanoma, glioma, sarcoma, carcinoma (e.g. colorectal, lung, breast, pancreatic, thyroid, renal, ovarian), lymphoma (e.g. histiocytic lymphoma), neurofibromatosis, myelodysplastic syndrome, leukemia, tumor angiogenesis; pain of neuropathic or inflammatory origin, including acute pain, chronic pain, cancer-related pain and migraine; and diseases associated with muscle regeneration or degeneration, including, but not limited to, vascular restenosis, sarcopenia, muscular dystrophies (including, but not limited to, Duchenne, Becker, Emery-Dreifuss, Limb-Girdle, Facioscapulohumeral, Myotonic, Oculopharyngeal, Distal and Congenital Muscular Dystrophies), motor neuron diseases (including, but not limited to, amyotrophic lateral sclerosis, infantile progressive spinal muscular atrophy, intermediate spinal muscular atrophy, juvenile spinal muscular atrophy, spinal bulbar muscular atrophy, and adult spinal muscular atrophy), inflammatory myopathies (including, but not limited to, dermatomyositis, polymyositis, and inclusion body myositis), diseases of the neuromuscular junction (including, but not limited to, myasthenia gravis, Lambert-Eaton syndrome, and congenital myasthenic syndrome), myopathies due to endocrine abnormalities (including, but not limited to, hyperthyroid myopathy and hypothyroid myopathy) diseases of peripheral nerve (including, but not limited to, Charcot-Marie-Tooth disease, Dejerine-Sottas disease, and Friedreich's ataxia), other myopathies (including, but not limited to, myotonia congenita, paramyotonia congenita, central core disease, nemaline myopathy, myotubular myopathy, and periodic paralysis), and metabolic diseases of muscle (including, but not limited to, phosphorylase deficiency, acid maltase deficiency, phosphofructokinase deficiency, debrancher enzyme deficiency, mitochondrial myopathy, carnitine deficiency, carnitine palmatyl transferase deficiency, phosphoglycerate kinase deficiency, phosphoglycerate mutase deficiency, lactate dehydrogenase deficiency, and myoadenylate deaminase deficiency).

B-Raf:

Target kinase B-Raf (i.e., v-raf murine sarcoma viral oncogene homolog B1) is a 84.4 kDa serine/threonine kinase encoded by chromosome 7q34 (symbol: BRAF). The mature protein comprises RBD (i.e., Ras binding domain), C1 (i.e., protein kinase C conserved region 1) and STK (i.e., serine/threonine kinase) domains.

Target kinase B-Raf is involved in the transduction of mitogenic signals from the cell membrane to the nucleus and may play a role in the postsynaptic responses of hippocampal neurons. As such, genes of the RAF family encode kinases that are regulated by Ras and mediate cellular responses to growth signals. Indeed, B-Raf kinase is a key component of the RAS->Raf->MEK->ERK/MAP kinase signaling pathway, which plays a fundamental role in the regulation of cell growth, division and proliferation, and, when constitutively activated, causes tumorigenesis. Among several isoforms of Raf kinase, the B-type, or B-Raf, is the strongest activator of the downstream MAP kinase signaling.

The BRAF gene is frequently mutated in a variety of human tumors, especially in malignant melanoma and colon carcinoma. The most common reported mutation was a missense thymine (T) to adenine (A) transversion at nucleotide 1796 (T1796A; amino acid change in the B-Raf protein is Val<600> to Glu<600>) observed in 80% of malignant melanoma tumors. Functional analysis reveals that this transversion is the only detected mutation that causes constitutive activation of B-Raf kinase activity, independent of RAS activation, by converting B-Raf into a dominant transforming protein. Based on precedents, human tumors develop resistance to kinase inhibitors by mutating a specific amino acid in the catalytic domain as the "gatekeeper". (Balak, et. al., Clin Cancer Res. 2006, 12:6494-501). Mutation of Thr-529 in BRAF to Ile is thus anticipated as a mechanism of resistance to BRAF inhibitors, and this can be envisioned as a transition in codon 529 from ACC to ATC.

Niihori et al., report that in 43 individuals with cardio-facio-cutaneous (CFC) syndrome, they identified two heterozygous KRAS mutations in three individuals and eight BRAF mutations in 16 individuals, suggesting that dysregulation of the RAS-RAF-ERK pathway is a common molecular basis for the three related disorders (Niihori et al., Nat Genet. 2006, 38(3):294-6).

c-Raf-1:

Target kinase c-Raf-1 (i.e., v-raf murine sarcoma viral oncogene homolog 1) is a 73.0 kDa STK encoded by chromosome 3p25 (symbol: RAF1). c-Raf-1 can be targeted to to the mitochondria by BCL2 (i.e., oncogene B-cell leukemia 2) which is a regulator of apoptotic cell death. Active c-Raf-1 improves BCL2-mediated resistance to apoptosis, and c-Raf-1 phosphorylates BAD (i.e., BCL2-binding protein). c-Raf-1 is implicated in carcinomas, including colorectal, ovarian, lung and renal cell carcinoma. C-Raf-1 is also implicated as an important mediator of tumor angiogenesis (Hood, J. D. et al., 2002, Science 296, 2404). C-Raf-1 inhibitors may also be useful for the treatment of acute myeloid leukemia and myelodysplastic syndromes (Crump, Curr Pharm Des 2002, 8(25):2243-8). Raf-1 activators may be useful as treatment for neuroendocrine tumors, such as medullary thyroid cancer, carcinoid, small cell lung cancer and pheochromocytoma (Kunnimalaiyaan et al., Anticancer Drugs 2006, 17(2): 139-42).

Raf inhibitors (A-Raf and/or B-Raf and/or c-Raf-1) may be useful in treating A-Raf-mediated, B-Raf-mediated or c-Raf-1-mediated disease or condition selected from the group consisting of neurologic diseases, including, but not limited to, multi-infarct dementia, head injury, spinal cord injury, Alzheimer's disease (AD), Parkinson's disease; neoplastic diseases including, but not limited to, melanoma, glioma, sarcoma, carcinoma (e.g. colorectal, lung, breast, pancreatic, thyroid, renal, ovarian), lymphoma (e.g. histiocytic lymphoma) neurofibromatosis, acute myeloid leukemia, myelodysplastic syndrome, leukemia, tumor angiogenesis, neuroendocrine tumors such as medullary thyroid cancer, carcinoid, small cell lung cancer and pheochromocytoma; pain of neuropathic or inflammatory origin, including, but not limited to, acute pain, chronic pain, cancer-related pain, and migraine; cardiovascular diseases, including, but not limited to, heart failure, ischemic stroke, cardiac hypertrophy, thrombosis (e.g. thrombotic microangiopathy syndromes), atherosclerosis, and reperfusion injury; inflammation including, but not limited to, psoriasis, arthritis and autoimmune diseases and conditions, osteoarthritis, endometriosis, scarring, vascular restenosis, fibrotic disorders, rheumatoid arthritis, inflammatory bowel disease (IBD); immunodeficiency diseases, including, but not limited to, organ transplant rejection, graft versus host disease; renal or prostatic diseases, including, but not limited to, diabetic nephropathy, polycystic kidney disease, nephrosclerosis, glomerulonephritis, prostate hyperplasia; metabolic disorders, including, but not limited to, obesity; infection, including, but not limited to, *Helicobacter pylori*, Hepatitis and Influenza viruses, fever, and sepsis; pulmonary diseases, including, but not limited to, chronic obstructive pulmonary disease (COPD) and acute respiratory distress syndrome (ARDS); genetic developmental diseases, including, but not limited to, Noonan's syndrome, Costello syndrome, (facio-cutaneoskeletal syndrome), LEOPARD syndrome, cardiofaciocutaneous syndrome (CFC), and neural crest syndrome abnormalities causing cardiovascular, skeletal, intestinal, skin, hair and endocrine diseases.

Kinase Activity Assays

A number of different assays for kinase activity can be utilized for assaying for active modulators and/or determining specificity of a modulator for a particular kinase or group or kinases. In addition to the assay mentioned in the Examples below, one of ordinary skill in the art will know of other assays that can be utilized and can modify an assay for a particular application. For example, numerous papers concerning kinases describe assays that can be used.

Additional alternative assays can employ binding determinations. For example, this sort of assay can be formatted either in a fluorescence resonance energy transfer (FRET) format, or using an AlphaScreen (amplified luminescent proximity homogeneous assay) format by varying the donor and acceptor reagents that are attached to streptavidin or the phosphor-specific antibody.

Organic Synthetic Techniques

A wide array of organic synthetic techniques exist in the art to facilitate the construction of potential modulators. Many of these organic synthetic methods are described in detail in standard reference sources utilized by those skilled in the art. One example of such a reference is March, 1994, *Advanced Organic Chemistry; Reactions, Mechanisms and Structure*, New York, McGraw Hill. Thus, the techniques useful to synthesize a potential modulator of kinase function are readily available to those skilled in the art of organic chemical synthesis.

Alternative Compound Forms or Derivatives

Compounds contemplated herein are described with reference to both generic formulae and specific compounds. In addition, invention compounds may exist in a number of different forms or derivatives, all within the scope of the present invention. Alternative forms or derivatives, include, for example, (a) prodrugs, and active metabolites (b) tautomers, isomers (including stereoisomers and regioisomers), and racemic mixtures (c) pharmaceutically acceptable salts and formulations and (d) solid forms, including different crystal forms, polymorphic or amorphous solids, including hydrates and solvates thereof, and other forms.

(a) Prodrugs and Metabolites

In addition to the present formulae and compounds described herein, the invention also includes prodrugs (generally pharmaceutically acceptable prodrugs), active metabolic derivatives (active metabolites), and their pharmaceutically acceptable salts.

Prodrugs are compounds or pharmaceutically acceptable salts thereof which, when metabolized under physiological conditions or when converted by solvolysis, yield the desired active compound. Prodrugs include, without limitation, esters, amides, carbamates, carbonates, ureides, solvates, or hydrates of the active compound. Typically, the prodrug is inactive, or less active than the active compound, but may provide one or more advantageous handling, administration, and/or metabolic properties. For example, some prodrugs are esters of the active compound; during metabolysis, the ester group is cleaved to yield the active drug. Esters include, for example, esters of a carboxylic acid group, or S-acyl or O-acyl derivatives of thiol, alcohol, or phenol groups. In this context, a common example is an alkyl ester of a carboxylic acid. Some prodrugs are activated enzymatically to yield the active compound, or a compound which, upon further chemical reaction, yields the active compound. Prodrugs may proceed from prodrug form to active form in a single step or may have one or more intermediate forms which may themselves have activity or may be inactive.

As described in *The Practice of Medicinal Chemistry*, Ch. 31-32 (Ed. Wermuth, Academic Press, San Diego, Calif., 2001), prodrugs can be conceptually divided into two non-exclusive categories, bioprecursor prodrugs and carrier prodrugs. Generally, bioprecursor prodrugs are compounds that are inactive or have low activity compared to the corresponding active drug compound, that contain one or more protective groups and are converted to an active form by metabolism or solvolysis. Both the active drug form and any released metabolic products should have acceptably low toxicity. Typically, the formation of active drug compound involves a metabolic process or reaction that is one of the follow types:

Oxidative Reactions:

Oxidative reactions are exemplified without limitation to reactions such as oxidation of alcohol, carbonyl, and acid functionalities, hydroxylation of aliphatic carbons, hydroxylation of alicyclic carbon atoms, oxidation of aromatic carbon atoms, oxidation of carbon-carbon double bonds, oxidation of nitrogen-containing functional groups, oxidation of silicon, phosphorus, arsenic, and sulfur, oxidative N-dealkylation, oxidative O- and S-dealkylation, oxidative deamination, as well as other oxidative reactions.

Reductive Reactions:

Reductive reactions are exemplified without limitation to reactions such as reduction of carbonyl functionalities, reduction of alcohol functionalities and carbon-carbon double bonds, reduction of nitrogen-containing functional groups, and other reduction reactions.

Reactions without Change in the Oxidation State:

Reactions without change in the state of oxidation are exemplified without limitation to reactions such as hydrolysis of esters and ethers, hydrolytic cleavage of carbon-nitrogen single bonds, hydrolytic cleavage of non-aromatic heterocycles, hydration and dehydration at multiple bonds, new atomic linkages resulting from dehydration reactions, hydrolytic dehalogenation, removal of hydrogen halide molecule, and other such reactions.

Carrier prodrugs are drug compounds that contain a transport moiety, e.g., that improves uptake and/or localized delivery to a site(s) of action. Desirably for such a carrier prodrug, the linkage between the drug moiety and the transport moiety is a covalent bond, the prodrug is inactive or less active than the drug compound, the prodrug and any release transport moiety are acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. (See, e.g., Cheng et al., U.S. Patent Publ. No. 20040077595, application Ser. No. 10/656, 838, incorporated herein by reference.) Such carrier prodrugs are often advantageous for orally administered drugs. In some instances, the transport moiety provides targeted delivery of the drug, for example the drug maybe conjugated to an antibody or antibody fragment. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of hydroxyl groups with lipophilic carboxylic acids, or of carboxylic acid groups with alcohols, e.g., aliphatic alcohols. Wermuth, supra.

Metabolites, e.g., active metabolites, overlap with prodrugs as described above, e.g., bioprecursor prodrugs. Thus, such metabolites are pharmacologically active compounds or compounds that further metabolize to pharmacologically active compounds that are derivatives resulting from metabolic processes in the body of a subject. Of these, active metabolites are such pharmacologically active derivative compounds. For prodrugs, the prodrug compound is generally inactive or of lower activity than the metabolic product. For active metabolites, the parent compound may be either an active compound or may be an inactive prodrug. For example, in some compounds, one or more alkoxy groups can be metabolized to hydroxyl groups while retaining pharmacologic activity and/or carboxyl groups can be esterified, e.g., glucuronidation. In some cases, there can be more than one metabolite, where an intermediate metabolite(s) is further metabolized to provide an active metabolite. For example, in some cases a derivative compound resulting from metabolic glucuronidation may be inactive or of low activity, and can be further metabolized to provide an active metabolite.

Metabolites of a compound may be identified using routine techniques known in the art, and their activities determined using tests such as those described herein. See, e.g., Bertolini et al., 1997, *J. Med. Chem.*, 40:2011-2016; Shan et al., 1997, *J Pharm Sci* 86(7):756-757; Bagshawe, 1995, *Drug Dev. Res.*, 34:220-230; Wermuth, supra.

(b) Tautomers, Stereoisomers, and Regioisomers

It is understood that some compounds may exhibit tautomerism. In such cases, the formulae provided herein expressly depict only one of the possible tautomeric forms. It is therefore to be understood that the formulae provided herein are intended to represent any tautomeric form of the depicted compounds and are not to be limited merely to the specific tautomeric form depicted by the drawings of the formulae.

Likewise, some of the compounds according to the present invention may exist as stereoisomers, i.e. having the same atomic connectivity of covalently bonded atoms yet differing in the spatial orientation of the atoms. For example, compounds may be optical stereoisomers, which contain one or more chiral centers, and therefore, may exist in two or more stereoisomeric forms (e.g. enantiomers or diastereomers). Thus, such compounds may be present as single stereoisomers (i.e., essentially free of other stereoisomers), racemates, and/or mixtures of enantiomers and/or diastereomers. As another example, stereoisomers include geometric isomers, such as cis- or trans-orientation of substituents on adjacent carbons of a double bond. All such single stereoisomers, racemates and mixtures thereof are intended to be within the scope of the present invention. Unless specified to the contrary, all such stereoisomeric forms are included within the formulae provided herein.

In some embodiments, a chiral compound of the present invention is in a form that contains at least 80% of a single isomer (60% enantiomeric excess ("e.e.") or diastereomeric excess ("d.e.")), or at least 85% (70% e.e. or d.e.), 90% (80% e.e. or d.e.), 95% (90% e.e. or d.e.), 97.5% (95% e.e. or d.e.), or 99% (98% e.e. or d.e.). As generally understood by those skilled in the art, an optically pure compound having one chiral center is one that consists essentially of one of the two possible enantiomers (i.e., is enantiomerically pure), and an optically pure compound having more than one chiral center is one that is both diastereomerically pure and enantiomerically pure. In some embodiments, the compound is present in optically pure form, such optically pure form being prepared and/or isolated by methods known in the art (e.g. by recrystallization techniques, chiral synthetic techniques (including synthesis from optically pure starting materials), and chromatographic separation using a chiral column.

(c) Pharmaceutically Acceptable Salts and Formulations

Unless specified to the contrary, specification of a compound herein includes pharmaceutically acceptable salts of such compound. Thus, compounds of Formula I can be in the form of pharmaceutically acceptable salts, or can be formulated as pharmaceutically acceptable salts. Contemplated pharmaceutically acceptable salt forms include, without limitation, mono, bis, tris, tetrakis, and so on. Pharmaceutically acceptable salts are non-toxic in the amounts and concentrations at which they are administered. The preparation of such salts can facilitate the pharmacological use by altering the physical characteristics of a compound without preventing it from exerting its physiological effect. Useful alterations in physical properties include lowering the melting point to facilitate transmucosal administration and increasing the solubility to facilitate administering higher concentrations of the drug. A compound of the invention may possess a sufficiently acidic, a sufficiently basic, or both functional groups, and accordingly react with any of a number of inorganic or organic bases, and inorganic and organic acids, to form a pharmaceutically acceptable salt.

Pharmaceutically acceptable salts include acid addition salts such as those containing chloride, bromide, iodide, hydrochloride, acetate, phenylacetate, acrylate, ascorbate, aspartate, benzoate, 2-phenoxybenzoate, 2-acetoxybenzoate, dinitrobenzoate, hydroxybenzoate, methoxybenzoate, methylbenzoate, bicarbonate, butyne-1,4 dioate, hexyne-1, 6-dioate, caproate, caprylate, chlorobenzoate, cinnamate, citrate, decanoate, formate, fumarate, glycolate, gluconate, glucarate, glucuronate, glucose-6-phosphate, glutamate, heptanoate, hexanoate, isethionate, isobutyrate, gamma-hydroxybutyrate, phenylbutyrate, lactate, malate, maleate, hydroxymaleate, methylmaleate, malonate, mandelate, nicotinate, nitrate, isonicotinate, octanoate, oleate, oxalate, pamoate, phosphate, monohydrogenphosphate, dihydrogenphosphate, orthophosphate, metaphosphate, pyrophosphate, 2-phosphoglycerate, 3-phosphoglycerate, phthalate, propionate, phenylpropionate, propiolate, pyruvate, quinate, salicylate, 4-aminosalicylate, sebacate, stearate, suberate, succinate, sulfate, pyrosulfate, bisulfate, sulfite, bisulfite, sulfamate, sulfonate, benzenesulfonate (i.e. besylate), ethanesulfonate (i.e. esylate), ethane-1,2-disulfonate, 2-hydroxyethanesulfonate (i.e. isethionate), methanesulfonate (i.e. mesylate), naphthalene-1-sulfonate, naphthalene-2-sulfonate (i.e. napsylate), propanesulfonate, p-toluenesulfonate (i.e. tosylate), xylenesulfonates, cyclohexylsulfamate, tartrate, and trifluoroacetate. These pharmaceutically acceptable acid addition salts can be prepared using the appropriate corresponding acid.

When acidic functional groups, such as carboxylic acid or phenol are present, pharmaceutically acceptable salts also include basic addition salts such as those containing benzathine, chloroprocaine, choline, ethanolamine, diethanolamine, triethanolamine, t-butylamine, dicyclohexylamine, ethylenediamine, N,N'-dibenzylethylenediamine, meglumine, hydroxyethylpyrrolidine, piperidine, morpholine, piperazine, procaine, aluminum, calcium, copper, iron, lithium, magnesium, manganese, potassium, sodium, zinc, ammonium, and mono-, di-, or tri-alkylamines, or salts derived from amino acids such as L-histidine, L-glycine, L-lysine, and L-arginine. For example, see *Remington's Pharmaceutical Sciences*, 19$^{th}$ ed., Mack Publishing Co., Easton, Pa., Vol. 2, p. 1457, 1995. These pharmaceutically acceptable base addition salts can be prepared using the appropriate corresponding base.

Pharmaceutically acceptable salts can be prepared by standard techniques. For example, the free-base form of a compound can be dissolved in a suitable solvent, such as an aqueous or aqueous-alcohol solution containing the appropriate acid and then isolated by evaporating the solution. In another example, a salt can be prepared by reacting the free base and acid in an organic solvent. If the particular compound is an acid, the desired pharmaceutically acceptable salt may be prepared by any suitable method, for example, treatment of the free acid with an appropriate inorganic or organic base.

The pharmaceutically acceptable salt of the different compounds may be present as a complex. Examples of complexes include 8-chlorotheophylline complex (analogous to, e.g., dimenhydrinate: diphenhydramine 8-chlorotheophylline (1:1) complex; Dramamine) and various cyclodextrin inclusion complexes.

(d) Other Compound Forms

In the case of agents that are solids, it is understood by those skilled in the art that the compounds and salts may exist in different crystal or polymorphic forms, or may be formulated as co-crystals, or may be in an amorphous form, or may be any combination thereof (e.g. partially crystalline, partially amorphous, or mixtures of polymorphs) all of which are intended to be within the scope of the present invention and specified formulae. Whereas salts are formed by acid/base addition, i.e. a free base or free acid of the compound of interest forms an acid/base reaction with a corresponding addition base or addition acid, respectively, resulting in an ionic charge interaction, co-crystals are a new chemical species that is formed between neutral compounds, resulting in the compound and an additional molecular species in the same crystal structure.

Additionally, the formulae are intended to cover hydrated or solvated as well as unhydrated or unsolvated forms of the identified structures. For example, the indicated structures include both hydrated and non-hydrated forms. Other examples of solvates include the structures in combination with a suitable solvent, such as isopropanol, ethanol, methanol, dimethylsulfoxide, ethyl acetate, acetic acid, or ethanolamine.

Administration

The methods and compounds will typically be used in therapy for human subjects. However, they may also be used to treat similar or identical indications in other animal subjects. Compounds of Formula I can be administered by different routes, including injection (i.e. parenteral, including intravenous, intraperitoneal, subcutaneous, and intramuscular), oral, transdermal, transmucosal, rectal, or inhalant. Such dosage forms should allow the compound to reach target cells. Other factors are well known in the art, and include considerations such as toxicity and dosage forms that retard the compound or composition from exerting its effects. Techniques and formulations generally may be found in Remington: *The Science and Practice of Pharmacy*, 21$^{st}$ edition, Lippincott, Williams and Wilkins, Philadelphia, Pa., 2005 (hereby incorporated by reference herein).

In some embodiments, compositions will comprise carriers or excipients, which may be chosen to facilitate administration of the compound by a particular route. Examples of carriers include calcium carbonate, calcium phosphate, various sugars such as lactose, glucose, or sucrose, types of starch, cellulose derivatives, gelatin, lipids, liposomes, nanoparticles, and the like. Carriers also include physiologically compatible liquids as solvents or for suspensions, including, for example, sterile solutions of water for injection (WFI), saline solution, dextrose solution, Hank's solution, Ringer's solution, vegetable oils, mineral oils, animal oils, polyethylene glycols, liquid paraffin, and the like.

In some embodiments, oral administration may be used. Pharmaceutical preparations for oral use can be formulated into conventional oral dosage forms such as capsules, tablets, and liquid preparations such as syrups, elixirs, and concentrated drops. Compounds of Formula I may be combined with solid excipients, optionally grinding a resulting mixture, and processing the mixture of granules, after adding suitable auxiliaries, if desired, to obtain, for example, tablets, coated tablets, hard capsules, soft capsules, solutions (e.g. aqueous, alcoholic, or oily solutions) and the like. Suitable excipients are, in particular, fillers such as sugars, including lactose, glucose, sucrose, mannitol, or sorbitol; cellulose preparations, for example, corn starch, wheat starch, rice starch, potato starch, gelatin, gum tragacanth, methyl cellulose, hydroxypropylmethyl-cellulose, sodium carboxymethylcellulose (CMC), and/or polyvinylpyrrolidone (PVP: povidone); oily excipients, including vegetable and animal oils, such as sunflower oil, olive oil, or codliver oil. The oral dosage formulations may also contain disintegrating agents, such as the cross-linked polyvinylpyrrolidone, agar, or alginic acid, or a salt thereof such as sodium alginate; a lubricant, such as talc or magnesium stearate; a plasticizer, such as glycerol or sorbitol; a sweetening such as sucrose, fructose, lactose, or aspartame; a natural or artificial flavoring agent, such as peppermint, oil of wintergreen, or cherry flavoring; or dye-stuffs or pigments, which may be used for identification or characterization of different doses or combinations. Also provided are dragee cores with suitable coatings. For this purpose, concentrated sugar solutions may be used, which may optionally contain, for example, gum arabic, talc, poly-vinylpyrrolidone, carbopol gel, polyethylene glycol, and/or titanium dioxide, lacquer solutions, and suitable organic solvents or solvent mixtures.

Pharmaceutical preparations that can be used orally include push-fit capsules made of gelatin ("gelcaps"), as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols.

In some embodiments, injection (parenteral administration) may be used, e.g., intramuscular, intravenous, intraperitoneal, and/or subcutaneous. Compounds of Formula I for injection may be formulated in sterile liquid solutions, preferably in physiologically compatible buffers or solutions, such as saline solution, Hank's solution, or Ringer's solution. Dispersions may also be prepared in non-aqueous solutions, such as glycerol, propylene glycol, ethanol, liquid polyethylene glycols, triacetin, and vegetable oils. Solutions may also contain a preservative, such as methylparaben, propylparaben, chlorobutanol, phenol, sorbic acid, thimerosal, and the like. In addition, the compounds may be formulated in solid form, including, for example, lyophilized forms, and redissolved or suspended prior to use.

In some embodiments, transmucosal, topical or transdermal administration may be used. In such formulations of compounds of Formula I, penetrants appropriate to the barrier to be permeated are used. Such penetrants are generally known in the art, and include, for example, for transmucosal administration, bile salts and fusidic acid derivatives. In addition, detergents may be used to facilitate permeation. Transmucosal administration, for example, may be through nasal sprays or suppositories (rectal or vaginal). Compositions of compounds of Formula I for topical administration may be formulated as oils, creams, lotions, ointments, and the like by choice of appropriate carriers known in the art. Suitable carriers include vegetable or mineral oils, white petrolatum (white soft paraffin), branched chain fats or oils, animal fats and high molecular weight alcohol (greater than $C_{12}$). In some embodiments, carriers are selected such that the active ingredient is soluble. Emulsifiers, stabilizers, humectants and antioxidants may also be included as well as agents imparting color or fragrance, if desired. Creams for topical application are preferably formulated from a mixture of mineral oil, self-emulsifying beeswax and water in which mixture the active ingredient, dissolved in a small amount of solvent (e.g., an oil), is admixed. Additionally, administration by transdermal means may comprise a transdermal patch or dressing such as a bandage impregnated with an active ingredient and optionally one or more carriers or diluents known in the art. To be administered in the form of a transdermal delivery system, the dosage administration will be continuous rather than intermittent throughout the dosage regimen.

In some embodiments, compounds are administered as inhalants. Compounds of Formula I may be formulated as dry powder or a suitable solution, suspension, or aerosol. Powders and solutions may be formulated with suitable additives known in the art. For example, powders may include a suitable powder base such as lactose or starch, and solutions may comprise propylene glycol, sterile water, ethanol, sodium chloride and other additives, such as acid, alkali and buffer salts. Such solutions or suspensions may be administered by inhaling via spray, pump, atomizer, or nebulizer, and the like. The compounds of Formula I may also be used in combination with other inhaled therapies, for example corticosteroids such as fluticasone proprionate, beclomethasone dipropionate, triamcinolone acetonide, budesonide, and mometasone furoate; beta agonists such as albuterol, salmeterol, and formoterol; anticholinergic agents such as ipratroprium bromide or tiotropium; vasodilators such as treprostinal and iloprost; enzymes such as DNAase; therapeutic proteins; immunoglobulin antibodies; an oligonucleotide, such as single or double stranded DNA or RNA, siRNA; antibiotics such as tobramycin; muscarinic receptor antagonists; leukotriene antagonists; cytokine antagonists; protease inhibitors; cromolyn sodium; nedocril sodium; and sodium cromoglycate.

The amounts of various compounds to be administered can be determined by standard procedures taking into account factors such as the compound activity (in vitro, e.g. the compound $IC_{50}$ vs. target, or in vivo activity in animal efficacy models), pharmacokinetic results in animal models (e.g. biological half-life or bioavailability), the age, size, and weight of the subject, and the disorder associated with the subject. The importance of these and other factors are well known to those of ordinary skill in the art. Generally, a dose will be in the range of about 0.01 to 50 mg/kg, also about 0.1 to 20 mg/kg of the subject being treated. Multiple doses may be used.

The compounds of Formula I may also be used in combination with other therapies for treating the same disease. Such combination use includes administration of the compounds and one or more other therapeutics at different times, or co-administration of the compound and one or more other therapies. In some embodiments, dosage may be modified for one or more of the compounds of the invention or other therapeutics used in combination, e.g., reduction in the amount dosed relative to a compound or therapy used alone, by methods well known to those of ordinary skill in the art.

It is understood that use in combination includes use with other therapies, drugs, medical procedures etc., where the other therapy or procedure may be administered at different times (e.g. within a short time, such as within hours (e.g. 1, 2, 3, 4-24 hours), or within a longer time (e.g. 1-2 days, 2-4 days, 4-7 days, 1-4 weeks)) than a compound of Formula I, or at the same time as a compound of Formula I. Use in combination also includes use with a therapy or medical procedure that is administered once or infrequently, such as surgery, along with a compound of Formula I administered within a short time or longer time before or after the other therapy or procedure. In some embodiments, the present invention provides for delivery of a compound of Formula I and one or more other drug therapeutics delivered by a different route of administration or by the same route of administration. The use in combination for any route of administration includes delivery of a compound of Formula I and one or more other drug therapeutics delivered by the same route of administration together in any formulation, including formulations where the two compounds are chemically linked in such a way that they maintain their therapeutic activity when administered. In one aspect, the other drug therapy may be co-administered with a compound of Formula I. Use in combination by co-administration includes administration of co-formulations or formulations of chemically joined compounds, or administration of two or more compounds in separate formulations within a short time of each other (e.g. within an hour, 2 hours, 3 hours, up to 24 hours), administered by the same or different routes. Co-administration of separate formulations includes co-administration by delivery via one device, for example the same inhalant device, the same syringe, etc., or administration from separate devices within a short time of each other. Co-formulations of a compound of Formula I and one or more additional drug therapies delivered by the same route includes preparation of the materials together such that they can be administered by one device, including the separate compounds combined in one formulation, or compounds that are modified such that they are chemically joined, yet still maintain their biological activity. Such chemically joined compounds may have a linkage that is substantially maintained in vivo, or the linkage may break down in vivo, separating the two active components.

EXAMPLES

Examples related to the present invention are described below. In most cases, alternative techniques can be used. The examples are intended to be illustrative and are not limiting or restrictive to the scope of the invention. In some examples, the mass spectrometry result indicated for a compound may have more than one value due to the isotope distribution of an atom in the molecule, such as a compound having a bromo or chloro substituent.

Unless specifically indicated otherwise, the Formula enumeration and R group enumeration used in the following examples is not related to such enumeration in other sections of this application. The reagents and solvents used in these examples can be readily substituted with appropriate alternatives as are known in the art and isolation of products is readily achieved by methods known in the art, including, but not limited to, extraction, crystallization, and chromatographic methods.

Example 1: Synthesis of Compound of Formula Ib or Id Wherein A is —C(O)—

Compounds of Formula Ib or Id, as defined in paragraphs [0010] and [0016], respectively, wherein A is —C(O)—, can be prepared in five steps as described in Scheme 1.

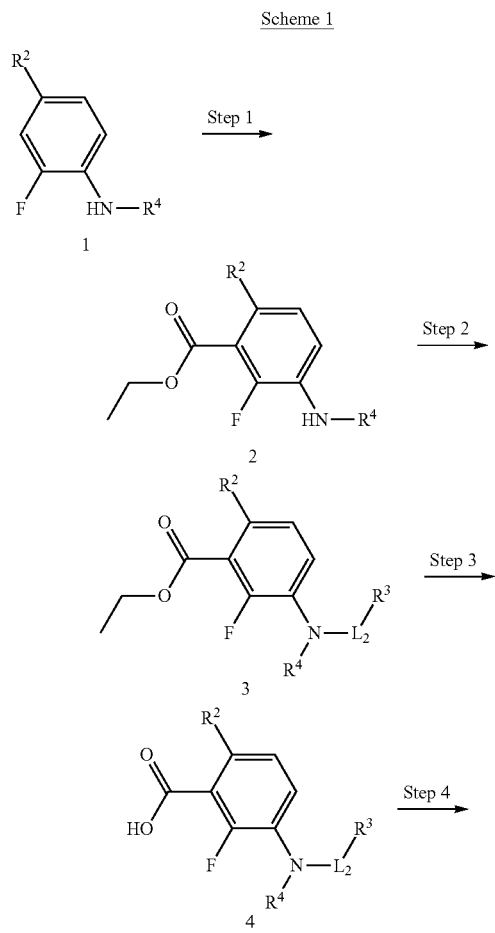

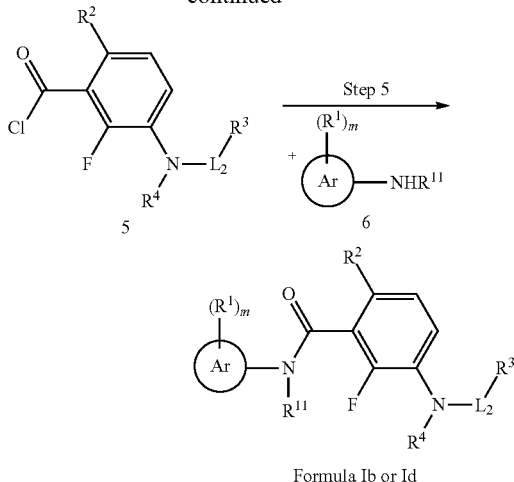

Step 1—Synthesis of Compound 2

Compound 1 ($R^2$ and $R^4$ as defined in paragraph [0004]) is dissolved in an anhydrous solvent (e.g. tetrahydrofuran) under nitrogen atmosphere. The solution is cooled down with the aid of a dry ice and acetone bath. To this solution is added a base (e.g. n-butyllithium), followed by 1,2-bis (chlorodimethylsilyl)ethane at low temperature (typically below −70° C.). The resulting mixture is stirred at low temperature for 1-2 hours. To this solution is added a base (e.g. n-butyllithium), followed by ethyl chloroformate. The resulting mixture is allowed to warm to room temperature and then stirred at room temperature for 1-3 days. The reaction mixture is quenched by an acid solution, stirred at room temperature for a couple of hours, and then basified. The mixture is extracted with an organic solvent (e.g. dichloromethane or ethyl acetate). The desired compound 2 is purified by chromatography.

Step 2—Synthesis of Compound 3

To compound 2 in an organic solvent (e.g. dichloromethane) is added pyridine, followed by an appropriate acylating agent, isocyanate, or sulfonyl chloride such as propane-1-sulfonylchloride. The reaction mixture is stirred at room temperature for over 12 hours and the mixture is then poured into water. The organic layer is separated and the aqueous layer is extracted with an appropriate organic solvent (e.g. dichloromethane). The desired compound 3 ($L_2$ and $R^3$ as defined in paragraph [0005], or $L_2$ is $S(O)_2$ for Formula Ib) is purified by chromatography.

Step 3—Synthesis of Compound 4

To compound 3 in a solvent mixture (e.g. tetrahydrofuran and water) is added a base (e.g. lithium hydroxide or sodium hydroxide). The resulting suspension is stirred in a heated oil bath for over 10 hours. The reaction mixture is cooled down to room temperature and then acidified with an acid solution such as concentrated hydrochloric acid. The aqueous layer is separated and extracted with an appropriate organic solvent (e.g. ethyl acetate). The desired compound 4 is purified by chromatography.

Step 4—Synthesis of Compound 5

To a suspension of compound 4 in an anhydrous solvent (e.g. dichloromethane), cooled with an ice and water bath, oxalyl chloride is added slowly, followed by dimethylformamide. The reaction mixture is stirred at room temperature for a few hours. After removal of the solvent and excess oxalyl chloride, the residue is used in the next step without further purification.

Step 5—Synthesis of Compound of Formula Ib or Id

To an appropriate amine 6 (Ar, m, $R^1$ and $R^{11}$ as defined in paragraph [0005]) in an anhydrous solvent (e.g. tetrahydrofuran) is added a base (e.g. triethylamine). To this mixture, cooled with an ice and salt bath, a solution of compound 5 in an anhydrous solvent (e.g. tetrahydrofuran) is added slowly. The resulting mixture was stirred at room temperature for over 12 hours. The desired compound of Formula Ib ($L_2$ is $S(O)_2$) or Id is purified by chromatography.

Example 2: Synthesis of Compound of Formula Ic or Ie

Compounds of Formula Ic or Ie, as defined in paragraphs [0015] and [0021], respectively, can be prepared in four steps as described in Scheme 2.

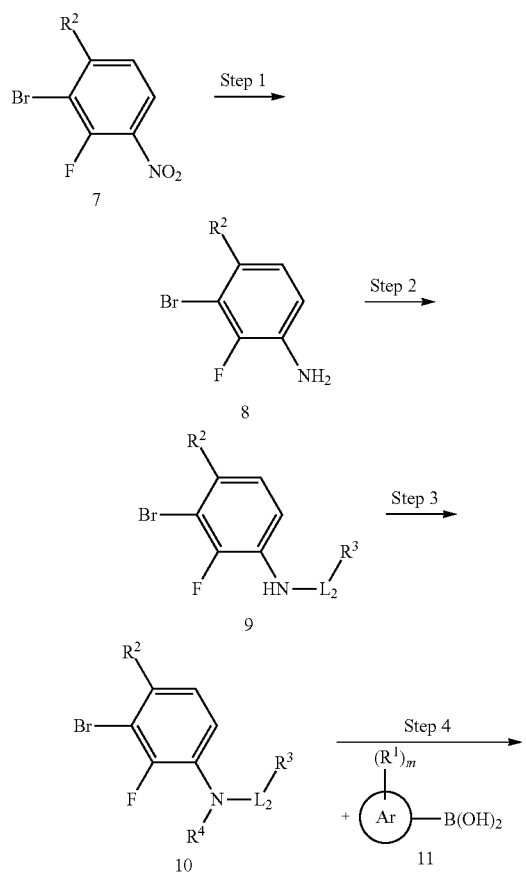

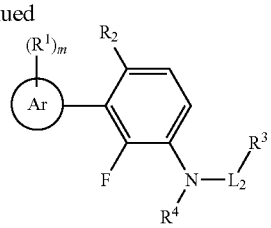

Formula Ic or Ie

Step 1—Synthesis of Compound 8

Compound 7 ($R^2$ as defined in paragraph [0005]) is dissolved in an appropriate solvent (e.g. methanol). To this solution is added catalyst (e.g. palladium on carbon). The suspension is then placed under a hydrogen atmosphere and shaken at room temperature for over 12 hours. The catalyst is removed by filtration on a pad of celite and washed with an appropriate solvent (e.g. methanol). The filtrate is concentrated under reduced pressure to give compound 8, which is used in the next step without further purification.

Step 2—Synthesis of Compound 9

To compound 8 in an organic solvent (e.g. dichloromethane) is added a base (e.g. pyridine) followed by an appropriate acylating agent, isocyanate, or sulfonyl chloride. The reaction mixture is stirred at room temperature for over 12 hours. The reaction mixture is then poured into water. The organic layer is collected and the aqueous layer is extracted with an appropriate organic solvent (e.g. dichloromethane). The organic solvents are then combined. The desired compound 9 ($L_2$ and $R^3$ as defined in paragraph [0005], or $L_2$ is $S(O)_2$ for Formula Ic) is purified by chromatography.

Step 3—Synthesis of Compound 10

To compound 9 in an organic solvent (e.g. tetrahydrofuran or dichloromethane) is added a base (e.g. sodium hydride) at low temperature, followed by an appropriate alkylating agent (e.g. halide). The reaction mixture is stirred at room temperature or heated in an oil bath as necessary, for a few hours. The reaction mixture is then poured into water. The organic layer is collected and the aqueous layer is extracted with an appropriate organic solvent (e.g. ethyl acetate or dichloromethane). The organic solvents are then combined. The desired compound 10 ($R^4$ as defined in paragraph [0005]) is purified by chromatography.

Step 4—Synthesis of Compound of Formula Ic or Ie

A mixture of compound 10, an appropriate boronic acid 11 (Ar, m and $R^1$ as defined in paragraph [0004]), and a catalyst (e.g. tetrakis(triphenylphosphine)palladium) in a mixture of base (e.g. aqueous solution of potassium carbonate) and an appropriate organic solvent (e.g. acetonitrile) is heated in an oil bath or is irradiated in a microwave system at over 100° C. for an appropriate time depending on starting materials. The reaction mixture is poured into water and then extracted with an appropriate organic solvent (e.g. dichloromethane or ethyl acetate). The organic solvents are then combined. The desired compound of Formula Ic ($L_2$ is $S(O)_2$) or Id is purified by chromatography.

Example 3: Synthesis of Compound of Formula I where $L_1$ is —$CH_2NR^{11}$—

Compounds of Formula I, as defined in paragraph [0005] where $L_1$ is —$CH_2NR^{11}$—, can be prepared in three steps as described in Scheme 3—Method A, or one step as described in Scheme 3—Method B.

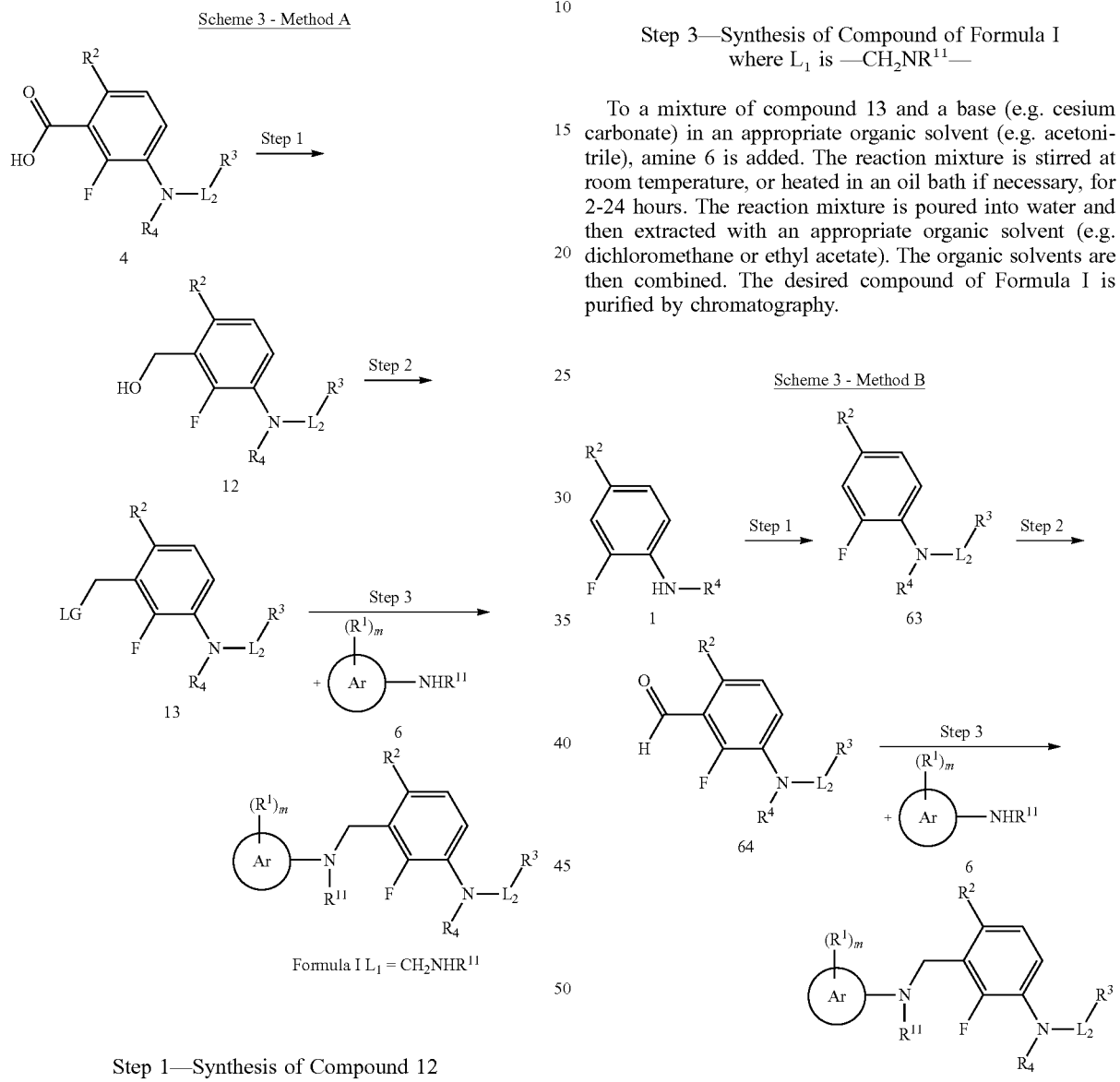

Step 1—Synthesis of Compound 12

Compound 4 (prepared as described in Scheme 1, Step 3 in Example 1) is dissolved in an appropriate solvent (e.g. tetrahydrofuran). To this solution is added an appropriate reducing agent (e.g. lithium tetrahydroaluminate) at low temperature (typically below −30° C.). The reaction mixture is then stirred at room temperature for 2-24 hours. Sodium sulfate is added and the mixture is stirred at room temperature for 30 minutes. The mixture is filtered through a pad of celite and washed with an appropriate solvent (e.g. ethyl acetate). The filtrate is concentrated under reduced pressure to give compound 12, which is used in the next step without further purification.

Step 2—Synthesis of Compound 13

Compound 13 (LG is a suitable leaving group) is prepared by converting compound 12 into a mesylate or triflate by reacting with the corresponding sulfonyl chloride in an appropriate organic solvent. It can also be converted into the corresponding bromide by reacting with an appropriate agent (e.g. phosphorous tribromide) in the presence of an appropriate base (e.g. pyridine).

Step 3—Synthesis of Compound of Formula I where $L_1$ is —$CH_2NR^{11}$—

To a mixture of compound 13 and a base (e.g. cesium carbonate) in an appropriate organic solvent (e.g. acetonitrile), amine 6 is added. The reaction mixture is stirred at room temperature, or heated in an oil bath if necessary, for 2-24 hours. The reaction mixture is poured into water and then extracted with an appropriate organic solvent (e.g. dichloromethane or ethyl acetate). The organic solvents are then combined. The desired compound of Formula I is purified by chromatography.

Step 1—Preparation of Compound 63

To substituted phenylamine 1 ($R^2$ and $R^4$ as defined in paragraph [0005]) in an appropriate solvent (e.g. tetrahydrofuran) are added a base (e.g. triethylamine) and acid halide (e.g. acid chloride or sulfonyl chloride) in an appropriate organic solvent under an atmosphere of nitrogen. The reaction is stirred at room temperature for 2-24 hours. The reaction mixture is then poured into an acid solution and extracted with an appropriate organic solvent (e.g. dichloromethane or ethyl acetate). The organic layers are combined. The desired compound 63 ($L_2$ and $R^3$ as defined in paragraph [0004]) is purified by crystallization or chromatography.

Step 2—Preparation of Compound 64

Compound 63 in an appropriate solvent (e.g. tetrahydrofuran) under an atmosphere of nitrogen is cooled in an acetone/dry ice bath. To this solution is added a base (e.g. lithium diisopropylamide) and then an appropriate reagent (e.g. N,N-dimethyl-formamide). The reaction mixture is stirred for 0.5 to 3 hours at low temperature (<50° C.) and then allowed to warm to room temperature. The reaction mixture is poured into water and extracted with an appropriate organic solvent (e.g. dichloromethane or ethyl acetate). The desired compound 64 is purified by chromatography.

Step 3—Synthesis of Compound of Formula I where $L_1$ is —$CH_2NR^{11}$—

To a mixture of compound 64 in an appropriate organic solvent (e.g. acetonitrile) is added amine 6 (Ar, m, $R^1$ and $R^{11}$ as defined in paragraph [0005]), and reducing agent (e.g. triethylsilane and trifluoroacetic acid). The reaction mixture is heated in an oil bath for 2-24 hours. The reaction mixture is concentrated, poured into water and then extracted with an appropriate organic solvent (e.g. dichloromethane or ethyl acetate). The organic layers are then combined. The desired compound of Formula I is purified by chromatography.

Alternatively, compounds of Formula I where $L_1$ is —$CH_2NR^{11}$— may be prepared by reduction of compounds of Formula Ib or Id wherein A is —C(O)— (e.g. prepared as described in Example 1) with an appropriate reducing agent (e.g. borane or diisobutylaluminum hydride).

Example 4: Synthesis of 6-chloro-2-fluoro-N-[6-(5-methyl-thiazol-2-ylamino)-pyridin-3-yl]-3-(propane-1-sulfonylamino)-benzamide P-0011

6-Chloro-2-fluoro-N-[6-(5-methyl-thiazol-2-ylamino)-pyridin-3-yl]-3-(propane-1-sulfonylamino)-benzamide P-0011 was synthesized in six steps from 4-chloro-2-fluoroaniline 14 as shown in Scheme 4.

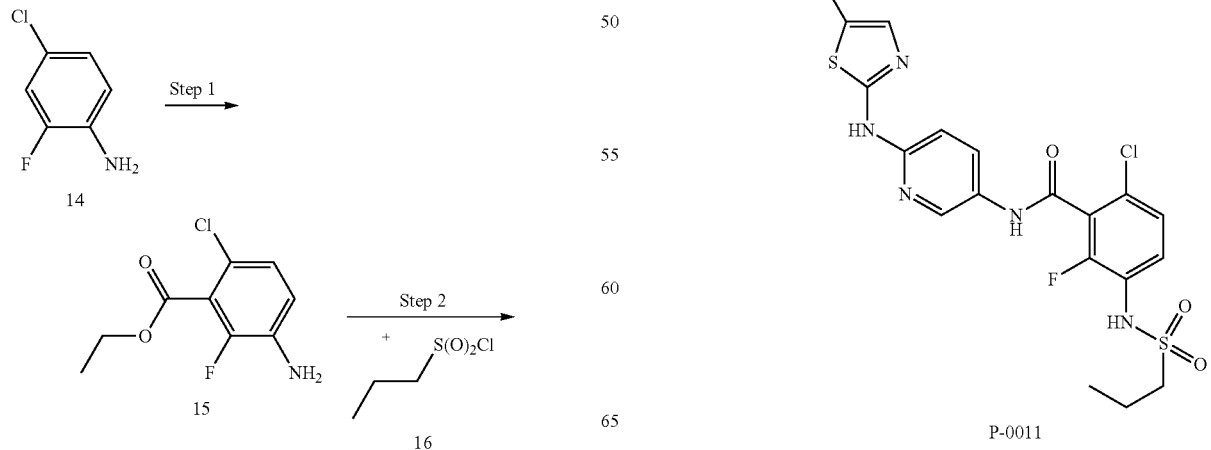

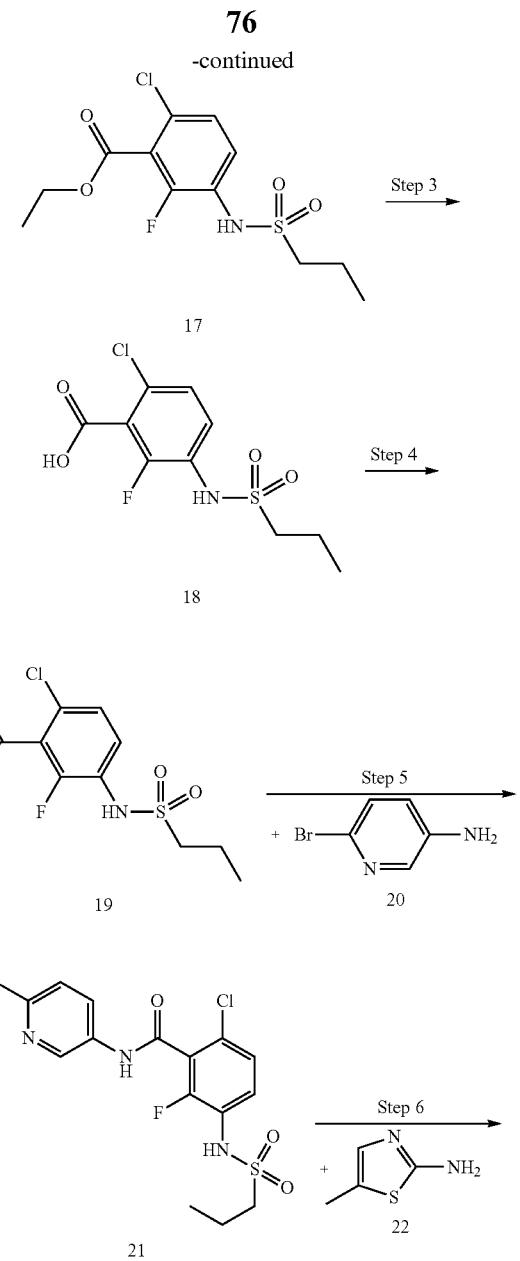

Step 1 Preparation 3-Amino-6-Chloro-2-Fluorobenzoic Acid Ethyl Ester (15)

4-Chloro-2-fluoroaniline (14, 12 mL) was dissolved in 200 mL of anhydrous tetrahydrofuran under a nitrogen atmosphere in a 1 L 3-neck round bottom flask. The mixture was cooled to −78° C. (dry ice/acetone bath) and n-butyl-lithium (2.5 M, 45 mL) was slowly added dropwise, maintaining the temperature below −70° C. The mixture was stirred at −70° C. for 30 minutes. 1,2-Bis(chlorodimethyl-silyl)ethane (24.80 g) was dissolved in 80 mL of anhydrous tetrahydrofuran and slowly added dropwise to the reaction mixture while maintaining the temperature below −70° C. The resulting mixture was stirred at −78° C. for 1 hour, then n-butyllithium (2.5 M, 45 mL) was slowly added dropwise maintaining the temperature below −70° C. The mixture was then stirred for 30 minutes at −78° C., then warmed up to 15° C. over 1 hour. The reaction mixture was cooled down to −78° C. and n-butyllithium (2.5 M, 50 mL) was slowly added dropwise maintaining the temperature below −70° C. The mixture was stirred at −70° C. for 90 minutes, then 13.40 mL of ethylchloroformate was slowly added dropwise maintaining the temperature below −70° C. The reaction mixture was slowly warmed to room temperature and stirred at room temperature for 64 hours. The reaction was quenched by careful addition of a solution of 50 mL of concentrated hydrochloric acid in 160 mL of water while cooling with an ice/water bath. The mixture was stirred at room temperature for 2 hours, then made basic by addition of potassium carbonate. The mixture was extracted with 3×100 mL of ethyl acetate and the combined organic extracts were washed with 50 mL of brine and dried with magnesium sulfate. After removal of the solvent, the residue was purified with silica gel column chromatography eluting with ethyl acetate in hexane to provide the desired compound (15, 17 g, 72%).

Step 2—Preparation 6-chloro-2-fluoro-3-(propane-1-sulfonylamino)-benzoic acid ethyl ester (17)

3-Amino-6-chloro-2-fluorobenzoic acid ethyl ester (15, 17 g) was dissolved in 785 mL of dichloromethane, to which 13.2 mL of pyridine was added, followed by propane-1-sulfonylchloride (16, 12.8 g). The reaction mixture was stirred at room temperature for 18 hours, then poured into 400 mL of water. The organic layer was separated and the aqueous layer was extracted with 200 mL of dichlormethane. The combined organic extracts were dried over magnesium sulfate to give an orange oil (41 g). Trituration in 150 mL of diethylether removed the pyridine salt as a white solid. The ether filtrate was concentrated to give orange oil, which was purified with silica gel column chromatography eluting with ethyl acetate in hexane to provide the desired compound as a pale yellow solid (17, 20 g, 57%).

Step 3 Preparation 6-Chloro-2-Fluoro-3-(Propane-1-Sulfonylamino)-Benzoic Acid (18)

6-Chloro-2-fluoro-3-(propane-1-sulfonylamino)-benzoic acid ethyl ester (17, 20 g) was dissolved in a mixture of 500 mL tetrahydrofuran and 150 mL water. Lithium hydroxide (12.95 g) was added and the resulting suspension was stirred at 90° C. for 17 hours. The mixture was cooled down to room temperature, then brought to pH=1 with concentrated hydrochloric acid (~36 mL). The aqueous layer was separated and extracted with 3×400 mL of ethyl acetate. The combined organic extracts were dried over magnesium sulfate and concentrated to give a beige solid (25 g). The solid was triturated in 100 mL of diethyl ether for 30 minutes, filtered, washed with 50 mL of diethyl ether and dried to provide the desired compound as a white solid (18, 16 g, 87%).

Step 4—Preparation 6-chloro-2-fluoro-3-(propane-1-sulfonylamino)-benzoyl chloride (19)

6-Chloro-2-fluoro-3-(propane-1-sulfonylamino)-benzoic acid 18 was suspended in anhydrous dichloromethane (30 mL/g). Dimethylformamide (2 drops) was added and the suspension cooled in an ice/water bath. Oxalyl chloride (5 eq) was slowly added dropwise. The bath was then removed and the reaction mixture stirred at room temperature for 2 to 3 hours and the solids slowly disappeared. Dichloromethane and excess oxalyl chloride were removed under reduced pressure and the residue was used without further purification in the next step.

Step 5 Preparation of N-(6-bromo-pyridin-3-yl)-6-chloro-2-fluoro-3-(propane-1-sulfonylamino)-benzamide (21)

6-Bromo-pyridin-3-ylamine (20, 3.16 g, 18.26 mmol) was dissolved in 55 mL of anhydrous tetrahydrofuran. Triethylamine (1.85 g, 2.55 mL, 18.26 mmol) was added and the mixture cooled in an ice/salt bath. A solution of 6-chloro-2-fluoro-3-(propane-1-sulfonylamino)-benzoyl chloride (19, 3.8 g, 12.17 mmol) in 55 mL of anhydrous tetrahydrofuran was slowly added dropwise to the reaction mixture. The resulting mixture was stirred at room temperature for 18 hours, then diluted with 180 mL of ethyl acetate, washed 2×70 mL with water and once with 110 mL brine, dried over magnesium sulfate and concentrated to give a brown residue. The residue was purified by silica gel flash chromatography, eluting with 1% methanol, to provide the desired compound as a yellow solid (21, 6.9 g, 66%).

Step 6—Preparation 6-chloro-2-fluoro-N-[6-(5-methyl-thiazol-2-ylamino)-pyridin-3-yl]-3-(propane-1-sulfonylamino)-benzamide (P-0011)

N-(6-bromo-pyridin-3-yl)-6-chloro-2-fluoro-3-(propane-1-sulfonylamino)-benzamide (21, 250 mg, 0.555 mmol) was placed in a microwave vial along with palladium acetate (12.5 mg, 0.055 mmol), BINAP (69 mg, 0.111 mmol), potassium tert-butoxide (124 mg, 1.11 mmol) and 2-amino-5-methyl-thiazole (22, 190 mg, 1.66 mmol). Dimethylformamide (2.5 mL) was added and the vial sealed. The mixture was then heated at 150° C. in a microwave for 3 hours. The black mixture was diluted with 50 mL of ethyl acetate and washed with 15 mL of water, then 15 mL of 0.67 M hydrochloric acid solution, 15 mL of water and finally 15 mL of brine. The organic phase was dried over magnesium sulfate. After removal of the solvent, the residue was purified by preparative TLC and then HPLC to provide the desired compound as a white solid (P-0011, 10 mg). MS (ESI) [M+H]+=483.8.

Example 5: Synthesis of 6-chloro-2-fluoro-N-(6-isopropylamino-pyridin-3-yl)-3-(propane-1-sulfonylamino)-benzamide P-0005

6-Chloro-2-fluoro-N-(6-isopropylamino-pyridin-3-yl)-3-(propane-1-sulfonylamino)-benzamide P-0005 was synthesized in three steps from 2-bromo-5-nitro-pyridine 23 as shown in Scheme 5.

Scheme 5

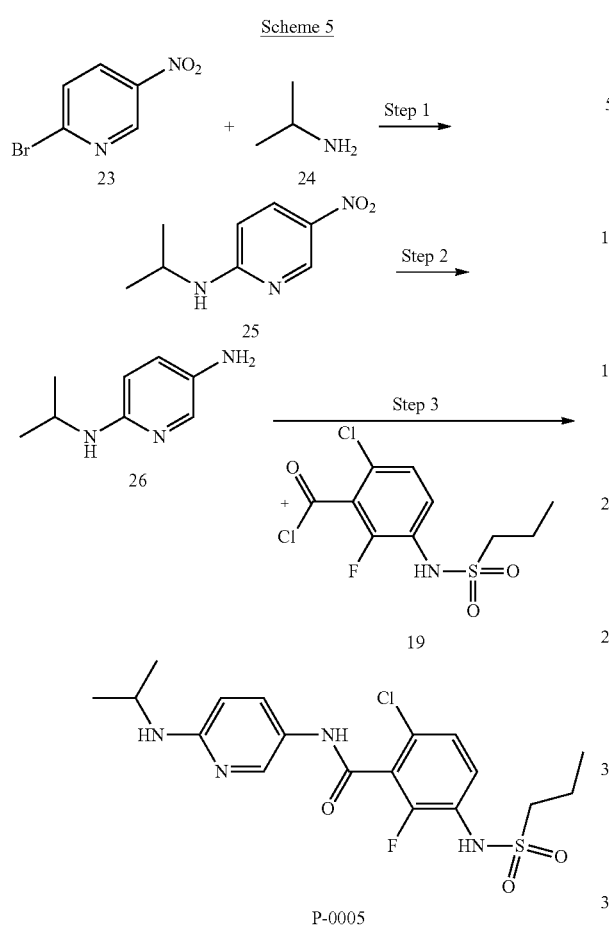

Step 1—Preparation of 6-isopropylamino-3-nitro pyridine (25)

2-Bromo-5-nitro-pyridine (23, 400 mg) was placed in a microwave vial. Isopropylamine (24, 3 mL) was added and the vial sealed. The mixture was then heated at 120° C. for 30 minutes using a Biotage Initiator EXP microwave. The crude mixture was then absorbed on a column and purified by silica gel chromatography. The fractions containing the desired compound were combined and concentrated to provide the desired compound as a yellow solid.

Step 2—Preparation of N*2*-isopropyl-pyridine-2,5-diamine (26)

The 6-isopropylamino-3-nitro pyridine 25 was dissolved in methanol (35 mL/g). Palladium on carbon catalyst (10%, wet, ~100 mg) was added and the suspension was placed under a hydrogen atmosphere at room temperature overnight (~18 hours). The catalyst was removed by filtration on a pad of celite and washed with 2×10 mL of methanol. The filtrate was concentrated under reduced pressure to provide the desired compound, which was used without further purification in the next step.

Step 3—Preparation of 6-chloro-2-fluoro-N-(6-isopropylamino-pyridin-3-yl)-3-(propane-1-sulfonylamino)-benzamide (P-0005)

N*2*-isopropyl-pyridine-2,5-diamine (26, 155 mg, 1.01 mmol) was dissolved in 4 mL of anhydrous tetrahydrofuran. Triethylamine (103 mg, 142 µL, 1.01 mmol) was added and the mixture cooled in an ice/salt bath. 6-Chloro-2-fluoro-3-(propane-1-sulfonylamino)-benzoyl chloride (19, 200 mg, 0.68 mmol) in 4 mL of anhydrous tetrahydrofuran was then slowly added dropwise. The resulting mixture was stirred at room temperature for 20 hours, then diluted with 30 mL of ethyl acetate, washed with 3×10 mL of water and 15 mL of brine. After removal of the solvent, the residue was purified by silica gel chromatography to provide the desired compound as a white solid (P-0005, 35 mg). MS (ESI) $[M+H^+]^+$=429.0.

6-Chloro-N-(6-cyclopentylamino-pyridin-3-yl)-2-fluoro-3-(propane-1-sulfonylamino)-benzamide P-0009, 6-Chloro-N-(6-cyclopropylamino-pyridin-3-yl)-2-fluoro-3-(propane-1-sulfonylamino)-benzamide P-0015, 6-Chloro-2-fluoro-3-(propane-1-sulfonylamino)-N-{6-[(thiophen-2-ylmethyl)-amino]-pyridin-3-yl}-benzamide P-0016, and N-(6-Benzylamino-pyridin-3-yl)-6-chloro-2-fluoro-3-(propane-1-sulfonylamino)-benzamide P-0017,

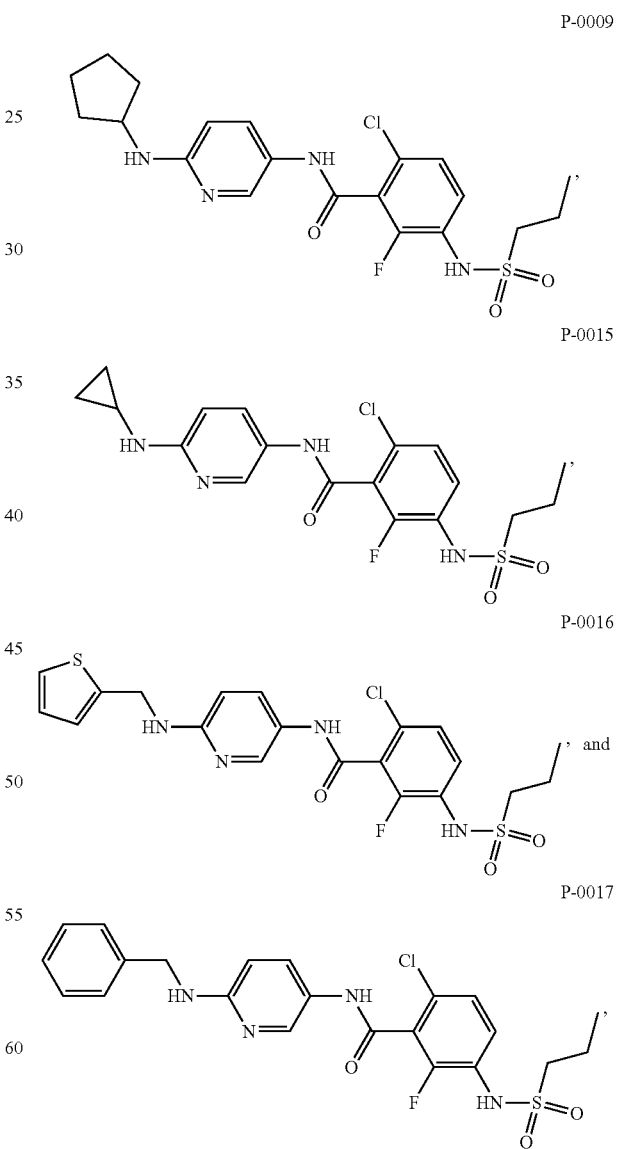

were prepared following the protocol of Scheme 5, replacing isopropylamine 24 with cyclopentylamine, cyclopropylamine, thiophen-2-yl-methylamine and benzylamine, respectively, in Step 1. MS (ESI) [M+H⁺]⁺ P-0009=455.2, P-0015=427.0, P-0016=483.2 and P-0017=477.2.

Example 6: Synthesis of N-(2-acetylamino-pyrimidin-5-yl)-6-chloro-2-fluoro-3-(propane-1-sulfonylamino)-benzamide P-0004

N-(2-Acetylamino-pyrimidin-5-yl)-6-chloro-2-fluoro-3-(propane-1-sulfonylamino)-benzamide P-0004 was synthesized in three steps from 2-amino-5-nitropyrimidine 27 as shown in Scheme 6.

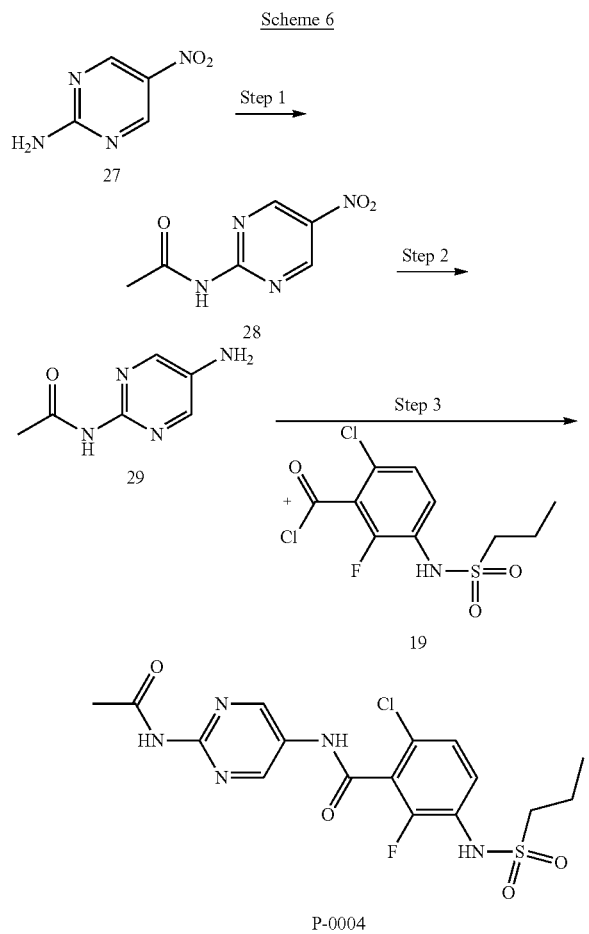 [SMILES: Nc1ncc([N+](=O)[O-])cn1 ; CC(=O)Nc1ncc([N+](=O)[O-])cn1 ; CC(=O)Nc1ncc(N)cn1 ; CCCS(=O)(=O)Nc1ccc(Cl)c(C(=O)Cl)c1F ; CCCS(=O)(=O)Nc1ccc(Cl)c(C(=O)Nc2cnc(NC(C)=O)nc2)c1F]

Step 1—Preparation of N-(5-nitro-pyrimidin-2-yl)-acetamide (28)

2-Amino-5-nitropyrimidine (27, 500 mg) was suspended in 5 mL of acetic anhydride. The mixture was heated at 160° C. for two hours, then cooled to room temperature. The solids were filtered and washed with 5 mL of water, then suspended in 10 mL of water and the pH was brought to 8-9 by addition of 25% ammonium hydroxide solution. The solids were filtered, washed with 2×10 mL cold water and recrystallized from ethyl acetate to provide the desired compound as beige needles (28, 382 mg, 58%).

Step 2—Preparation of N-(5-amino-pyrimidin-2-yl)-acetamide (29)

N-(5-Nitro-pyrimidin-2-yl)-acetamide (28, 620 mg) was suspended in 31 mL of methanol. Palladium on carbon catalyst (10%, wet, 60 mg) was added and the suspension was placed under hydrogen atmosphere for 17 hours. The catalyst was filtered off on a pad of celite and washed with 2×30 mL of methanol. The filtrate was concentrated under reduced pressure to provide the desired compound as pale yellow needles (29, 520 mg, 100%).

Step 3—Preparation of N-(2-acetylamino-pyrimidin-5-yl)-6-chloro-2-fluoro-3-(propane-1-sulfonylamino)-benzamide P-0004

N-(5-amino-pyrimidin-2-yl)-acetamide (29, 154 mg, 1.01 mmol) was dissolved in 3 mL of anhydrous tetrahydrofuran. Triethylamine (103 mg, 142 µL, 1.01 mmol) was added and the mixture cooled in an ice/salt bath. 6-Chloro-2-fluoro-3-(propane-1-sulfonylamino)-benzoyl chloride (19, 200 mg, 0.68 mmol) in 3 mL of anhydrous tetrahydrofuran was then slowly added dropwise. The resulting mixture was stirred at room temperature for 18 hours, then diluted with 20 mL of ethyl acetate, washed with 2×10 mL of water and 10 mL of brine. The organic layer was dried over magnesium sulfate. After removal of the solvent, the residue was purified by silica gel chromatography to provide the desired compound as a white solid (P-0004, 55 mg, 19%). MS (ESI) [M+H⁺]⁺=430.2.

Example 7: Synthesis of N-(6-acetylamino-pyridin-3-yl)-2,6-difluoro-3-(propane-1-sulfonylamino)-benzamide P-0008

N-(6-Acetylamino-pyridin-3-yl)-2,6-difluoro-3-(propane-1-sulfonylamino)-benzamide P-0008 was synthesized in three steps from 2,6-difluoro-3-nitro-benzoic acid 30 and N-(5-amino-pyridin-2-yl)-acetamide 31 as shown in Scheme 7.

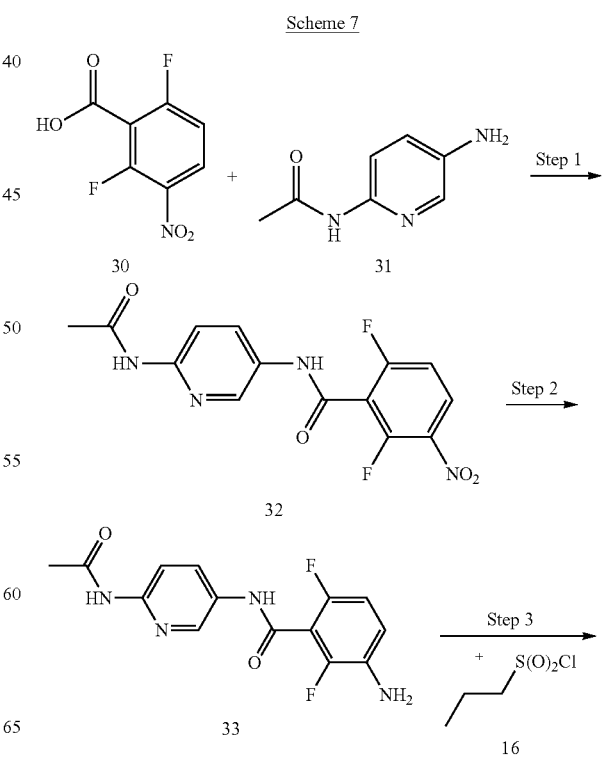

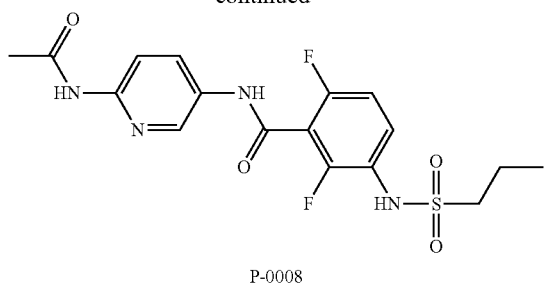

P-0008

Step 1—Preparation of N-(6-acetylamino-pyridin-3-yl)-2,6-difluoro-3-nitro-benzamide (32)

2,6-difluoro-3-nitro-benzoic acid (30, 500 mg) was dissolved in 15 mL of anhydrous dichloromethane. N,N-Dimethylformamide (1 drop) was then added and the mixture cooled to 5° C. in an ice/water bath. Oxalyl chloride (1.1 mL, 5 eq) was slowly added dropwise. The reaction mixture was stirred at room temperature for two hours, then concentrated under reduced pressure to give a yellow solid residue, which was dissolved in 5 mL of anhydrous tetrahydrofuran and slowly added dropwise to a solution of N-(5-amino-pyridin-2-yl)-acetamide (31, 558 mg, 1.5 eq) and triethylamine (0.52 mL) in 10 mL of anhydrous tetrahydrofuran. The resulting suspension was stirred at room temperature overnight. The mixture was diluted with 50 mL of ethyl acetate, washed with 2×25 mL of water, then 25 mL brine, dried over magnesium sulfate and concentrated to provide the crude desired compound as a brown solid (32, 980 mg, 84%), which was used in the next step without further purification.

Step 2—Preparation of N-(6-acetylamino-pyridin-3-yl)-3-amino-2,6-difluoro-benzamide (33)

N-(6-Acetylamino-pyridin-3-yl)-2,6-difluoro-3-nitro-benzamide (32, 950 mg) was suspended in 15 mL of methanol. Palladium on carbon catalyst (10%, wet, 100 mg) was added and the suspension was placed under hydrogen atmosphere for 17 hours. The catalyst was filtered off on a pad of celite and washed with 2×20 mL of methanol. The filtrate was concentrated under reduced pressure to provide the desired compound as a black solid (33, 750 mg, 86%).

Step 3—Preparation of N-(6-acetylamino-pyridin-3-yl)-2,6-difluoro-3-(propane-1-sulfonylamino)-benzamide (P-0008)

N-(6-Acetylamino-pyridin-3-yl)-3-amino-2,6-difluoro-benzamide (33, 700 mg) was dissolved in 35 mL of pyridine. 4-dimethyl-amino-pyridine (1 eq) was added followed by propane-1-sulfonyl chloride (16, 0.80 g, 2.3 eq). The resulting mixture was stirred at room temperature for 3 days, then at 70° C. for 18 hours. The pyridine was removed under reduced pressure and the residue purified by silica gel column chromatography eluting with ethyl acetate in hexanes to provide the desired compound as a yellow solid (P-0008, 10 mg, 1%). MS (ESI) [M+H$^+$]$^+$=412.9.

Additional compounds may be prepared following the protocol of Scheme 7, replacing propane-1-sulfonyl chloride 16 with a suitable sulfonyl chloride in Step 3. The following compounds may be prepared by this method:

N-(6-Acetylamino-pyridin-3-yl)-2,6-difluoro-3-(2-fluoro-benzenesulfonylamino)-benzamide (P-0097), N-(6-Acetylamino-pyridin-3-yl)-2,6-difluoro-3-(3-fluoro-benzenesulfonylamino)-benzamide (P-0098), N-(6-Acetylamino-pyridin-3-yl)-3-(2,6-difluoro-benzenesulfonylamino)-2,6-difluoro-benzamide (P-0099), N-(6-Acetylamino-pyridin-3-yl)-3-(2,4-difluoro-benzenesulfonylamino)-2,6-difluoro-benzamide (P-0100), N-(6-Acetylamino-pyridin-3-yl)-3-(2,5-difluoro-benzenesulfonylamino)-2,6-difluoro-benzamide (P-0101), 6-Acetylamino-N-[2,6-difluoro-3-(3-fluoro-4-methoxy-benzenesulfonylamino)-phenyl]-nicotinamide (P-0102), N-(6-Acetylamino-pyridin-3-yl)-2,6-difluoro-3-(4-trifluoromethyl-benzenesulfonylamino)-benzamide (P-0103), N-(6-Acetylamino-pyridin-3-yl)-3-(4-difluoromethoxy-benzenesulfonylamino)-2,6-difluoro-benzamide (P-0104), N-(6-Acetylamino-pyridin-3-yl)-3-(3-difluoromethoxy-benzenesulfonylamino)-2,6-difluoro-benzamide (P-0105), N-(6-Acetylamino-pyridin-3-yl)-2,6-difluoro-3-(4-isopropyl-benzenesulfonylamino)-benzamide (P-0106), N-(6-Acetylamino-pyridin-3-yl)-3-(4-tert-butyl-benzenesulfonylamino)-2,6-difluoro-benzamide (P-0107), N-(6-Acetylamino-pyridin-3-yl)-2,6-difluoro-3-(4-propyl-benzenesulfonylamino)-benzamide (P-0108), N-(6-Acetylamino-pyridin-3-yl)-2,6-difluoro-3-(pyridine-2-sulfonylamino)-benzamide (P-0109), N-(6-Acetylamino-pyridin-3-yl)-2,6-difluoro-3-(pyridine-3-sulfonylamino)-benzamide (P-0110), N-(6-Acetylamino-pyridin-3-yl)-2,6-difluoro-3-(dimethylaminosulfonylamino)-benzamide (P-0111), N-(6-Acetylamino-pyridin-3-yl)-2,6-difluoro-3-(piperidine-1-sulfonylamino)-benzamide (P-0112), N-(6-Acetylamino-pyridin-3-yl)-2,6-difluoro-3-(morpholine-4-sulfonylamino)-benzamide (P-0113), N-(6-Acetylamino-pyridin-3-yl)-2,6-difluoro-3-(tetrahydropyran-4-sulfonylamino)-benzamide (P-0114), N-(6-Acetylamino-pyridin-3-yl)-3-cyclopentanesulfonylamino-2,6-difluoro-benzamide (P-0115), N-(6-Acetylamino-pyridin-3-yl)-2,6-difluoro-3-(pyrrolidine-1-sulfonylamino)-benzamide (P-0116), and N-(6-Acetylamino-pyridin-3-yl)-2,6-difluoro-3-(3,3,3-trifluoro-propane-1-sulfonylamino)-benzamide (P-0117).

The following table indicates the compound number in Column 1, the sulfonyl chloride used in Step 3 in Column 2, and the resulting compound in Column 3:

| Compound number | Sulfonyl Chloride in Step 3 | Compound |
|---|---|---|
| P-0097 | 2-fluorobenzenesulfonyl chloride | N-(6-acetamidopyridin-3-yl)-2,6-difluoro-3-((2-fluorophenyl)sulfonamido)benzamide |
| P-0098 | 3-fluorobenzenesulfonyl chloride | N-(6-acetamidopyridin-3-yl)-2,6-difluoro-3-((3-fluorophenyl)sulfonamido)benzamide |
| P-0099 | 2,6-difluorobenzenesulfonyl chloride | N-(6-acetamidopyridin-3-yl)-3-((2,6-difluorophenyl)sulfonamido)-2,6-difluorobenzamide |
| P-0100 | 2,4-difluorobenzenesulfonyl chloride | N-(6-acetamidopyridin-3-yl)-3-((2,4-difluorophenyl)sulfonamido)-2,6-difluorobenzamide |
| P-0101 | 2,5-difluorobenzenesulfonyl chloride | N-(6-acetamidopyridin-3-yl)-3-((2,5-difluorophenyl)sulfonamido)-2,6-difluorobenzamide |
| P-0102 | 3-fluoro-4-methoxybenzenesulfonyl chloride | N-(6-acetamidopyridin-3-yl)-2,6-difluoro-3-((3-fluoro-4-methoxyphenyl)sulfonamido)benzamide |
| P-0103 | 4-(trifluoromethyl)benzenesulfonyl chloride | N-(6-acetamidopyridin-3-yl)-2,6-difluoro-3-((4-(trifluoromethyl)phenyl)sulfonamido)benzamide |

-continued

| Compound number | Sulfonyl Chloride in Step 3 | Compound |
|---|---|---|
| P-0104 | 4-(difluoromethoxy)benzenesulfonyl chloride | N-(6-acetamidopyridin-3-yl)-3-((4-(difluoromethoxy)phenyl)sulfonamido)-2,6-difluorobenzamide |
| P-0105 | 3-(difluoromethoxy)benzenesulfonyl chloride | N-(6-acetamidopyridin-3-yl)-3-((3-(difluoromethoxy)phenyl)sulfonamido)-2,6-difluorobenzamide |
| P-0106 | 4-isopropylbenzenesulfonyl chloride | N-(6-acetamidopyridin-3-yl)-2,6-difluoro-3-((4-isopropylphenyl)sulfonamido)benzamide |
| P-0107 | 4-tert-butylbenzenesulfonyl chloride | N-(6-acetamidopyridin-3-yl)-3-((4-(tert-butyl)phenyl)sulfonamido)-2,6-difluorobenzamide |
| P-0108 | 4-propylbenzenesulfonyl chloride | N-(6-acetamidopyridin-3-yl)-2,6-difluoro-3-((4-propylphenyl)sulfonamido)benzamide |
| P-0109 | pyridine-2-sulfonyl chloride | N-(6-acetamidopyridin-3-yl)-2,6-difluoro-3-(pyridine-2-sulfonamido)benzamide |
| P-0110 | pyridine-3-sulfonyl chloride | N-(6-acetamidopyridin-3-yl)-2,6-difluoro-3-(pyridine-3-sulfonamido)benzamide |

| Compound number | Sulfonyl Chloride in Step 3 | Compound |
|---|---|---|
| P-0111 | dimethylsulfamoyl chloride | N-(6-acetamidopyridin-3-yl)-3-((N,N-dimethylsulfamoyl)amino)-2,6-difluorobenzamide |
| P-0112 | piperidine-1-sulfonyl chloride | N-(6-acetamidopyridin-3-yl)-2,6-difluoro-3-((piperidin-1-ylsulfonyl)amino)benzamide |
| P-0113 | morpholine-4-sulfonyl chloride | N-(6-acetamidopyridin-3-yl)-2,6-difluoro-3-((morpholin-4-ylsulfonyl)amino)benzamide |
| P-0114 | tetrahydro-2H-pyran-4-sulfonyl chloride | N-(6-acetamidopyridin-3-yl)-2,6-difluoro-3-(((tetrahydro-2H-pyran-4-yl)sulfonyl)amino)benzamide |
| P-0115 | cyclopentanesulfonyl chloride | N-(6-acetamidopyridin-3-yl)-3-((cyclopentylsulfonyl)amino)-2,6-difluorobenzamide |
| P-0116 | pyrrolidine-1-sulfonyl chloride | N-(6-acetamidopyridin-3-yl)-2,6-difluoro-3-((pyrrolidin-1-ylsulfonyl)amino)benzamide |
| P-0117 | 3,3,3-trifluoropropane-1-sulfonyl chloride | N-(6-acetamidopyridin-3-yl)-2,6-difluoro-3-(((3,3,3-trifluoropropyl)sulfonyl)amino)benzamide |

Example 8: Synthesis of pyrrolidine-1-carboxylic acid {5-[6-chloro-2-fluoro-3-(propane-1-sulfonylamino)-benzoylamino]-pyridin-2-yl}-amide P-0006

Pyrrolidine-1-carboxylic acid {5-[6-chloro-2-fluoro-3-(propane-1-sulfonylamino)-benzoylamino]-pyridin-2-yl}-amide P-0006 was synthesized in four steps from 2-amino-5-nitro-pyridine 34 as shown in Scheme 8.

Scheme 8

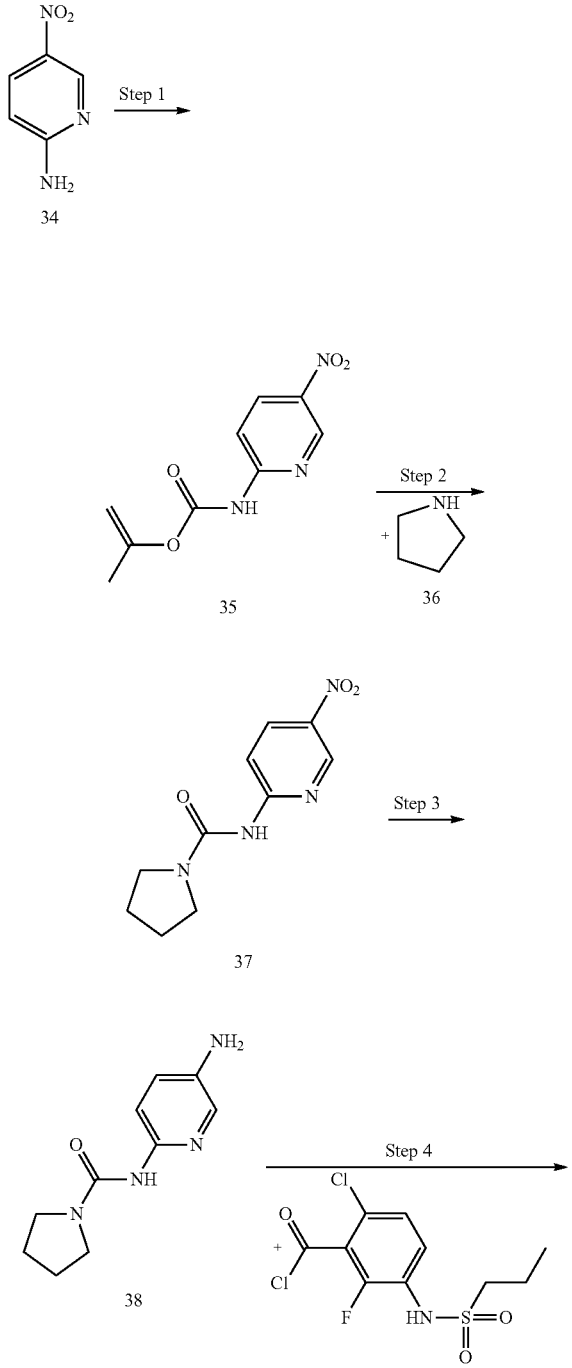

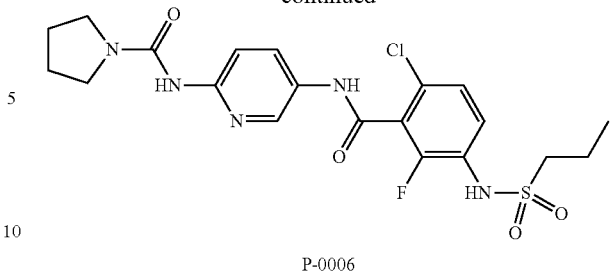

P-0006

Step 1—Preparation (5-nitro-pyridin-2-yl)-carbamic acid isopropenyl ester (35)

2-Amino-5-nitro-pyridine (34, 500 mg) was dissolved in 5 mL of anhydrous tetrahydrofuran. N-Methyl morpholine (436 mg, 1.2 eq) was added and the mixture cooled to −10° C. in an ice/salt acetone bath. A solution of isopropenyl chloroformate (520 mg) in 5 mL of tetrahydrofuran was then slowly added dropwise while maintaining the temperature below −10° C. The reaction mixture was stirred at room temperature overnight, then diluted with 25 mL of ethyl acetate and 20 mL of water. The aqueous layer was separated and extracted with 2×25 mL of ethyl acetate. The combined organic extracts were washed with 25 mL of half saturated brine and dried over magnesium sulfate. After removal of the solvent, the residue was purified with silica gel column chromatography eluting with ethyl acetate in hexane to provide the desired compound as a white solid (35, 0.52 g, 65%).

Step 2—Preparation of pyrrolidine-1-carboxylic acid (5-nitro-pyridin-2-yl)-amide (37)

(5-Nitro-pyridin-2-yl)-carbamic acid isopropenyl ester (35, 160 mg) was dissolved in 2 mL of anhydrous tetrahydrofuran. N-Methylpyrrolidine (6 mg, 0.1 eq) was added, followed by pyrrolidine (36, 51 mg, 1 eq). The mixture was stirred at room temperature overnight, forming a precipitate. The precipitate was filtered off, washed with 1 mL of tetrahydrofuran and dried to give a white solid. Additional compound was obtained by concentration of the filtrate under reduced pressure and trituration of the residue in diethyl ether (~5 mL) to provide the desired compound as a beige solid (37, 0.12 g, 71%).

Step 3—Preparation of pyrrolidine-1-carboxylic acid (5-amino-pyridin-2-yl)-amide (38)

Pyrrolidine-1-carboxylic acid (5-nitro-pyridin-2-yl)-amide (37, 115 mg) was dissolved in 10 mL of methanol. Palladium on carbon catalyst was added and the suspension placed under a hydrogen atmosphere for 64 hours. The catalyst was filtered over a pad of celite and washed with 2×10 mL of methanol. The filtrate was concentrated under reduced pressure to provide the desired compound as a grey solid (38, 0.1 g, 100%).

Step 4—Preparation of pyrrolidine-1-carboxylic acid {5-[6-chloro-2-fluoro-3-(propane-1-sulfonylamino)-benzoylamino]-pyridin-2-yl}-amide (P-0006)

Pyrrolidine-1-carboxylic acid (5-amino-pyridin-2-yl)-amide (38, 100 mg, 0.48 mmol) was dissolved in 2 mL of anhydrous tetrahydrofuran. Triethylamine (49 mg, 67 µL, 0.48 mmol) was added and the mixture cooled in an ice/salt bath. 6-Chloro-2-fluoro-3-(propane-1-sulfonylamino)-benzoyl chloride (19, 100 mg, 0.34 mmol) in 1 mL of anhydrous tetrahydrofuran was then slowly added dropwise. The resulting mixture was stirred at room temperature for 60 hours, then diluted with 20 mL of ethyl acetate, washed with 2×10 mL of water and 10 mL of brine. The organic layer was dried over magnesium sulfate. After removal of solvent, the residue was purified by silica gel column chromatography eluting with ethyl acetate in hexanes to provide the desired compound as a white solid (P-0006, 5 mg, 3%). MS (ESI) [M+H$^+$]$^+$=484.0.

Example 9: Synthesis of 6-chloro-2-fluoro-3-(propane-1-sulfonylamino)-N-quinolin-3-yl-benzamide P-0013

6-Chloro-2-fluoro-3-(propane-1-sulfonylamino)-N-quinolin-3-yl-benzamide P-0013 was synthesized in one step from 3-aminoquinoline 39 as shown in Scheme 9.

Scheme 9

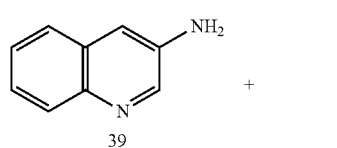

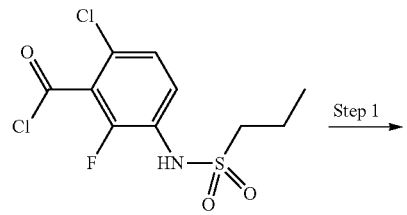

Step 1—Preparation of 6-chloro-2-fluoro-3-(propane-1-sulfonylamino)-N-quinolin-3-yl-benzamide (P-0013)

3-Aminoquinoline (39, 172 mg, 1.19 mmol) was dissolved in 5 mL of anhydrous tetrahydrofuran. Triethylamine (120 mg, 170 µL, 1.19 mmol) was added and the mixture cooled in an ice/salt bath. 6-chloro-2-fluoro-3-(propane-1-sulfonylamino)-benzoyl chloride (19, 250 mg, 0.80 mmol) in 5 mL of anhydrous tetrahydrofuran was slowly added dropwise. The resulting mixture was stirred at room temperature for 20 hours, then diluted with 30 mL of ethyl acetate, washed with 3×10 mL of water and 15 mL of brine. The organic layer was dried over magnesium sulfate and concentrated to give a pale yellow residue (400 mg), which was further triturated in ethyl acetate to provide the desired compound as a white solid (P-0013, 110 mg, 32%). MS (ESI) [M+H$^+$]$^+$=421.9.

N-(6-Acetylamino-pyridin-3-yl)-6-chloro-2-fluoro-3-(propane-1-sulfonylamino)-benzamide P-0002, 6-Chloro-2-fluoro-N-(6-methoxy-pyridin-3-yl)-3-(propane-1-sulfonylamino)-benzamide P-0003, 6-Chloro-N-(3,5-dimethyl-isoxazol-4-yl)-2-fluoro-3-(propane-1-sulfonylamino)-benzamide P-0007, 6-chloro-N-[5-(4-chloro-phenyl)-2H-pyrazol-3-yl]-2-fluoro-3-(propane-1-sulfonylamino)-benzamide P-0010, 6-chloro-N-[5-(4-chloro-benzyl)-[1,3,4]thiadiazol-2-yl]-2-fluoro-3-(propane-1-sulfonylamino)-benzamide P-0012, [2-[6-Chloro-2-fluoro-3-(propane-1-sulfonylamino)-benzoylamino]-4H-[1,3,4]thiadiazin-(5E)-ylidene]-acetic acid ethyl ester P-0014, and 6-Chloro-2-fluoro-N-imidazo[1,2-a]pyridin-3-yl-3-(propane-1-sulfonylamino)-benzamide P-0018,

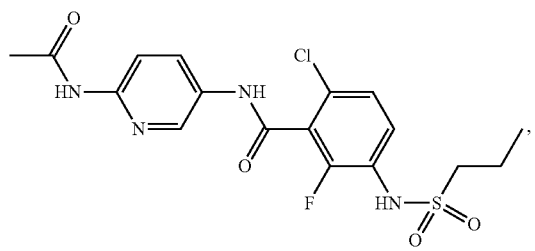

P-0002

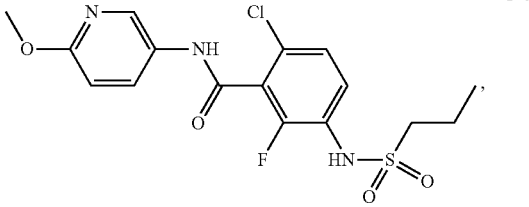

P-0003

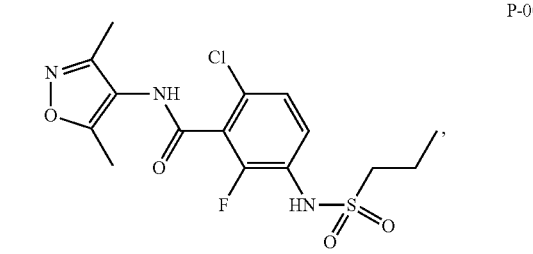

P-0007

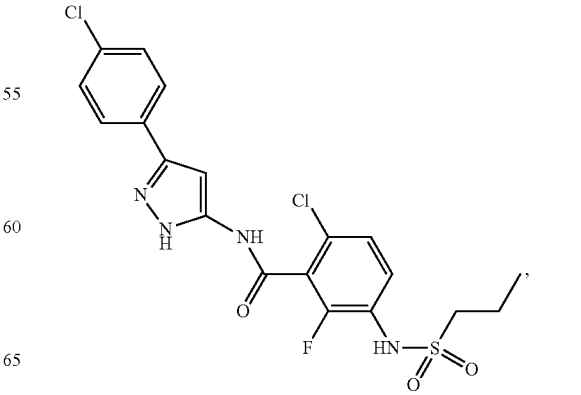

P-0010

-continued

P-0012

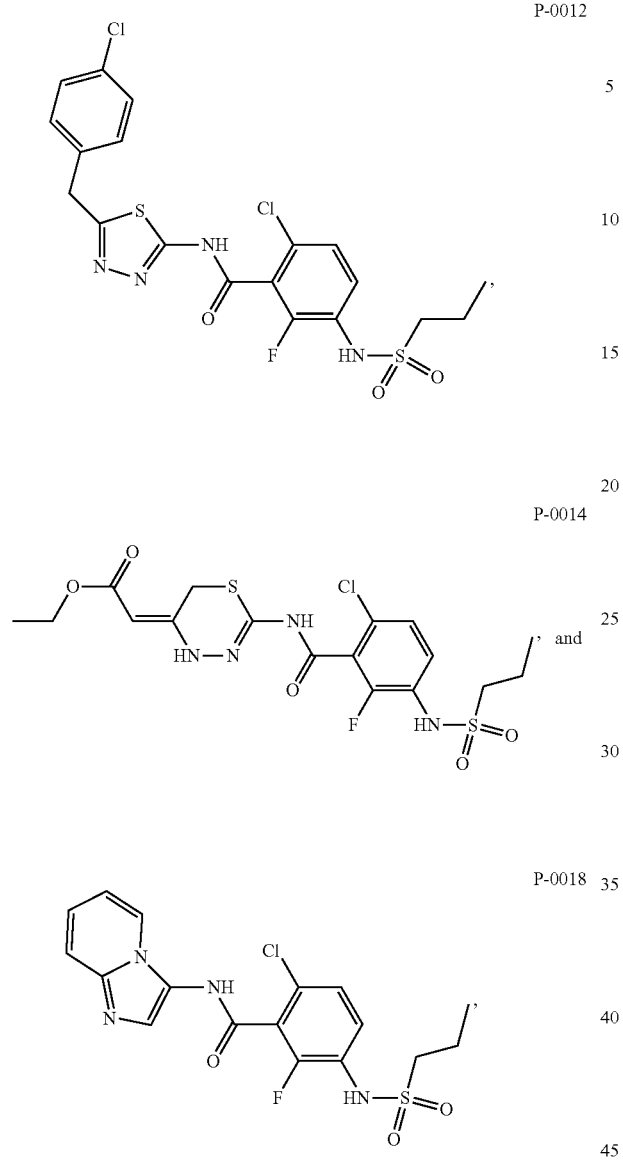

P-0014

P-0018 were prepared following the protocol of Scheme 9, replacing 3-aminoquinoline 39 with N-(5-amino-pyridin-2-yl)-acetamide; 6-methoxy-pyridin-3-ylamine; 3,5-dimethyl-isoxazol-4-ylamine; 5-(4-chloro-phenyl)-2H-pyrazol-3-ylamine; 5-(4-chloro-benzyl)-[1,3,4]thiadiazol-2-ylamine; [2-amino-4H-[1,3,4]thiadiazin-(5E)-ylidene]-acetic acid ethyl ester; and imidazo[1,2-a]pyridin-3-ylamine, respectively. MS (ESI) [M+H⁺]⁺ P-0002=429.2, P-0003=402.2, P-0007=389.9, P-0010=471.2, P-0012=503.0, P-0014=478.9 and P-0018=411.0.

Example 10: Synthesis of 6-chloro-2-fluoro-3-(propane-1-sulfonylamino)-N-pyridin-3-yl-benzamide P-0001

6-Chloro-2-fluoro-3-(propane-1-sulfonylamino)-N-pyridin-3-yl-benzamide P-0001 was synthesized in two steps from 6-chloro-2-fluoro-3-(propane-1-sulfonylamino)-benzoic acid 18 as shown in Scheme 10.

Scheme 10

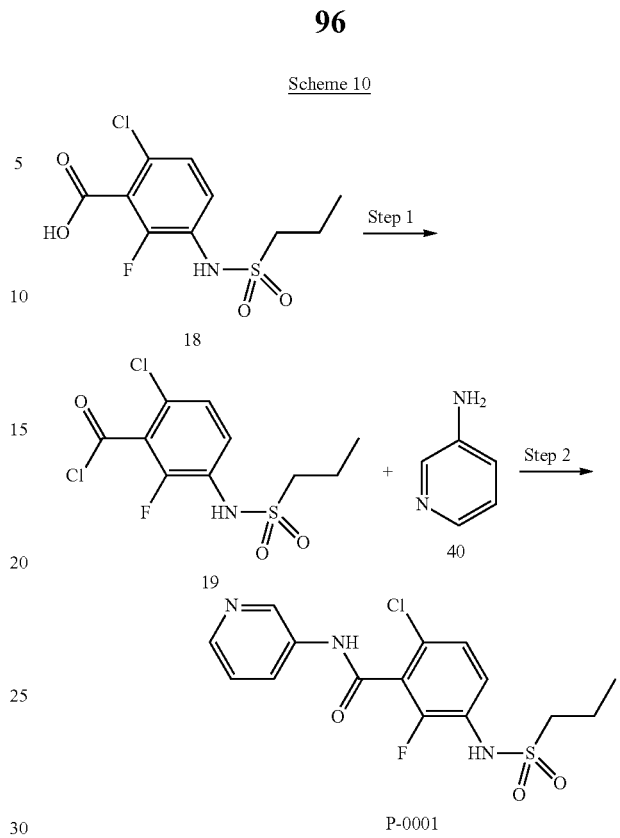

Step 1—Preparation of 6-chloro-2-fluoro-3-(propane-1-sulfonylamino)-benzoyl chloride (19)

To 6-chloro-2-fluoro-3-(propane-1-sulfonylamino)-benzoic acid (18, 502 mg, 1.70 mmol, prepared as in Step 3 of Scheme 4, Example 4) in 35 mL of dichloromethane, oxalyl chloride (5 mL, 2.0 M in dichloromethane) and N,N-dimethylformamide (100 μL, 0.001 mol) were added. The reaction mixture was stirred at room temperature for 2 hours. The reaction was concentrated to give compound 19, used without further purification.

Step 2—Preparation of 6-chloro-2-fluoro-3-(propane-1-sulfonylamino)-N-pyridin-3-yl-benzamide (P-0001)

To 6-chloro-2-fluoro-3-(propane-1-sulfonylamino)-benzoyl chloride (19, 0.200 g, 0.64 mmol) in 10.0 mL of dichloromethane, pyridin-3-ylamine (40, 0.126 g, 1.34 mmol) and 4-dimethylaminopyridine (7.8 mg, 0.064 mmol) were added. The reaction was stirred at room temperature overnight. The reaction mixture was poured into water and extracted with ethyl acetate. The organic layer was washed with brine, dried over anhydrous sodium sulfate and filtered. The filtrate was concentrated and purified with silica gel column chromatography eluting 5% methanol in dichloromethane to provide the desired compound (P-0001, 0.15 g, 63%). MS (ESI) [M+H⁺]⁺=371.1.

Example 11: Synthesis of propane-1-sulfonic acid {2,4-difluoro-3-[(5-methyl-isoxazol-3-ylamino)-methyl]-phenyl}-amide P-0019

Propane-1-sulfonic acid {2,4-difluoro-3-[(5-methyl-isoxazol-3-ylamino)-methyl]-phenyl}-amide P-0019 was synthesized in three steps from 2,4-difluoro-phenylamine 41 as shown in Scheme 11.

Scheme 11

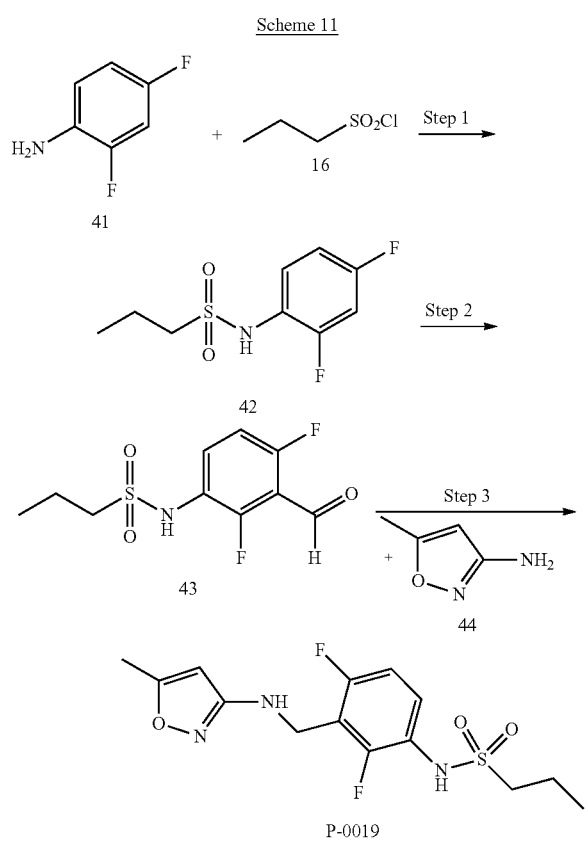

Step 1—Preparation of propane-1-sulfonic acid (2,4-difluoro-phenyl)-amide (42)

To 2,4-difluoro-phenylamine (41, 3.0 mL, 29.8 mmol) in 50 mL of tetrahydrofuran, triethylamine (9.13 mL, 65.5 mmol) and propane-1-sulfonyl chloride (16, 2.90 mL, 25.8 mmol) were added under an atmosphere of nitrogen. The reaction was stirred at room temperature overnight. The reaction was poured into 1 M HCl and extracted with ethyl acetate. The organic layer was washed with brine, dried over anhydrous sodium sulfate and filtered. The filtrate was concentrated to provide the desired compound (42, 2.0 g, 28%), which was used without further purification in the next step.

Step 2—Preparation of propane-1-sulfonic acid (2,4-difluoro-3-formyl-phenyl)-amide (43)

To propane-1-sulfonic acid (2,4-difluoro-phenyl)-amide (42, 1.5 g, 6.38 mmol) in 10 mL of tetrahydrofuran under an atmosphere of nitrogen, cooled in a −78° C. acetone/dry ice bath, lithium diisopropylamide (0.80 M in tetrahydrofuran, 24 mL, freshly prepared from n-butyllithium and diisopropylamine) was added. After 30 minutes, N,N-dimethylformamide (542 μL, 7.018 mmol) was added dropwise to the reaction. The reaction was stirred for 30 minutes at −78° C. and then allowed to warm to room temperature for 40 minutes. The reaction was poured into water and extracted with ethyl acetate. The organic layer was washed with brine, dried over anhydrous sodium sulfate and filtered. The filtrate was concentrated and purified by silica gel column chromatography eluting with 5% ethyl acetate in hexane to give a light yellow solid (43, 300 mg, 18%). MS(ESI) [M−H⁺]⁻=262.3.

Step 3—Preparation of propane-1-sulfonic acid {2,4-difluoro-3-[(5-methyl-isoxazol-3-ylamino)-methyl]-phenyl}-amide (P-0019)

To 5-methyl-isoxazol-3-ylamine (44, 0.13 g, 1.3 mmol) in 20 mL of acetonitrile, propane-1-sulfonic acid (2,4-difluoro-3-formyl-phenyl)-amide (43, 0.35 g, 1.3 mmol), triethylsilane (1 mL, 7 mmol) and trifluoroacetic acid (0.5 mL, 7 mmol) were added. The reaction mixture was stirred at 80° C. overnight. The reaction mixture was concentrated, then poured into aqueous potassium carbonate and extracted with ethyl acetate. The organic layer was dried over anhydrous sodium sulfate. After removal of drying agent and then solvent, the residue was purified by silica gel column chromatography to provide the desired compound as a white solid (P-0019, 0.22 g, 48%). MS (ESI) [M−H⁺]=346.95.

N-{5-[2,6-Difluoro-3-(propane-1-sulfonylamino)-benzylamino]-pyridin-2-yl}-acetamide P-0020, propane-1-sulfonic acid [2,4-difluoro-3-(quinolin-3-ylaminomethyl)-phenyl]-amide P-0021, propane-1-sulfonic acid {3-[(6-chloropyridin-3-ylamino)-methyl]-2,4-difluoro-phenyl}-amide P-0022, and propane-1-sulfonic acid {2,4-difluoro-3-[(6-methoxy-pyridin-3-ylamino)-methyl]-phenyl}-amide P-0023,

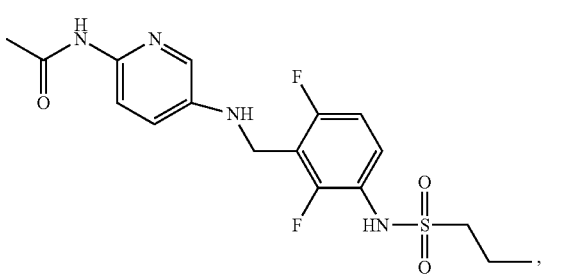
,
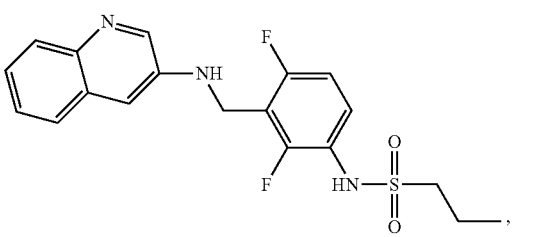
,
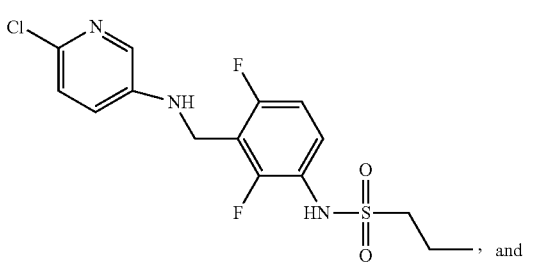
, and

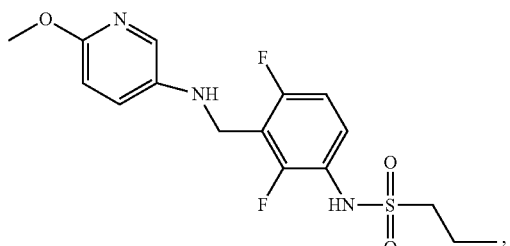

P-0023 were prepared following the protocol of Scheme 11, replacing 5-methyl-isoxazol-3-ylamine 44 with N-(5-amino-pyridin-2-yl)-acetamide, quinolin-3-ylamine, 6-chloro-pyridin-3-ylamine, and 6-methoxy-pyridin-3-ylamine, respectively. MS (ESI) [M+H⁺]⁺ P-0020=399.35, P-0021=392.40, P-0022=376.95, and P-0023=372.55.

Example 12: Synthesis of quinoline-3-carboxylic acid [2,6-difluoro-3-(propane-1-sulfonylamino)-phenyl]-amide P-0024 and propane-1-sulfonic acid {2,4-difluoro-3-[(quinolin-3-ylmethyl)-amino]-phenyl}-amide P-0025

Quinoline-3-carboxylic acid [2,6-difluoro-3-(propane-1-sulfonylamino)-phenyl]-amide P-0024 and propane-1-sulfonic acid {2,4-difluoro-3-[(quinolin-3-ylmethyl)-amino]-phenyl}-amide P-0025 were synthesized in three steps from propane-1-sulfonic acid (2,4-difluoro-3-formyl-phenyl)-amide 43 as shown in Scheme 12.

Scheme 12

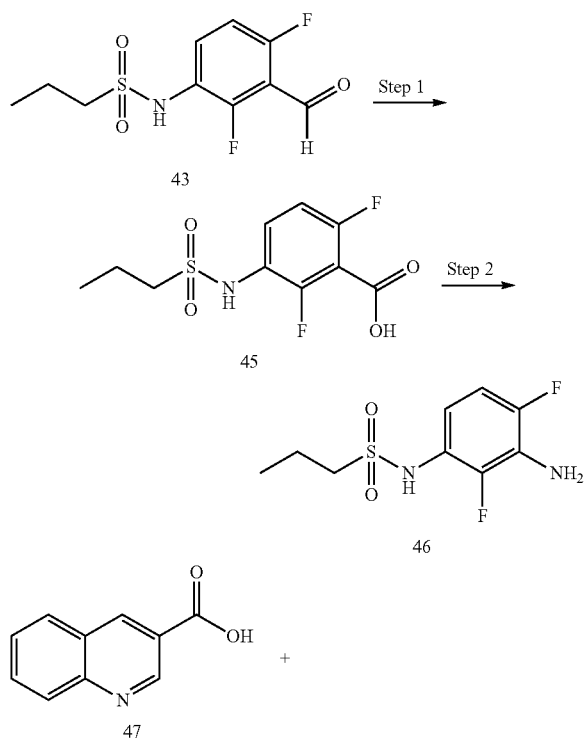

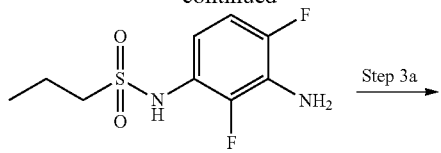

46

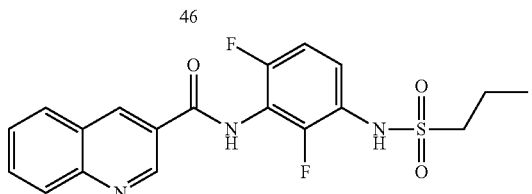

P-0024

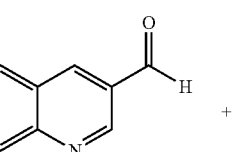

48

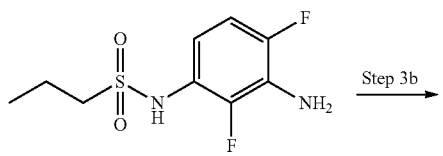

46

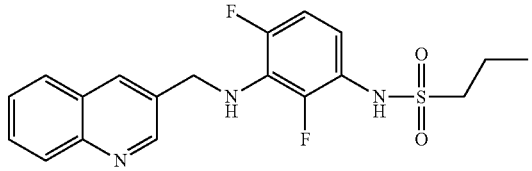

P-0025

Step 1—Preparation of 2,6-difluoro-3-(propane-1-sulfonylamino)-benzoic acid (45)

To a reaction flask, propane-1-sulfonic acid (2,4-difluoro-3-formyl-phenyl)-amide (43, 3.00 g, 11.4 mmol) and oxone (9.10 g, 14.8 mmol) and 30 mL of anhydrous N,N-dimethylformamide were added under nitrogen. The mixture was stirred at room temperature overnight, then quenched with 250 mL of 1 M hydrochloric acid solution and extracted with 250 mL of ethyl acetate. The organic layers were washed with 3×100 mL of 1M hydrochloric acid solution and dried over magnesium sulfate. After removal of drying agent and solvent, the residue was dried in vacuo to provide the desired compound (45, 2.9 g, 91%).

Step 2—Preparation of propane-1-sulfonic acid (3-amino-2,4-difluoro-phenyl)-amide (46)

To a reaction flask, 2,6-difluoro-3-(propane-1-sulfonylamino)-benzoic acid (45, 2.88 g, 10.3 mmol), triethylamine (2.09 g, 20.6 mmol) and diphenylphosphoryl azide (3.21 g, 11.7 mmol) and 84 mL of anhydrous tert-butanol were added under nitrogen. The reaction mixture was heated in an oil bath at 105° C. overnight, then cooled to room temperature and diluted with ethyl acetate. The organic layer was washed with 3×250 mL of water, 250 mL of brine, dried over magnesium sulfate, filtered and concentrated in vacuo to provide 4.1 g of crude Boc-protected amine, which was purified by silica gel column chromatography using hexane:ethyl acetate as eluant to provide 3.3 g of the Boc-protected amine. This was dissolved in 50 mL of dichloromethane and 16 mL of trifluoroacetic acid was added and the reaction stirred at room temperature until there was no starting material by TLC. The reaction was neutralized by pouring into a cooled saturated solution of sodium bicarbonate and extracted into 3×150 mL of dichloromethane. The combined organic extracts were washed with 50 mL of brine, dried over magnesium sulfate, filtered and concentrated in vacuo to provide the desired compound (46, 1.94 g, 75%).

Step 3a—Preparation of quinoline-3-carboxylic acid [2,6-difluoro-3-(propane-1-sulfonylamino)-phenyl]-amide (P-0024)

To a reaction vessel, 3-quinoline carboxylic acid (47, 39.1 mg, 0.23 mmol), 1.5 mL of anhydrous tetrahydrofuran, 1 drop of anhydrous N,N-dimethylformamide and oxalyl chloride (86 mg, 0.68 mmol) were added under nitrogen. The reaction was stirred at room temperature for 1.5 hours, then concentrated to dryness and the residue was diluted with 2 mL of anhydrous tetrahydrofuran. To this solution, triethylamine (15.8 mg, 0.16 mmol) and propane-1-sulfonic acid (3-amino-2,4-difluoro-phenyl)-amide (46, 100 mg, 0.40 mmol) were added and the reaction was stirred at room temperature over weekend. The reaction mixture was diluted with 5 mL of water and extracted into 3×10 mL of ethyl acetate. The organic extracts were dried over magnesium sulfate, filtered and concentrated in vacuo, then purified by silica gel column chromatography (hexane:ethyl acetate gradient) to provide the desired compound (P-0024, 33 mg, 36%). MS (ESI) [M+H$^+$]$^+$=406.1.

Step 3b—Preparation of propane-1-sulfonic acid {2,4-difluoro-3-[(quinolin-3-ylmethyl)-amino]-phenyl}-amide (P-0025)

To a reaction vessel, propane-1-sulfonic acid (3-amino-2,4-difluoro-phenyl)-amide (46, 155 mg, 0.62 mmol), 2 mL of anhydrous acetonitrile, 3-quinoline carboxaldehyde (48, 100 mg, 0.64 mmol), trifluoroacetic acid (431 mg, 3.78 mmol) and triethylsilane (425 mg, 3.65 mmol) were added under nitrogen. The reaction was heated at 80° C. overnight, then cooled to room temperature and concentrated in vacuo, to which 10 mL of an aqueous solution of 10% potassium carbonate was added. This was extracted into 3×15 mL of ethyl acetate. The combined organic extracts were washed with 15 mL of brine, dried over magnesium sulfate, filtered and concentrated in vacuo. The residue was purified by silica gel column chromatography (hexane:ethyl acetate gradient) to provide the desired compound (P-0025, 70 mg, 29%). MS (ESI) [M+H$^+$]$^+$=392.0.

Example 13: Synthesis of propane-1-sulfonic acid [2,4-difluoro-3-(quinolin-3-yloxymethyl)-phenyl]-amide P-0026

Propane-1-sulfonic acid [2,4-difluoro-3-(quinolin-3-yloxymethyl)-phenyl]-amide P-0026 was synthesized in three steps from propane-1-sulfonic acid (2,4-difluoro-3-formyl-phenyl)-amide 43 as shown in Scheme 13.

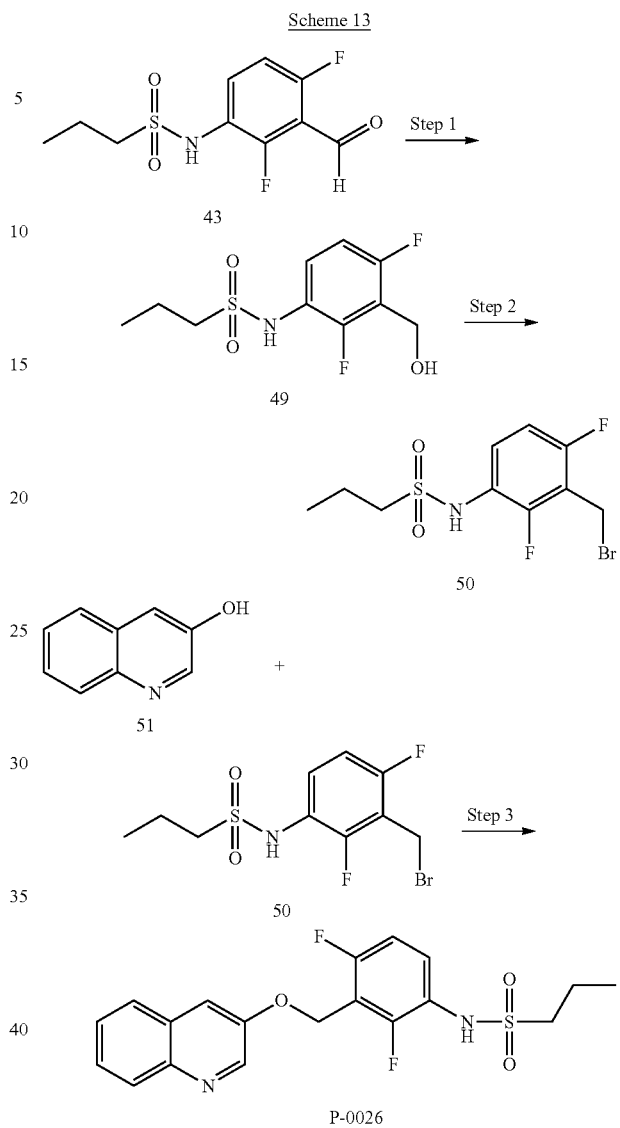

Step 1—Preparation of propane-1-sulfonic acid (2,4-difluoro-3-hydroxymethyl-phenyl)-amide (49)

To a reaction vessel, propane-1-sulfonic acid (2,4-difluoro-3-formyl-phenyl)-amide (43, 1.00 g, 3.80 mmol), 20 mL of methanol, and sodium borohydride (0.29 g, 7.60 mmol) were added under nitrogen. The reaction was stirred at room temperature for 1 hour, then poured onto 50 mL of aqueous 10% sodium dihydrogenphosphate. The mixture was extracted with 3×50 mL of dichloromethane and the combined organic extracts were dried over magnesium sulfate, filtered and concentrated in vacuo to provide the desired compound (49, 0.97 g, 96%), used in the next step without further purification.

Step 2—Preparation of propane-1-sulfonic acid (3-bromomethyl-2,4-difluoro-phenyl)-amide (50)

To a reaction vessel under nitrogen containing polymer-supported triphenylphosphine (2.45 g, 4.41 mmol) in 5 mL of acetonitrile, bromine (0.70 g, 4.41 mmol) was added, followed by a solution of propane-1-sulfonic acid (2,4-difluoro-3-hydroxymethyl-phenyl)-amide (49, 0.97 g, 3.67 mmol) in 5 mL of acetonitrile. The reaction mixture was stirred at 60° C. for approximately 3 hours. The reaction mixture was filtered and the polymer washed with 5 mL of ethyl acetate. The filtrate and wash were concentrated in vacuo to provide the desired compound (50, 0.91 g, 76%), used in the next step without further purification.

Step 3—Preparation of propane-1-sulfonic acid [2,4-difluoro-3-(quinolin-3-yloxymethyl)-phenyl]-amide (P-0026)

To reaction vessel, 3-hydroxyquinoline (51, 442 mg, 3.05 mmol) and 5 mL of anhydrous N,N-dimethylformamide were added under nitrogen. Sodium hydride (60% dispersion in mineral oil, 183 mg, 4.57 mmol) was added in portions. The reaction was stirred at room temperature for 30 minutes, then propane-1-sulfonic acid (3-bromomethyl-2,4-difluoro-phenyl)-amide (50, 500 mg, 1.52 mmol) was added and the reaction stirred at room temperature overnight. The reaction mixture was neutralized with acetic acid and extracted into 3×20 mL of ethyl acetate. The combined organic extracts were dried over magnesium sulfate, filtered and concentrated in vacuo. The residue was purified by silica gel column chromatography (hexane: ethyl acetate gradient), followed by second purification by silica gel column chromatography to provide the desired compound (P-0026, 50 mg, 8%). MS (ESI) $[M+H^+]^+$=393.0.

Additional compounds may be prepared following the protocol of Scheme 13, optionally replacing propane-1-sulfonic acid (2,4-difluoro-3-formyl-phenyl)-amide 43 with N-(2,4-difluoro-3-formyl-phenyl)-4-trifluoromethyl-benzenesulfonamide (prepared following the protocol of Scheme 11, Example 11, steps 1 and 2 using 4-trifluoromethyl-benzenesulfonyl chloride in Step 1 in place of propane-1-sulfonyl chloride 16) in Step 1 and 3-hydroxyquinoline 51 with a suitable alcohol in Step 3. The following compounds may be prepared by this method:

N-{5-[2,6-Difluoro-3-(propane-1-sulfonylamino)-benzyloxy]-pyridin-2-yl}-acetamide (P-0091),
Propane-1-sulfonic acid [3-(2-amino-pyridin-3-yloxymethyl)-2,4-difluoro-phenyl]-amide (P-0092),
Propane-1-sulfonic acid [2,4-difluoro-3-(1H-pyrrolo[2,3-b]pyridin-5-yloxymethyl)-phenyl]-amide (P-0093),
N-{5-[2,6-Difluoro-3-(4-trifluoromethyl-benzenesulfonylamino)-benzyloxy]-pyridin-2-yl}-acetamide (P-0094),
N-[3-(2-Amino-pyridin-3-yloxymethyl)-2,4-difluoro-phenyl]-4-trifluoromethyl-benzenesulfonamide (P-0095), and
N-[2,4-Difluoro-3-(1H-pyrrolo[2,3-b]pyridin-5-yloxymethyl)-phenyl]-4-trifluoromethyl-benzenesulfonamide (P-0096).

The following table indicates the compound number in Column 1, the aldehyde used in Step 1 in Column 2, the alcohol used in Step 3 in Column 3, and the resulting compound in Column 4:

| | |
|---|---|
| P-0096 | 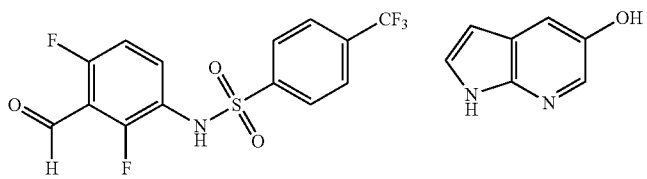 |
| Compound number | Compound |
|---|---|
| P-0091 | 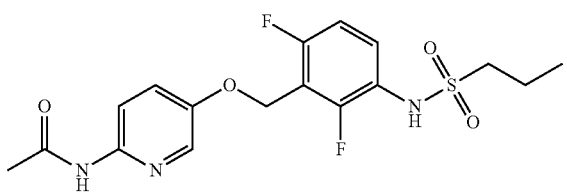 [SMILES: CCCS(=O)(=O)Nc1ccc(F)c(COc2ccc(NC(C)=O)nc2)c1F] |
| P-0092 | 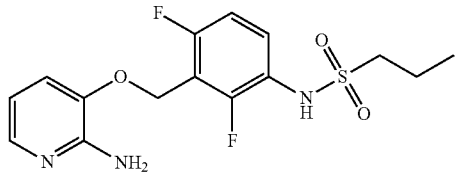 [SMILES: CCCS(=O)(=O)Nc1ccc(F)c(COc2cccnc2N)c1F] |
| P-0093 | 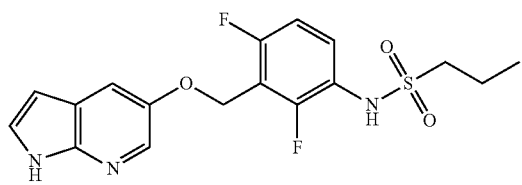 [SMILES: CCCS(=O)(=O)Nc1ccc(F)c(COc2cnc3[nH]ccc3c2)c1F] |
| P-0094 | 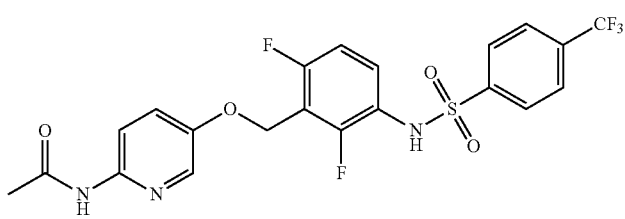 [SMILES: CC(=O)Nc1ccc(OCc2c(F)ccc(NS(=O)(=O)c3ccc(C(F)(F)F)cc3)c2F)cn1] |
| P-0095 | 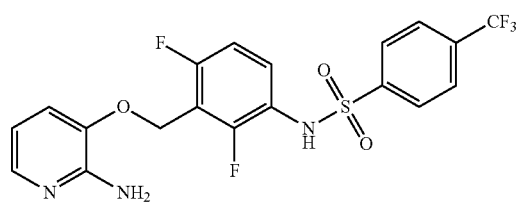 [SMILES: Nc1ncccc1OCc1c(F)ccc(NS(=O)(=O)c2ccc(C(F)(F)F)cc2)c1F] |
| P-0096 | 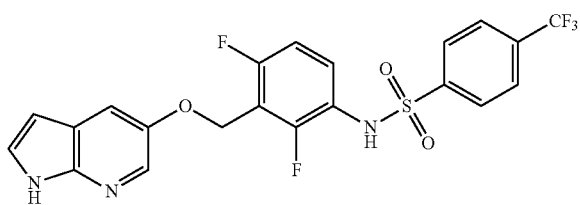 [SMILES: O=S(=O)(Nc1ccc(F)c(COc2cnc3[nH]ccc3c2)c1F)c1ccc(C(F)(F)F)cc1] |

Example 14: Synthesis of 2,6-difluoro-3-(propane-1-sulfonylamino)-N-quinolin-3-yl-benzamide P-0027

2,6-Difluoro-3-(propane-1-sulfonylamino)-N-quinolin-3-yl-benzamide P-0027 was synthesized in one step from 2,6-difluoro-3-(propane-1-sulfonylamino)-benzoic acid 45 as shown in Scheme 14.

Scheme 14

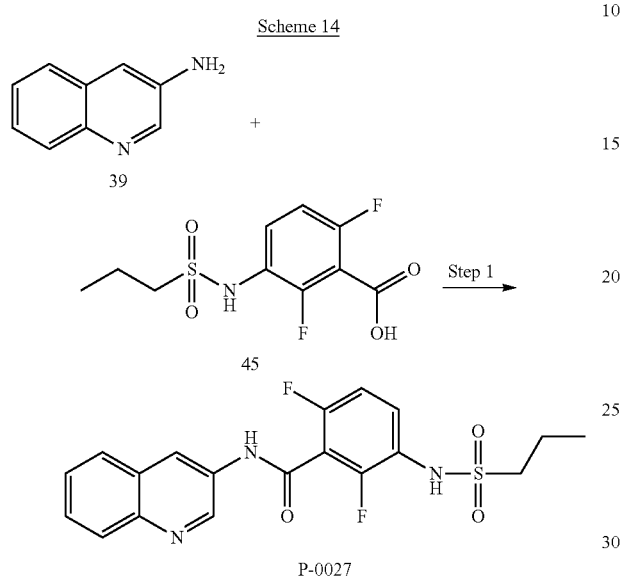

P-0027

Step 1—Preparation of 2,6-difluoro-3-(propane-1-sulfonylamino)-N-quinolin-3-yl-benzamide (P-0027)

To reaction vessel, 2,6-difluoro-3-(propane-1-sulfonylamino)-benzoic acid (45, 250 mg, 0.90 mmol), 5 mL of anhydrous dichloromethane and anhydrous N,N-dimethylformamide (6.54 mg, 0.09 mmol) were added under nitrogen. The reaction mixture was cooled to 0° C. and oxalyl chloride (568 mg, 4.48 mmol) was added dropwise. This was stirred at room temperature for 3 hours, then concentrated in vacuo. The residue was diluted with 5 mL of anhydrous tetrahydrofuran and triethylamine (136 mg, 1.34 mmol) and 3-aminoquinoline (39, 194 mg, 1.34 mmol) were added. The reaction mixture was stirred at room temperature over the weekend, then concentrated in vacuo. The residue was purified by silica gel column chromatography (hexane:ethyl acetate gradient) to provide the desired compound (P-0027, 163 mg, 45%). MS (ESI) [M+H$^+$]$^+$=406.1.

Example 15: Synthesis of Additional Compounds

Additional compounds may be synthesized in six steps according to the following Scheme 15 or in four steps according the following Scheme 16.

Scheme 15

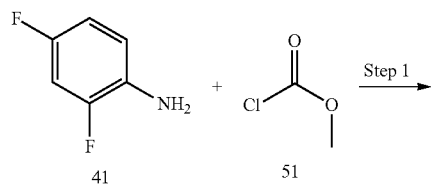

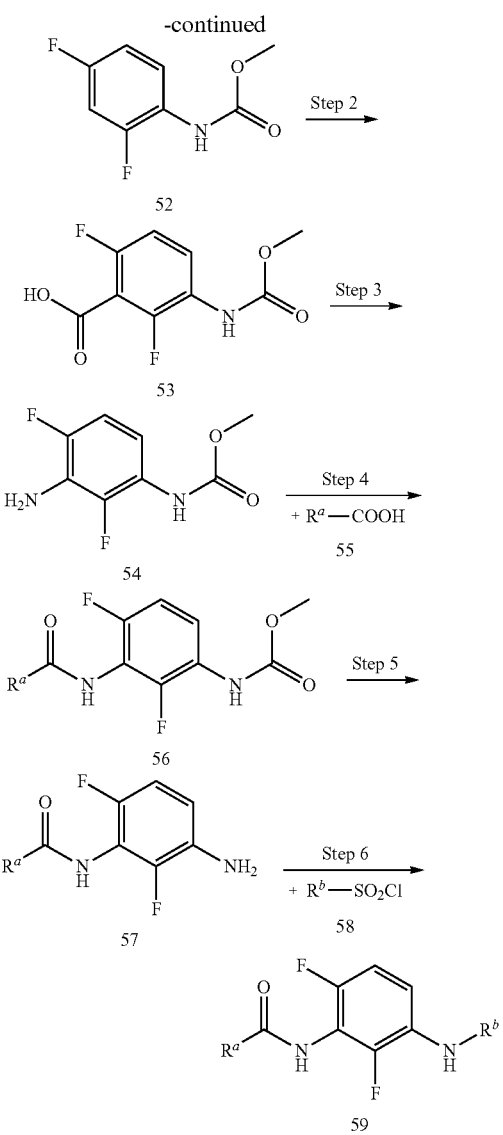

Step 1—Preparation of (2,4-difluoro-phenyl)-carbamic acid methyl ester (52)

To 2,4-difluoroaniline 41, potassium carbonate, and water, methyl chloroformate 51 is added slowly dropwise. The reaction is stirred at 0° C. and then allowed to come to room temperature. The reaction mixture is extracted with ethyl acetate and washed with diluted HCl (pH=2), twice with saturated sodium bicarbonate, twice with brine, and dried with magnesium sulfate. Removal of solvent provides the desired compound as a crude solid.

Step 2—Preparation of 2,6-difluoro-3-methoxycarbonylamino-benzoic acid (53)

To (2,4-difluoro-phenyl)-carbamic acid methyl ester 52 in tetrahydrofuran at −78° C., 2.5 eq. of lithium diisopropylamide is added. After 15 minutes, solid carbon dioxide is added and the reaction is allowed to warm to room temperature. The reaction mixture is extracted with ethyl acetate and washed with diluted HCl (pH=2). The desired compound is isolated by silica gel column chromatography.

Step 3—Preparation of (3-amino-2,4-difluoro-phenyl)-carbamic acid methyl ester (54)

To 2,6-difluoro-3-methoxycarbonylamino-benzoic acid 53, anhydrous tert-butanol, and triethylamine, diphenylphosphoryl azide is added. The action is heated in an oil bath at 105° C. overnight. The reaction is cooled to room temperature and diluted with ethyl acetate. The organic layer is washed 3× with water, then 1× with brine, dried over magnesium sulfate and filtered and concentrated in vacuo to provide crude Boc-protected amine, which is purified by silica gel column chromatography. The purified Boc-protected amine is dissolved in dichloromethane, trifluoroacetic acid is added and the reaction stirred at room temperature, monitoring by TLC for the disappearance of starting material. The completed reaction is neutralised by pouring into a cooled saturated solution of sodium hydrogen carbonate and then extracted 3× into dichloromethane. The combined organic extracts are washed with brine, dried over magnesium sulfate, filtered and concentrated in vacuo to provide the desired compound.

Step 4—Preparation of Compound 56

To a reaction vessel, carboxylic acid 55 ($R^a$ is optionally substituted heteroaryl), anhydrous tetrahydrofuran, 1 drop anhydrous dimethylformamide, and oxalyl chloride are added under nitrogen. The reaction mixture is allowed to stir at room temperature for 1.5 hours, then concentrated to dryness. The resulting residue is diluted with anhydrous tetrahydrofuran, then triethylamine and (3-amino-2,4-difluoro-phenyl)-carbamic acid methyl ester 54 are added and allowed to stir at room temperature overnight. The reaction is diluted with water extracted 3× into ethyl acetate. The organic extracts are dried over magnesium sulfate, filtered and concentrated in vacuo to provide the desired compound as a crude solid, which is purified by silica gel column chromatography (hexane: ethyl acetate gradient).

Step 5—Preparation of Compound 57

To compound 56 in dioxane, an equal volume of 1 N lithium hydroxide is added. The reaction is allowed to stir at 60° C. and monitored by TLC. When complete, reaction is extracted with 1N aqueous HCl and ethyl acetate. The organic layer is dried over anhydrous magnesium sulfate, filtered and volatile solvents removed to provide the desired compound as a crude solid.

Step 6—Preparation of Compound 59

To compound 57, tetrahydrofuran is added, followed by addition of compound 58 ($R^b$ is di-alkylamino, optionally substituted lower alkyl, optionally substituted cycloalkyl, optionally substituted heterocycloalkyl, optionally substituted aryl or optionally substituted heteroaryl) as a solution in tetrahydrofuran, then adding pyridine. The reaction vial is allowed to stir at room temperature. After 23 hours, the reaction is poured into water and 1N aqueous HCl and extracted with ethyl acetate. The organic layer is washed with brine, dried over anhydrous magnesium sulfate and filtered. The filtrate is concentrated and purified by silica gel column chromatography (hexane: ethyl acetate gradient) to provide the desired compound.

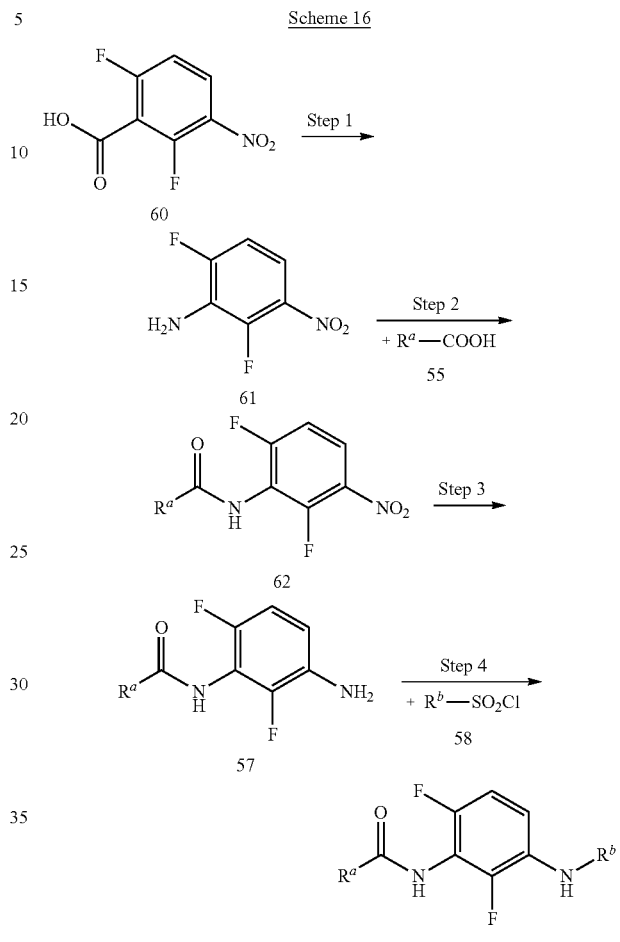

Scheme 16

Step 1—Preparation of 2,6-difluoro-3-nitro-phenylamine (61)

2,6-Difluoro-3-nitrobenzoic acid 60 is converted to 2,6-difluoro-3-nitro-phenylamine 61 following the methods described in Scheme 15, Step 3.

Step 2—Preparation of Compound 62

2,6-Difluoro-3-nitro-phenylamine 61 is reacted with compound 55 following the methods described in Scheme 15, Step 4 to provide the desired compound 62.

Step 3—Preparation of Compound 57

To compound 62 in ethanol and tetrahydrofuran, ~3 cc of raney nickle slurry in water is added. The reaction is placed in a parr hydrogenator under hydrogen at 35 psi and monitored by TLC until all starting material is consumed. The reaction is filtered and all volatile solvents are removed to provide the desired compound as a crude solid.

Step 4—Preparation of Compound 59

Compound 57 is reacted with compound 58 following the methods described in Scheme 15, Step 6 to provide the desired compound 59.

The following compounds may be made following the protocol of either Scheme 15 or Scheme 16:

6-Acetylamino-N-[2,6-difluoro-3-(2-fluoro-benzenesulfonylamino)-phenyl]-nicotinamide (P-0028),
6-Acetylamino-N-[2,6-difluoro-3-(3-fluoro-benzenesulfonylamino)-phenyl]-nicotinamide (P-0029),
6-Acetylamino-N-[3-(2,6-difluoro-benzenesulfonylamino)-2,6-difluoro-phenyl]-nicotinamide (P-0030),
6-Acetylamino-N-[3-(2,4-difluoro-benzenesulfonylamino)-2,6-difluoro-phenyl]-nicotinamide (P-0031),
6-Acetylamino-N-[3-(2,5-difluoro-benzenesulfonylamino)-2,6-difluoro-phenyl]-nicotinamide (P-0032),
6-Acetylamino-N-[2,6-difluoro-3-(3-fluoro-4-methoxy-benzenesulfonylamino)-phenyl]-nicotinamide (P-0033),
6-Acetylamino-N-[2,6-difluoro-3-(4-trifluoromethyl-benzenesulfonylamino)-phenyl]-nicotinamide (P-0034),
6-Acetylamino-N-[3-(4-difluoromethoxy-benzenesulfonylamino)-2,6-difluoro-phenyl]-nicotinamide (P-0035),
6-Acetylamino-N-[3-(3-difluoromethoxy-benzenesulfonylamino)-2,6-difluoro-phenyl]-nicotinamide (P-0036),
6-Acetylamino-N-[2,6-difluoro-3-(4-isopropyl-benzenesulfonylamino)-phenyl]-nicotinamide (P-0037),
6-Acetylamino-N-[3-(4-tert-butyl-benzenesulfonylamino)-2,6-difluoro-phenyl]-nicotinamide (P-0038),
6-Acetylamino-N-[2,6-difluoro-3-(4-propyl-benzenesulfonylamino)-phenyl]-nicotinamide (P-0039),
6-Acetylamino-N-[2,6-difluoro-3-(pyridine-2-sulfonylamino)-phenyl]-nicotinamide (P-0040),
6-Acetylamino-N-[2,6-difluoro-3-(pyridine-3-sulfonylamino)-phenyl]-nicotinamide (P-0041),
6-Acetylamino-N-[2,6-difluoro-3-(dimethylaminosulfonylamino)-phenyl]-nicotinamide (P-0042),
6-Acetylamino-N-[2,6-difluoro-3-(piperidine-1-sulfonylamino)-phenyl]-nicotinamide (P-0043),
6-Acetylamino-N-[2,6-difluoro-3-(morpholine-4-sulfonylamino)-phenyl]-nicotinamide (P-0044),
6-Acetylamino-N-[2,6-difluoro-3-(tetrahydro-pyran-4-sulfonylamino)-phenyl]-nicotinamide (P-0045),
6-Acetylamino-N-(3-cyclopentanesulfonylamino-2,6-difluoro-phenyl)-nicotinamide (P-0046),
6-Acetylamino-N-[2,6-difluoro-3-(pyrrolidine-1-sulfonylamino)-phenyl]-nicotinamide (P-0047),
6-Acetylamino-N-[2,6-difluoro-3-(3,3,3-trifluoro-propane-1-sulfonylamino)-phenyl]-nicotinamide (P-0048),
1H-Pyrrolo[2,3-b]pyridine-5-carboxylic acid [2,6-difluoro-3-(2-fluoro-benzenesulfonylamino)-phenyl]-amide (P-0049),
1H-Pyrrolo[2,3-b]pyridine-5-carboxylic acid [2,6-difluoro-3-(3-fluoro-benzenesulfonylamino)-phenyl]-amide (P-0050),
1H-Pyrrolo[2,3-b]pyridine-5-carboxylic acid [3-(2,6-difluoro-benzenesulfonylamino)-2,6-difluoro-phenyl]-amide (P-0051),
1H-Pyrrolo[2,3-b]pyridine-5-carboxylic acid [3-(2,4-difluoro-benzenesulfonylamino)-2,6-difluoro-phenyl]-amide (P-0052),
1H-Pyrrolo[2,3-b]pyridine-5-carboxylic acid [3-(2,5-difluoro-benzenesulfonylamino)-2,6-difluoro-phenyl]-amide (P-0053),
1H-Pyrrolo[2,3-b]pyridine-5-carboxylic acid [2,6-difluoro-3-(3-fluoro-4-methoxy-benzenesulfonylamino)-phenyl]-amide (P-0054),
1H-Pyrrolo[2,3-b]pyridine-5-carboxylic acid [2,6-difluoro-3-(4-trifluoromethyl-benzenesulfonylamino)-phenyl]-amide (P-0055),
1H-Pyrrolo[2,3-b]pyridine-5-carboxylic acid [3-(4-difluoromethoxy-benzenesulfonylamino)-2,6-difluoro-phenyl]-amide (P-0056),
1H-Pyrrolo[2,3-b]pyridine-5-carboxylic acid [3-(3-difluoromethoxy-benzenesulfonylamino)-2,6-difluoro-phenyl]-amide (P-0057),
1H-Pyrrolo[2,3-b]pyridine-5-carboxylic acid [2,6-difluoro-3-(4-isopropyl-benzenesulfonylamino)-phenyl]-amide (P-0058),
1H-Pyrrolo[2,3-b]pyridine-5-carboxylic acid [3-(4-tert-butyl-benzenesulfonylamino)-2,6-difluoro-phenyl]-amide (P-0059),
1H-Pyrrolo[2,3-b]pyridine-5-carboxylic acid [2,6-difluoro-3-(4-propyl-benzenesulfonylamino)-phenyl]-amide (P-0060),
1H-Pyrrolo[2,3-b]pyridine-5-carboxylic acid [2,6-difluoro-3-(pyridine-2-sulfonylamino)-phenyl]-amide (P-0061),
1H-Pyrrolo[2,3-b]pyridine-5-carboxylic acid [2,6-difluoro-3-(pyridine-3-sulfonylamino)-phenyl]-amide (P-0062),
1H-Pyrrolo[2,3-b]pyridine-5-carboxylic acid [2,6-difluoro-3-(dimethylaminosulfonylamino)-phenyl]-amide (P-0063),
1H-Pyrrolo[2,3-b]pyridine-5-carboxylic acid [2,6-difluoro-3-(piperidine-1-sulfonylamino)-phenyl]-amide (P-0064),
1H-Pyrrolo[2,3-b]pyridine-5-carboxylic acid [2,6-difluoro-3-(morpholine-4-sulfonylamino)-phenyl]-amide (P-0065),
1H-Pyrrolo[2,3-b]pyridine-5-carboxylic acid [2,6-difluoro-3-(tetrahydro-pyran-4-sulfonylamino)-phenyl]-amide (P-0066),
1H-Pyrrolo[2,3-b]pyridine-5-carboxylic acid (3-cyclopentanesulfonylamino-2,6-difluoro-phenyl)-amide (P-0067),
1H-Pyrrolo[2,3-b]pyridine-5-carboxylic acid [2,6-difluoro-3-(pyrrolidine-1-sulfonylamino)-phenyl]-amide (P-0068),
1H-Pyrrolo[2,3-b]pyridine-5-carboxylic acid [2,6-difluoro-3-(3,3,3-trifluoro-propane-1-sulfonylamino)-phenyl]-amide (P-0069),
3H-Imidazo[4,5-b]pyridine-6-carboxylic acid [2,6-difluoro-3-(2-fluoro-benzenesulfonylamino)-phenyl]-amide (P-0070),
3H-Imidazo[4,5-b]pyridine-6-carboxylic acid [2,6-difluoro-3-(3-fluoro-benzenesulfonylamino)-phenyl]-amide (P-0071),
3H-Imidazo[4,5-b]pyridine-6-carboxylic acid [3-(2,6-difluoro-benzenesulfonylamino)-2,6-difluoro-phenyl]-amide (P-0072),
3H-Imidazo[4,5-b]pyridine-6-carboxylic acid [3-(2,4-difluoro-benzenesulfonylamino)-2,6-difluoro-phenyl]-amide (P-0073),
3H-Imidazo[4,5-b]pyridine-6-carboxylic acid [3-(2,5-difluoro-benzenesulfonylamino)-2,6-difluoro-phenyl]-amide (P-0074),
3H-Imidazo[4,5-b]pyridine-6-carboxylic acid [2,6-difluoro-3-(3-fluoro-4-methoxy-benzenesulfonylamino)-phenyl]-amide (P-0075),
3H-Imidazo[4,5-b]pyridine-6-carboxylic acid [2,6-difluoro-3-(4-trifluoromethyl-benzenesulfonylamino)-phenyl]-amide (P-0076),
3H-Imidazo[4,5-b]pyridine-6-carboxylic acid [3-(4-difluoromethoxy-benzenesulfonylamino)-2,6-difluoro-phenyl]-amide (P-0077),
3H-Imidazo[4,5-b]pyridine-6-carboxylic acid [3-(3-difluoromethoxy-benzenesulfonylamino)-2,6-difluoro-phenyl]-amide (P-0078), 3H-Imidazo[4,5-b]pyridine-6-carboxylic acid [2,6-difluoro-3-(4-isopropyl-benzenesulfonylamino)-phenyl]-amide (P-0079), 3H-Imidazo[4,5-b]pyridine-6-carboxylic acid [3-(4-tert-butyl-benzenesulfonylamino)-2,6-difluoro-phenyl]-amide (P-0080), 3H-Imidazo[4,5-b]pyridine-6-carboxylic acid [2,6-difluoro-3-(4-propyl-benzenesulfonylamino)-phenyl]-amide (P-0081), 3H-Imidazo[4,5-b]pyridine-6-carboxylic acid [2,6-difluoro-3-(pyridine-2-sulfonylamino)-phenyl]-amide (P-0082), 3H-Imidazo[4,5-b]pyridine-6-carboxylic acid [2,6-difluoro-3-(pyridine-3-sulfonylamino)-phenyl]-amide (P-0083), 3H-Imidazo[4,5-b]pyridine-6-carboxylic acid [2,6-difluoro-3-(dimethylaminosulfonylamino)-phenyl]-amide (P-0084), 3H-Imidazo[4,5-b]pyridine-6-carboxylic acid [2,6-difluoro-3-(piperidine-1-sulfonylamino)-phenyl]-amide (P-0085), 3H-Imidazo[4,5-b]pyridine-6-carboxylic acid [2,6-difluoro-3-(morpholine-4-sulfonylamino)-phenyl]-amide (P-0086), 3H-Imidazo[4,5-b]pyridine-6-carboxylic acid [2,6-difluoro-3-(tetrahydro-pyran-4-sulfonylamino)-phenyl]-amide (P-0087), 3H-Imidazo[4,5-b]pyridine-6-carboxylic acid (3-cyclopentanesulfonylamino-2,6-difluoro-phenyl)-amide (P-0088), 3H-Imidazo[4,5-b]pyridine-6-carboxylic acid [2,6-difluoro-3-(pyrrolidine-1-sulfonylamino)-phenyl]-amide (P-0089), 3H-Imidazo[4,5-b]pyridine-6-carboxylic acid [2,6-difluoro-3-(3,3,3-trifluoro-propane-1-sulfonylamino)-phenyl]-amide (P-0090), 6-Acetylamino-N-[2,6-difluoro-3-(propane-1-sulfonylamino)-phenyl]-nicotinamide (P-0118), 1H-Pyrrolo[2,3-b]pyridine-5-carboxylic acid [2,6-difluoro-3-(propane-1-sulfonylamino)-phenyl]-amide (P-0119), and 3H-Imidazo[4,5-b]pyridine-6-carboxylic acid [2,6-difluoro-3-(propane-1-sulfonylamino)-phenyl]-amide (P-0120).

These compounds are shown in the following table, where column 1 provides the compound number, column 2 the carboxylic acid compound 55 used in either Step 4 of Scheme 15 or Step 2 of Scheme 16, column 3 the sulfonyl chloride compound 58 used in either Step 6 of Scheme 15 or Step 4 of Scheme 16, and column 4 the resulting compound 59.

| Compound number | Compound 55 | Compound 58 |
|---|---|---|
| P-0028 | | |
| P-0029 | | |
| P-0030 | | |
| P-0031 | | |
| P-0032 | | |

-continued
P-0033 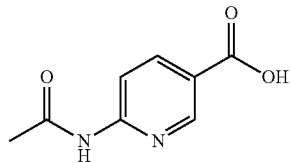 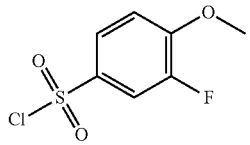
P-0034 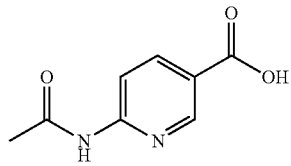 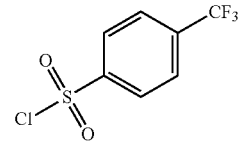 [SMILES: O=S(=O)(Cl)c1ccc(C(F)(F)F)cc1]
P-0035 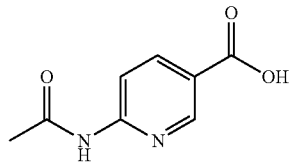 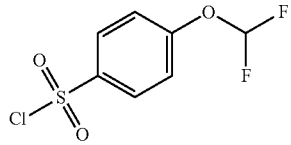 [SMILES: O=S(=O)(Cl)c1ccc(OC(F)F)cc1]
P-0036 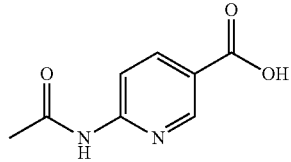 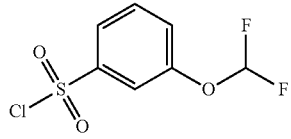 [SMILES: O=S(=O)(Cl)c1cccc(OC(F)F)c1]
P-0037 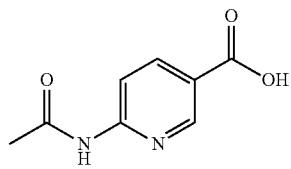 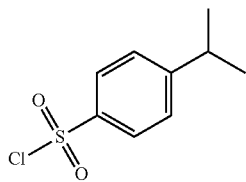
P-0038 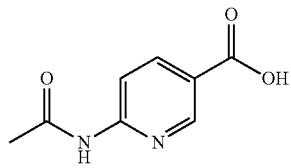 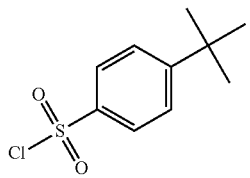
P-0039 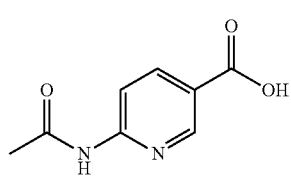 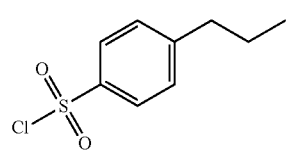
P-0040 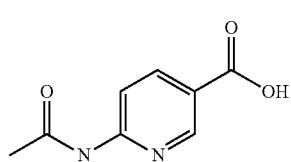 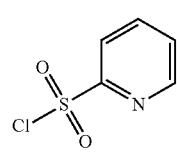
P-0041 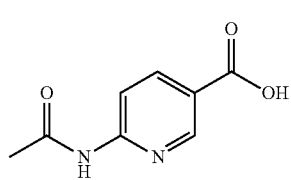 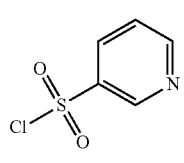

| | | |
|---|---|---|
| P-0042 | 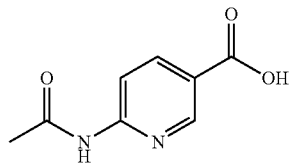 | 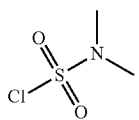 |
| P-0043 | 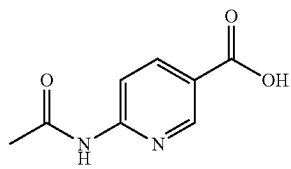 | 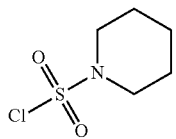 |
| P-0044 | 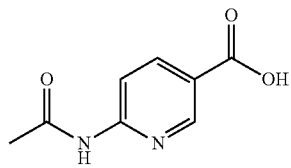 | 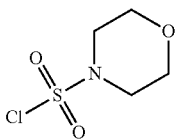 |
| P-0045 | 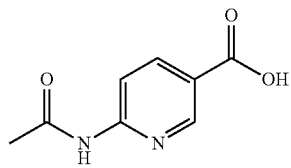 | 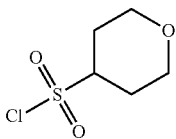 |
| P-0046 | 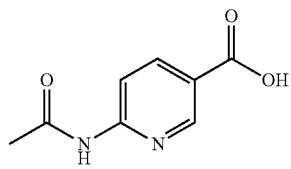 | 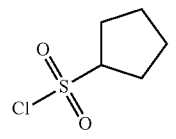 |
| P-0047 | 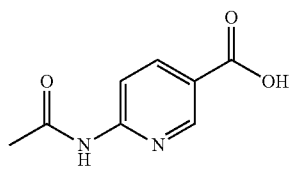 | 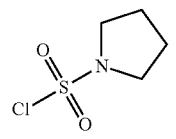 |
| P-0048 | 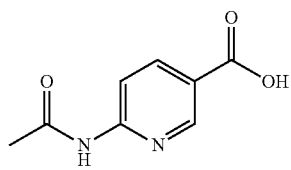 | 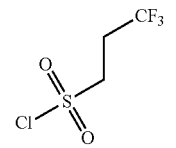 |
| P-0118 | 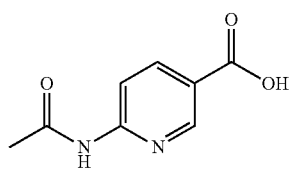 | 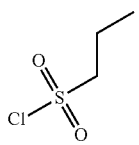 |
| P-0049 | 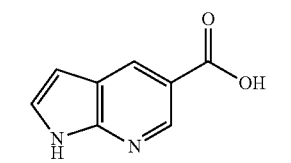 [SMILES: O=C(O)c1cnc2[nH]ccc2c1] | 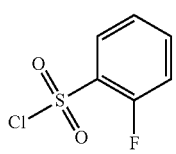 [SMILES: O=S(=O)(Cl)c1ccccc1F] |

-continued
P-0050 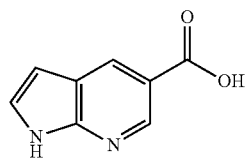 [SMILES: O=C(O)c1cnc2[nH]ccc2c1] 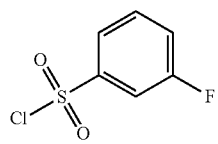 [SMILES: O=S(=O)(Cl)c1cccc(F)c1]
P-0051 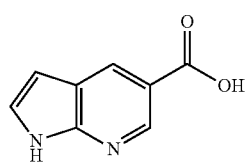 [SMILES: O=C(O)c1cnc2[nH]ccc2c1] 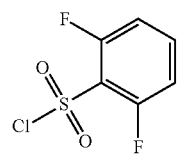 [SMILES: O=S(=O)(Cl)c1c(F)cccc1F]
P-0052 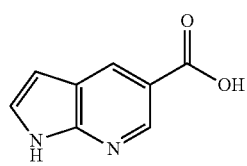 [SMILES: O=C(O)c1cnc2[nH]ccc2c1] 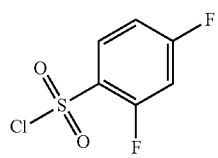 [SMILES: O=S(=O)(Cl)c1ccc(F)cc1F]
P-0053 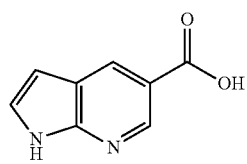 [SMILES: O=C(O)c1cnc2[nH]ccc2c1] 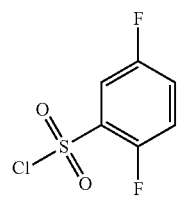 [SMILES: O=S(=O)(Cl)c1cc(F)ccc1F]
P-0054 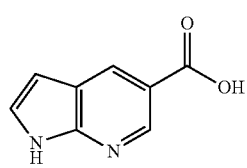 [SMILES: O=C(O)c1cnc2[nH]ccc2c1] 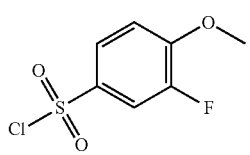
P-0055 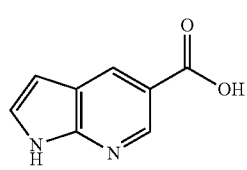 [SMILES: O=C(O)c1cnc2[nH]ccc2c1] 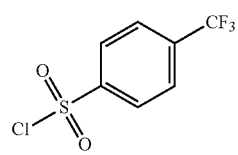 [SMILES: O=S(=O)(Cl)c1ccc(C(F)(F)F)cc1]
P-0056 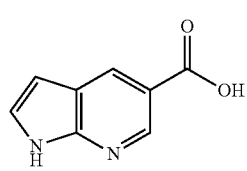 [SMILES: O=C(O)c1cnc2[nH]ccc2c1] 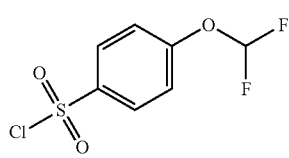 [SMILES: O=S(=O)(Cl)c1ccc(OC(F)F)cc1]
P-0057 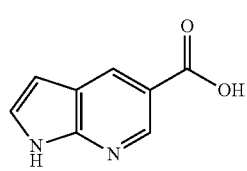 [SMILES: O=C(O)c1cnc2[nH]ccc2c1] 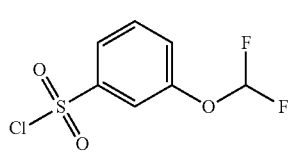 [SMILES: O=S(=O)(Cl)c1cccc(OC(F)F)c1]
P-0058 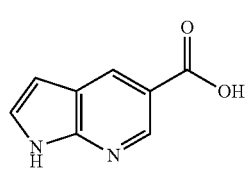 [SMILES: O=C(O)c1cnc2[nH]ccc2c1] 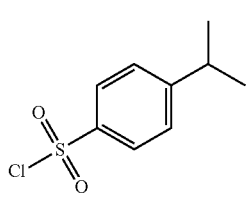

-continued
P-0059 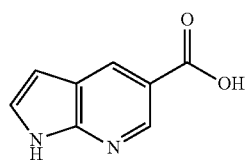 [SMILES: O=C(O)c1cnc2[nH]ccc2c1] 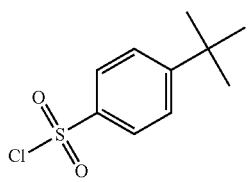
P-0060 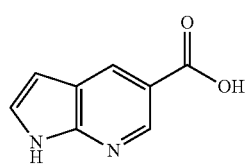 [SMILES: O=C(O)c1cnc2[nH]ccc2c1] 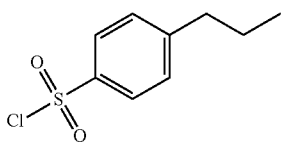
P-0061 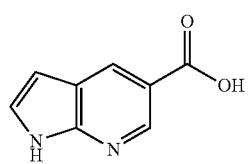 [SMILES: O=C(O)c1cnc2[nH]ccc2c1] 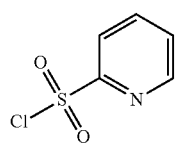
P-0062 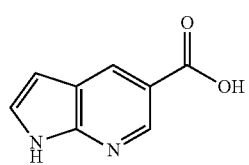 [SMILES: O=C(O)c1cnc2[nH]ccc2c1] 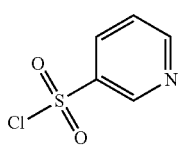
P-0063 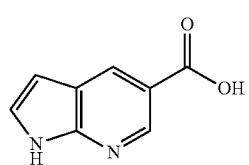 [SMILES: O=C(O)c1cnc2[nH]ccc2c1] 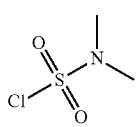
P-0064  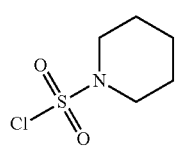
P-0065 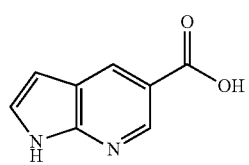 [SMILES: O=C(O)c1cnc2[nH]ccc2c1] 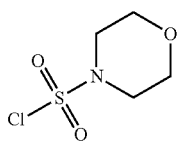
P-0066 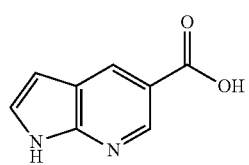 [SMILES: O=C(O)c1cnc2[nH]ccc2c1] 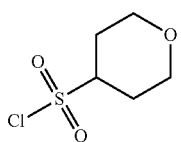
P-0067 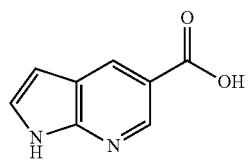 [SMILES: O=C(O)c1cnc2[nH]ccc2c1] 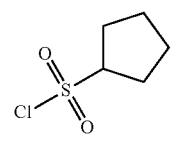

-continued
| | | |
|---|---|---|
| P-0068 | 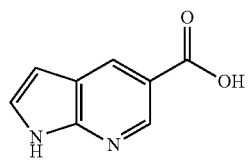 [SMILES: O=C(O)c1cnc2[nH]ccc2c1] | 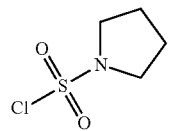 |
| P-0069 | 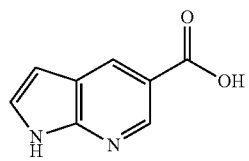 [SMILES: O=C(O)c1cnc2[nH]ccc2c1] | 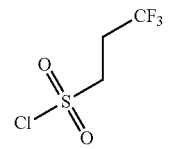 |
| P-0119 | 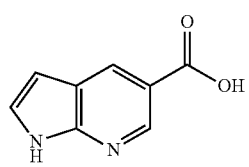 [SMILES: O=C(O)c1cnc2[nH]ccc2c1] | 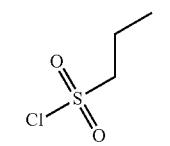 |
| P-0070 | 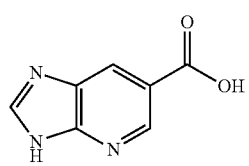 [SMILES: O=C(O)c1cnc2[nH]cnc2c1] | 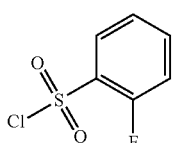 |
| P-0071 | 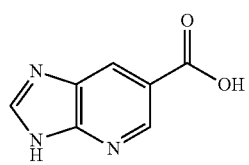 [SMILES: O=C(O)c1cnc2[nH]cnc2c1] | 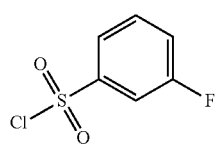 [SMILES: O=S(=O)(Cl)c1cccc(F)c1] |
| P-0072 | 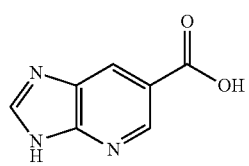 [SMILES: O=C(O)c1cnc2[nH]cnc2c1] | 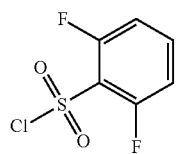 [SMILES: O=S(=O)(Cl)c1c(F)cccc1F] |
| P-0073 | 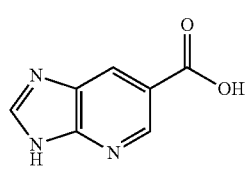 [SMILES: O=C(O)c1cnc2[nH]cnc2c1] | 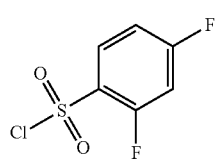 [SMILES: O=S(=O)(Cl)c1ccc(F)cc1F] |
| P-0074 | 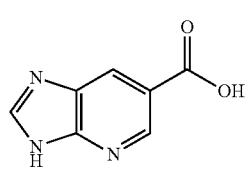 [SMILES: O=C(O)c1cnc2[nH]cnc2c1] | 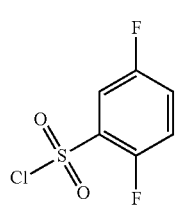 [SMILES: O=S(=O)(Cl)c1cc(F)ccc1F] |
| P-0075 | 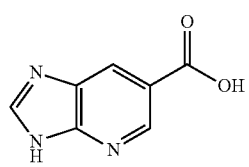 [SMILES: O=C(O)c1cnc2[nH]cnc2c1] | 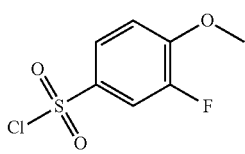 |

-continued
| | | |
|---|---|---|
| P-0076 | 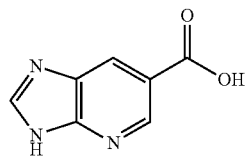 [SMILES: O=C(O)c1cnc2[nH]cnc2c1] | 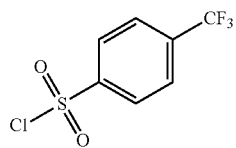 [SMILES: O=S(=O)(Cl)c1ccc(C(F)(F)F)cc1] |
| P-0077 | 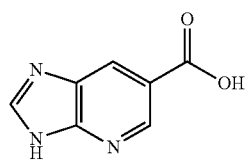 [SMILES: O=C(O)c1cnc2[nH]cnc2c1] | 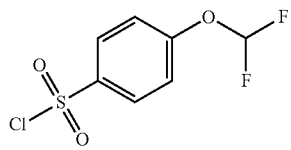 [SMILES: O=S(=O)(Cl)c1ccc(OC(F)F)cc1] |
| P-0078 | 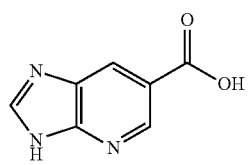 [SMILES: O=C(O)c1cnc2[nH]cnc2c1] | 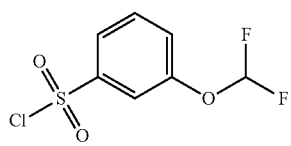 [SMILES: O=S(=O)(Cl)c1cccc(OC(F)F)c1] |
| P-0079 | 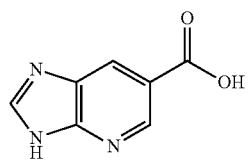 [SMILES: O=C(O)c1cnc2[nH]cnc2c1] | 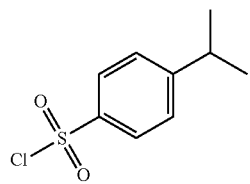 |
| P-0080 | 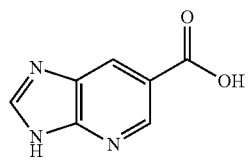 [SMILES: O=C(O)c1cnc2[nH]cnc2c1] | 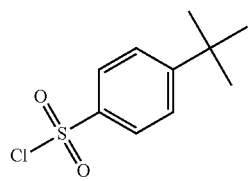 |
| P-0081 | 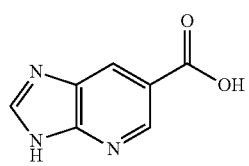 [SMILES: O=C(O)c1cnc2[nH]cnc2c1] | 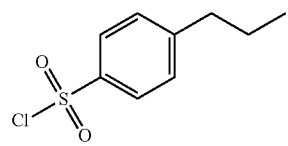 |
| P-0082 | 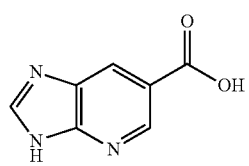 | 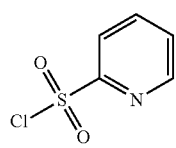 |
| P-0083 | 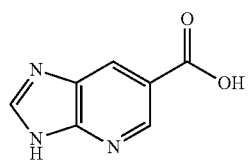 [SMILES: O=C(O)c1cnc2[nH]cnc2c1] | 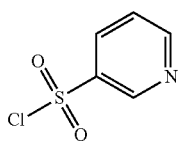 |
| P-0084 | 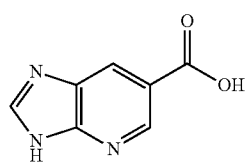 [SMILES: O=C(O)c1cnc2[nH]cnc2c1] | 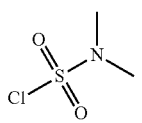 |

-continued
| | | |
|---|---|---|
| P-0085 | 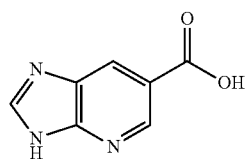 [SMILES: O=C(O)c1cnc2[nH]cnc2c1] | 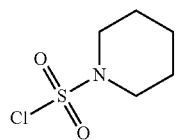 |
| P-0086 | 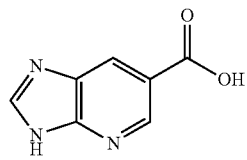 [SMILES: O=C(O)c1cnc2[nH]cnc2c1] | 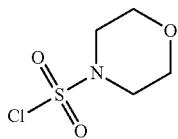 |
| P-0087 | 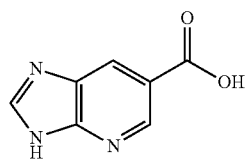 [SMILES: O=C(O)c1cnc2[nH]cnc2c1] | 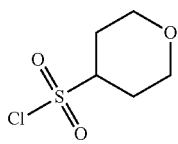 |
| P-0088 | 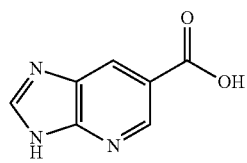 [SMILES: O=C(O)c1cnc2[nH]cnc2c1] | 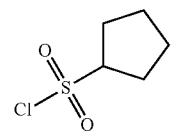 |
| P-0089 | 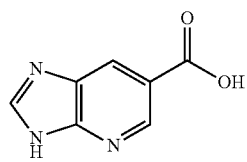 [SMILES: O=C(O)c1cnc2[nH]cnc2c1] | 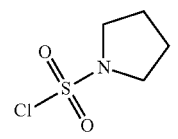 |
| P-0090 | 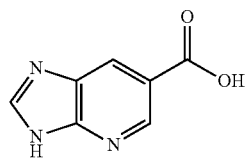 [SMILES: O=C(O)c1cnc2[nH]cnc2c1] | 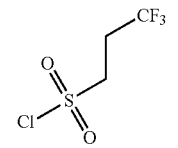 |
| P-0120 | 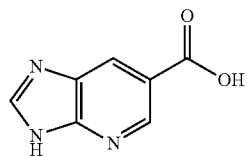 [SMILES: O=C(O)c1cnc2[nH]cnc2c1] | 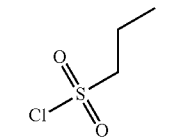 |
| Compound number | Resulting Compound 59 |
|---|---|
| P-0028 | 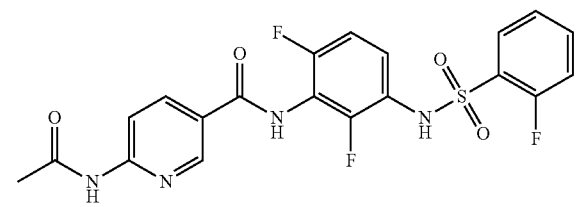 [SMILES: CC(=O)Nc1ccc(C(=O)Nc2c(F)ccc(NS(=O)(=O)c3ccccc3F)c2F)cn1] |

P-0029 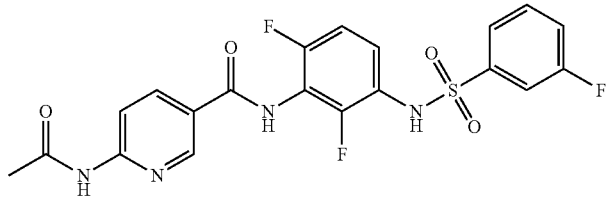 [SMILES: CC(=O)Nc1ccc(C(=O)Nc2c(F)ccc(NS(=O)(=O)c3cccc(F)c3)c2F)cn1]
P-0030 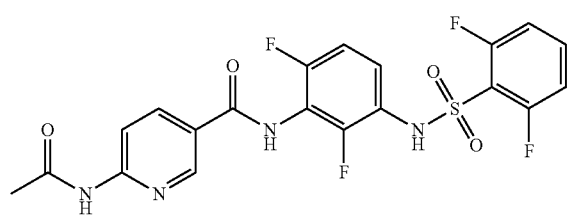 [SMILES: CC(=O)Nc1ccc(C(=O)Nc2c(F)ccc(NS(=O)(=O)c3c(F)cccc3F)c2F)cn1]
P-0031 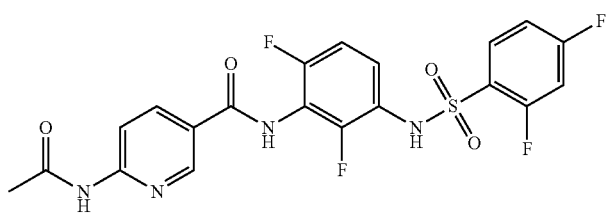 [SMILES: CC(=O)Nc1ccc(C(=O)Nc2c(F)ccc(NS(=O)(=O)c3ccc(F)cc3F)c2F)cn1]
P-0032 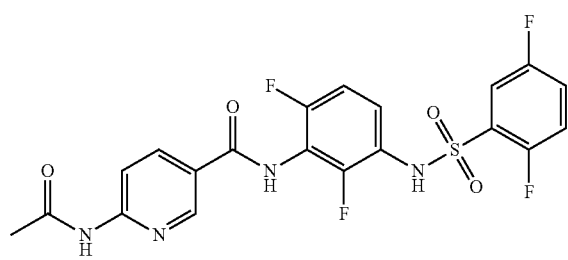 [SMILES: CC(=O)Nc1ccc(C(=O)Nc2c(F)ccc(NS(=O)(=O)c3cc(F)ccc3F)c2F)cn1]
P-0033 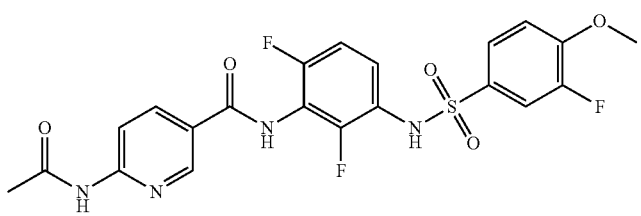 [SMILES: COc1ccc(S(=O)(=O)Nc2ccc(F)c(NC(=O)c3ccc(NC(C)=O)nc3)c2F)cc1F]
P-0034 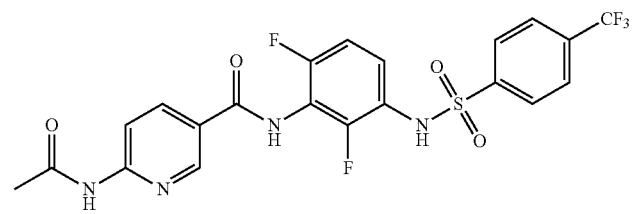 [SMILES: CC(=O)Nc1ccc(C(=O)Nc2c(F)ccc(NS(=O)(=O)c3ccc(C(F)(F)F)cc3)c2F)cn1]
P-0035 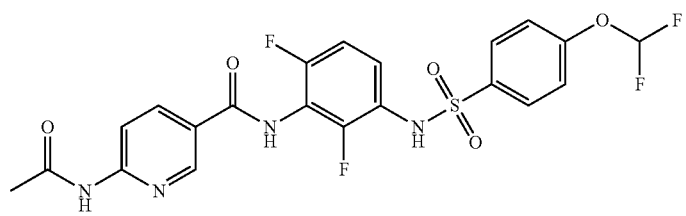 [SMILES: CC(=O)Nc1ccc(C(=O)Nc2c(F)ccc(NS(=O)(=O)c3ccc(OC(F)F)cc3)c2F)cn1]

-continued
P-0036
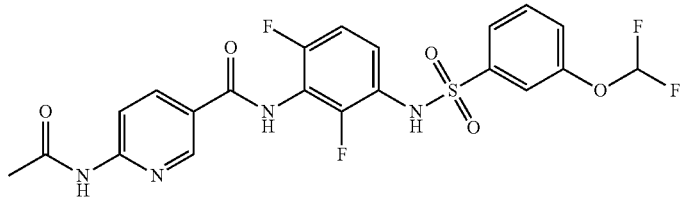 [SMILES: CC(=O)Nc1ccc(C(=O)Nc2c(F)ccc(NS(=O)(=O)c3cccc(OC(F)F)c3)c2F)cn1]
P-0037
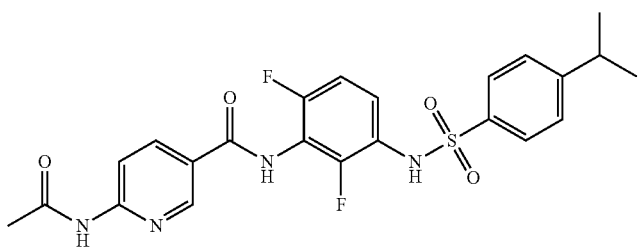 [SMILES: CC(=O)Nc1ccc(C(=O)Nc2c(F)ccc(NS(=O)(=O)c3ccc(C(C)C)cc3)c2F)cn1]
P-0038
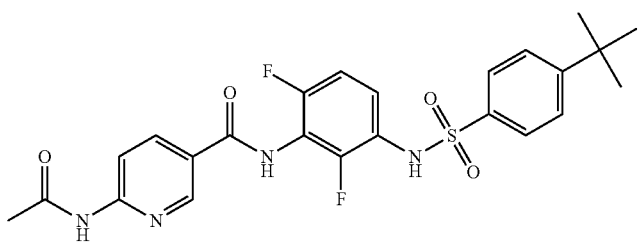 [SMILES: CC(=O)Nc1ccc(C(=O)Nc2c(F)ccc(NS(=O)(=O)c3ccc(C(C)(C)C)cc3)c2F)cn1]
P-0039
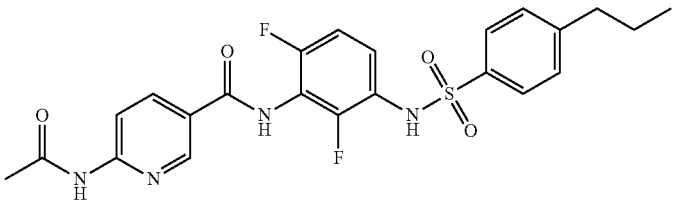 [SMILES: CCCc1ccc(S(=O)(=O)Nc2ccc(F)c(NC(=O)c3ccc(NC(C)=O)nc3)c2F)cc1]
P-0040
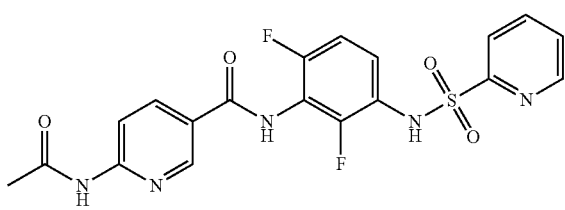 [SMILES: CC(=O)Nc1ccc(C(=O)Nc2c(F)ccc(NS(=O)(=O)c3ccccn3)c2F)cn1]
P-0041
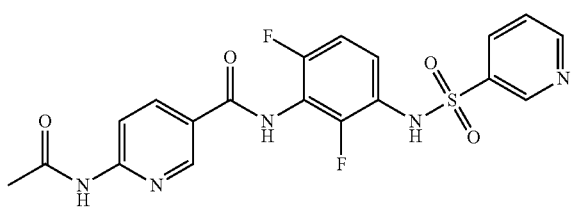 [SMILES: CC(=O)Nc1ccc(C(=O)Nc2c(F)ccc(NS(=O)(=O)c3cccnc3)c2F)cn1]
P-0042
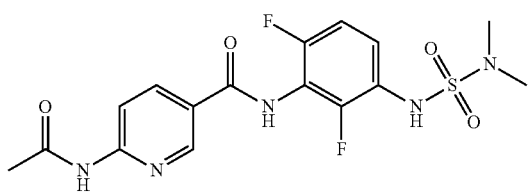 [SMILES: CC(=O)Nc1ccc(C(=O)Nc2c(F)ccc(NS(=O)(=O)N(C)C)c2F)cn1]

P-0043 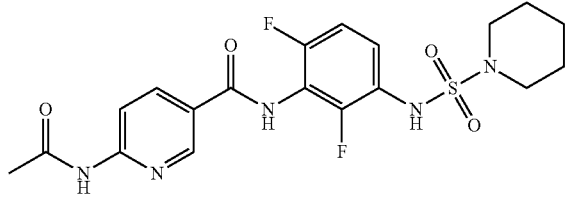 [SMILES: CC(=O)Nc1ccc(C(=O)Nc2c(F)ccc(NS(=O)(=O)N3CCCCC3)c2F)cn1]
P-0044 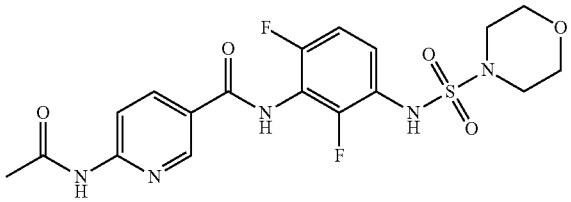 [SMILES: CC(=O)Nc1ccc(C(=O)Nc2c(F)ccc(NS(=O)(=O)N3CCOCC3)c2F)cn1]
P-0045 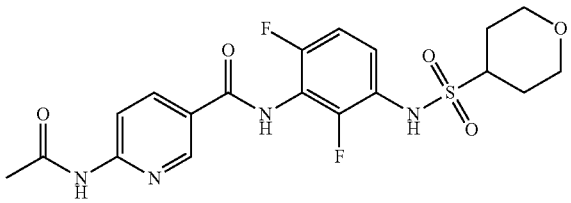 [SMILES: CC(=O)Nc1ccc(C(=O)Nc2c(F)ccc(NS(=O)(=O)C3CCOCC3)c2F)cn1]
P-0046 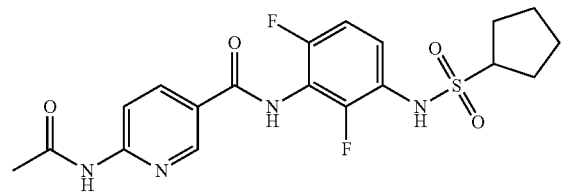 [SMILES: CC(=O)Nc1ccc(C(=O)Nc2c(F)ccc(NS(=O)(=O)C3CCCC3)c2F)cn1]
P-0047 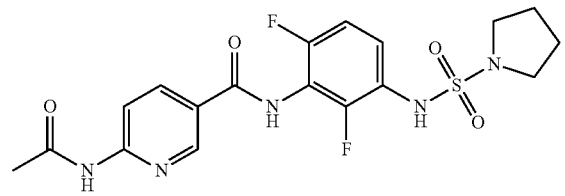 [SMILES: CC(=O)Nc1ccc(C(=O)Nc2c(F)ccc(NS(=O)(=O)N3CCCC3)c2F)cn1]
P-0048 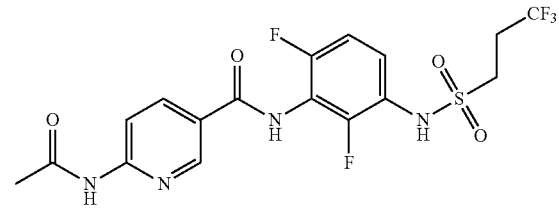 [SMILES: CC(=O)Nc1ccc(C(=O)Nc2c(F)ccc(NS(=O)(=O)CCC(F)(F)F)c2F)cn1]
P-0118 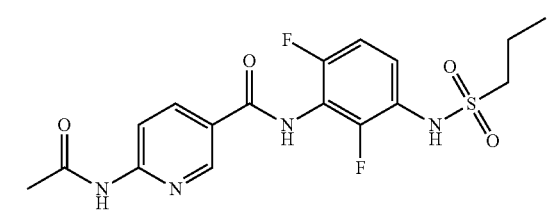 [SMILES: CCCS(=O)(=O)Nc1ccc(F)c(NC(=O)c2ccc(NC(C)=O)nc2)c1F]

P-0049
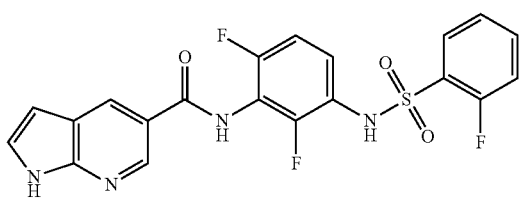 [SMILES: O=C(Nc1c(F)ccc(NS(=O)(=O)c2ccccc2F)c1F)c1cnc2[nH]ccc2c1]
P-0050
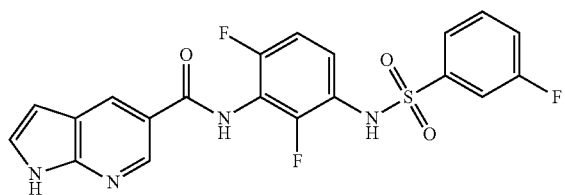 [SMILES: O=C(Nc1c(F)ccc(NS(=O)(=O)c2cccc(F)c2)c1F)c1cnc2[nH]ccc2c1]
P-0051
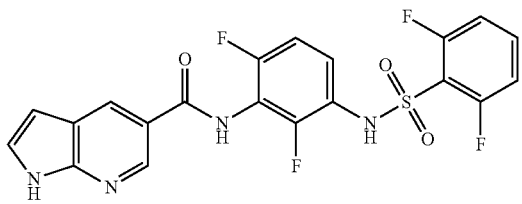 [SMILES: O=C(Nc1c(F)ccc(NS(=O)(=O)c2c(F)cccc2F)c1F)c1cnc2[nH]ccc2c1]
P-0052
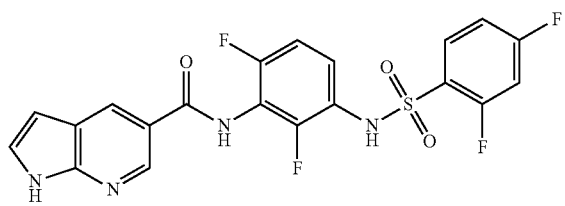 [SMILES: O=C(Nc1c(F)ccc(NS(=O)(=O)c2ccc(F)cc2F)c1F)c1cnc2[nH]ccc2c1]
P-0053
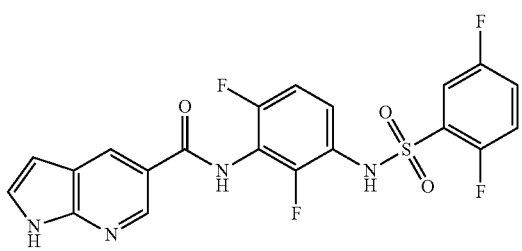 [SMILES: O=C(Nc1c(F)ccc(NS(=O)(=O)c2cc(F)ccc2F)c1F)c1cnc2[nH]ccc2c1]
P-0054
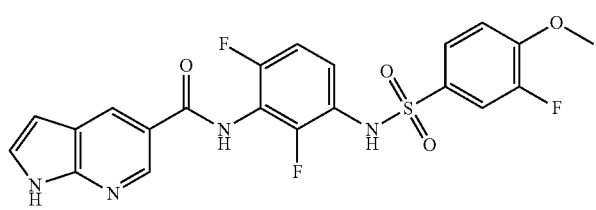 [SMILES: COc1ccc(S(=O)(=O)Nc2ccc(F)c(NC(=O)c3cnc4[nH]ccc4c3)c2F)cc1F]
P-0055
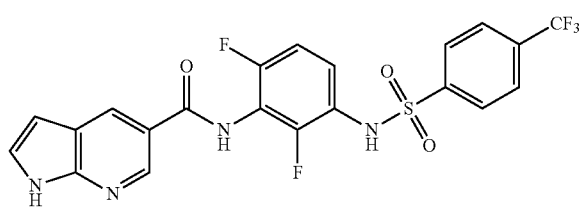 [SMILES: O=C(Nc1c(F)ccc(NS(=O)(=O)c2ccc(C(F)(F)F)cc2)c1F)c1cnc2[nH]ccc2c1]

P-0056 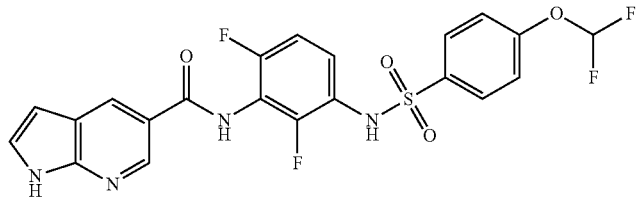 [SMILES: O=C(Nc1c(F)ccc(NS(=O)(=O)c2ccc(OC(F)F)cc2)c1F)c1cnc2[nH]ccc2c1]
P-0057 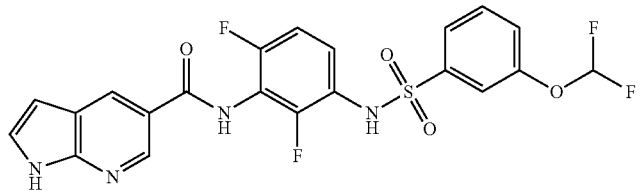 [SMILES: O=C(Nc1c(F)ccc(NS(=O)(=O)c2cccc(OC(F)F)c2)c1F)c1cnc2[nH]ccc2c1]
P-0058 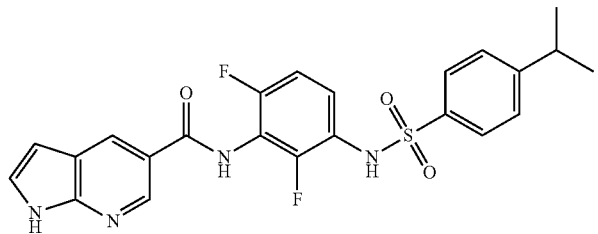 [SMILES: CC(C)c1ccc(S(=O)(=O)Nc2ccc(F)c(NC(=O)c3cnc4[nH]ccc4c3)c2F)cc1]
P-0059 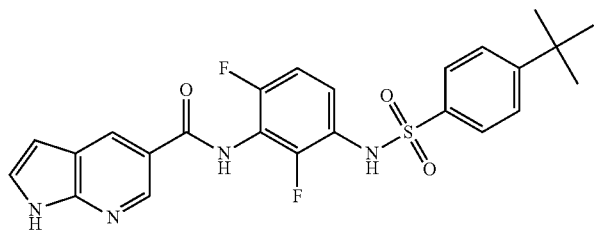 [SMILES: CC(C)(C)c1ccc(S(=O)(=O)Nc2ccc(F)c(NC(=O)c3cnc4[nH]ccc4c3)c2F)cc1]
P-0060 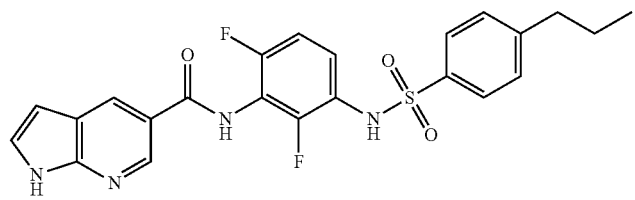 [SMILES: CCCc1ccc(S(=O)(=O)Nc2ccc(F)c(NC(=O)c3cnc4[nH]ccc4c3)c2F)cc1]
P-0061 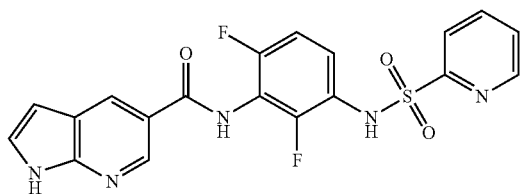 [SMILES: O=C(Nc1c(F)ccc(NS(=O)(=O)c2ccccn2)c1F)c1cnc2[nH]ccc2c1]
P-0062 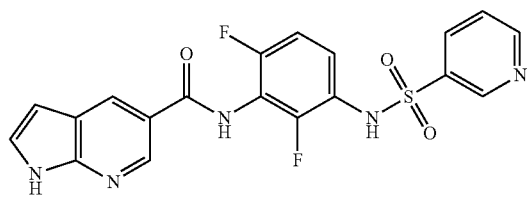 [SMILES: O=C(Nc1c(F)ccc(NS(=O)(=O)c2cccnc2)c1F)c1cnc2[nH]ccc2c1]

P-0063 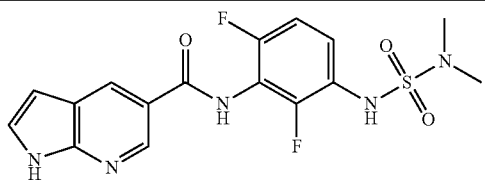
P-0064 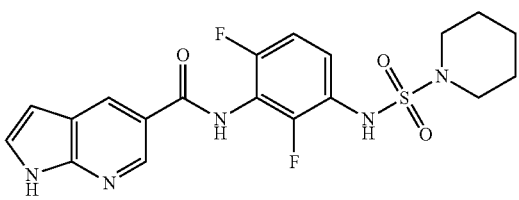 [SMILES: O=C(Nc1c(F)ccc(NS(=O)(=O)N2CCCCC2)c1F)c1cnc2[nH]ccc2c1]
P-0065 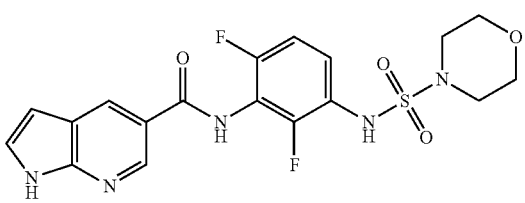
P-0066 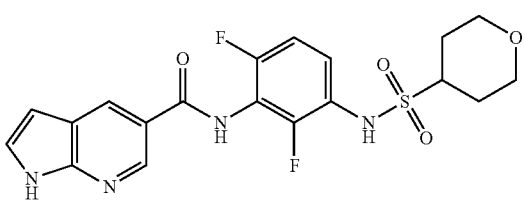 [SMILES: O=C(Nc1c(F)ccc(NS(=O)(=O)N2CCOCC2)c1F)c1cnc2[nH]ccc2c1]
P-0067 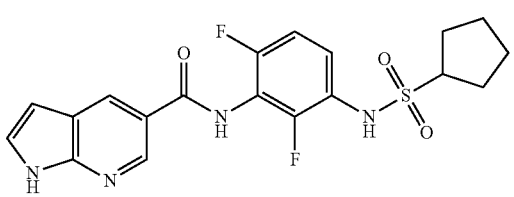 [SMILES: O=C(Nc1c(F)ccc(NS(=O)(=O)C2CCCC2)c1F)c1cnc2[nH]ccc2c1]
P-0068 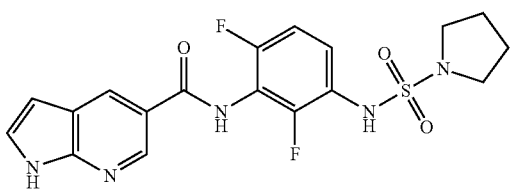
P-0069 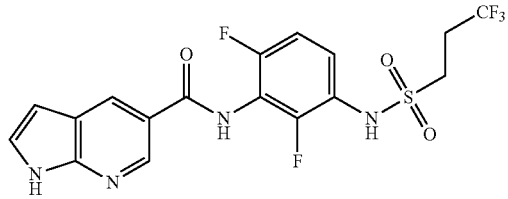 [SMILES: O=C(Nc1c(F)ccc(NS(=O)(=O)CCC(F)(F)F)c1F)c1cnc2[nH]ccc2c1]
P-0119 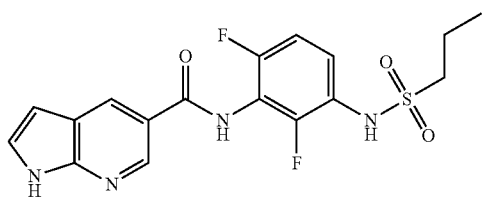 [SMILES: CCCS(=O)(=O)Nc1ccc(F)c(NC(=O)c2cnc3[nH]ccc3c2)c1F]

P-0070 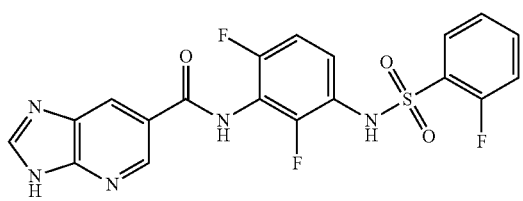 [SMILES: O=C(Nc1c(F)ccc(NS(=O)(=O)c2ccccc2F)c1F)c1cnc2[nH]cnc2c1]
P-0071 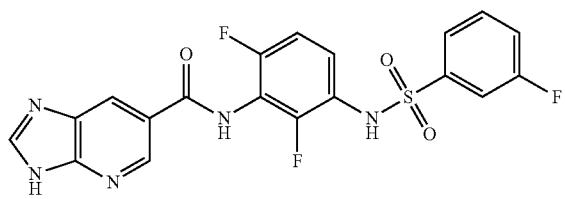 [SMILES: O=C(Nc1c(F)ccc(NS(=O)(=O)c2cccc(F)c2)c1F)c1cnc2[nH]cnc2c1]
P-0072 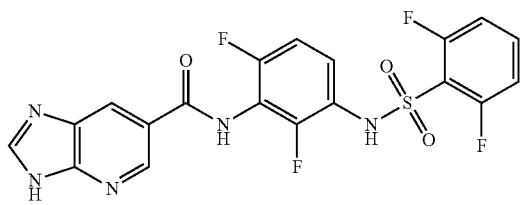 [SMILES: O=C(Nc1c(F)ccc(NS(=O)(=O)c2c(F)cccc2F)c1F)c1cnc2[nH]cnc2c1]
P-0073 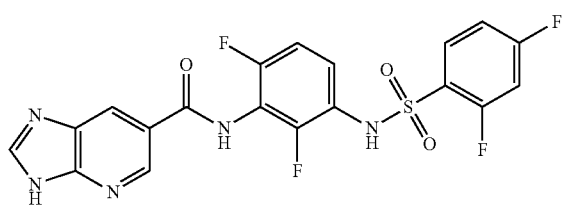 [SMILES: O=C(Nc1c(F)ccc(NS(=O)(=O)c2ccc(F)cc2F)c1F)c1cnc2[nH]cnc2c1]
P-0074 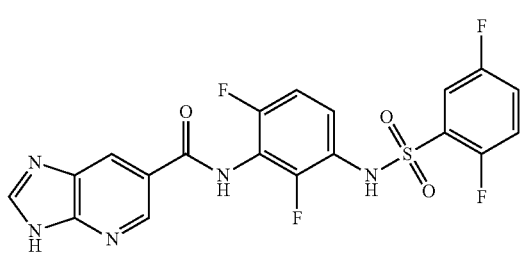 [SMILES: O=C(Nc1c(F)ccc(NS(=O)(=O)c2cc(F)ccc2F)c1F)c1cnc2[nH]cnc2c1]
P-0075 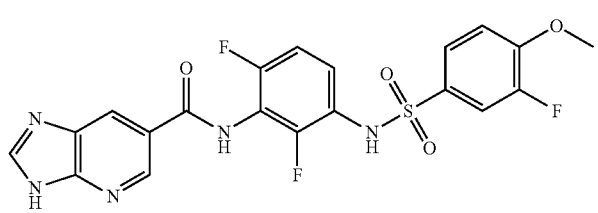 [SMILES: COc1ccc(S(=O)(=O)Nc2ccc(F)c(NC(=O)c3cnc4[nH]cnc4c3)c2F)cc1F]
P-0076 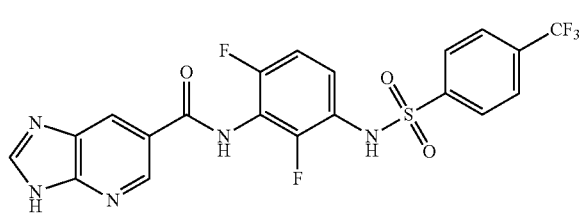

-continued
P-0077
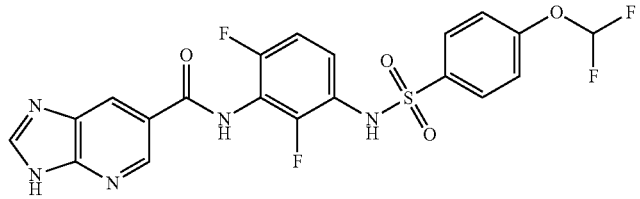 [SMILES: O=C(Nc1c(F)ccc(NS(=O)(=O)c2ccc(OC(F)F)cc2)c1F)c1cnc2[nH]cnc2c1]
P-0078
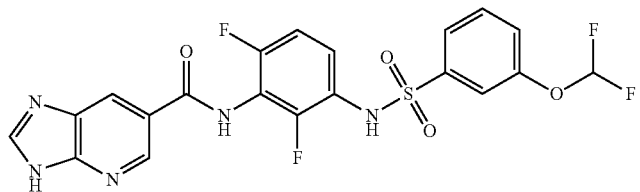 [SMILES: O=C(Nc1c(F)ccc(NS(=O)(=O)c2cccc(OC(F)F)c2)c1F)c1cnc2[nH]cnc2c1]
P-0079
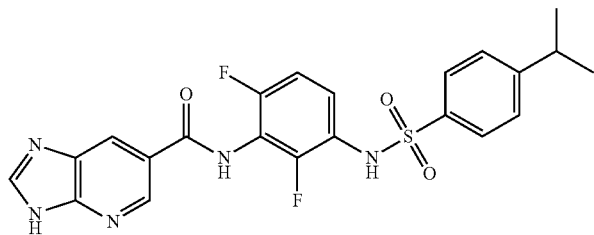 [SMILES: CC(C)c1ccc(S(=O)(=O)Nc2ccc(F)c(NC(=O)c3cnc4[nH]cnc4c3)c2F)cc1]
P-0080
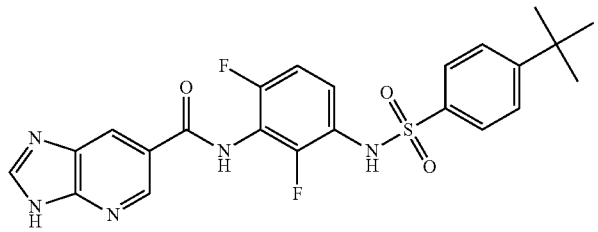
P-0081
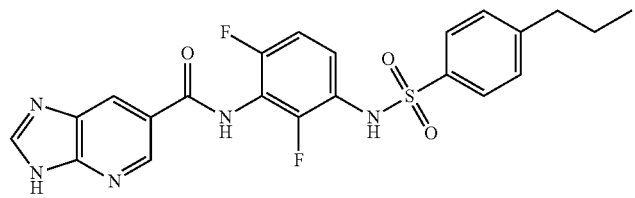 [SMILES: CCCc1ccc(S(=O)(=O)Nc2ccc(F)c(NC(=O)c3cnc4[nH]cnc4c3)c2F)cc1]
P-0082
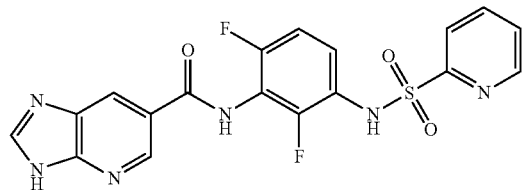 [SMILES: O=C(Nc1c(F)ccc(NS(=O)(=O)c2ccccn2)c1F)c1cnc2[nH]cnc2c1]
P-0083
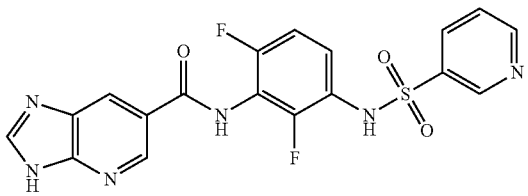 [SMILES: O=C(Nc1c(F)ccc(NS(=O)(=O)c2cccnc2)c1F)c1cnc2[nH]cnc2c1]

-continued
P-0084 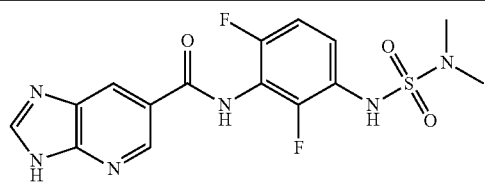
P-0085 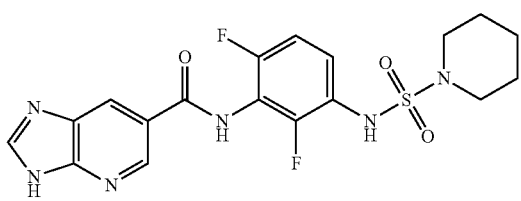 [SMILES: O=C(Nc1c(F)ccc(NS(=O)(=O)N2CCCCC2)c1F)c1cnc2[nH]cnc2c1]
P-0086 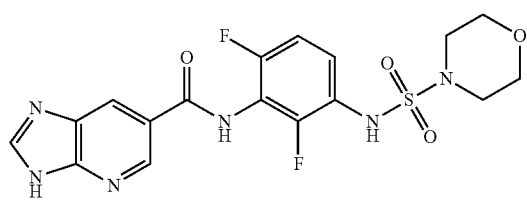 [SMILES: O=C(Nc1c(F)ccc(NS(=O)(=O)N2CCOCC2)c1F)c1cnc2[nH]cnc2c1]
P-0087 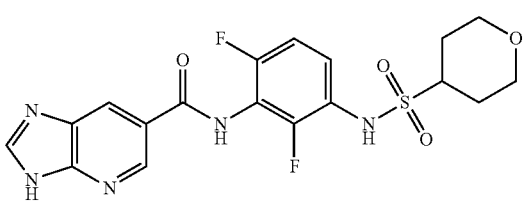 [SMILES: O=C(Nc1c(F)ccc(NS(=O)(=O)C2CCOCC2)c1F)c1cnc2[nH]cnc2c1]
P-0088 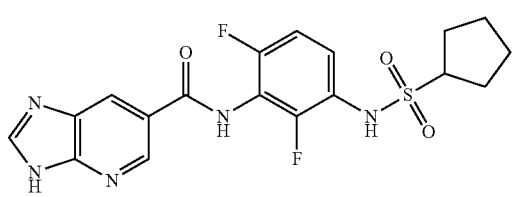
P-0089 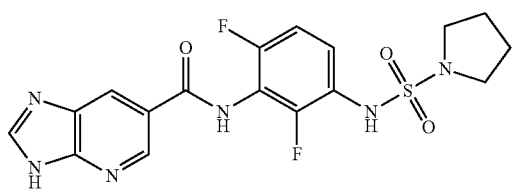 [SMILES: O=C(Nc1c(F)ccc(NS(=O)(=O)C2CCCC2)c1F)c1cnc2[nH]cnc2c1]
P-0090 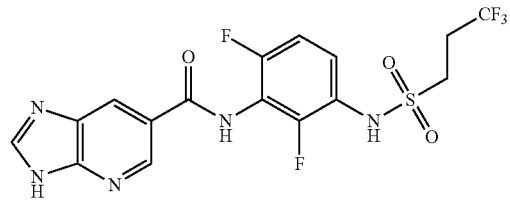 [SMILES: O=C(Nc1c(F)ccc(NS(=O)(=O)CCC(F)(F)F)c1F)c1cnc2[nH]cnc2c1]
P-0120 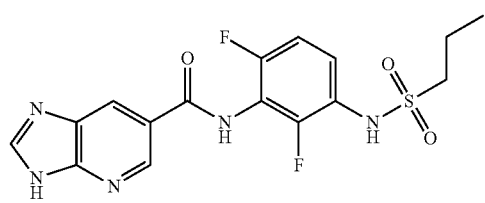 [SMILES: CCCS(=O)(=O)Nc1ccc(F)c(NC(=O)c2cnc3[nH]cnc3c2)c1F]

Example 12: Kinase Activity Assays

Assays for the activity of kinases, including, but not limited to, Fms, Kit, B-Raf, B-Raf V600E, B-Raf V600E/T529I and c-Raf-1 are known in the art, for example as described in US Patent Publication Number US20070032519 and U.S. patent application Ser. No. 11/473,347 (see also, PCT publication WO2007002433), the disclosures of which are hereby incorporated by reference in their entireties including all specifications, figures, and tables, and for all purposes.

Representative compounds screened by at least one of the methods described above, or by similar methods, having $IC_{50}$ of less than 10 µM under the test conditions employed are shown in tables 2a (A-Raf), 2b (B-Raf), 2c (B-Raf V600E), 2d (c-Raf-1), 2e (Brk), 2f (Btk), 2 g (Csk), 2h (Fak), 2i (Fms), 2j (Kdr), 2k (Kit), 2i (Lck), 2m (Lyn), 2n (Src), 2o (TrkA), and 2p (Yes).

TABLE 2a

Representative compounds with activity toward kinase A-Raf with $IC_{50} \leq 10$ µM under the test conditions employed.

| | |
|---|---|
| A-Raf | P-0001, P-0002, P-0004, P-0005, P-0006, P-0008, P-0009, P-0010, P-0011, P-0012, P-0013, P-0015, P-0016, P-0017, P-0020, P-0021, P-0025, P-0026, P-0027 |

TABLE 2b

Representative compounds with activity toward kinase B-Raf with $IC_{50} \leq 10$ µM under the test conditions employed.

| | |
|---|---|
| B-Raf | P-0002, P-0004, P-0008, P-0011, P-0013, P-0015, P-0016, P-0017, P-0018, P-0027 |

TABLE 2c

Representative compounds with activity toward kinase B-Raf V600E with $IC_{50} \leq 10$ µM under the test conditions employed.

| | |
|---|---|
| B-Raf V600E | P-0001, P-0002, P-0004, P-0005, P-0008, P-0011, P-0013, P-0015, P-0016, P-0017, P-0018, P-0020, P-0021, P-0025, P-0026, P-0027 |

TABLE 2d

Representative compounds with activity toward kinase c-Raf-1 with $IC_{50} \leq 10$ µM under the test conditions employed.

| | |
|---|---|
| c-Raf-1: | P-0001, P-0002, P-0004, P-0008, P-0009, P-0011, P-0013, P-0015, P-0016, P-0017, P-0020, P-0021, P-0027 |

TABLE 2e

Representative compounds with activity toward kinase Brk with $IC_{50} \leq 10$ µM under the test conditions employed.

| | |
|---|---|
| Brk: | P-0002 |

TABLE 2f

Representative compounds with activity toward kinase Btk with $IC_{50} \leq 10$ µM under the test conditions employed.

| | |
|---|---|
| Btk: | P-0011 |

TABLE 2g

Representative compounds with activity toward kinase Csk with $IC_{50} \leq 10$ µM under the test conditions employed.

| | |
|---|---|
| Csk: | P-0002 |

TABLE 2h

Representative compounds with activity toward kinase Fak with $IC_{50} \leq 10$ µM under the test conditions employed.

| | |
|---|---|
| Fak: | P-0002 |

TABLE 2i

Representative compounds with activity toward kinase Fms with $IC_{50} \leq 10$ µM under the test conditions employed.

| | |
|---|---|
| Fms: | P-0010, P-0026 |

TABLE 2j

Representative compounds with activity toward kinase Kdr with $IC_{50} \leq 10$ µM under the test conditions employed.

| | |
|---|---|
| Kdr: | P-0011 |

TABLE 2k

Representative compounds with activity toward kinase Kit with $IC_{50} \leq 10$ µM under the test conditions employed.

| | |
|---|---|
| Kit: | P-0011 |

TABLE 2l

Representative compounds with activity toward kinase Lck with $IC_{50} \leq 10$ µM under the test conditions employed.

| | |
|---|---|
| Lck: | P-0002 |

TABLE 2m

Representative compounds with activity toward kinase Lyn with $IC_{50} \leq 10$ µM under the test conditions employed.

| | |
|---|---|
| Lyn: | P-0002 |

TABLE 2n

Representative compounds with activity toward
kinase Src with $IC_{50} \leq 10$ μM under
the test conditions employed.

| Src: | P-0002, P-0011 |
|---|---|

TABLE 2o

Representative compounds with activity toward
kinase TrkA with $IC_{50} \leq 10$ μM under
the test conditions employed.

| TrkA: | P-0002, P-0011 |
|---|---|

TABLE 2p

Representative compounds with activity toward
kinase Yes with $IC_{50} \leq 10$ μM under
the test conditions employed.

| Yes: | P-0002 |
|---|---|

Example 13: Efficacy of Compounds in
Combination with Standard-of-Care
Chemotherapeutic Agents in Four Human Cancer
Cell Lines Compounds of the invention, such as compounds of Formula I, in combination with a standard chemotherapeutic agent, such as 5-fluorouracil, carboplatin, dacarbazine, gefitinib, oxaliplatin, paclitaxel, SN-38, temozolomide, or vinblastine, can be assessed for their effectiveness in killing human tumor cells. Such assays are known in the art, for example, as described in U.S. patent application Ser. No. 11/473,347.

Additional examples of certain methods contemplated by the present invention may be found in the following applications: U.S. Patent Publ. No. 2006/058339; U.S. Patent Publ. No. 2006/058340; U.S. Patent Publ. No. 2007/0032519; and U.S. patent application Ser. No. 11/473,347, filed Jun. 21, 2006 (Equivalent to PCT published as WO 2007/002433), each of which are hereby incorporated by reference herein in their entireties including all specifications, figures, and tables, and for all purposes.

All patents and other references cited in the specification are indicative of the level of skill of those skilled in the art to which the invention pertains, and are incorporated by reference in their entireties, including any tables and figures, to the same extent as if each reference had been incorporated by reference in its entirety individually.

One skilled in the art would readily appreciate that the present invention is well adapted to obtain the ends and advantages mentioned, as well as those inherent therein. The methods, variances, and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. Thus, for an embodiment of the invention using one of the terms, the invention also includes another embodiment wherein one of these terms is replaced with another of these terms. In each embodiment, the terms have their established meaning. Thus, for example, one embodiment may encompass a method "comprising" a series of steps, another embodiment would encompass a method "consisting essentially of" the same steps, and a third embodiment would encompass a method "consisting of" the same steps. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Also, unless indicated to the contrary, where various numerical values are provided for embodiments, additional embodiments are described by taking any 2 different values as the endpoints of a range. Such ranges are also within the scope of the described invention.

Thus, additional embodiments are within the scope of the invention and within the following claims.

What is claimed is:

1. A method for treating a subject with melanoma, thyroid cancer, or colorectal cancer, said method comprising administering to the subject:

an effective amount of a compound of formula (Ia):

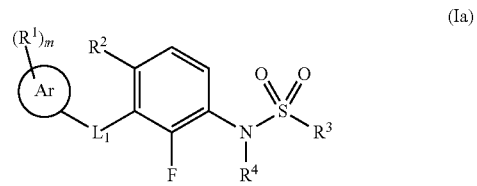

or a pharmaceutically acceptable salt thereof,
wherein:
$L_1$ is a bond or —N(H)C(O)—;
each $R^1$ is —N($R^5$)—C(X)—$R^7$, lower alkyl, or optionally substituted heteroaryl;
$R^2$ is hydrogen or halogen;
$R^4$ is hydrogen;
$R^3$ is optionally substituted lower alkyl or optionally substituted aryl;
m is 0, 1, 2, or 3;
Ar is a monocyclic heteroaryl containing 5 to 6 atoms wherein at least one atom is nitrogen;
$R^5$ is hydrogen;
X is O; and
$R^7$ is lower alkyl.

2. The method of claim 1, wherein $R^2$ is hydrogen.

3. The method of claim 1, wherein $R^2$ is halogen.

4. The method of claim 1, wherein $R^3$ is optionally substituted phenyl.

5. The method of claim 1, wherein $R^3$ is phenyl substituted with one or more substituents selected from the group consisting of fluoro, lower alkyl, fluoro substituted lower alkyl, lower alkoxy, fluoro substituted lower alkoxy, lower alkylthio, and fluoro substituted lower alkylthio.

6. The method of claim 1, wherein $R^3$ is phenyl substituted with one or more fluoro.

7. The method of claim 1, wherein one of the $R^1$ substituents is lower alkyl containing 1-4 carbon atoms.

8. The method of claim 1, wherein one of the $R^1$ substituents is optionally substituted heteroaryl.

9. The method of claim 1, further comprising administering a chemotherapeutic agent in combination with the compound of formula (Ia).

10. The method of claim 6, further comprising administering a chemotherapeutic agent in combination with the compound of formula (Ia), and wherein the chemotherapeutic agent is a kinase inhibitor.

11. The method of claim 7, further comprising administering a chemotherapeutic agent in combination with the compound of formula (Ia), and wherein the chemotherapeutic agent is a kinase inhibitor.

12. The method of claim 8, further comprising administering a chemotherapeutic agent in combination with the compound of formula (Ia), and wherein the chemotherapeutic agent is a kinase inhibitor.

13. The method of claim 10, wherein the subject has melanoma.

14. The method of claim 10, wherein the melanoma is melanoma having a B-Raf V600E mutation.

15. A method for treating a subject with melanoma, thyroid cancer, or colorectal cancer, said method comprising administering to the subject:
an effective amount of a compound of formula (Ia):

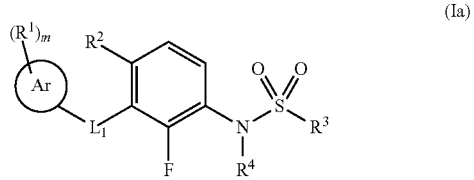

(Ia)

or a pharmaceutically acceptable salt thereof,
wherein:
$L_1$ is a bond;
each $R^1$ is —N($R^5$)—C(X)—$R^7$, lower alkyl, or optionally substituted heteroaryl;
$R^2$ is hydrogen or halogen;
$R^4$ is hydrogen;
$R^3$ is optionally substituted lower alkyl or optionally substituted aryl;
m is 0, 1, 2, or 3;
Ar is a monocyclic heteroaryl containing 5 to 6 atoms wherein at least one atom is nitrogen;
$R^5$ is hydrogen;
X is O; and
$R^7$ is lower alkyl.

16. The method of claim 15, wherein $R^2$ is hydrogen.

17. The method of claim 15, wherein $R^2$ is halogen.

18. The method of claim 15, wherein $R^3$ is optionally substituted phenyl.

19. The method of claim 15, wherein $R^3$ is phenyl substituted with one or more substituents selected from the group consisting of fluoro, lower alkyl, fluoro substituted lower alkyl, lower alkoxy, fluoro substituted lower alkoxy, lower alkylthio, and fluoro substituted lower alkylthio.

20. The method of claim 15, wherein $R^3$ is phenyl substituted with one or more fluoro.

21. The method of claim 15, wherein one of the $R^1$ substituents is lower alkyl containing 1-4 carbon atoms.

22. The method of claim 15, wherein one of the $R^1$ substituents is optionally substituted heteroaryl.

23. The method of claim 15, further comprising administering a chemotherapeutic agent in combination with the compound of formula (Ia).

24. The method of claim 20, further comprising administering a chemotherapeutic agent in combination with the compound of formula (Ia), and wherein the chemotherapeutic agent is a kinase inhibitor.

25. The method of claim 21, further comprising administering a chemotherapeutic agent in combination with the compound of formula (Ia), and wherein the chemotherapeutic agent is a kinase inhibitor.

26. The method of claim 22, further comprising administering a chemotherapeutic agent in combination with the compound of formula (Ia), and wherein the chemotherapeutic agent is a kinase inhibitor.

27. The method of claim 24, wherein the subject has melanoma.

28. The method of claim 24, wherein the melanoma is melanoma having a B-Raf V600E mutation.

29. A method for treating a subject with non-small cell lung cancer, said method comprising administering to the subject:
an effective amount of a compound of formula (Ia):

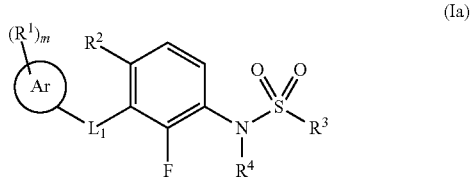

(Ia)

or a pharmaceutically acceptable salt thereof,
wherein:
$L_1$ is a bond or —N(H)C(O)—;
each $R^1$ is —N($R^5$)—C(X)—$R^7$, lower alkyl, or optionally substituted heteroaryl;
$R^2$ is hydrogen or halogen;
$R^4$ is hydrogen;
$R^3$ is optionally substituted lower alkyl or optionally substituted aryl;
m is 0, 1, 2, or 3;
Ar is a monocyclic heteroaryl containing 5 to 6 atoms wherein at least one atom is nitrogen;
$R^5$ is hydrogen;
X is O; and
$R^7$ is lower alkyl.

30. The method of claim 29, wherein $R^2$ is hydrogen.

31. The method of claim 29, wherein $R^2$ is halogen.

32. The method of claim 29, wherein $R^3$ is optionally substituted phenyl.

33. The method of claim 29, wherein $R^3$ is phenyl substituted with one or more substituents selected from the group consisting of fluoro, lower alkyl, fluoro substituted lower alkyl, lower alkoxy, fluoro substituted lower alkoxy, lower alkylthio, and fluoro substituted lower alkylthio.

34. The method of claim 29, wherein $R^3$ is phenyl substituted with one or more fluoro.

35. The method of claim 29, wherein one of the $R^1$ substituents is lower alkyl containing 1-4 carbon atoms.

36. The method of claim 29, wherein one of the $R^1$ substituents is optionally substituted heteroaryl.

37. The method of claim 29, further comprising administering a chemotherapeutic agent in combination with the compound of formula (Ia).

38. The method of claim 34, further comprising administering a chemotherapeutic agent in combination with the compound of formula (Ia), and wherein the chemotherapeutic agent is a kinase inhibitor.

39. The method of claim 35, further comprising administering a chemotherapeutic agent in combination with the compound of formula (Ia), and wherein the chemotherapeutic agent is a kinase inhibitor.

40. The method of claim 36, further comprising administering a chemotherapeutic agent in combination with the compound of formula (Ia), and wherein the chemotherapeutic agent is a kinase inhibitor.

41. A method for treating a subject with non-small cell lung cancer, said method comprising administering to the subject:
an effective amount of a compound of formula (Ia):

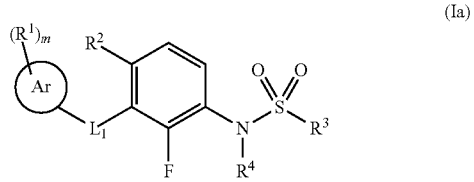

(Ia)

or a pharmaceutically acceptable salt thereof,
wherein:
$L_1$ is a bond;
each $R^1$ is —N($R^5$)—C(X)—$R^7$, lower alkyl, or optionally substituted heteroaryl;
$R^2$ is hydrogen or halogen;
$R^4$ is hydrogen;
$R^3$ is optionally substituted lower alkyl or optionally substituted aryl;
m is 0, 1, 2, or 3;
Ar is a monocyclic heteroaryl containing 5 to 6 atoms wherein at least one atom is nitrogen;
$R^5$ is hydrogen;
X is O; and
$R^7$ is lower alkyl.

42. The method of claim 41, wherein $R^2$ is hydrogen.

43. The method of claim 41, wherein $R^2$ is halogen.

44. The method of claim 41, wherein $R^3$ is optionally substituted phenyl.

45. The method of claim 41, wherein $R^3$ is phenyl substituted with one or more substituents selected from the group consisting of fluoro, lower alkyl, fluoro substituted lower alkyl, lower alkoxy, fluoro substituted lower alkoxy, lower alkylthio, and fluoro substituted lower alkylthio.

46. The method of claim 41, wherein $R^3$ is phenyl substituted with one or more fluoro.

47. The method of claim 41, wherein one of the $R^1$ substituents is lower alkyl containing 1-4 carbon atoms.

48. The method of claim 41, wherein one of the $R^1$ substituents is optionally substituted heteroaryl.

49. The method of claim 41, further comprising administering a chemotherapeutic agent in combination with the compound of formula (Ia).

50. The method of claim 46, further comprising administering a chemotherapeutic agent in combination with the compound of formula (Ia), and wherein the chemotherapeutic agent is a kinase inhibitor.

51. The method of claim 47, further comprising administering a chemotherapeutic agent in combination with the compound of formula (Ia), and wherein the chemotherapeutic agent is a kinase inhibitor.

52. The method of claim 48, further comprising administering a chemotherapeutic agent in combination with the compound of formula (Ia), and wherein the chemotherapeutic agent is a kinase inhibitor.

* * * * *